US010253338B2

(12) United States Patent
Beckham et al.

(10) Patent No.: US 10,253,338 B2
(45) Date of Patent: Apr. 9, 2019

(54) CONVERSION OF BIOMASS TO USEFUL INTERMEDIATES

(71) Applicant: Alliance for Sustainable Energy, LLC, Golden, CO (US)

(72) Inventors: Gregg Tyler Beckham, Golden, CO (US); Christopher W. Johnson, Denver, CO (US); Derek R. Vardon, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/467,761

(22) Filed: Mar. 23, 2017

(65) Prior Publication Data
US 2017/0275655 A1    Sep. 28, 2017

Related U.S. Application Data

(60) Provisional application No. 62/312,065, filed on Mar. 23, 2016.

(51) Int. Cl.
| C12P 7/44 | (2006.01) |
| C12N 9/10 | (2006.01) |
| C12N 15/52 | (2006.01) |
| C12N 9/02 | (2006.01) |
| C12N 9/04 | (2006.01) |
| C12N 9/18 | (2006.01) |
| C12N 9/90 | (2006.01) |
| C12N 9/88 | (2006.01) |

(52) U.S. Cl.
CPC ............. *C12P 7/44* (2013.01); *C12N 9/0006* (2013.01); *C12N 9/0008* (2013.01); *C12N 9/0069* (2013.01); *C12N 9/13* (2013.01); *C12N 9/18* (2013.01); *C12N 9/88* (2013.01); *C12N 9/90* (2013.01); *C12N 15/52* (2013.01); *C12Y 101/01312* (2013.01); *C12Y 102/01085* (2015.07); *C12Y 113/11001* (2013.01); *C12Y 113/11003* (2013.01); *C12Y 113/11008* (2013.01); *C12Y 208/03006* (2013.01); *C12Y 301/01024* (2013.01); *C12Y 301/01057* (2013.01); *C12Y 307/01009* (2013.01); *C12Y 401/01044* (2013.01); *C12Y 401/01045* (2013.01); *C12Y 401/01077* (2013.01); *C12Y 402/01083* (2013.01); *C12Y 503/02* (2013.01); *C12Y 503/02006* (2015.07); *C12Y 503/03004* (2013.01); *C12Y 505/01001* (2013.01); *C12Y 505/01002* (2013.01)

(58) Field of Classification Search
None
See application file for complete search history.

(56) References Cited

U.S. PATENT DOCUMENTS

| 4,952,501 A | 8/1990 | Jasin et al. |
| 5,487,987 A | 1/1996 | Frost et al. |
| 2016/0017381 A1 | 1/2016 | Beckham et al. |

FOREIGN PATENT DOCUMENTS

WO    WO 2013/163230 A2    10/2013

OTHER PUBLICATIONS

Wheelis et al., "The Genetic Control of Dissimilatory Pathways in Pseudomonas Putida" 66 Genetics 245-266 (1970).*
Göbel et al., "Degradation of Aromatics and Chloroaromatics by Pseudomonas sp. Strain B13: Cloning Characterization, and Analysis of Sequences Encoding 3-Oxoadipate:Succinyl-Coenzyme A (CoA) Transferase and 3-Oxoadipyl-CoA Thiolase" 184(1) Journal of Bacteriology 216-223 (2002).*
Draths et al., "Environmentally Compatible Synthesis of Adipic Acid from D-glucose", Journal of the American Chemical Society, Jan. 1994, vol. 116, No. 1, pp. 399-400.
Gürbüz et al., "Dual-bed Catalyst System for C—C Coupling of Biomass-derived Oxygenated Hydrocarbons to Fuel-grade Compounds", Green Chemistry, 2010, vol. 12, No. 2, pp. 223-227.
Gürbüz et al., "Integration of C—C Coupling Reactions of Biomass-derived Oxygenates to Fuel-grade Compounds", Applied Catalysis B: Environmental, Feb. 2010, vol. 94, Nos. 1-2, pp. 134-141.
Harayama et al., "The meta cleavage operon of TOL degradative plasmid pWW0 comprises 13 genes", Molecular & General Genetics MGG, Mar. 1990, vol. 221, No. 1, pp. 113-120.
Kasiai et al., "Uncovering the Protocatechuate 2,3-Cleavage Pathway Genes", Journal of Bacteriology, Nov. 2009, vol. 191, No. 21, pp. 6758-6768.
Linger et al., "Lignin Valorization Though Integrated Biological Funneling and Chemical Catalysis", Proceedings of the National Academy of Sciences, Aug. 2014, vol. 111, No. 33, pp. 12013-12018.
Ozokwelu, "High Efficiency Modular Chemical Processes (HEMCP) Modular Process Intensification", Advanced Manufacturing Office—U.S. Department of Energy, Energy Efficiency & Renewable Energy, Sep. 27, 2014, pp. 1-12.
Vardon et al., "Adipic Acid Production from Lignin", Energy & Environmental Science, 2015, vol. 8, pp. 617-628.

(Continued)

Primary Examiner — Nancy J Leith
(74) Attorney, Agent, or Firm — Sam J. Barkley; Michael A. McIntyre

(57) ABSTRACT

An aspect of the present disclosure is a microbial cell that includes a genetic modification resulting in the expression of a deficient form of an endogenous dioxygenase, and a gene encoding an exogenous dioxygenase and a promoter sequence, where the endogenous dioxygenase includes PcaH and PcaG, the exogenous dioxygenase includes LigA and LigB, the microbial cell is capable of growth utilizing at least one of a cellulose decomposition molecule or a lignin decomposition molecule, and the microbial cell is capable of producing 2-hydroxy-2H-pyran-4,6-dicarboxylic acid.

12 Claims, 6 Drawing Sheets
Specification includes a Sequence Listing.

(56) References Cited

OTHER PUBLICATIONS

Weber et al., "Biosynthesis of cis,cis-Muconic Acid and Its Aromatic Precursors, Catechol and Protocatechuic Acid, from Renewable Feedstocks by *Saccharomyces cerevisiae*", Applied and Environmental Microbiology, Dec. 2012, vol. 78, No. 23, pp. 8421-8430.
Compound Summary for CID 440647, 2-hydroxy-2H-pyran-4,6-dicarboxylic acid, Open Chemistry Database, accessed at https://pubchem.ncbi.nlm.nih.gov/compound/440647 on Oct. 4, 2017, pp. 1-9.
Masai et al., "Genetic and Biochemical Investigations on Bacterial Catabolic Pathways for Lignin-Derived Aromatic Compounds", Bioscience, Biotechnology, and Biochemistry, 2007, vol. 71, No. 1, pp. 1-15.
International Search Report and Written Opinion for International (PCT) Application No. PCT/US17/23878, dated Dec. 19, 2017, pp. 1-12.

\* cited by examiner

10 → 10a

11 → 11a

CONVERSION OF BIOMASS TO USEFUL INTERMEDIATES

CROSS-REFERENCE TO RELATED APPLICATIONS

This application claims priority to U.S. Provisional Application No. 62/312,065 filed Mar. 23, 2016, the contents of which are incorporated herein by reference in its entirety.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy, created on Mar. 23, 2017, is named 14-45_ST25.txt, and is 235 kilobytes in size.

BACKGROUND

Many petrochemicals and polymers are manufactured by environmentally unfriendly processes that produce significant amounts of waste (e.g. adipic acid manufacturing requires $HNO_3$-oxidation of cyclohexanol/cyclohexane, resulting in massive amounts of green-house gas emissions). Since petrochemical manufacturing requires such energy intensive, environmentally damaging processes, there is clearly a need for new approaches that produce petrochemical replacements from renewable feedstocks such as lignocellulose.

SUMMARY

An aspect of the present disclosure is a microbial cell that includes a genetic modification resulting in the expression of a deficient form of an endogenous dioxygenase, and a gene encoding an exogenous dioxygenase and a promoter sequence, where the endogenous dioxygenase includes PcaH (nucleic acid sequence represented by SEQ ID NO:29, amino acid sequence represented by SEQ ID NO:30) and PcaG (nucleic acid sequence represented by SEQ ID NO:31, amino acid sequence represented by SEQ ID NO:32), the exogenous dioxygenase includes LigA (nucleic acid sequence represented by SEQ ID NO:1, amino acid sequence represented by SEQ ID NO:2) and LigB (nucleic acid sequence represented by SEQ ID NO:3, amino acid sequence represented by SEQ ID NO:4), the microbial cell is capable of growth utilizing at least one of a cellulose decomposition molecule or a lignin decomposition molecule, and the microbial cell is capable of producing 2-hydroxy-2H-pyran-4,6-dicarboxylic acid.

An aspect of the present disclosure is a microbial cell that includes a genetic modification resulting in the expression of a deficient form of an endogenous dioxygenase and a gene encoding an exogenous dioxygenase, an exogenous dehydrogenase, and a promoter sequence, where the endogenous dioxygenase includes PcaH and PcaG, the exogenous dioxygenase includes LigA and LigB, the exogenous dehydrogenase includes LigC (nucleic acid sequence represented by SEQ ID NO:5, amino acid sequence represented by SEQ ID NO:6), the microbial cell is capable of growth utilizing at least one of a cellulose decomposition molecule or a lignin decomposition molecule, and the microbial cell is capable of producing 2-oxo-2H-pyran-4,6-dicarboxylic acid.

An aspect of the present disclosure is a microbial cell that includes a first genetic modification resulting in the expression of a deficient form of an endogenous dioxygenase, a second genetic modification resulting in the expression of deficient forms of an endogenous tautomerase, an endogenous hydratase, and an endogenous decarboxylase, and a gene encoding an exogenous dioxygenase, an exogenous dehydrogenase, an exogenous hydrolase, and a promoter sequence, where the endogenous dioxygenase includes PcaH and PcaG, the endogenous tautomerase, the endogenous hydratase, and the endogenous decarboxylase include GalD (nucleic acid sequence represented by SEQ ID NO:15, amino acid sequence represented by SEQ ID NO:16), GalB (nucleic acid sequence represented by SEQ ID NO:17, amino acid sequence represented by SEQ ID NO:18), and GalC (nucleic acid sequence represented by SEQ ID NO:19, amino acid sequence represented by SEQ ID NO:20) respectively, the exogenous dioxygenase includes LigA and LigB, the exogenous dehydrogenase includes LigC, the exogenous hydrolase includes LigI (nucleic acid sequence represented by SEQ ID NO:7, amino acid sequence represented by SEQ ID NO:8), the microbial cell is capable of growth utilizing at least one of a cellulose decomposition molecule or a lignin decomposition molecule, and the microbial cell is capable of producing (1E,3E)-4-hydroxybuta-1,3-diene-1,2,4-tricarboxylic acid.

An aspect of the present disclosure is a microbial cell that includes a first genetic modification resulting in the expression of a deficient form of an endogenous dioxygenase, a second genetic modification resulting in the expression of a deficient form of an endogenous tautomerase, an endogenous hydratase, and an endogenous decarboxylase, and a gene encoding an exogenous dioxygenase, an exogenous dehydrogenase, an exogenous hydrolase, an exogenous tautomerase, and a promoter sequence, where the endogenous dioxygenase includes PcaH and PcaG, the endogenous tautomerase, the endogenous hydratase, and the endogenous decarboxylase include GalD, GalB, and GalC respectively, the exogenous dioxygenase includes LigA and LigB, the exogenous dehydrogenase includes LigC, the exogenous hydrolase includes LigI, the exogenous tautomerase includes LigU (nucleic acid sequence represented by SEQ ID NO:9, amino acid sequence represented by SEQ ID NO:10), the microbial cell is capable of growth utilizing at least one of a cellulose decomposition molecule or a lignin decomposition molecule, and the microbial cell is capable of producing (1E)-4-oxobut-1-ene-1,2,4-tricarboxylic acid.

An aspect of the present disclosure is a microbial cell that includes a first genetic modification resulting in the expression of a deficient form of an endogenous dioxygenase, a second genetic modification resulting in the expression of a deficient form of an endogenous tautomerase, an endogenous hydratase, and an endogenous decarboxylase, and a gene encoding an exogenous dioxygenase, an exogenous dehydrogenase, an exogenous hydrolase, an exogenous tautomerase, an exogenous hydratase, and a promoter sequence, where the endogenous dioxygenase includes PcaH and PcaG, the endogenous tautomerase, the endogenous hydratase, and the endogenous decarboxylase include GalD, GalB, and GalC respectively, the exogenous dioxygenase includes LigA and LigB, the exogenous dehydrogenase includes LigC, the exogenous hydrolase includes LigI, the exogenous tautomerase includes LigU, the exogenous hydratase includes LigJ (nucleic acid sequence represented by SEQ ID NO:11, amino acid sequence represented by SEQ ID NO:12), the microbial cell is capable of growth utilizing at least one of a cellulose decomposition molecule or a lignin decomposition molecule, and the microbial cell is capable of producing 2-hydroxy-4-oxobutane-1,2,4-tricarboxylic acid.

An aspect of the present disclosure is a microbial cell that includes a genetic modification resulting in the expression of a deficient form of an endogenous enol-lactonase, a deficient form of an endogenous decarboxylase, and a deficient form of an endogenous cycloisomerase, where the endogenous enol-lactonase includes PcaD (nucleic acid sequence represented by SEQ ID NO:37, amino acid sequence represented by SEQ ID NO:38), the endogenous decarboxylase includes PcaC (nucleic acid sequence represented by SEQ ID NO:35, amino acid sequence represented by SEQ ID NO:36), the endogenous cycloisomerase includes PcaB (nucleic acid sequence represented by SEQ ID NO:33, amino acid sequence represented by SEQ ID NO:34), the microbial cell is capable of growth utilizing at least one of a cellulose decomposition molecule or a lignin decomposition molecule, and the microbial cell is capable of producing (1E, 3Z)-buta-1,3-diene-1,2,4-tricarboxylic acid.

An aspect of the present disclosure is a microbial cell that includes a genetic modification resulting in the expression of a deficient form of an endogenous enol-lactonase and a deficient form of an endogenous decarboxylase, where the endogenous enol-lactonase includes PcaD, the endogenous decarboxylase includes PcaC, the microbial cell is capable of growth utilizing at least one of a cellulose decomposition molecule or a lignin decomposition molecule, and the microbial cell is capable of producing 2-carboxy-5-oxo-2,5-dihydrofuran-2-carboxylic acid.

An aspect of the present disclosure is a microbial cell that includes a genetic modification resulting in the expression of a deficient form of an endogenous enol-lactonase, where the endogenous enol-lactonase includes PcaD, the microbial cell is capable of growth utilizing at least one of a cellulose decomposition molecule or a lignin decomposition molecule, and the microbial cell is capable of producing 2-(2-oxo-3H-furan-5-yl)acetic acid.

An aspect of the present disclosure is a microbial cell that includes a genetic modification resulting in the expression of a deficient form of an endogenous transferase, where the endogenous transferase includes PcaI (nucleic acid sequence represented by SEQ ID NO:39, amino acid sequence represented by SEQ ID NO:40) and PcaJ (nucleic acid sequence represented by SEQ ID NO:41, amino acid sequence represented by SEQ ID NO:42), the microbial cell is capable of growth utilizing at least one of a cellulose decomposition molecule or a lignin decomposition molecule, and the microbial cell is capable of producing 3-oxohexanedioic acid.

An aspect of the present disclosure is a microbial cell that includes a genetic modification resulting in the expression of a deficient form of an endogenous dioxygenase and a gene encoding an exogenous dioxygenase and a promoter sequence, where the endogenous dioxygenase includes PcaH and PcaG, the exogenous dioxygenase includes PraA, the microbial cell is capable of growth utilizing at least one of a cellulose decomposition molecule or a lignin decomposition molecule, and the microbial cell is capable of producing (2E,4E)-2-formyl-5-hydroxyhexa-2,4-dienedioic acid.

An aspect of the present disclosure is a microbial cell that includes a first genetic modification resulting in the expression of a deficient form of a first endogenous dioxygenase, a second genetic modification resulting in the expression of a deficient form of a second endogenous dioxygenase, a third genetic modification resulting in the expression of a deficient form of an endogenous muconate cycloisomerase, a deficient form of an endogenous muconolactone isomerase, and a deficient form of a third endogenous dioxygenase, a first gene encoding a first exogenous dioxygenase, an exogenous decarboxylase, and a first promoter sequence, and a second gene encoding a second exogenous dioxygenase and a second promoter sequence, where the first endogenous dioxygenase includes PcaH and PcaG, the second endogenous dioxygenase includes CatA2 (nucleic acid sequence represented by SEQ ID NO:23, amino acid sequence represented by SEQ ID NO:24), the endogenous muconate cycloisomerase includes CatB (nucleic acid sequence represented by SEQ ID NO:25, amino acid sequence represented by SEQ ID NO:26), the endogenous muconolactone isomerase includes CatC (nucleic acid sequence represented by SEQ ID NO:27, amino acid sequence represented by SEQ ID NO:28), the third endogenous dioxygenase includes CatA (nucleic acid sequence represented by SEQ ID NO:21, amino acid sequence represented by SEQ ID NO:22), the first exogenous dioxygenase includes PraA, the exogenous decarboxylase includes PraH (nucleic acid sequence represented by SEQ ID NO:47, amino acid sequence represented by SEQ ID NO:48), the second exogenous dioxygenase includes XylE, the microbial cell is capable of growth utilizing at least one of a cellulose decomposition molecule or a lignin decomposition molecule, and the microbial cell is capable of producing (2Z,4E)-2-hydroxy-6-oxohexa-2,4-dienoic acid.

An aspect of the present disclosure is a microbial cell that includes a first genetic modification resulting in the expression of a deficient form of a first endogenous dioxygenase, a second genetic modification resulting in the expression of a deficient form of a second endogenous dioxygenase, a third genetic modification resulting in the expression of a deficient form of an endogenous muconate cycloisomerase, a deficient form of an endogenous muconolactone isomerase, and a deficient form of a third endogenous dioxygenase, a first gene encoding a first exogenous dioxygenase, an exogenous decarboxylase, and a first promoter sequence, and a second gene encoding a second exogenous dioxygenase, an exogenous dehydrogenase, and a second promoter sequence, where the first endogenous dioxygenase includes PcaH and PcaG, the second endogenous dioxygenase includes CatA2, the endogenous muconate cycloisomerase includes CatB, the endogenous muconolactone isomerase includes CatC, the third endogenous dioxygenase includes CatA, the first exogenous dioxygenase includes PraA (nucleic acid sequence represented by SEQ ID NO:45, amino acid sequence represented by SEQ ID NO:46), the exogenous decarboxylase includes PraH, the second exogenous dioxygenase includes XylE (nucleic acid sequence represented by SEQ ID NO:49, amino acid sequence represented by SEQ ID NO:50), the exogenous dehydrogenase includes XylG (nucleic acid sequence represented by SEQ ID NO:53, amino acid sequence represented by SEQ ID NO:54), the microbial cell is capable of growth utilizing at least one of a cellulose decomposition molecule or a lignin decomposition molecule, and the microbial cell is capable of producing (2Z,4E)-2-hydroxyhexa-2,4-dienedioic acid.

An aspect of the present disclosure is a microbial cell that includes a first genetic modification resulting in the expression of a deficient form of a first endogenous dioxygenase, a second genetic modification resulting in the expression of a deficient form of a second endogenous dioxygenase, a third genetic modification resulting in the expression of a deficient form of an endogenous muconate cycloisomerase, a deficient form of an endogenous muconolactone isomerase, and a deficient form of a third endogenous dioxygenase, a first gene encoding a first exogenous dioxygenase, an exogenous decarboxylase, and a first promoter sequence, and a second gene encoding a second exogenous dioxygenase, an exogenous dehydrogenase, an exogenous tautomerase, and a second promoter sequence, where the first endogenous dioxygenase comprises PcaH and PcaG, the second endogenous dioxygenase includes CatA2, the endogenous muconate cycloisomerase includes CatB, the endogenous muconolactone isomerase includes CatC, the third endogenous dioxygenase includes CatA, the first exogenous dioxygenase includes PraA, the exogenous decarboxylase includes PraH, the second exogenous dioxygenase includes XylE, the exogenous dehydrogenase includes XylG, the exogenous tautomerase includes XylH (nucleic acid sequence represented by SEQ ID NO:55, amino acid sequence represented by SEQ ID NO:56), the microbial cell is capable of growth utilizing at least one of a cellulose decomposition molecule or a lignin decomposition molecule, and the microbial cell is capable of producing (3E)-2-oxohex-3-enedioic acid.

An aspect of the present disclosure is a microbial cell that includes a first genetic modification resulting in the expression of a deficient form of a first endogenous dioxygenase, a second genetic modification resulting in the expression of a deficient form of a second endogenous dioxygenase, a third genetic modification resulting in the expression of a deficient form of an endogenous muconate cycloisomerase, a deficient form of an endogenous muconolactone isomerase, and a deficient form of a third endogenous dioxygenase, a first gene encoding a first exogenous dioxygenase, an exogenous decarboxylase, and a first promoter sequence, and a second gene encoding a second exogenous dioxygenase, an exogenous hydrolase, and a second promoter sequence, where the first endogenous dioxygenase includes PcaH and PcaG, the second endogenous dioxygenase includes CatA2, the endogenous muconate cycloisomerase includes CatB, the endogenous muconolactone isomerase includes CatC, the third endogenous dioxygenase includes CatA, the first exogenous dioxygenase includes PraA, the exogenous decarboxylase includes PraH, the second exogenous dioxygenase includes XylE, the exogenous hydrolase includes XylF (nucleic acid sequence represented by SEQ ID NO:51, amino acid sequence represented by SEQ ID NO:52), the microbial cell is capable of growth utilizing at least one of a cellulose decomposition molecule or a lignin decomposition molecule, and the microbial cell is capable of producing (2E)-2-hydroxypenta-2,4-dienoic acid.

An aspect of the present disclosure is a microbial cell that includes a first genetic modification resulting in the expression of a deficient form of a first endogenous dioxygenase, a second genetic modification resulting in the expression of a deficient form of a second endogenous dioxygenase, a third genetic modification resulting in the expression of a deficient form of an endogenous muconate cycloisomerase, a deficient form of an endogenous muconolactone isomerase, and a deficient form of a third endogenous dioxygenase, a first gene encoding a first exogenous dioxygenase, an exogenous decarboxylase, and a first promoter sequence, and a second gene encoding a second exogenous dioxygenase, an exogenous dehydrogenase, an exogenous tautomerase, an exogenous hydrolase, an exogenous hydratase, an exogenous decarboxylase, and a second promoter sequence, where the first endogenous dioxygenase includes PcaH and PcaG, the second endogenous dioxygenase includes CatA2, the endogenous muconate cycloisomerase includes CatB, the endogenous muconolactone isomerase includes CatC, the third endogenous dioxygenase includes CatA, the first exogenous dioxygenase includes PraA, the exogenous decarboxylase includes PraH, the second exogenous dioxygenase includes XylE, the exogenous dehydrogenase includes XylG, the exogenous tautomerase includes XylH, the exogenous hydrolase includes XylF, the exogenous hydratase includes XylJ (nucleic acid sequence represented by SEQ ID NO:59, amino acid sequence represented by SEQ ID NO:60), the exogenous decarboxylase includes XylI (nucleic acid sequence represented by SEQ ID NO:57, amino acid sequence represented by SEQ ID NO:58), the microbial cell is capable of growth utilizing at least one of a cellulose decomposition molecule or a lignin decomposition molecule, and the microbial cell is capable of producing 4-hydroxy-2-oxopentanoic acid.

BRIEF DESCRIPTION OF THE DRAWINGS

Some embodiments are illustrated in referenced figures of the drawings. It is intended that the embodiments and figures disclosed herein are to be considered illustrative rather than limiting.

DETAILED DESCRIPTION

Figure 1:
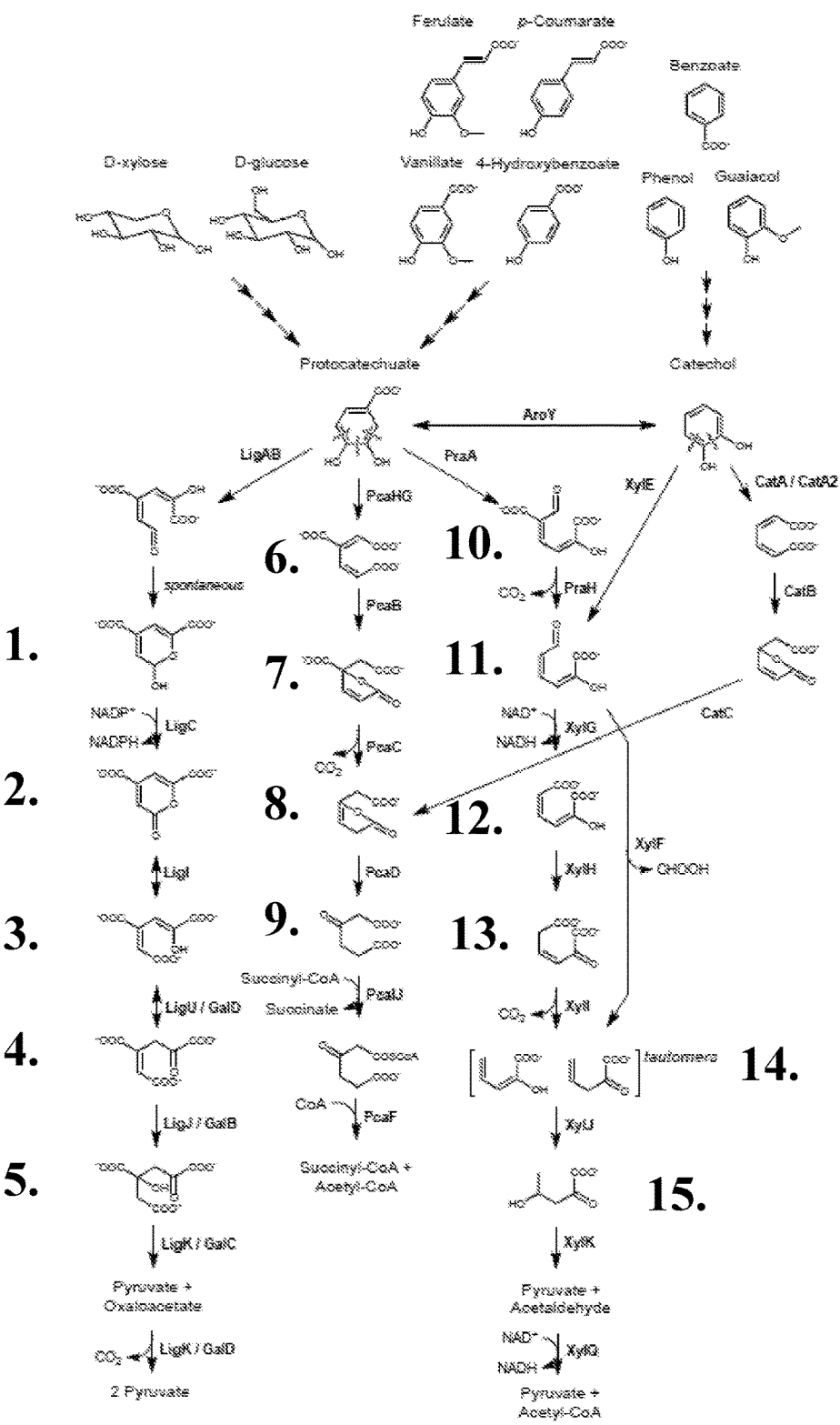
FIG. 1 illustrates a schematic of protocatechuate and catechol degradation pathways and the 15 molecules targeted for production by the engineered strains described herein, according to some embodiments of the present disclosure.

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

SEQ ID NOS: 1-66 provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis*, *B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei*, *T. viride*, *T. koningii*, or *T. harzianum*), *Penicillium* (e.g., *P. funiculosum*), *Humicola* (e.g., *H. insolens*), *Chrysosporium* (e.g., *C. lucknowense*), *Gliocladium*, *Aspergillus* (e.g., *A. niger*, *A. nidulans*, *A. awamori*, or *A. aculeatus*), *Fusarium*, *Neurospora*, *Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, *miscanthus*, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Exemplary culture/fermentation conditions and reagents are provided in the Table 2 below. Media may be supplemented with aromatic substrates like guaiacol, guaethol or anisole for dealkylation reactions.

The nucleic acid molecules described herein encode the enzymes with amino acid sequences such as those represented by the SEQ ID NOs presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein, or may include up to a certain integer number of amino acid alterations. Such protein or polypeptide variants retain functionality as enzymes, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

The present disclosure relates to genetically modified microorganisms including Pseudomonads (including *Pseudomonas putida*), *Acinetobacter* sp., various Rhodococci (e.g., *Rhodococcus erythryopohs*), *Sphingobium* sp., *Saccharomyces cerevisiae*, *Zygosaccharomyces bailii*, *Pichia kudriavzevii*, and *Candida glabrata* that have been metabolically engineered to direct various lignin, cellulose, and hemicellulose derived intermediates such as catechol and protcatechuate to a variety of novel molecules, which may be reacted to produce polymers and/or copolymers. Genetically modified strains of microorganisms have been developed for the production of each of the following molecules:

1. 2-hydroxy-2H-pyran-4,6-dicarboxylic acid;
2. 2-oxo-2H-pyran-4,6-dicarboxylic acid;
3. (1E,3E)-4-hydroxybuta-1,3-diene-1,2,4-tricarboxylic acid;
4. (1E)-4-oxobut-1-ene-1,2,4-tricarboxylic acid;
5. 2-hydroxy-4-oxobutane-1,2,4-tricarboxylic acid;
6. (1E,3Z)-buta-1,3-diene-1,2,4-tricarboxylic acid;
7. 2-carboxy-5-oxo-2,5-dihydrofuran-2-carboxylic acid;
8. 2-(2-oxo-3H-furan-5-yl)acetic acid;
9. 3-oxohexanedioic acid;
10. (2E,4E)-2-formyl-5-hydroxyhexa-2,4-dienedioic acid;
10a. pyridine-2,5-dicarboxylic acid;
11. (2Z,4E)-2-hydroxy-6-oxohexa-2,4-dienoic acid;
11a. pyridine-2-carboxylic acid;
12. (2Z,4E)-2-hydroxyhexa-2,4-dienedioic acid;
13. (3E)-2-oxohex-3-enedioic acid;
14. (2E)-2-hydroxypenta-2,4-dienoic acid; and
15. 4-hydroxy-2-oxopentanoic acid.

These seventeen molecules will be referred to by their respective numbers throughout the remainder of this disclosure. For example, 3-oxohexanedioic acid will be referred to as "molecule #9" or "#9" or "(#9)" or "9". Referring to FIG. 1, 3-oxohexanedioic acid is shown in the middle vertical pathway, labeled "9". Collectively, these seventeen molecules have properties suitable as precursors of direct polymer replacements and/or for advanced polymeric materials. They can be reacted with themselves to form homopolymers, with one another in novel combinations to form tailored copolymers, or with other conventional polymer precursors and cross-linking molecules to generate a new class of materials derived from lignocellulosic biomass.

Referring to FIG. 1, microorganisms capable of metabolizing catechol and/or protocatechuate may cleave the aromatic ring of these molecules in either the ortho (intradiol) or meta (extradiol) position relative to two hydroxyl groups. The cleavage of these molecules at different positions yields different products that may be metabolized through different "lower pathways" to enter the tricarboxylic acid (TCA) cycle. These lower pathways may be referred to according to the dioxygenase that initiates them; e.g. the pathway responsible for metabolism of the product of 4,5 meta cleavage of protocatechuate can be referred to as the protocatechuate 4,5 meta-cleavage pathway.

The present disclosure relates to the construction of fifteen different P. putida strains (e.g. P. putida KT2440) engineered to produce the seventeen different molecules (listed above) that are intermediates in these "lower pathways". For example, the deletion of genes encoding enzymes responsible for advancing a molecule through the catechol or protocatechuate ortho-cleavage pathways may eliminate the targeted enzyme, resulting in the accumulation of a molecule that would normally be eliminated by conversion to the next molecule in the pathway. Alternatively, genes encoding one of the endogenous dioxygenases (e.g. CatA and CatA2 or PcaG and PcaH) may be deleted from the genome and genes encoding part of one of the meta-cleavage pathways from organisms such as P. putida mt-2, Paenibacillus sp. strain JJ-1b, or Sphingobium sp. strain SYK-6 may be integrated in its place, so that catechol or protocatechuate may be metabolized by the introduced pathway, converting it to the final intermediate produced by the incomplete, exogenously-expressed pathway. In some cases, endogenous genes encoding enzymes such as GalB, GalC, and GalD, which may catalyze the same reactions of LigU, LigJ, and LigK (nucleic acid sequence represented by SEQ ID NO:13, amino acid sequence represented by SEQ ID NO:14), may be deleted so as not to interfere with the exogenous enzymes. Alternatively, endogenous enzymes may be used to produce the targeted molecules.

While the present disclosure relates to engineered strains that utilize enzymes from P. putida KT2440, P. putida mt-2, Sphingobium sp. strain SYK-6, and Paenibacillus sp. strain JJ-1b, similar strains could be constructed in different hosts using different endogenous or exogenous enzymes that catalyze the same reactions described herein. Thus, variations to these pathways present in other organisms that may enable the production of the compounds targeted here, or related molecules not described herein, are considered within the scope of the present disclosure. In eukaryotes, for example, the product of protocatechuate ring cleavage (molecule #6) is converted to 3-carboxymuconolactone instead of 4-carboxymuconolactone (molecule #7) before being converted directly to 3-oxoadipate (molecule #9). In some species of Rhodococcus and Streptomyces, an enzyme that appears to represent a fusion of the 4-carboxymuconolactone decarboxylase PcaD and the 3-oxoadipate enol-lactonase and PcaC catalyzes the direct conversion of 4-carboxymuconolactone (molecule #7) to 3-oxoadipate (molecule #9).

The seventeen molecules reported herein utilize fifteen engineered P. Putida strains, which were produced in fermentation broths using p-coumarate or benzoate as the starting raw material. Referring again to FIG. 1, p-coumarate and benzoate are metabolized through protocatechuate and catechol intermediates, respectively. However, the seventeen molecules may be produced from any substrates that may be converted, biologically or otherwise, to either of these molecules. For example, some aromatic molecules such as p-coumarate, ferulate, 4-hydroxybenzoate, and vanillate may be metabolized through protocatechuate, while others such as benzoate and phenol may be metabolized through catechol. Further examples include 3-dehydroshikimate and chorismate, intermediates in the shikimate pathway for aromatic amino acid synthesis, which may be converted to protocatechuate through several routes. Phenylalanine, another product of the shikimate pathway, may be converted through lignin biosynthesis pathways to cinnamate, p-coumarate, caffeate, ferulate and molecules derived from these, which may then be metabolized through protocatechuate and/or catechol. Thus, any carbon source that may be converted to these amino acids, aromatic carbons, sugars, glycerol, etc., may be converted to protocatechuate or catechol, which may be subsequently converted to any of the seventeen molecules described herein, by the appropriate use of the enzymatic reactions described herein.

FIG. 1 illustrates pathways that lead to the various target molecules, per embodiments of the present disclosure. The first (left-most) pathway, referred to as the protocatechuate 4,5 meta-cleavage pathway, may produce any of the first five target molecules: 2-hydroxy-2H-pyran-4,6-dicarboxylic acid (#1); 2-oxo-2H-pyran-4,6-dicarboxylic acid (#2); (1E, 3E)-4-hydroxybuta-1,3-diene-1,2,4-tricarboxylic acid (#3); (1E)-4-oxobut-1-ene-1,2,4-tricarboxylic acid (#4); and 2-hydroxy-4-oxobutane-1,2,4-tricarboxylic acid (#5). Referring to FIG. 1, protocatechuate may be cleaved at the 4,5 meta position by a dioxygenase, for example a protocatechuate 4,5-dioxygenase (e.g. LigA and LigB, two subunits that assemble to form the functional enzyme) to produce 2-hydroxy-4-carboxymuconate-6-semialdehyde, which spontaneously converts to 2-hydroxy-2H-pyran-4,6-dicarboxylic acid (#1). 2-hydroxy-2H-pyran-4,6-dicarboxylic acid (#1) may be converted to 2-oxo-2H-pyran-4,6-dicarboxylic acid (#2) by a dehydrogenase, for example a 4-carboxy-2-hydroxymuconate-6-semialdehyde dehydrogenase (e.g. LigC). 2-oxo-2H-pyran-4,6-dicarboxylic acid (#2) may be converted to (1E,3E)-4-hydroxybuta-1,3-diene-1,2,4-tricarboxylic acid (#3) by a hydrolase, for example a 2-pyrone-4,6-dicarboxylic acid hydrolase (e.g. LigI). (1E,3E)-4-hydroxybuta-1,3-diene-1,2,4-tricarboxylic acid (#3) may be converted to (1E)-4-oxobut-1-ene-1,2,4-tricarboxylic acid (#4) by a tautomerase, for example a 4-oxalomesaconate tautomerase (e.g. LigU). (1E)-4-oxobut-1-ene-1,2,4-tricarboxylic acid (#4) may be converted to 2-hydroxy-4-oxobutane-1,2,4-tricarboxylic acid (#5) by a hydratase, for example a 4-oxalomesaconate hydratase (e.g. LigJ). In addition, molecules #1 through #5 may also be produced through catechol, for example, by the conversion of catechol to protecatechuate by a carboxylase (e.g. AroY) (nucleic acid sequence represented by SEQ ID NO:65, amino acid sequence represented by SEQ ID NO:66).

The middle vertical pathway shown in FIG. 1 illustrates the catechol and protocatechuate ortho-cleavage pathways, which, in P. putida KT2440, converge at molecule 8. These pathways may produce four of the target molecules: (1E, 3Z)-buta-1,3-diene-1,2,4-tricarboxylic acid (#6); 2-carboxy- 5-oxo-2,5-dihydrofuran-2-carboxylic acid (#7); 2-(2-oxo-3H-furan-5-yl)acetic acid (#8); and 3-oxohexanedioic acid (#9). Referring to FIG. 1, protocatechuate may be cleaved at the ortho position by a dioxygenase, for example protocatechuate 3,4-dioxygenase (e.g. PcaH and PcaG are two subunits that assemble to form the functional enzyme) to produce (1E,3Z)-buta-1,3-diene-1,2,4-tricarboxylic acid (#6). (1E,3Z)-buta-1,3-diene-1,2,4-tricarboxylic acid (#6) may be converted to 2-carboxy-5-oxo-2,5-dihydrofuran-2-carboxylic acid (#7) by a cycloisomerase, for example 3-carboxy-cis,cis-muconate cycloisomerase (e.g. PcaB). 2-carboxy-5-oxo-2,5-dihydrofuran-2-carboxylic acid (#7) may be converted to 2-(2-oxo-3H-furan-5-yl)acetic acid (#8) by decarboxylase, for example 4-carboxymuconolactone decarboxylase. 2-(2-oxo-3H-furan-5-yl)acetic acid (#8) may be converted to 3-oxohexanedioic acid (#9) by a lactonase, for example 3-oxoadipate enol-lactonase. In addition, molecules #6 through #9 may also be produced through catechol, for example, by the conversion of catechol to protecatechuate by a carboxylase (e.g. AroY). In addition, 2-(2-oxo-3H-furan-5-yl)acetic acid (#8) may be produced by the conversion of catechol to cis,cis-muconate by a dioxygenase, for example a catechol 1,2-dioxygenase (e.g. CatA and/or CatA2), followed by the conversion of cis,cis-muconate to muconolactone by a cycloisomerase, for example a mucanolactone isomerase (e.g. Cat B), followed by conversion of muconolactone to 2-(2-oxo-3H-furan-5-yl) acetic acid (#8) by an isomerase, for example a muconolactone isomerase (e.g. CatC).

The final vertical pathways shown in FIG. 1 illustrates the catechol meta-cleavage and protocatechuate 2,3 meta-cleavage pathways. These pathways may result in five of the target molecules: (2E,4E)-2-formyl-5-hydroxyhexa-2,4-dienedioic acid/pyridine-2,5-dicarboxylic acid (#10); (2Z,4E)-2-hydroxy-6-oxohexa-2,4-dienoic acid/pyridine-2-carboxylic acid (#11); (2Z,4E)-2-hydroxyhexa-2,4-dienedioic acid (#12); (3E)-2-oxohex-3-enedioic acid (#13); (2E)-2-hydroxypenta-2,4-dienoic acid (#14); and 4-hydroxy-2-oxopentanoic acid (#15). Referring to FIG. 1, protocatechuate may be cleaved at the 2,3 meta position by a dioxygenase, for example a protocatechuate 2,3-dioxygenase (e.g. PraA) to produce (2E,4E)-2-formyl-5-hydroxyhexa-2,4-dienedioic acid (#10). (2E,4E)-2-formyl-5-hydroxyhexa-2,4-dienedioic acid (#10) may be converted to (2Z,4E)-2-hydroxy-6-oxohexa-2,4-dienoic acid (#11) by a decarboxylase, for example a 5-carboxy-2-hydroxymuconate-6-semialdehyde decarboxylase (e.g. PraH). (2Z,4E)-2-hydroxy-6-oxohexa-2,4-dienoic acid (#11) may be converted to (2Z,4E)-2-hydroxyhexa-2,4-dienedioic acid (#12) by a dehydrogenase, for example a 2-hydroxymuconate semialdehyde dehydrogenase (e.g. XylG). (2Z,4E)-2-hydroxyhexa-2,4-dienedioic acid (#12) may be converted to (3E)-2-oxohex-3-enedioic acid (#13) by a tautomerase, for example a 4-oxalocrotonate tautomerase (e.g. XylH). (3E)-2-oxohex-3-enedioic acid (#13) may be converted to (2E)-2-hydroxypenta-2,4-dienoic acid (#14) by a decarboxylase, for example an 4-oxalocrotonate decarboxylase (e.g. XylI). (2E)-2-hydroxypenta-2,4-dienoic acid (#14) may be converted to 4-hydroxy-2-oxopentanoic acid (#15) by a hydratase, for example a 2-hydroxypent-2,4-dienoate hydratase (e.g. XylJ).

In addition, molecules #10 through #15 may also be produced through catechol, for example, by the conversion of catechol to protocatechuate by a carboxylase (e.g. AroY), followed by the conversion of protocatechuate to (2E,4E)-2-formyl-5-hydroxyhexa-2,4-dienedioic acid (#10) by a dioxygenase, for example a protocatechuate 2,3-dioxygenase (e.g. PraA). In addition, (2Z,4E)-2-hydroxy-6-oxohexa-2,4-dienoic acid (#11) may be produced by converting catechol directly to (2Z,4E)-2-hydroxy-6-oxohexa-2,4-dienoic acid (#11) utilizing a dioxygenase, for example a catechol 2,3 dioxygenase (e.g. XylE). In addition, (2Z,4E)-2-hydroxy-6-oxohexa-2,4-dienoic acid (#11) may be converted directly to (2E)-2-hydroxypenta-2,4-dienoic acid (#14) utilizing a hydrolase, for example a 2-hydroxymuconic semialdehyde hydrolase (e.g. XylF). Further details are provided below for all of the pathways shown in FIG. 1.

Figure 2:
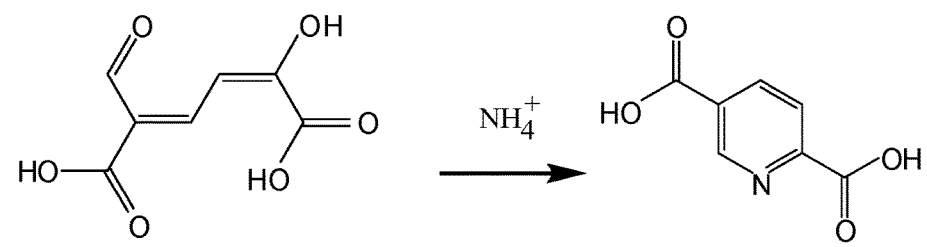
FIG. 2 illustrates reactions of molecules #10 and #11 in the presence of ammonium to produce molecules #10a and #11a respectively, according to some embodiments of the present disclosure.
Figure 2:
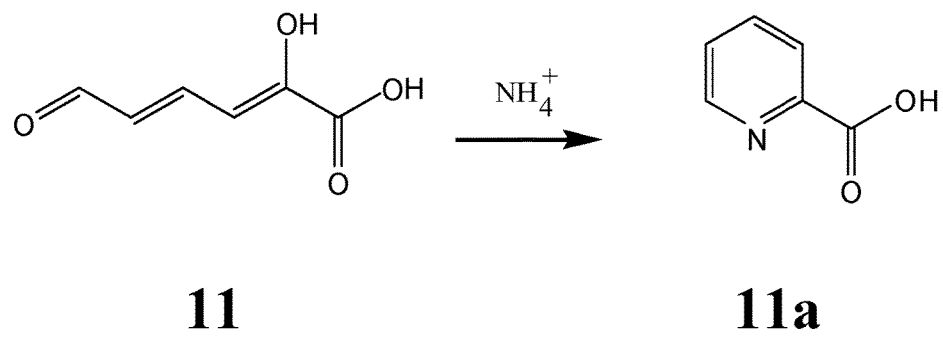
Figure 3:
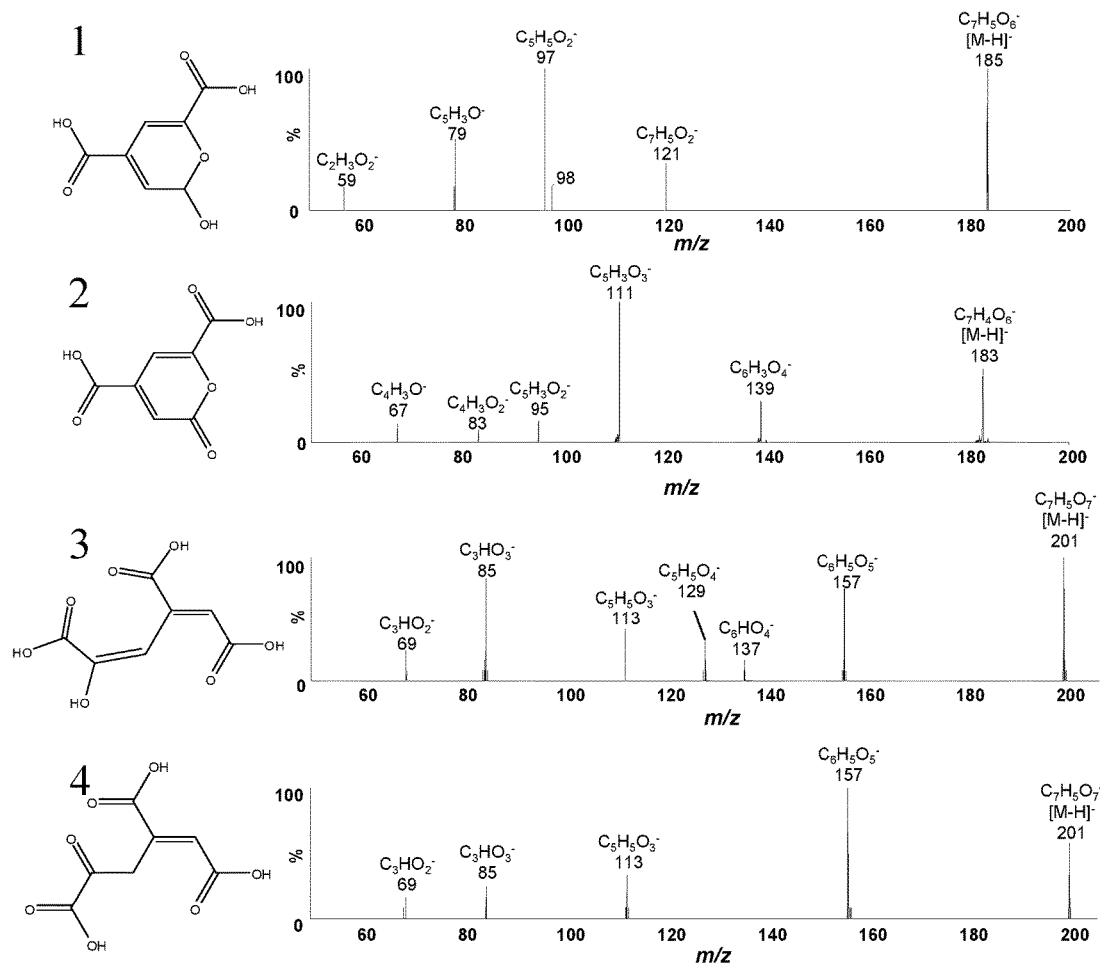
FIGS. 3 through 6 illustrate MS-MS data validating the production of molecules #1, #2, #3, #4, #5, #6, #7, #8, #9, #10, #11, #12, #13, #14, and #15 by engineered microorganisms as described herein, according to some embodiments of the present disclosure.
Figure 4:
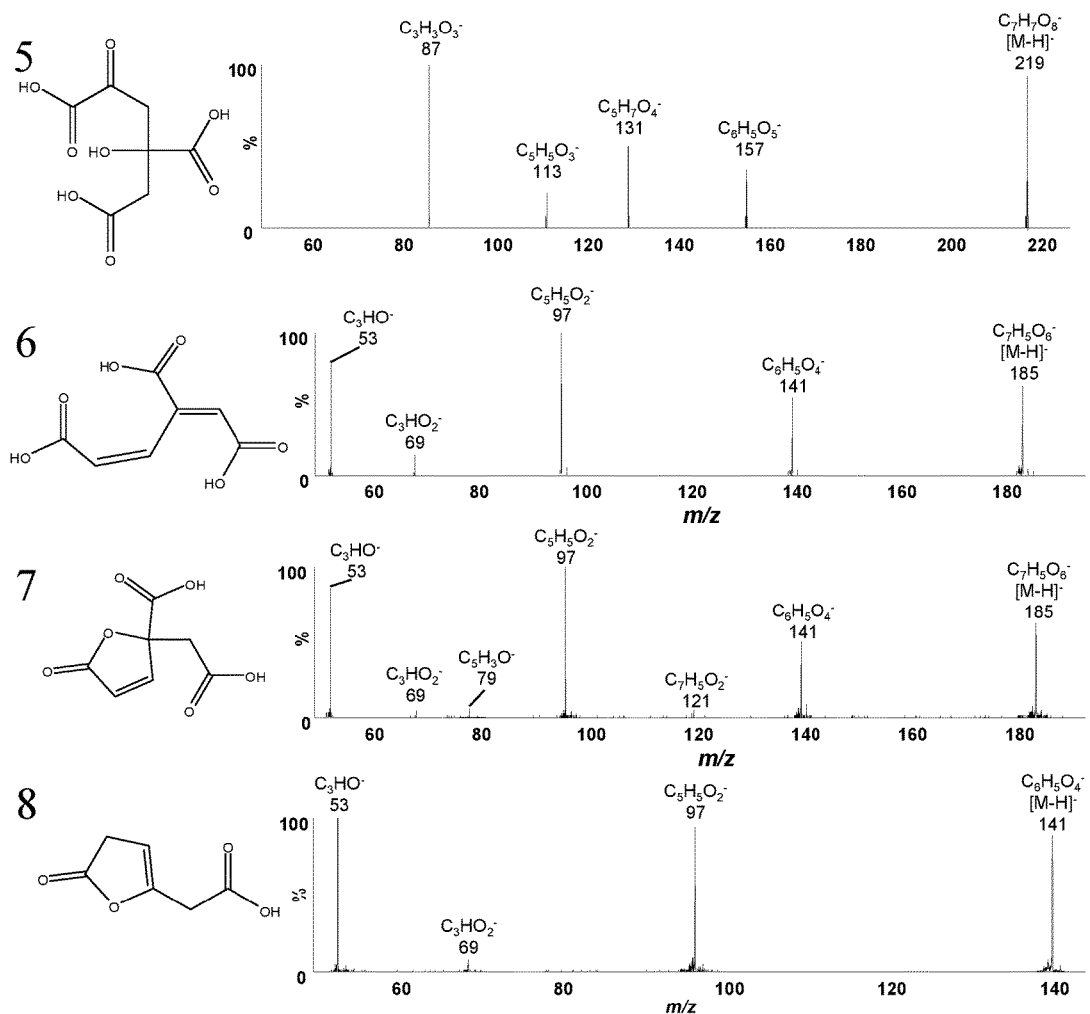
Figure 5:
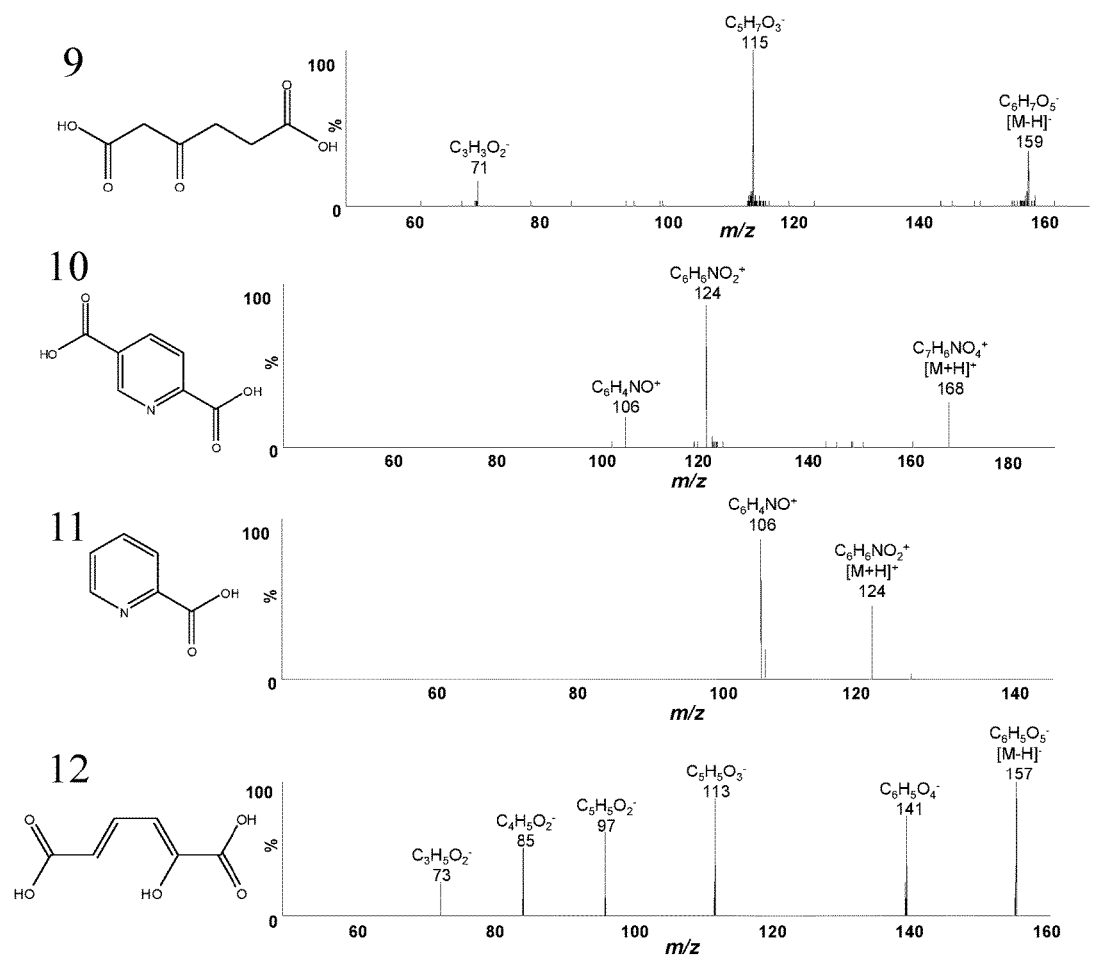
Figure 6:
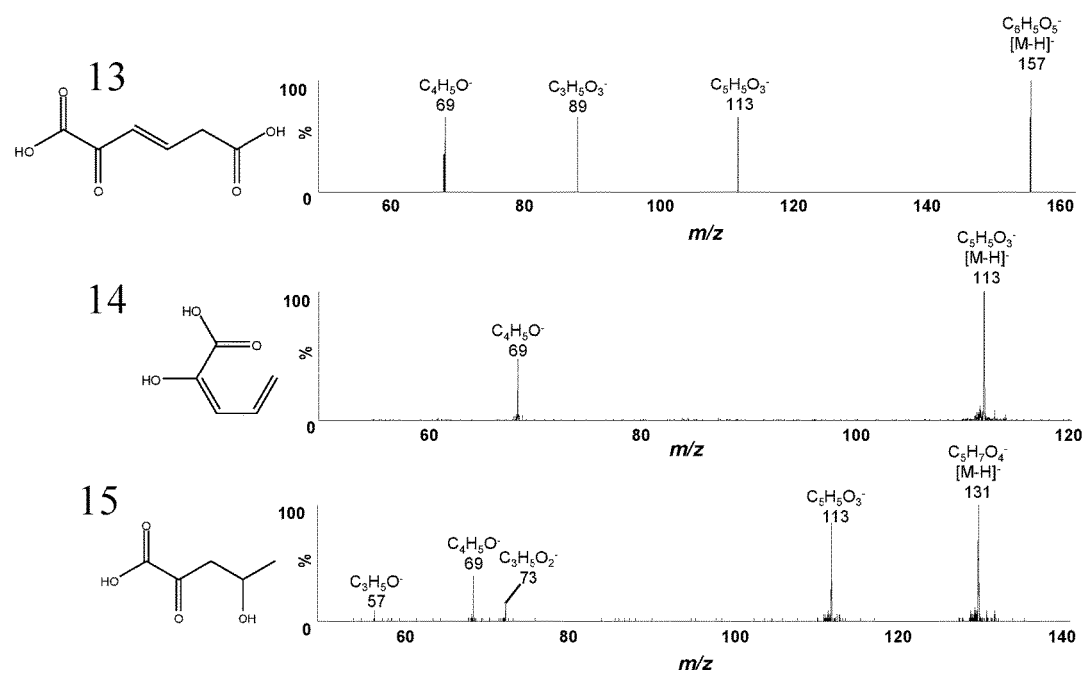

It should be noted that (2E,4E)-2-formyl-5-hydroxyhexa-2,4-dienedioic acid (molecule #10) and (2Z,4E)-2-hydroxy-6-oxohexa-2,4-dienoic acid (molecule #11) are spontaneously converted to pyridine-2,5-dicarboxylic acid (molecule #10a) and pyridine-2-carboxylic acid (molecule #11a), respectively, in the presence of the $NH_4$ (ammonium) in the M9 minimal medium they are produced in, so these are the products that were ultimately detected in the media of cultures producing #10 and #11. This cyclisation could also be accomplished with $NH_3$ (ammonia). See FIG. 2 for details.

As stated above, genetically modified strains of *P. Putida* KT2440 were engineered to produce each of the fifteen target molecules listed above. All strains were made by genetic modification to *P. Putida* KT2440. Other methods for gene modification are considered within the scope of the present disclosure; e.g. gene addition and/or over-expression by the addition of non-native plasmids, etc. Examples of each engineered *P. Putida* KT2440 strain, for each of the fifteen target molecules, are provided below.

Note regarding nomenclature: Modifications to *P. Putida* KT2440 will be summarized in "short-hand" notation as follows. First, the gene or genes immediately following a Δ symbol have been deleted from the genome. A double-colon following the deleted gene(s) refers to replacing the deleted gene(s) with the genetic element, gene or genes that immediately follow the double-colon. Finally, the single colon refers to genetic fusion of the gene before the colon to the gene following the colon, where one genetic element or gene immediately precedes the next.

Molecule #1: Strain CJ249—*P. putida* KT2440 ΔpcaHG:: Ptac:ligAB

A modified *P. Putida* KT2440 strain for the production of 2-hydroxy-2H-pyran-4,6-dicarboxylic acid (#1) was engineered by deletion of the genes encoding a protocatechuate 3,4-dioxygenase (e.g. PcaH and PcaG combine to form the functional enzyme) and replacing them with a DNA sequence encoding the Ptac promoter (nucleic acid sequence represented by SEQ ID NO:67) fused to and upstream (5') of the DNA sequences encoding two subunits of a protocatechuate 4,5-dioxygenases (e.g. LigA and LigB, which assemble to form the functional enzyme). This example illustrates that a genetically modified strain of *P. Putida* capable of producing 2-hydroxy-2H-pyran-4,6-dicarboxylic acid (#1) may be engineered by the replacement of an endogenous dioxygenase with a sequence of DNA consisting of a suitable promoter fused to genes encoding an exogenous dioxygenase.

Molecule #2: Strain CJ251—*P. putida* KT2440 ΔpcaHG:: Ptac:ligABC

A modified *P. Putida* KT2440 strain for the production of 2-oxo-2H-pyran-4,6-dicarboxylic acid (#2) was engineered by deletion of the genes encoding a protocatechuate 3,4-dioxygenase (e.g. PcaH and PcaG assemble to form the functional enzyme) and replacing them with a DNA sequence encoding the Ptac promoter fused to the DNA sequences encoding two subunits of a protocatechuate 4,5-dioxygenases (e.g. LigA and LigB, which assemble to form the functional enzyme), and a 4-carboxy-2-hydroxymuconate-6-semialdehyde dehydrogenase (e.g. LigC). This example illustrates that a genetically modified strain of *P. Putida* capable of producing 2-oxo-2H-pyran-4,6-dicarboxylic acid (#2) may be engineered by the replacement of an endogenous dioxygenase with a sequence of DNA consisting of a suitable promoter fused to genes encoding an exogenous dioxygenase, and an exogenous dehydrogenase.

Molecule #3: Strain CJ350—*P. putida* KT2440 ΔpcaHG::Ptac:ligABCI ΔgalBCD

A modified *P. Putida* KT2440 strain for the production of (1E,3E)-4-hydroxybuta-1,3-diene-1,2,4-tricarboxylic acid (#3) was engineered by deletion of the genes encoding a protocatechuate 3,4-dioxygenase (e.g. PcaH and PcaG combine to form the functional enzyme) and replacing them with a DNA sequence encoding the Ptac promoter fused to the DNA sequences encoding two subunits of a protocatechuate 4,5-dioxygenase (e.g. LigA and LigB, which assemble to form the functional enzyme), a 4-carboxy-2-hydroxymuconate-6-semialdehyde dehydrogenase (e.g. LigC), and a 2-pyrone-4,6-dicarboxylic acid hydrolase (e.g. LigI). In addition, the genes encoding a 4-oxalomesaconate tautomerase (e.g. GalD), a 4-oxalomesaconate hydratase (e.g. GalB), and a 4-Carboxy-4-hydroxy-2-oxoadipate aldolase/oxaloacetate decarboxylase (e.g. GalC) were deleted from *P. Putida* KT2440. This example illustrates that a genetically modified strain of *P. Putida* capable of producing (1E,3E)-4-hydroxybuta-1,3-diene-1,2,4-tricarboxylic acid (#3) may be engineered by the replacement of an endogenous dioxygenase with a sequence of DNA consisting of a suitable promoter fused to genes encoding an exogenous dioxygenase, an exogenous dehydrogenase, and an exogenous hydrolase, and by the deletion of an endogenous tautomerase, an endogenous hydratase, and an endogenous decarboxylase.

Molecule #4: Strain CJ328—*P. putida* KT2440 ΔpcaHG::Ptac:ligABCIU ΔgalBCD

A modified *P. Putida* KT2440 strain for the production of (1E)-4-oxobut-1-ene-1,2,4-tricarboxylic acid (#4) was engineered by deletion of the genes encoding a protocatechuate 3,4-dioxygenase (e.g. PcaH and PcaG combine to form the functional enzyme) and replacing them with a DNA sequence encoding the Ptac promoter fused to the DNA sequences encoding two subunits of a protocatechuate 4,5-dioxygenase (e.g. LigA and LigB, which assemble to form the functional enzyme), a 4-carboxy-2-hydroxymuconate-6-semialdehyde dehydrogenase (e.g. LigC), a 2-pyrone-4,6-dicarboxylic acid hydrolase (e.g. LigI), and a 4-oxalomesaconate tautomerase (e.g. LigU). In addition, the genes encoding a 4-oxalomesaconate tautomerase (e.g. GalD), a 4-oxalomesaconate hydratase (e.g. GalB), and a 4-Carboxy-4-hydroxy-2-oxoadipate aldolase/oxaloacetate decarboxylase (e.g. GalC) were deleted from *P. Putida* KT2440. This example illustrates that a genetically modified strain of *P. Putida* capable of producing (1E)-4-oxobut-1-ene-1,2,4-tricarboxylic acid (#4) may be engineered by the replacement of an endogenous dioxygenase with a sequence of DNA encoding a suitable promoter fused to genes encoding an exogenous dioxygenase, an exogenous dehydrogenase, an exogenous hydrolase, and an exogenous tautomerase, and by the deletion of an endogenous tautomerase, an endogenous hydratase, and an endogenous decarboxylase.

In additional modified *P. Putida* KT2440 strain can be envisioned for the production of (1E)-4-oxobut-1-ene-1,2,4-tricarboxylic acid (#4), with the strain described as follows:

*P. putida* KT2440 ΔpcaHG::Ptac:ligABCI ΔgalBC.

In this example, molecule (#4) may be produced by a modified *P. Putida* KT2440 strain by deleting the genes encoding a protocatechuate 3,4-dioxygenase (e.g. PcaH and PcaG combine to form the functional enzyme) and replacing them with a DNA sequence encoding the Ptac promoter fused to the DNA sequences encoding two subunits of a protocatechuate 4,5-dioxygenase (e.g. LigA and LigB, which assemble to form the functional enzyme), a 4-carboxy-2-hydroxymuconate-6-semialdehyde dehydrogenase (e.g. LigC), and a 2-pyrone-4,6-dicarboxylic acid hydrolase (e.g. LigI). In addition, for this strain to produce molecule (#4), the genes encoding a 4-oxalomesaconate hydratase (e.g. GalB) and a 4-Carboxy-4-hydroxy-2-oxoadipate aldolase/oxaloacetate decarboxylase (e.g. GalC) are deleted from *P. Putida* KT2440.

Molecule #5: Strain CJ329—*P. putida* KT2440 ΔpcaHG::Ptac:ligABCIUJ ΔgalBCD

A modified *P. Putida* KT2440 strain for the production of 2-hydroxy-4-oxobutane-1,2,4-tricarboxylic acid (#5) was engineered by deletion of the genes encoding a protocatechuate 3,4-dioxygenase (e.g. PcaH and PcaG combine to form the functional enzyme) and replacing them with a DNA sequence encoding the Ptac promoter fused to the DNA sequences encoding two subunits of a protocatechuate 4,5-dioxygenase (e.g. LigA and LigB, which assemble to form the functional enzyme), a 4-carboxy-2-hydroxymuconate-6-semialdehyde dehydrogenase (e.g. LigC), a 2-pyrone-4,6-dicarboxylic acid hydrolase (e.g. LigI), a 4-oxalomesaconate tautomerase (e.g. LigU), and a 4-oxalomesaconate hydratase (e.g. LigJ). In addition, the genes encoding a 4-oxalomesaconate tautomerase (e.g. GalD), a 4-oxalomesaconate hydratase (e.g. GalB), and a 4-Carboxy-4-hydroxy-2-oxoadipate aldolase/oxaloacetate decarboxylase (e.g. GalC) were deleted from *P. Putida* KT2440. This example illustrates that a genetically modified strain of *P. Putida* capable of producing 2-hydroxy-4-oxobutane-1,2,4-tricarboxylic acid (#5) may be engineered by the replacement of an endogenous dioxygenase with a sequence of DNA consisting of a suitable promoter fused to genes encoding an exogenous dioxygenases, an exogenous dehydrogenase, an exogenous hydrolase, an exogenous tautomerase, and an exogenous hydrotase, and by the deletion of an endogenous tautomerase, an endogenous hydratase, and an endogenous decarboxylase.

In additional modified *P. Putida* KT2440 strain can be envisioned for the production of of 2-hydroxy-4-oxobutane-1,2,4-tricarboxylic acid (#5), with the strain described as follows:

*P. putida* KT2440 ΔpcaHG::Ptac:ligABCI ΔgalC.

In this example, molecule (#5) may be produced by a modified *P. Putida* KT2440 strain by deleting the genes encoding a protocatechuate 3,4-dioxygenase (e.g. PcaH and PcaG combine to form the functional enzyme) and replacing them with a DNA sequence encoding the Ptac promoter fused to the DNA sequences encoding two subunits of a protocatechuate 4,5-dioxygenase (e.g. LigA and LigB, which assemble to form the functional enzyme), a 4-carboxy-2-hydroxymuconate-6-semialdehyde dehydrogenase (e.g. LigC), and a 2-pyrone-4,6-dicarboxylic acid hydrolase (e.g. LigI). In addition, for this strain to produce molecule (#5), the gene encoding a 4-Carboxy-4-hydroxy-2-oxoadipate aldolase/oxaloacetate decarboxylase (e.g. GalC) is deleted from *P. Putida* KT2440.

Molecule #6: Strain CJ257—*P. putida* KT2440 ΔpcaBDC

A modified *P. Putida* KT2440 strain for the production of (1E,3Z)-buta-1,3-diene-1,2,4-tricarboxylic acid (#6) was engineered by deletion of the genes encoding a 3-oxoadipate enol-lactonase (e.g. pcaD), a 4-carboxymuconolactone decarboxylase (e.g. pcaC), and a 3-carboxy-cis,cis-muconate cycloisomerase (e.g. pcaB). This example illustrates that a genetically modified strain of *P. Putida* capable of producing (1E,3Z)-buta-1,3-diene-1,2,4-tricarboxylic acid (#6) may be engineered by the deletion of genes encoding an endogenous enol-lactonase, an endogenous decarboxylase, and an endogeneous cycloisomerase.

Molecule #7: Strain CJ259—*P. putida* KT2440 ΔpcaDC

A modified *P. Putida* KT2440 strain for the production of 2-carboxy-5-oxo-2,5-dihydrofuran-2-carboxylic acid (#7) was engineered by deletion of the genes encoding a 3-oxoadipate enol-lactonase (e.g. pcaD) and a 4-carboxymuconolactone decarboxylase (e.g. pcaC). This example illustrates that a genetically modified strain of *P. Putida* capable of producing 2-carboxy-5-oxo-2,5-dihydrofuran-2-carboxylic acid (#7) may be engineered by the deletion of genes encoding an endogenous enol-lactonase and an endogenous decarboxylase.

Molecule #8: Strain CJ261—*P. putida* KT2440 ΔpcaD

A modified *P. Putida* KT2440 strain for the production of 2-(2-oxo-3H-furan-5-yl)acetic acid (#8) was engineered by deletion of the gene encoding 3-oxoadipate enol-lactonase (e.g. pcaD). This example illustrates that a genetically modified strain of *P. Putida* capable of producing 2-(2-oxo-3H-furan-5-yl)acetic acid (#8) may be engineered by the deletion of genes encoding an endogeneous enol-lactonase.

Molecule #9: Strain CJ263—*P. putida* KT2440 ΔpcaIJ

A modified *P. Putida* KT2440 strain for the production of 3-oxohexanedioic acid (#9) was engineered by deletion of the genes encoding two subunits of a 3-oxoadipate CoA-transferase (e.g. PcaI and PcaJ combine to form the functional enzyme). This example illustrates that a genetically modified strain of *P. Putida* capable of producing 3-oxohexanedioic acid (#9) may be engineered by the deletion of genes encoding an endogenous transferase.

Molecule #10: Strain CJ265—*P. putida* KT2440 ΔpcaHG::Ptac:praA

A modified *P. Putida* KT2440 strain for the production of (2E,4E)-2-formyl-5-hydroxyhexa-2,4-dienedioic acid (#10) was engineered by deletion of the genes encoding two subunits of a protocatechuate 3,4-dioxygenase (e.g. PcaH and PcaG combine to form the functional enzyme), which were replaced with the DNA sequence consisting of the Ptac promoter fused to the exogenous gene encoding a protocatechuate 2,3-dioxygenase (e.g. PraA). This example illustrates that a genetically modified strain of *P. Putida* capable of producing (2E,4E)-2-formyl-5-hydroxyhexa-2,4-dienedioic acid (#10) may be engineered by the replacement of endogenous genes encoding an endogenous dioxygenase with a sequence of DNA consisting of a suitable promoter fused to genes encoding an exogenous gene encoding a dioxygenase.

Molecule #11: Strain CJ146—*P. putida* KT2440 ΔcatA2 ΔpcaHG::Ptac:praAH ΔcatBCA::Ptac:xylE A modified *P. Putida* KT2440 strain for the production of (2Z,4E)-2-hydroxy-6-oxohexa-2,4-dienoic acid (#11) was engineered by deletion of the gene encoding a catechol 1,2-dioxygenase (e.g. catA2). In addition, the genes encoding two subunits of a protocatechuate 3,4-dioxygenase (e.g. PcaH and PcaG combine to form the functional enzyme) were also deleted and replaced with a DNA sequence consisting of the Ptac promoter fused to exogenous genes encoding a protocatechuate 2,3-dioxygenase (e.g. PraA) and a 5-carboxy-2-hydroxymuconate-6-semialdehyde decarboxylase (e.g. PraH). In addition, the genes encoding a catechol 1,2-dioxygenase (e.g. CatA), a muconate cycloisomerase (e.g. CatB), and a muconolactone isomerase (e.g. CatC) were also deleted and replaced with a DNA sequence consisting of the Ptac promoter fused to an exogenous gene encoding a catechol 2,3-dioxygenase (e.g. XylE). This example illustrates that a genetically modified strain of *P. Putida* capable of producing (2Z,4E)-2-hydroxy-6-oxohexa-2,4-dienoic acid (#11) may be engineered by the deletion of an endogenous gene encoding a dioxygenase, the replacement of endogenous genes encoding a dioxygenase with exogenous genes encoding a dioxygenase and a decarboxylase, and the replacement of endogenous genes encoding a dioxygenase, a cycloisomerase, and an isomerase with an exogenous gene encoding a dioxygenase.

Molecule #12: Strain CJ266—*P. putida* KT2440 ΔcatA2 ΔpcaHG::Ptac:praAH ΔcatBCA::Ptac:xylEG A modified *P. Putida* KT2440 strain for the production of (2Z,4E)-2-hydroxyhexa-2,4-dienedioic acid (#12) was engineered by deletion of the gene encoding a catechol 1,2-dioxygenase (e.g. CatA2). In addition, the genes encoding two subunits of a protocatechuate 3,4-dioxygenase (e.g. PcaH and PcaG combine to form the functional enzyme) were also deleted and replaced with a DNA sequence consisting of the Ptac promoter fused to exogenous genes encoding a protocatechuate 2,3-dioxygenase (e.g. PraA) and a 5-carboxy-2-hydroxymuconate-6-semialdehyde decarboxylase (e.g. PraH). In addition, the genes encoding a catechol 1,2-dioxygenase (e.g. CatA), a muconate cycloisomerase (e.g. CatB), and a muconolactone isomerase (e.g. CatC) were also deleted and replaced with a DNA sequence including the Ptac promoter fused to exogenous genes encoding a catechol 2,3 dioxygenase (e.g. XylE), and a 2-hydroxymuconate semialdehyde dehydrogenase (e.g. XylG). This example illustrates that a genetically modified strain of *P. Putida* capable of producing (2Z,4E)-2-hydroxyhexa-2,4-dienedioic acid (#12) may be engineered by the deletion of an endogenous gene encoding a dioxygenase, the replacement of endogenous genes encoding a dioxygenase with exogenous genes encoding a dioxygenase and a decarboxylase, and the replacement of endogenous genes encoding a dioxygenase, a cycloisomerase, and an isomerase with exogenous genes encoding a dioxygenase, and a dehydrogenase.

Molecule #13: Strain CJ267—*P. putida* KT2440 ΔcatA2 ΔpcaHG::Ptac:praAH ΔcatBCA::Ptac:xylEGH A modified *P. Putida* KT2440 strain for the production of (3E)-2-oxohex-3-enedioic acid (#13) was engineered by deletion of the gene encoding a catechol 1,2-dioxygenase (e.g. CatA2). In addition, the genes encoding two subunits of a protocatechuate 3,4-dioxygenase (e.g. PcaH and PcaG combine to form the functional enzyme) were also deleted and replaced with a DNA sequence including the Ptac promoter fused to exogenous genes encoding a protocatechuate 2,3-dioxygenase (e.g. PraA) and a 5-carboxy-2-hydroxymuconate-6-semialdehyde decarboxylase (e.g. PraH). In addition, the genes encoding a catechol 1,2-dioxygenase (e.g. CatA), a muconate cycloisomerase (e.g. CatB), and a muconolactone isomerase (e.g. CatC) were also deleted and replaced with the DNA sequence including the Ptac promoter fused to the exogenous genes encoding a catechol 2,3 dioxygenase (e.g. XylE), a 2-hydroxymuconate semialdehyde dehydrogenase (e.g. XylG), and a 4-oxalocrotonate tautomerase (e.g. XylH). This example illustrates that a genetically modified strain of *P. Putida* capable of producing (3E)-2-oxohex-3-enedioic acid (#13) may be engineered by the deletion of an endogenous gene encoding a dioxygenase, the replacement of endogenous genes encoding a dioxygenase with exogenous genes encoding a dioxygenase and a decarboxylase, and the replacement of endogenous genes encoding a dioxygenase, a cycloisomerase, and an isomerase with exogenous genes encoding a dioxygenase, a dehydrogenase, and a tautomerase.

Molecule #14: Strain CJ270—*P. putida* KT2440 ΔcatA2 ΔpcaHG::Ptac:praAH ΔcatBCA::Ptac:xylEF A modified *P. Putida* KT2440 strain for the production of (2E)-2-hydroxypenta-2,4-dienoic acid (#14) was engineered by deletion of the gene encoding a catechol 1,2-dioxygenase (e.g. CatA2). In addition, the genes encoding two subunits of a protocatechuate 3,4-dioxygenases (e.g. PcaH and PcaG combine to form the functional enzyme) were also deleted and replaced with a DNA sequence including the Ptac promoter fused to exogenous genes encoding a protocatechuate 2,3-dioxygenase (e.g. PraA) and a 5-carboxy-2-hydroxymuconate-6-semialdehyde decarboxylase (e.g. PraH). In addition, the genes encoding a catechol 1,2-dioxygenase (e.g. CatA), a muconate cycloisomerase (e.g. CatB), and a muconolactone isomerase (e.g. CatC) were also deleted and replaced with the DNA sequence including the Ptac promoter fused to exogenous genes encoding a catechol 2,3 dioxygenase (e.g. XylE), and a 2-hydroxymuconic semialdehyde hydrolase (e.g. XylF). This example illustrates that a genetically modified strain of *P. Putida* capable of producing (2E)-2-hydroxypenta-2,4-dienoic acid (#14) may be engineered by the deletion of an endogenous gene encoding a dioxygenase, the replacement of endogenous genes encoding a dioxygenase with exogenous genes encoding a dioxygenase and a decarboxylase, and the replacement of endogenous genes encoding a dioxygenase, a cycloisomerase, and an isomerase with exogenous genes encoding a dioxygenase, and a hydrolase.

Molecule #15: Strain CJ268—*P. putida* KT2440 ΔcatA2 ΔpcaHG::Ptac:praAH ΔcatBCA::Ptac:xylEGFJIH A modified *P. Putida* KT2440 strain for the production of 4-hydroxy-2-oxopentanoic acid (#15) was engineered by deletion of the genes encoding a catechol 1,2-dioxygenase (e.g. CatA2). In addition, the genes encoding two subunits of a protocatechuate 3,4-dioxygenases (e.g. PcaH and PcaG combine to form the functional enzyme) were also deleted and replaced with the DNA sequence including the Ptac promoter fused to exogenous genes encoding a protocatechuate 2,3-dioxygenase (e.g. PraA) and a 5-carboxy-2-hydroxymuconate-6-semialdehyde decarboxylase (e.g. PraH). In addition, the genes encoding a catechol 1,2-dioxygenase (e.g. CatA), a muconate cycloisomerase (e.g. CatB), and a muconolactone isomerase (e.g. CatC) were also deleted and replaced with the DNA sequence including the Ptac promoter fused to the exogenous genes encoding a catechol 2,3 dioxygenase (e.g. XylE), a 2-hydroxymuconic semialdehyde hydrolase (e.g. XylF), a 2-hydroxymuconate semialdehyde dehydrogenase (e.g. XylG), a 4-oxalocrotonate tautomerase (e.g. XylH), a 4-oxalocrotonate decarboxylase (e.g. XylI), and a 2-hydroxypent-2,4-dienoate hydratase (e.g. XylJ). This example illustrates that a genetically modified strain of *P. Putida* capable of producing 4-hydroxy-2-oxopentanoic acid (#15) may be engineered by the deletion of an endogenous gene encoding a dioxygenase, the replacement of endogenous genes encoding a dioxygenase with exogenous genes encoding a dioxygenase and a decarboxylase, and the replacement of endogenous genes encoding a dioxygenase, a cycloisomerase, and an isomerase with exogenous genes encoding a dioxygenase, a hydrolase, a dehydrogenase, a tautomerase, a decarboxylase, and a hydratase.

In the examples described above, the Ptac promoter is utilized to express the various exogenous genes introduced into the engineered strains of *P. Putida*. Other promoters may be used in addition to the Ptac promoter and/or instead of the Ptac promoter, with examples including Plac (nucleic acid sequence represented by SEQ ID NO:68), PBAD (nucleic acid sequence represented by SEQ ID NO:69), Pcat (nucleic acid sequence represented by SEQ ID NO:70), and Ppca (nucleic acid sequence represented by SEQ ID NO:71).

The above examples illustrate engineered strains of microorganisms where one or more endogenous genes were deleted and replaced with one or more exogenous genes. However, in some embodiments of the present disclosure, an endogenous gene may be deleted or inactivated or rendered deficient by some other method. For example, an endogenous gene may be rendered inactive/deficient by deleting a portion of the gene, by inserting another genetic element into the endogenous gene's sequence, and/or by changing the endogenous gene in such a way that the resultant protein (e.g. enzyme) does not function properly (e.g. doesn't fold properly, active sites no longer available, etc.). Thus, engineered microorganisms designed to produce the 17 molecules disclosed herein may be achieved by inactivating or omitting targeted endogenous genes by methods other than deletion of the targeted endogenous genes, and are considered within the scope of the present disclosure.

Experimental Method—Strain Engineering:

To construct strains for the production of the fifteen target molecules, the host strain, *P. putida* (ATCC 47054), was engineered by replacing or deleting regions of the genome using an antibiotic/sucrose method of selection and counter-selection. Cassettes consisting of the DNA fragments to be integrated flanked by ~1 kb fragments of DNA with sequences identical to those 5' and 3' of the location in the genome targeted for deletion or replacement (5' and 3' targeting regions) were assembled in vectors pCM433 or pK18mobsacB using NEBuilder® HiFi DNA Assembly Master Mix (New England Biolabs), which cannot replicate in *P. putida* KT2440. For replacements, additional genetic elements or genes were assembled between the 5' and 3' targeting regions. For deletions, no additional genetic elements or genes were assembled between the 5' and 3' targeting regions. These plasmids (see Table 1) were transformed into *P. putida* KT2440 or strains derived thereof and isolates in which the plasmid, containing an antibiotic-resistance gene, had recombined into the genome by homologous recombination within either the 5' or 3' targeting region were selected on solid LB (Lennox) medium supplemented with 50 µg/mL kanamycin for pCM433-based plasmids or 30 µg/mL tetracycline for pK18mobsacB-based plasmids. These isolates were then streaked on YT+25% sucrose plates containing 10 g/L yeast extract, 20 g/L tryptone, 250 g/L sucrose, and 18 g/L agar to select isolates in which the plasmid backbone, containing the sacB gene that is lethal in the presence of sucrose, had recombined out of the genome at either the, now duplicated, 5' or 3' targeting regions. Depending on whether these recombinations occur at the 5' or 3' targeting regions, the genomes of these sucrose-resistant isolates will either contain the wild-type sequence that was originally between the targeting regions or the deleted or replaced sequence. Diagnostic colony PCR was used to distinguish between these possibilities by amplifying with primers that are either specific to the replaced sequence or exhibit a change in the size of the product amplified and identify strains containing the required gene replacement(s). The sequences of all primers used in construction of the gene deletion or replacement plasmids and the identification of strains containing these deletions or replacements by diagnostic colony PCR are provided (See Table 2). The sequences of all primers used in construction of the gene replacement plasmids and the identification of strains containing these replacements by diagnostic colony PCR are provided (See Table 3). Additional details regarding the endogenous gene deletions and exogenous gene additions are summarized in Tables 4-6. Gene sequences and the resultant amino acid sequences are provided in the accompanying sequence listings.

Experimental Method—Strain Validation/Molecule Production:

Strains confirmed to contain the required genetic deletions or replacements were then evaluated for production of the targeted molecules in shake-flask experiments. 125 mL baffled shake flasks containing 25 mL modified M9 minimal media (pH 7.2) containing 13.56 g/L disodium phosphate, 6 g/L monopotassium phosphate, 1 g/L NaCl, 2 g/L NH4Cl, 2 mM MgSO4, 100 μM CaCl2, and 18 μM FeSO4 supplemented with 20 mM Na benzoate (Sigma-Aldrich) or p-coumaric acid (Sigma-Aldrich) neutralized with NaOH. These flasks were incubated shaking at 225 rpm, 30° C. and fed an additional 10 mM glucose after 24 and 48 hrs. After 72 hours, the cultures were transferred to 50 mL conical tubes and centrifuged to pellet the cells. The supernatants were filtered through 0.22 μm filters and analyzed for the presence of the targeted compound using a Waters Acquity ultra performance liquid chromatography (UPLC) system coupled to an Acquity tunable UV (TUV) detector and a Waters Micromass Q-T of Micro™ mass spectrometer (Waters Corp., Milford, Mass.). Samples were injected undiluted at a volume of 20 μL and analytes were separated on an Aminex HPX-87H 9 μm, 7.8 mm i.d.×300 mm column (Bio-Rad Laboratories, Hercules, Calif.) using an isocratic mobile phase of 25 mM formic acid at a flow rate of 0.6 mL min' and a column temperature of 55° C. Metabolites were monitored post-column by 254 nm TUV and mass spectrometry (MS) in series. Positive- and negative-ion electrospray (ESI)-MS and tandem mass spectrometry (MS/MS) in centroid data collection mode was performed. For both ion modes, the nebulization gas was set to 550 L $h^{-1}$ at a temperature of 250° C., the cone gas was set to 10 L $h^{-1}$ and the source temperature was set to 110° C. For negative-ion mode, the capillary and cone voltages were set to 2650 V and 25 V, respectively and for positive-ion mode the capillary voltage was 3000 V and the cone voltage was 35 V. For MS experiments, data was collected between m/z 20-500 with collision energy of 8 eV and an acquisition rate of 0.4 sec spectrum$^{-1}$. MS/MS experiments were performed by increasing the collision energy to 15-35 eV, specific to each analyte. MS-MS data validating the production of each of the 15 target molecules are summarized in FIGS. 3 through 6.

TABLE 1

Plasmid Construction

| Plasmid | Utility | Plasmid Construction Details |
|---|---|---|
| pCJ004 | Deletion of catA2 in *P. putida* KT2440 and strains derived from it | The 5' targeting region was amplified from *P. putida* KT2440 genomic DNA with primer pair oCJ038/oCJ039 (1,037 bp) and the 3' targeting region was amplified using primer pair oCJ040/oCJ041 (1,042 bp). These fragments were then assembled into pCM433 digested with AatII and SacI (7,991 bp). |
| pCJ005 | Replacement of catBCA with Ptac:xylE in *P. putida* KT2440 and strains derived from it | The 5' targeting region was amplified from *P. putida* KT2440 genomic DNA with primer pair oCJ042/oCJ043 (1,104 bp, which incorporated the tac promoter), xylE (969 bp) was amplified from *P. putida* mt-2 (ATCC 23973) genomic DNA with primer pair oCJ044/oCJ045, and the 3' targeting region was amplified using primer pair oCJ046/oCJ047 (1,033 bp). These fragments were then assembled into pCM433 digested with AatII and SacI (7,991 bp). |
| pCJ008 | Replacement of catBCA with Ptac:xylEGFJQKIH in *P. putida* KT2440 and strains derived from it and as an intermediate in construction of other plasmids | The 5' targeting region was amplified from *P. putida* KT2440 genomic DNA with primers pair oCJ042/oCJ043 (1,104 bp, which incorporated the tac promoter). The xylEGFJQKIH operon was amplified from *P. putida* mt-2 (ATCC 23973) genomic DNA using primers oCJ044/oCJ048 (7,133 bp). The 3' homology region was amplified using primers oCJ046 and oCJ047 (1033 bp). These fragments were then assembled into pCM433 digested with AatII and SacI (7,991 bp). |
| pCJ011 | Deletion of pcaHG in *P. putida* KT2440 and strains derived from it and as an intermediate in construction of other plasmids | The 5' targeting region was amplified from *P. putida* KT2440 genomic DNA with primer pair oCJ100/oCJ101 (981 bp) and the 3' tageting region was amplified using primer pair oCJ102/oCJ103 (1,040 bp). These fragments were then assembled into pCM433 digested with AatII and SacI (7,991 bp). |
| pCJ019 | To replace pcaHG in *P. putida* KT2440 and strains derived from it with Ptac:ligABCIUJK | The ligABCIUJK genes from *Sphingobium* sp. SYK-6 were codon optimized for expression in *P. putida* KT2440 and synthesized as two DNA fragments, ligABCI and ligUJK, in which Shine-Delgamo consensus RBSs (AGGAGGACAGCT) were included 5' of the start codon of each gene. ligABCI was amplified from the synthesized fragment with primer pair oCJ154(which incorportes the tac promoter)/oCJ157 (3,297 bp) while ligUJK was amplified from the other synthesized fragment with primer pair oCJ158/oCJ155 (2,851 bp). These fragments were then assembled in pCJ011 digested with BglII and NotI (9,948 bp). |
| pCJ032 | Replacement of pcaHG with Ptac:praAH in *P. putida* KT2440 and strains derived from it | The praA and praH genes from *Paenibacillus* sp.JJ-1b were codon optimized for expression in *P. putida* KT2440 and synthesized as a DNA fragment containing synthetic RBSs for each gene. This fragment was amplified with oCJ251 and oCJ252 and assembled into pCJ011 digested with BglII and NotI (9,934 bp). |
| pCJ051 | Replacement of pcaHG with Ptac:ligAB in *P. putida* KT2440 and strains derived from it | Ptac:ligAB was amplified from pCJ019 with primer pair oCJ330/oCJ331 (1,480 bp) and assembled into pCJ019 digested with BglII and NotI (,9942 bp). |
| pCJ052 | Replacement of pcaHG with Ptac:ligABC in *P. putida* KT2440 and strains derived from it | Ptac:ligABC was amplified from pCJ019 with primer pair oCJ330/oCJ332 (2,440 bp) and assembled into pCJ019 digested with BglII and NotI (9,942 bp). |
| pCJ053 | Replacement of pcaHG with Ptac:ligABCI in *P. putida* KT2440 and strains derived from it. | Ptac:ligABCI was amplified from pCJ019 with primer pair oCJ330/oCJ333 (3,334 bp) and assembled into pCJ019 digested with BglII and NotI (9,942 bp). |
| pCJ054 | Replacement of pcaHG with Ptac:ligABCIU in *P. putida* KT2440 and strains derived from it. | Ptac:ligABCIU was amplified from pCJ019 with primer pair oCJ330/oCJ334 (4,402 bp) and assembled into pCJ019 digested with BglII and NotI (9,942 bp). |

TABLE 1-continued

Plasmid Construction

| Plasmid | Utility | Plasmid Construction Details |
|---|---|---|
| pCJ055 | Replacement of pcaHG with Ptac:ligABCIUJ in *P. putida* KT2440 and strains derived from it. | Ptac:ligABCIUJ was amplified from pCJ019 with primer pair oCJ330/oCJ335 (5,440 bp) and assembled into pCJ019 digested with BgIII and NotI (9,942 bp). |
| pCJ056 | Deletion of pcaBDC in *P. putida* KT2440 and strains derived from it | The 5' targeting region was amplified with primer pair oCJ346/oCJ347 (1,045 bp) while the 3' targeting region was amplified with primer pair oCJ348/oCJ349 (1,053 bp) and these fragments were assembled into pK18mobsacB amplified with primer pair oCJ345/oCJ289 and digested with EcoRI and BamHI (5,391 bp). |
| pCJ057 | Deletion of pcaDC in *P. putida* KT2440 and strains derived from it | The 5' targeting region was amplified with primer pair oCJ351/oCJ352 (1,045 bp) while the 3' targeting region was amplified with primer pair oCJ353/oCJ349 (1,052 bp) and these fragments were assembled into pK18mobsacB amplified with primer pair oCJ345/oCJ289 and digested with EcoRI and BamHI (5,391 bp). |
| pCJ058 | Deletion of pcaD in *P. putida* KT2440 and strains derived from it | The 5' targeting region was amplified with primer pair oCJ351/oCJ357 (1,046 bp) while the 3 targeting region (1,068 bp) was amplified with primer pair oCJ358/oCJ359 (1052 bp) and these fragments were assembled into pK18mobsacB amplified with primer pair oCJ345/oCJ289 and digested with EcoRI and BamHI (5391 bp). |
| pCJ059 | Deletion of pcaJ in *P. putida* KT2440 and strains derived from it | The 5' targeting region was amplified with primer pair oCJ361/oCJ362 (1,049 bp) while the 3 targeting region (1,068 bp) was amplified with primer pair oCJ363/oCJ364 (1,049 bp) and these fragments were assembled into pK18mobsacB amplified with primer pair oCJ345/oCJ289 and digested with EcoRI and BamHI (5,391 bp). |
| pCJ060 | Replacement of pcaHG with Ptac:praA in *P. putida* KT2440 and strains derived from it | Ptac:praA was amplified from pCJ032 with primer pair oCJ251/oCJ354 (936 bp) and assembled into pCJ019 digested with BgIII and NotI (9,942). |
| pCJ061 | Replacement of catBCA with Ptac:xylEG in *P. putida* KT2440 and strains derived from it | Ptac:xylEG was amplified from pCJ008 with primer pair oCJ336/oCJ337 (2,213 bp) and assembled into pCJ008 digested with NdeI and NotI (10,337 bp). |
| pCJ062 | Replacement of catBCA with Ptac:xylEGH in *P. putida* KT2440 and strains derived from it. | Ptac:xylEGH was amplified from pCJ008 with primer pair oCJ336/oCJ338 (2,229 bp) and assembled into pCJ008 digested with NdeI and XmaI (10,565 bp). |
| pCJ064 | Replacement of catBCA with Ptac:xylEGF in *P. putida* KT2440 and strains derived from it | Ptac:xylEGF was amplified from pCJ008 with primer pair oCJ336/oCJ342 (3,072 bp) and assembled into pCJ008 digested with NdeI and NotI (10,337 bp). |
| pCJ065 | Replacement of catBCA with Ptac:xylEGFJIH in *P. putida* KT2440 and strains derived from it | Ptac:xylEGFJIH was amplified from pCJ008 with primer pair oCJ336/oCJ343 (3,862 bp) and xylIH was amplified from pCJ008 with primer pair oCJ344/oCJ341 (1,090 bp). These fragments were then and assembled into pCJ008 digested with NdeI and NotI (10,337 bp). |
| pCJ081 | Deletion of galBCD in *P. putida* KT2440 and strains derived from it | The 5' targeting region was amplified from *P. putida* KT2440 genomic DNA with primer pair oCJ435/oCJ436 (1060 bp) while the 3' targeting region was amplified from *P. putida* KT2440 genomic DNA with primer pair oCJ437/oCJ438 (1,050 bp) and these fragments were assembled into pK18mobsacB amplified with primer pair oCJ345/oCJ289 and digested with EcoRI and BamHI (5,391 bp). |
| pCJ124 | Replacement of galBC with the tac promoter upstream of galD in *P. putida* KT2440 and strains derived from it | The 3' targeting region containing galD was amplified from *P. putida* KT2440 genomic DNA with primers oCJ624/oCJ625 (1,235 bp, which incorporated the tac promoter upstream of galD) and assembled into pCJ081 digested with NotI and BamHI (6,399 bp). |
| pCJ125 | Deletion of galC and integration of the tac promoter upstream of galBD in *P. putida* KT2440 and strains derived from it | galB was amplified from *P. putida* KT2440 genomic DNA with primers oCJ626/oCJ627 (855 bp) and assembled into pCJ124 digested with SpeI (7,572 bp). |

TABLE 2

Strain Construction

| Target Molecule | Strain | Genotype | Strain Construction Details | Medium Used For Evaluation of Molecule Production |
|---|---|---|---|---|
| 1: 2-hydroxy-2H-pyran-4,6-dicarboxylic acid | CJ249 | P. putida KT2440 ΔpcaHG::Ptac:ligAB | pcaHG was replaced with Ptac:ligAB in P. putida KT2440 with pCJ051. This strain was confirmed to contain this gene replacement by diagnostic colony PCR amplification of a 1,056 bp product with primer pair oCJ106/oCJ055 and a 2,428 bp product with primer pair oCJ054/oCJ107. | M9 + 20 mM p-coumarate + 20 mM Glucose |
| 2: 2-oxo-2H-pyran-4,6-dicarboxylic acid | CJ251 | P. putida KT2440 ΔpcaHG::Ptac:ligABC | pcaHG was replaced with Ptac:ligABC in P. putida KT2440 with pCJ052. This strain was confirmed to contain this gene replacement by diagnostic colony PCR amplification of a 1,056 bp product with primer pair oCJ106/oCJ055 and a 3,388 bp product with primer pair oCJ054/oCJ107. | M9 + 20 mM p-coumarate + 20 mM Glucose |
| 3: (1E,3E)-4-hydroxybuta-1,3-diene-1,2,4-tricarboxylic acid | CJ350 | P. putida KT2440 ΔpcaHG::Ptac:ligABCI ΔgalBCD | pcaHG was replaced with Ptac:ligABCI in P. putida KT2440 with pCJ053. This strain was confirmed to contain this gene replacement by diagnostic colony PCR amplification of a 1,056 bp product with primer pair oCJ106/oCJ055 and a 1,298 bp product with primer pair oCJ149/oCJ107. galBCD was deleted from P. putida KT2440 with pCJ252 with pCJ081. This deletion was confirmed by diagnostic colony PCR amplification of a 2071 bp product with primer pair oCJ439/oCJ440. | M9 + 20 mM p-coumarate + 20 mM Glucose |
| 4: (1E)-4-oxobut-1-ene-1,2,4-tricarboxylic acid | CJ328 | P. putida KT2440 ΔpcaHG::Ptac:ligABCIU ΔgalBCD | pcaHG was replaced with Ptac:ligABCIU in P. putida KT2440 with pCJ054. This strain was confirmed to contain this gene replacement by diagnostic colony PCR amplification of a 1,056 bp product with primer pair oCJ106/oCJ055 and a 2,366 bp product with primer pair oCJ149/oCJ107. galBCD was deleted from this strain with pCJ081. This deletion was confirmed by diagnostic colony PCR amplification of a 2071 bp product with primer pair oCJ439/oCJ440. | M9 + 20 mM p-coumarate + 20 mM Glucose |
|  | CJ491 | P. putida KT2440 ΔpcaHG::Ptac:ligABCIU ΔgalBC::Ptac:galD | pcaHG was replaced with Ptac:ligABCIU in P. putida KT2440 with pCJ054. This strain was confirmed to contain this gene replacement by diagnostic colony PCR amplification of a 1,056 bp product with primer pair oCJ106/oCJ055 and a 2,366 bp product with primer pair oCJ149/oCJ107. galBC was deleted and the tac promoter was integrated upstream of galD using pCJ124 and this replacement was confirmed by amplification of 3,242 bp product with primer pair OCJ439/OCJ440. | M9 + 20 mM p-coumarate + 20 mM Glucose |
| 5: 2-hydroxy-4-oxobutane-1,2,4-tricarboxylic acid | CJ329 | P. putida KT2440 ΔpcaHG::Ptac:ligABCIUJ ΔgalBCD | pcaHG was replaced with Ptac:ligABCIUJ in P. putida KT2440 with pCJ055. This strain was confirmed to contain this gene replacement by diagnostic colony PCR amplification of a 1,056 bp product with primer pair oCJ106/oCJ055 and a 3,392 bp product with primer pair oCJ149/oCJ107. galBCD was deleted from this strain with pCJ081. This deletion was confirmed by diagnostic colony PCR amplification of a 2071 bp product with primer pair oCJ439/oCJ440. | M9 + 20 mM p-coumarate + 20 mM Glucose |
|  | CJ507 | P. putida KT2440 ΔpcaHG::Ptac:ligABCIUJ ΔgalC::Ptac:galBD | pcaHG was replaced with Ptac:ligABCIUJ in P. putida KT2440 with pCJ055. This strain was confirmed to contain this gene replacement by diagnostic colony PCR amplification of a 1,056 bp product with primer pair oCJ106/oCJ055 and a 3,392 bp product with primer pair oCJ149/oCJ107. galC was deleted and the tac promoter was integrated upstream of galBD in this strain using pCJ125 and this replacement was confirmed by amplification of a 4031 bp product using primers oCJ1440/oCJ440. | M9 + 20 mM p-coumarate + 20 mM Glucose |
| 6: (1E,3Z)-buta-1,3-diene-1,2,4-tricarboxylic acid | CJ257 | P. putida KT2440 ΔpcaBDC | pcaBDC was deleted from P. putida KT2440 with pCJ056. This deletion was confirmed by diagnostic colony PCR amplification of a 2,067 bp product with primer pair oCJ355/oCJ356. | M9 + 20 mM p-coumarate + 20 mM Glucose |
| 7: 2-carboxy-5-oxo-2,5-dihydrofuran-2-carboxylic acid | CJ259 | P. putida KT2440 ΔpcaDC | pcaDC was deleted from P. putida KT2440 with pCJ057. This deletion was confirmed by diagnostic colony PCR amplification of a 3,429 bp product with primer pair oCJ355/oCJ356. | M9 + 20 mM p-coumarate + 20 mM Glucose |
| 8: 2-(2-oxo-3H-furan-5-yl)acetic acid | CJ261 | P. putida KT2440 ΔpcaD | pcaD was deleted from P. putida KT2440 with pCJ058. This deletion was confirmed by diagnostic colony PCR amplification of a 3,835 bp product with primer pair oCJ355/oCJ356. | M9 + 20 mM p-coumarate + 20 mM Glucose |
| 9: 3-oxohexanedioic acid | CJ263 | P. putida KT2440 ΔpcaJ | pcaJ was deleted from P. putida KT2440 with pCJ059. This deletion was confirmed by diagnostic colony PCR amplification of a 2,037 bp product with primer pair oCJ366/oCJ367. | M9 + 20 mM p-coumarate + 20 mM Glucose |
| 10: (2E,4E)-2-formyl-5-hydroxyhexa-2,4-dienedioic acid/ | CJ265 | P. putida KT2440 ΔpcaHG::Ptac:praA | pcaHG was replaced with Ptac:praA in P. putida KT2440 with pCJ060. This strain was confirmed to contain this gene replacement by diagnostic colony PCR amplification of a 2,923 bp product with primer pair oCJ106/oCJ107. | M9 + 20 mM p-coumarate + 20 mM Glucose |

TABLE 2-continued

| Target Molecule | Strain | Genotype | Strain Construction Details | Medium Used For Evaluation of Molecule Production |
|---|---|---|---|---|
| pyridine 2,5-dicarboxylic acid 11: (2Z,4E)-2-hydroxy-6-oxohexa-2,4-dienoic acid/ pyridine-5-carboxylic acid | CJ146 | P. putida KT2440 ΔcaA2 ΔcatBCA::Ptac:xylE ΔpcaHG::Ptac:praAH | catA2 deleted from P. putida KT2440 using pCJ004 and this deletion was confirmed by diagnostic colony PCR amplification of a 2,089 bp product with primer pair oCJ084/oCJ085. catBCA was replaced with Ptac:xylE using pCJ005 and this gene replacement was confirmed by diagnostic colony PCR amplification of a 3,078 bp product with primer pair oCJ086/oCJ087. pcaHG was replaced with praAH from Paenibacillus sp.JJ-1b using plasmid pCJ032 and this replacement was confirmed by diagnostic colony PCR amplification of a 3,888 bp product with primer pair oCJ106/oCJ107. | M9 + 20 mM benzoate + 20 mM Glucose |
| 12: (2Z,4E)-2-hydroxyhexa-2,4-dienedioic acid | CJ266 | P. putida KT2440 ΔcatA2 ΔpcaHG::Ptac:praAH ΔcatBCA::Ptac:xylEG | catBCA was replaced with Ptac:xylEG in CJ146 with pCJ061. This strain was confirmed to contain this gene replacement by diagnostic colony PCR amplification of a 2,057 bp product with primer pair oCJ086/oCJ091 and a 1,517 bp product with primer pair oCJ061/oCJ087. | M9 + 20 mM benzoate + 20 mM Glucose |
| 13: (3E)-2-oxohex-3-enedioic acid | CJ267 | P. putida KT2440 ΔcatA2 ΔpcaHG::Ptac:praAH ΔcatBCA::Ptac:xylEGH | catBCA was replaced with Ptac:xylEGH in CJ146 with pCJ062. This strain was confirmed to contain this gene replacement by diagnostic colony PCR amplification of a 2,057 bp product with primer pair oCJ086/oCJ091 and a 1,761 bp product with primer pair oCJ061/oCJ087. | M9 + 20 mM benzoate + 20 mM Glucose |
| 14: (2E)-2-hydroxypenta-2,4-dienoic acid | CJ270 | P. putida KT2440 ΔcatA2 ΔpcaHG::Ptac:praAH ΔcatBCA::Ptac:xylEGF | catBCA was replaced with Ptac:xylEGF in CJ146 with pCJ064. This strain was confirmed to contain this gene replacement by diagnostic colony PCR amplification of a 2,057 bp product with primer pair oCJ086/oCJ091 and a 1,869 bp product with primer pair oCJ062/oCJ087. | M9 + 20 mM benzoate + 20 mM Glucose |
| 15: 4-hydroxy-2-oxopentanoic acid | CJ268 | P. putida KT2440 ΔcatA2 ΔpcaHG::Ptac:praAH ΔcatBCA::Ptac:xylEGFJIH | catBCA was replaced with Ptac:xylEGFJIH in CJ146 with pCJ065. This strain was confirmed to contain this gene replacement by diagnostic colony PCR amplification of a 2,057 bp product with primer pair oCJ086/oCJ091 and a 1,330 bp product with primer pair oCJ070/oCJ087. | M9 + 20 mM benzoate + 20 mM Glucose |

TABLE 3

Primer Sequences

| Primer | SEQ ID: NO | Sequence (5'→3') |
|---|---|---|
| oCJ038 | 72 | ccgaaaagtgccacctGACGTCcttcatcgccggcctg |
| oCJ039 | 73 | GCCGCagctcgAGATCTgtcttgttctgttcggttcagg |
| oCJ040 | 74 | AGATCTcgagctGCGGCCGCtccaccgagtgggctg |
| oCJ041 | 75 | gctggatcctctagtGAGCTCggttttcatgggcttcatggc |
| oCJ042 | 76 | ccgaaaagtgccacctGACGTCcctgttgctcgatcaacgc |
| oCJ043 | 77 | tcataAGATCTctcctgtgtgaaattgttatccgctcacaattccacacat tatacgagccgatgattaattgtcaacagctctgttgccaggtcccgtc |
| oCJ044 | 78 | aggagAGATCTtatgaacaaaggtgtaatgcgacc |
| oCJ045 | 79 | cgaacGCGGCCGCgcaataagtcgtaccggaccatc |
| oCJ046 | 80 | attgcGCGGCCGCgttcgaggttatgtcactgtgattttg |
| oCJ047 | 81 | gctggatcctctagtGAGCTCcgcctgctccaggttg |
| oCJ048 | 82 | cgaacGCGGCCGCgcaattcagcgtctgaccttgctg |
| oCJ054 | 83 | ATCGGCTCGTATAATGTGTGG |
| oCJ055 | 84 | TCCGCTCACAATTCCACAC |
| oCJ061 | 85 | AATTTCGGCCCGCTGATC |
| oCJ062 | 86 | GCAGCAAAGCCCTGAAATC |
| oCJ070 | 87 | AACATCACCGTGCGCTAC |
| oCJ084 | 88 | CCTCAATGGCTTTGCCAG |
| oCJ085 | 89 | GTACAACACACTGCCAGC |
| oCJ086 | 90 | TGTGGGCATGGTGTGTTC |
| oCJ087 | 91 | TCTTCAAAGCGTCCGGTG |
| oCJ091 | 92 | ACGAAGGCACCGCTAATG |
| oCJ100 | 93 | ccgaaaagtgccacctGACGTCggccttgctgctgcag |
| oCJ101 | 94 | GCCGCagctcgAGATCTggaattgtgagaacgcctgg |
| oCJ102 | 95 | AGATCTcgagctGCGGCCGCggtgaagcttggggcc |
| oCJ103 | 96 | gctggatcctctagtGAGCTCacgatttccccattgccag |
| oCJ106 | 97 | ATCTTGAACCAACGCACC |
| oCJ107 | 98 | CACAAGGCAATCCTGATCG |
| oCJ154 | 99 | ggcgttctcacaattccAGATCTgagctgttgacaattaatcatcggctcg tataatgtgtggaattgtgagcggataacaatttcacacAGGAGGACAGCT atgaccgagaagaaagaacgcatcg |
| oCJ155 | 100 | gcggccccaagcttcaccGCGGCCGCTcagacgtacttcaggccctc |
| oCJ157 | 101 | tcacatttcctccgaccagtacag |
| oCJ158 | 102 | actggtcggaggaaatgtgaAGGAGGACAGCTatgccaggc |
| oCJ251 | 103 | ccaggcgttctcacaattccAGATCTgagctgttgacaattaatcatcgg |
| oCJ252 | 104 | gagcggccccaagcttcaccGCGGCCGCt |
| oCJ289 | 105 | CTAACTCACATTAATTGCGTTGCGCTCACTG |
| oCJ330 | 106 | gcccaggcgttctcacaattcc |
| oCJ331 | 107 | cgcagagcggccccaagcttcaccGCGGCCGCtcaggcctgggccagg |
| oCJ332 | 108 | cgcagagcggccccaagcttcaccGCGGCCGCtcagccctgcttttccagc tg |
| oCJ333 | 109 | cgcagagcggccccaagcttcaccGCGGCCGCtcacatttcctccgaccag tacagg |
| oCJ334 | 110 | cgcagagcggccccaagcttcaccGCGGCCGCtcagccgaacacgatgccg |
|  | 111 | cgcagagcggccccaagcttcaccGCGGCCGCtcacaggcacgggctttc a |
|  | 112 | aactggagcgggatctgatggc |
|  | 113 | aatcacagtgacataaccctcgaacGCGGCCGCtcaaagtttcacacagatg tttttcagctcgg |
|  | 114 | ggtgtgcctcctgaagaagaggccgCCCGGGcagggcggccggatggctca aagtttcacacagatgttttttcagctcgg |
|  | 115 | tgacataaccctcgaacGCGGCC |
|  | 116 | aatcacagtgacataaccctcgaacGCGGCCGCtcaggaatggagggcgtcg g |
|  | 117 | tcatgcctgttgctccttcagatgaagcgcacggaggc |
|  | 118 | gcgcttcatctgaaggagcaacaggcatgaatcgtacc |
|  | 119 | GAATTCctgcagtctagaGGATCCctagcttcacgctgccgcaag |
|  | 120 | cgcaacgcaattaatgtgagttagGAATTCgtgcttcggctccctgatgat c |
|  | 121 | tcacggtGCGGCCGCttaatcatcatggtgcaggtacgccg |
|  | 122 | caccatgatgattaaGCGGCCGCaccgtgatcacgggcagg |
|  | 123 | gtgcttgcggcagcgtgaagctagGGATCCgaaccgctatatcaagggtga caacgtc |
|  | 124 | cgcaacgcaattaatgtgagttagGAATTCgcgcgatgccctcgatttgat c |
|  | 125 | tcacggtGCGGCCGCtcaggcagtgaaacgttgatgttcgg |
|  | 126 | gtttcactgcctgaGCGGCCGCaccgtgatcacgggcagg |
|  | 127 | cagagcggccccaagcttcaccGCGGCCGCttagctgacgaaggagatgat ggcg |
|  | 128 | CTGATGATCTCGGTGCTG |
|  | 129 | GACTTCAACTTCGCCACC |
|  | 130 | tgtcctcaGCGGCCGCtcaggcagtgaaacgttgatgttcgg |
|  | 131 | gtttcactgcctgaGCGGCCGCtgaggacaacgcatggacgag |
|  | 132 | gtgcttgcggcagcgtgaagctagGGATCCaacagggaggcacaacaatga aaaccc |

TABLE 3-continued

Primer Sequences

| | | |
|---|---|---|
| | 133 | cgcaacgcaattaatgtgagttagGAATTCgtagttgtcgcccgactcgg |
| | 134 | gtcttcctggaGCGGCCGCggttgttcctggagttgtggttgtc |
| | 135 | caggaacaaccGCGGCCGCtccaggaagacttagggctttccatg |
| | 136 | gtgcttgcggcagcgtgaagctagGGATCCtgaccacagccacccagtgc |
| | 137 | CCCAGCCCATGCTGAATTTG |
| | 138 | CGATTGCGCCATGAACAG |
| | 139 | agtgagcgcaacgcaattaatgtgagttagGAATTCgcccgcggcaacacc |
| | 140 | agcaaccattgatgagGCGGCCGCtggcctgtgcagggcactaatg |
| | 141 | aggccaGCGGCCGCctcatcaatggttgcttggggtttcaaaaatg |
| | 142 | ccctgagtgcttgcggcagcgtgaagctagGGATCCgacaccccccggcgtg |
| | 143 | GAAGCAGTTGTCGAGCAG |
| | 144 | ATTGGTGAAAAcccGcAG |
| | 145 | tgaacgcattagtgccctgcacaggccaGCgagctgttgacaattaatcatcggctcgtataatgtgtggaattgtgagcggataacaatttcacACTAGTCCTAAGGAGATCTAAatgggccagacccgcatacc |
| | 146 | ccctgagtgcttgcggcagcgtgaagctagGGATCCtcacttctccggcccaccc |
| | 147 | tgtgagcggataacaatttcacACTAGTTAAGGGGGAAAAatgacatcctgcgcccaccc |
| | 148 | aggcagggtatgcgggtctggcccatTTTTTCCTCCGTtcatgccaggttctccgtcacg |

| Primer | SEQ ID: NO | Description |
|---|---|---|
| oCJ038 | 72 | catA2 replacement 5' homology F with AatII and pCM433 overlap |
| oCJ039 | 73 | catA2 replacement 5' homology R with BglII and 3' overlap |
| oCJ040 | 74 | catA2 replacement 3' homology F with NotI and 5' overlap |
| oCJ041 | 75 | catA2 replacement 3' homology R with SacI and pCM433 overlap |
| oCJ042 | 76 | catBCA replacement 5' homology F with AatII and pCM433 overlap |
| oCJ043 | 77 | catBCA replacement 5' homology R with Ptac, BglII and xylE overlap |
| oCJ044 | 78 | xylE F with BglII and 5' overlap |
| oCJ045 | 79 | xylE R with NotI and 3' overlap |
| oCJ046 | 80 | catBCA replacement 3' homology F with NotI and xylE overlap |
| oCJ047 | 81 | catBCA replacement 3' homology R with SacI and pCM433 overlap |
| oCJ048 | 82 | xylH R with NotI and 3' overlap |
| oCJ054 | 83 | Diagnostic: pTac F |
| oCJ055 | 84 | Diagnostic: pTac R |
| oCJ061 | 85 | Diagnostic: xylG F |
| oCJ062 | 86 | Diagnostic: xylF F |
| oCJ070 | 87 | Diagnostic: xylI F |
| oCJ084 | 88 | Diagnostic: BenK F |
| oCJ085 | 89 | Diagnostic: BenE2 R |
| oCJ086 | 90 | Diagnostic: catR F |
| oCJ087 | 91 | Diagnostic: catBCA 3' homology R |
| oCJ091 | 92 | Diagnostic: xylG R |
| oCJ100 | 93 | pcaGH deletion 5' homology F with AatII and pCM433 overlap |
| oCJ101 | 94 | pcaGH deletion 5' homology R with BglII and 3' overlap |
| oCJ102 | 95 | pcaGH deletion 3' homology F with NotI and 5' overlap |
| oCJ103 | 96 | pcaGH deletion 3' homology R with SacI and pCM433 overlap |
| oCJ106 | 97 | Diagnostic: PP_4567 outside homology F |
| oCJ107 | 98 | Diagnostic: trmA R outside homology F |
| oCJ154 | 99 | ligABCI fragment F with BglII, Ptac and overlap with pcaHG 5' homology |
| oCJ155 | 100 | ligUJK fragment R with NotI and overlap with pcaHG 3' homology |
| oCJ157 | 101 | ligABCI fragment R and ligUJK fragment overlap |
| oCJ158 | 102 | ligUJK fragment F and ligABCI overlap |
| oCJ251 | 103 | Ptac: praAH(opt P.p.) F with pCJ011 overlap |
| oCJ252 | 104 | Ptac: praAH(opt P.p.) R with pCJ011 overlap |
| oCJ289 | 105 | pK18mobsacB around the world R |
| oCJ330 | 106 | lig operon F with ΔpcaHG upstream targeting overlap |
| oCJ331 | 107 | ligB R with ΔpcaHG upstream targeting overlap |
| oCJ332 | 108 | ligC R with ΔpcaHG upstream targeting overlap |
| oCJ333 | 109 | high R with ΔpcaHG upstream targeting overlap |
| oCJ334 | 110 | ligU R with ΔpcaHG upstream targeting overlap |
| | 111 | ligJ R with ΔpcaHG upstream targeting overlap |
| | 112 | xylE F (partial) with xylE upstream targeting overlap |
| | 113 | xylG R with ΔcatBCA downstream targeting overlap |
| | 114 | xylG R with xyIH overlap |
| | 115 | ΔcatBCA downstream targeting overlap |
| | 116 | xylF R with ΔcatBCA downstream targeting overlap |
| | 117 | xylJ R with xylI overlap |
| | 118 | xylI F with xylJ overlap |
| | 119 | pK18mobsacB around the world F with EcoRI XbaI PstI BamHI sites |
| | 120 | Targeting upstream of pcaB F with pK18mobsacB overlap |
| | 121 | Targeting upstream of pcaB R with targeting downstream of pcaC overlap |
| | 122 | Targeting downstream of pcaC F with targeting upstream of pcaB |

TABLE 3-continued

Primer Sequences

| | |
|---|---|
| | overlap |
| 123 | Targeting downstream of pcaC R with pK18mobsacB overlap |
| 124 | Targeting upstream of pcaD F with pK18mobsacB overlap |
| 125 | Targeting upstream of pcaD R with targeting downstream of pcaC overlap |
| 126 | Targeting downstream of pcaC F with targeting upstream of pcaD overlap |
| 127 | praA R with pCJ011 overlap |
| 128 | Diagnostic: outside targeting region upstream of pcaB |
| 129 | Diagnostic: PCR outside targeting region downstream of pcaC |
| 130 | Targeting upstream of pcaD R with targeting downstream of pcaD overlap |
| 131 | Targeting downstream of pcaD F with targeting upstream of pcaD overlap |
| 132 | Targeting downstream of pcaD R with pK18mobsacB overlap |
| 133 | Targeting upstream of pcaI F with pK18mobsacB overlap |
| 134 | Targeting upstream of pcaI R with targeting downstream of pcaJ overlap |
| 135 | Targeting downstream of pcaJ F with targeting upstream of pcaI overlap |
| 136 | Targeting downstream of pcaJ R with pK18mobsacB overlap |
| 137 | Diagnostic: outisde targeting region upstream of pcaI F |
| 138 | Diagnostic: outside targeting region upstream of pcaI F |
| 139 | galBCD upstream targeting F with pK18mobsacBmod overlap |
| 140 | galBCD upstream targeting R with NotI and downstream targeting overlap |
| 141 | galBCD downstream targeting F with NotI and upstream targeting overlap |
| 142 | galBCD downstream targeting R with pK18mobsacBmod targeting overlap |
| 143 | Diagnostic: outside galBCD upstream targeting region F |
| 144 | Diagnostic: outside galBCD downstream targeting region R |
| 145 | galD F with Ptac, RBS, and upstream targeting overlap |
| 146 | galD R with BamHI pK18mobsacBmod overlap |
| 147 | galB F with RBS and Ptac overlap |
| 148 | galB R with RBS and galD overlap |

TABLE 4

Protocatechuate 4,5 meta-cleavage pathway

| EC Number | Enzyme Name | Example | NCBI-Protein | Genbank Nucleotide |
|---|---|---|---|---|
| 1.13.11.8 | protocatechuate 4,5-dioxygenase | LigA, *Sphingobium* sp. SYK-6 | WP_014075577.1 | n/a, optimized sequence |
| | | LigB, *Sphingobium* sp. SYK-6 | WP_014075576.1 | n/a, optimized sequence |
| 1.1.1.312 | 4-carboxy-2-hydroxymuconate-6-semialdehyde dehydrogenase | LigC, *Sphingobium* sp. SYK-6 | WP_014075575.1 | n/a, optimized sequence |
| 3.1.1.57 | 2-pyrone-4,6-dicarboxylic acid hydrolase | LigI, *Sphingobium* sp. SYK-6 | WP_014075583.1 | n/a, optimized sequence |
| 5.3.2.8 | 4-oxalomesaconate tautomerase | LigU, *Sphingobium* sp. SYK-6 | WP_014075582.1 (YP_004834388.1) | n/a, optimized sequence |
| 4.2.1.83 | 4-oxalomesaconate hydratase | LigJ, *Sphingobium* sp. SYK-6 | WP_014075578.1 | n/a, optimized sequence |
| 4.1.3.17, 1.1.1.38/ 4.1.1.3 | 4-Carboxy-4-hydroxy-2-oxoadipate aldolase/oxaloacetate decarboxylase | LigK, *Sphingobium* sp. SYK-6 | WP_014075581.1 (YP_004834387.1) | n/a, optimized sequence |
| 5.3.2.8 | 4-oxalomesaconate tautomerase | GalD (PP_2513), *Pseudomonas putida* KT2440 | NP_744661.1 | NC_002947.3: 2860243..2861328 complement |
| 4.2.1.83 | 4-oxalomesaconate hydratase | GalB (PP_2515), *Pseudomonas putida* KT2440 | NP_744663.1 | NC_002947.3: 2862044..2862820 complement |
| 4.1.3.17, 1.1.1.38/ 4.1.1.3 | 4-Carboxy-4-hydroxy-2-oxoadipate aldolase/oxaloacetate decarboxylase | GalC (PP_2514), *Pseudomonas putida* KT2440 | NP_744662.1 | NC_002947.3: 2861331..2862047 complement |

TABLE 5

Catechol and protocatechuate ortho-cleavage pathways

| EC Number | Enzyme Name | Example | NCBI-Protein | Genbank Nucleotide |
|---|---|---|---|---|
| 1.13.11.1 | catechol 1,2-dioxygenase | CatA, *Pseudomonas putida* KT2440 | NP_745846.1 | NC_002947.3: 4235833..4236768 complement |

TABLE 5-continued

Catechol and protocatechuate ortho-cleavage pathways

| EC Number | Enzyme Name | Example | NCBI-Protein | Genbank Nucleotide |
|---|---|---|---|---|
| 1.13.11.1 | catechol 1,2-dioxygenase | CatA2 (PP_3166), *Pseudomonas putida* KT2440 | NP_745310.1 | NC_002947.3: 3587162..3588076 |
| 5.5.1.1 | muconate cycloisomerase | CatB, *Pseudomonas putida* KT2440 | NP_745848.1 | NC_002947.3: 4237124..4238245 complement |
| 5.3.3.4 | muconolactone isomerase | CatC, *Pseudomonas putida* KT2440 | NP_745847.1 | NC_002947.3: 4236812..4237102 complement |
| 1.13.11.3 | protocatechuate 3,4-dioxygenase | PcaH, *Pseudomonas putida* KT2440 | NP_746765.1 | NC_002947.3: 5281619..5282338 complement |
|  |  | PcaG, *Pseudomonas putida* KT2440 | NP_746764.1 | NC_002947.3: 5281003..5281608 complement |
| 5.5.1.2 | 3-carboxy-cis,cis-muconate cycloisomerase | PcaB, *Pseudomonas putida* KT2440 | NP_743538.1 | NC_002947.3: 1571875..1573227 |
| 4.1.1.44 | 4-carboxymuconolactone decarboxylase | PcaC, *Pseudomonas putida* KT2440 | NP_743540.1 | NC_002947.3: 1574041..1574433 |
| 3.1.1.24 | 3-oxoadipate enol-lactonase | PcaD, *Pseudomonas putida* KT2440 | NP_743539.1 | NC_002947.3: 1573239..1574030 |
| 2.8.3.6 | 3-oxoadipate CoA-transferase | PcaI, *Pseudomonas putida* KT2440 | NP_746081.1 | NC_002947.3: 4457362..4458057 |
|  |  | PcaJ, *Pseudomonas putida* KT2440 | NP_746082.1 | NC_002947.3: 4458066..4458707 |
| 2.3.1.174 | beta-ketoadipyl CoA thiolase | PcaF, *Pseudomonas putida* KT2440 | NP_743536.1 | NC_002947.3: 1569186..1570388 |

TABLE 6

Catechol meta-cleavage and protocatechuate 2,3 meta-cleavage pathways

| EC Number | Enzyme Name | Example | NCBI-Protein | Genbank Nucleotide |
|---|---|---|---|---|
| 1.13.11.— | protocatechuate 2,3-dioxygenase | PraA, *Paenibacillus* sp. JJ-1b | BAH79099.1 | n/a, optimized sequence |
| — | 5-carboxy-2-hydroxymuconate-6-semialdehyde decarboxylase | PraH, *Paenibacillus* sp. JJ-1b | BAH79106.1 | n/a, optimized sequence |
| 1.13.11.2 | catechol 2,3 dioxygenase | XylE, *Pseudomonas putida* mt-2 | NP_542866.1 | AJ344068.1: 50914..51837 complement |
| 3.7.1.9 | 2-hydroxymuconic semialdehyde hydrolase | XylF, *Pseudomonas putida* mt-2 | NP_542864.1 | AJ344068.1: 48563..49408 complement |
| 1.2.1.85 |  | XylG, *Pseudomonas putida* mt-2 | NP_542865.1 | AJ344068.1: 49419..50879 complement |
| 5.3.2.6 | 4-Oxalocrotonate Tautomerase | XylH, *Pseudomonas putida* mt-2 | NP_542859.1 | AJ344068.1: 44734..44925 complement |
| 4.1.1.77 | 4-oxalocrotonate decarboxylase | XylI, *Pseudomonas putida* mt-2 | NP_542860.1 | AJ344068.1: 44975..45769 complement |
| 4.2.1.80 | 2-hydroxypent-2,4-dienoate hydratase | XylJ, *Pseudomonas putida* mt-2 | NP_542863.1 | AJ344068.1: 47883..48551 complement |
| 4.1.3.39 | 4-hydroxy-2-ketovalerate aldolase | XylK, *Pseudomonas putida* mt-2 | NP_542861.1 | AJ344068.1: 45766..46803 complement |
| 1.2.1.10 | acetaldehyde dehydrogenase | XylQ, *Pseudomonas putida* mt-2 | NP_542862.1 | AJ344068.1: 46814..47752 complement |

Note:
XylG is a 2-hydroxymuconate semialdehyde dehydrogenase.

EXAMPLES: PROTOCATECHUATE 4,5 META-CLEAVAGE PATHWAYS

Example 1

A microbial cell comprising: a first genetic modification resulting in the expression of a deficient form of an endogenous dioxygenase; and a gene encoding an exogenous dioxygenase, wherein: the microbial cell is capable of growth utilizing at least one of a cellulose decomposition molecule or a lignin decomposition molecule, and the microbial cell is capable of producing a target molecule.

Example 2

The microbial cell of Example 1, wherein the endogenous dioxygenase comprises a protocatechuate 3,4-dioxygenase.

Example 3

The microbial cell of Example 2, wherein the protocatechuate 3,4-dioxygenase comprises PcaH.

Example 4

The microbial cell of Example 2, wherein the protocatechuate 3,4-dioxygenase comprises PcaG.

Example 5

The microbial cell of Example 2, wherein the protocatechuate 3,4-dioxygenase is PcaH and PcaG.

Example 6

The microbial cell of Example 1, wherein the exogenous dioxygenase comprises a protocatechuate 3,4-dioxygenase.

Example 7

The microbial cell of Example 6, wherein the protocatechuate 3,4-dioxygenase comprises LigA.

Example 8

The microbial cell of Example 6, wherein the protocatechuate 3,4-dioxygenase comprises LigB.

Example 9

The microbial cell of Example 6, wherein the protocatechuate 3,4-dioxygenase is LigA and LigB.

Example 10

The microbial cell of Example 1, wherein the gene is operably linked to a promoter.

Example 11

The microbial cell of Example 10, wherein the promoter is Ptac.

Example 12

The microbial cell of Example 1, wherein the target molecule is 2-hydroxy-2H-pyran-4,6-dicarboxylic acid (molecule #1).

Example 13

The microbial cell of Example 1, further comprising a gene encoding an exogenous dehydrogenase.

Example 14

The microbial cell of Example 13, wherein the exogenous dehydrogenase comprises a 4-carboxy-2-hydroxymuconate-6-semialdehyde dehydrogenase.

Example 15

The microbial cell of Example 14, wherein the 4-carboxy-2-hydroxymuconate-6-semialdehyde is LigC.

Example 16

The microbial cell of Example 13, wherein the target molecule is 2-oxo-2H-pyran-4,6-dicarboxylic acid (molecule #2).

Example 17

The microbial cell of Example 13, further comprising:
a second genetic modification resulting in the expression of a deficient form of an endogenous tautomerase; and
a gene encoding an exogenous hydrolase.

Example 18

The microbial cell of Example 17, wherein the exogenous hydrolase comprises a 2-pyrone-4,6-dicarboxylic acid hydrolase.

Example 19

The microbial cell of Example 18, wherein the 2-pyrone-4,6-dicarboxylic acid hydrolase is LigI.

Example 20

The microbial cell of Example 17, wherein the endogenous tautomerase comprises a 4-oxalomesaconate tautomerase.

Example 21

The microbial cell of Example 20, wherein the 4-oxalomesaconate tautomerase is GalD.

Example 22

The microbial cell of Example 17, wherein the second genetic modification further results in the expression of a deficient form of an endogenous hydratase.

Example 23

The microbial cell of Example 22, wherein the endogenous hydratase comprises a 4-oxalomesaconate hydratase.

Example 24

The microbial cell of Example 23, wherein the 4-oxalomesaconate hydratase is GalB.

Example 25

The microbial cell of Example 22, wherein the second genetic modification further results in the expression of a deficient form of an endogenous decarboxylase.

Example 26

The microbial cell of Example 25, wherein the endogenous decarboxylase comprises a 4-carboxy-4-hydroxy-2-oxoadipate aldolase/oxaloacetate decarboxylase.

Example 27

The microbial cell of Example 26, wherein the 4-carboxy-4-hydroxy-2-oxoadipate aldolase/oxaloacetate decarboxylase is GalC.

Example 28

The microbial cell of Example 17, wherein the second genetic modification further results in the expression of a deficient form of an endogenous hydratase and a deficient form of an endogenous decarboxylase.

Example 29

The microbial cell of Example 28, wherein the endogenous hydratase is GalB and the endogenous decarboxylase is GalC.

Example 30

The microbial cell of Example 28, wherein the target molecule is (1E,3E)-4-hydroxybuta-1,3-diene-1,2,4-tricarboxylic acid (molecule #3).

Example 31

The microbial cell of Example 28, further comprising a gene encoding an exogeneous tautomerase.

Example 32

The microbial cell of Example 31, wherein the exogenous tautomerase comprises a 4-oxalomesaconate tautomerase.

Example 33

The microbial cell of Example 32, wherein the 4-oxalomesaconate tautomerase is LigU.

Example 34

The microbial cell of Example 31, wherein the target molecule is (1E)-4-oxobut-1-ene-1,2,4-tricarboxylic acid (molecule #4).

Example 35

The microbial cell of Example 31, further comprising a gene encoding an exogenous hydratase.

Example 36

The microbial cell of Example 35, wherein the exogenous hydratase comprises a 4-oxalomesaconate hydratase.

Example 37

The microbial cell of Example 36, wherein the 4-oxalomesaconate hydratase is LigJ.

Example 38

The microbial cell of Example 35, wherein the target molecule is 2-hydroxy-4-oxobutane-1,2,4-tricarboxylic acid (molecule #5).

Example 39

The microbial cell of Example 1, wherein the microbial cell is from at least one of a fungus, a bacterium, or a yeast.

Example 40

The microbial cell of Example 39, wherein the microbial cell is from a bacterium.

Example 41

The microbial cell of Example 40, wherein the bacterium is from the genus *Psuedomonas*.

Example 42

The microbial cell of Example 41, wherein the bacterium comprises a strain from at least one of *P. putida*, *P. fluorescens*, or *P. stutzeri*.

Example 43

The microbial cell of Example 42, wherein the strain comprises *P. putida* KT2440.

Example 44

The microbial cell of Example 1, wherein the cellulose decomposition molecule comprises a sugar molecule.

Example 45

The microbial cell of Example 44, wherein the sugar molecule comprises at least one of D-xylose or D-glucose.

Example 46

The microbial cell of Example 1, wherein the lignin decomposition molecule comprises an aromatic molecule.

Example 47

The microbial cell of Example 46, wherein the aromatic molecule comprises at least one of protocatechuate, ferulate, p-coumarate, vanillate, or 4-hydroxybenzoate

Example 48

The microbial cell of Example 47, wherein the aromatic molecule comprises protocatechuate.

Example 49

The microbial cell of Example 46, wherein the aromatic molecule comprises at least one of catechol, protocatechuate, benzoate, phenol, or guaiacol.

Example 50

The microbial cell of Example 49, wherein the aromatic molecule comprises catechol and protocatechuate.

Example 51

The microbial cell of Example 1, wherein the first genetic modification comprises at least one of a full deletion of the endogenous dioxygenase, a partial deletion of the endogenous dioxygenase, an insertion into the endogenous dioxygenase, or a replacement of the endogenous dioxygenase.

Example 52

The microbial cell of Example 1, further comprising a gene encoding an exogenous carboxylase.

Example 53

The microbial cell of Example 52, wherein the exogenous carboxylase is AroY.

EXAMPLES: CATECHOL AND PROTOCATECHUATE ORTHO-CLEAVAGE PATHWAYS

Example 1

A microbial cell comprising a genetic modification resulting in the expression of a deficient form of an endogenous enol-lactonase, wherein:
the microbial cell is capable of growth utilizing at least one of a cellulose decomposition molecule or a lignin decomposition molecule, and

Example 2

The microbial cell of Example 1, wherein the endogenous enol-lactonase comprises a 3-oxoadipate enol-lactonase.

Example 3

The microbial cell of Example 2, wherein the 3-oxoadipate enol-lactonase is PcaD.

Example 4

The microbial cell of Example 1, wherein the target molecule is 2-(2-oxo-3H-furan-5-yl)acetic acid (molecule #8).

Example 5

The microbial cell of Example 1, wherein the genetic modification further results in the expression of a deficient form of an endogenous decarboxylase.

Example 6

The microbial cell of Example 5, wherein the endogenous decarboxylase comprises a 4-carboxymuconolactone decarboxylase.

Example 7

The microbial cell of Example 6, wherein the 4-carboxymuconolactone decarboxylase is PcaC.

Example 8

The microbial cell of Example 5, wherein the target molecule is 2-carboxy-5-oxo-2,5-dihydrofuran-2-carboxylic acid (molecule #7).

Example 9

The microbial cell of Example 5, wherein the genetic modification further results in the expression of a deficient form of an endogenous cycloisomerase.

Example 10

The microbial cell of Example 9, wherein the endogenous cycloisomerase comprises a 3-carboxy-cis,cis-muconate cycloisomerase.

Example 11

The microbial cell of Example 10, wherein the 3-carboxy-cis,cis-muconate cycloisomerase is PcaB.

Example 12

The microbial cell of Example 9, wherein the target molecule is (1E,3Z)-buta-1,3-diene-1,2,4-tricarboxylic acid (molecule #6).

Example 13

The microbial cell of Example 1, wherein the microbial cell is from at least one of a fungus, a bacterium, or a yeast.

Example 14

The microbial cell of Example 13, wherein the microbial cell is from a bacterium.

Example 15

The microbial cell of Example 14, wherein the bacterium is from the genus *Psuedomonas*.

Example 16

The microbial cell of Example 15, wherein the bacterium comprises a strain from at least one of *P. putida, P. fluorescens*, or *P. stutzeri*.

Example 17

The microbial cell of Example 16, wherein the strain comprises *P. putida* KT2440.

Example 18

The microbial cell of Example 1, wherein the cellulose decomposition molecule comprises a sugar molecule.

Example 19

The microbial cell of Example 18, wherein the sugar molecule comprises at least one of D-xylose or D-glucose.

Example 20

The microbial cell of Example 1, wherein the lignin decomposition molecule comprises an aromatic molecule.

Example 21

The microbial cell of Example 20, wherein the aromatic molecule comprises at least one of protecatechuate, ferulate, p-coumarate, vanillate, or 4-hydroxybenzoate

Example 22

The microbial cell of Example 21, wherein the aromatic molecule comprises protocatechuate.

Example 23

The microbial cell of Example 20, wherein the aromatic molecule comprises at least one of catechol, protecatechuate, benzoate, phenol, or guaiacol.

Example 24

The microbial cell of Example 23, wherein the aromatic molecule comprises catechol and protocatechuate.

Example 25

The microbial cell of Example 1, wherein the genetic modification comprises at least one of a full deletion of the endogenous enol-lactonase, a partial deletion of the endog-

Example 26

The microbial cell of Example 1, further comprising a gene encoding an exogenous carboxylase.

Example 27

The microbial cell of Example 26, wherein the exogenous carboxylase is AroY.

Example 28

A microbial cell comprising a genetic modification resulting in the expression of a deficient form of an endogenous transferase, wherein:
the microbial cell is capable of growth utilizing at least one of a cellulose decomposition molecule or a lignin decomposition molecule, and
the microbial cell is capable of producing a target molecule.

Example 29

The microbial cell of Example 28, wherein the endogenous transferase comprises a 3-oxoadipate CoA-transferase.

Example 30

The microbial cell of Example 29, wherein the 3-oxoadipate CoA-transferase comprises PcaI.

Example 31

The microbial cell of Example 29, wherein the 3-oxoadipate CoA-transferase comprises PcaJ.

Example 32

The microbial cell of Example 29, wherein the 3-oxoadipate CoA-transferase is PcaI and PcaJ.

Example 33

The microbial cell of Example 28, wherein the target molecule is 3-oxohexanedioic acid (molecule #9).

Example 34

The microbial cell of Example 28, wherein the microbial cell is from at least one of a fungus, a bacterium, or a yeast.

Example 35

The microbial cell of Example 34, wherein the microbial cell is from a bacterium.

Example 36

The microbial cell of Example 35, wherein the bacterium is from the genus *Psuedomonas*.

Example 37

The microbial cell of Example 36, wherein the bacterium comprises a strain from at least one of *P. putida, P. fluorescens*, or *P. stutzeri*.

Example 38

The microbial cell of Example 37, wherein the strain comprises *P. putida* KT2440.

Example 39

The microbial cell of Example 28, wherein the cellulose decomposition molecule comprises a sugar molecule.

Example 40

The microbial cell of Example 39, wherein the sugar molecule comprises at least one of D-xylose or D-glucose.

Example 41

The microbial cell of Example 28, wherein the lignin decomposition molecule comprises an aromatic molecule.

Example 42

The microbial cell of Example 41, wherein the aromatic molecule comprises at least one of protecatechuate, ferulate, p-coumarate, vanillate, or 4-hydroxybenzoate

Example 43

The microbial cell of Example 42, wherein the aromatic molecule comprises protocatechuate.

Example 44

The microbial cell of Example 41, wherein the aromatic molecule comprises at least one of catechol, protocatechuate, benzoate, phenol, or guaiacol.

Example 45

The microbial cell of Example 44, wherein the aromatic molecule comprises catechol and protocatechuate.

Example 46

The microbial cell of Example 28, wherein the genetic modification comprises at least one of a full deletion of the endogenous transferase, a partial deletion of the endogenous transferase, an insertion into the endogenous transferase, or a replacement of the endogenous transferase.

Example 47

The microbial cell of Example 28, further comprising a gene encoding an exogenous carboxylase.

Example 48

The microbial cell of Example 47, wherein the exogenous carboxylase is AroY.

EXAMPLES: CATECHOL META-CLEAVAGE AND PROTOCATECHUATE 2,3 META-CLEAVAGE PATHWAYS

Example 1

A microbial cell comprising:
a first genetic modification resulting in the expression of a deficient form of a first endogenous dioxygenase; and
a gene encoding a first exogenous dioxygenase, wherein:
the microbial cell is capable of growth utilizing at least one of a cellulose decomposition molecule or a lignin decomposition molecule, and
the microbial cell is capable of producing a target molecule.

Example 2

The microbial cell of Example 1, wherein the first endogenous dioxygenase comprises a protocatechuate 3,4-dioxygenase.

Example 3

The microbial cell of Example 2, wherein the protocatechuate 3,4-dioxygenase comprises PcaH.

Example 4

The microbial cell of Example 2, wherein the protocatechuate 3,4-dioxygenase comprises PcaG.

Example 5

The microbial cell of Example 2, wherein the protocatechuate 3,4-dioxygenase is PcaH and PcaG.

Example 6

The microbial cell of Example 1, wherein the first exogenous dioxygenase comprises a protocatechuate 2,3-dioxygenase.

Example 7

The microbial cell of Example 6, wherein the protocatechuate 2,3-dioxygenase is PraA.

Example 8

The microbial cell of Example 1, wherein the gene is operably linked to a first promoter.

Example 9

The microbial cell of Example 8, wherein the first promoter is
Ptac.

Example 10

The microbial cell of Example 1, wherein the target molecule is (2E,4E)-2-formyl-5-hydroxyhexa-2,4-dienedioic acid (molecule #10).

Example 11

The microbial cell of Example 1, further comprising a gene encoding an exogenous decarboxylase.

Example 12

The microbial cell of Example 11, wherein the exogenous decarboxylase comprises a 5-carboxy-2-hydroxymuconate-6-semialdehyde decarboxylase.

Example 13

The microbial cell of Example 12, wherein the 5-carboxy-2-hydroxymuconate-6-semialdehyde decarboxylase is PraH.

Example 14

The microbial cell of Example 11, further comprising a second genetic modification resulting in the expression of a deficient form of a second endogenous dioxygenase.

Example 15

The microbial cell of Example 14, wherein the second endogenous dioxygenase comprises a catechol 1,2-dioxygenase.

Example 16

The microbial cell of Example 15, wherein the catechol 1,2-dioxygenase is CatA2.

Example 17

The microbial cell of Example 14, further comprising a third genetic modification resulting in the expression of a deficient form of an endogenous cycloisomerase.

Example 18

The microbial cell of Example 17, wherein the endogenous cycloisomerase comprises a muconate cycloisomerase.

Example 19

The microbial cell of Example 18, wherein the muconate cycloisomerase is CatB.

Example 20

The microbial cell of Example 17, wherein the third genetic modification further results in the expression of a deficient form of an endogenous isomerase.

Example 21

The microbial cell of Example 20, wherein the endogenous isomerase comprises a muconolactone isomerase.

Example 22

The microbial cell of Example 21, wherein the muconolactone isomerase is CatC.

Example 23

The microbial cell of Example 17, wherein the third genetic modification further results in the expression of a deficient form of a third endogenous dioxygenase.

Example 24

The microbial cell of Example 23, wherein the third endogenous dioxygenase is CatA.

Example 25

The microbial cell of Example 23, further comprising a gene encoding a second exogenous dioxygenase.

Example 26

The microbial cell of Example 25, wherein the second exogenous dioxygenase comprises a catechol 2,3-dioxygenase.

Example 27

The microbial cell of Example 26, wherein the catechol 2,3-dioxygenase sequence is XylE.

Example 28

The microbial cell of Example 25, wherein the gene encoding the second exogenous dioxygenase is operably linked to a second promoter.

Example 29

The microbial cell of Example 28, wherein the second promoter is
Ptac.

Example 30

The microbial cell of Example 28, wherein the target molecule is (2Z,4E)-2-hydroxy-6-oxohexa-2,4-dienoic acid (molecule #11).

Example 31

The microbial cell of Example 28, further comprising a gene encoding an exogenous dehydrogenase.

Example 32

The microbial cell of Example 31, wherein the exogenous dehydrogenase comprises a 2-hydroxymuconate semialdehyde dehydrogenase.

Example 33

The microbial cell of Example 32, wherein the 2-hydroxymuconate semialdehyde dehydrogenase is XylG.

Example 34

The microbial cell of Example 31, wherein the target molecule is (2Z,4E)-2-hydroxyhexa-2,4-dienedioic acid (molecule #12).

Example 35

The microbial cell of Example 31, further comprising a gene encoding an exogenous tautomerase.

Example 36

The microbial cell of Example 35, wherein the exogenous tautomerase comprises a 4-oxalocrotonate tautomerase.

Example 37

The microbial cell of Example 36, wherein the 4-oxalocrotonate tautomerase is XylH.

Example 38

The microbial cell of Example 35, wherein the target molecule is (3E)-2-oxohex-3-enedioic acid (molecule #13).

Example 39

The microbial cell of Example 28, further comprising a gene encoding an exogenous hydrolase.

Example 40

The microbial cell of Example 39, wherein the exogenous hydrolase comprises 2-hydroxymuconic semialdehyde hydrolase.

Example 41

The microbial cell of Example 40, wherein the 2-hydroxymuconic semialdehyde hydrolase is XylF.

Example 42

The microbial cell of Example 39, wherein the target molecule is (2E)-2-hydroxypenta-2,4-dienoic acid (molecule #14).

Example 43

The microbial cell of Example 35, further comprising a gene encoding an exogenous hydratase.

Example 44

The microbial cell of Example 43, wherein the exogenous hydratase comprises a 2-hydroxypent-2,4-dienoate hydratase.

Example 45

The microbial cell of Example 39, wherein the 2-hydroxypent-2,4-dienoate hydratase is XylJ.

Example 46

The microbial cell of Example 43, further comprising a gene encoding an exogenous decarboxylase.

Example 47

The microbial cell of Example 46, wherein the exogenous decarboxylase comprises a 4-oxalocrotonate decarboxylase.

Example 48

The microbial cell of Example 47, wherein the 4-oxalocrotonate decarboxylase is XylI.

Example 49

The microbial cell of Example 46, further comprising a gene encoding an exogenous hydrolase.

Example 50

The microbial cell of Example 49, wherein the exogenous hydrolase comprises a 2-hydroxymuconic semialdehyde hydrolase.

Example 51

The microbial cell of Example 45, wherein the 2-hydroxymuconic semialdehyde hydrolase is XylF.

Example 52

The microbial cell of Example 49, wherein the target molecule is 4-hydroxy-2-oxopentanoic acid (molecule #15).

Example 53

The microbial cell of Example 1, wherein the microbial cell is from at least one of a fungus, a bacterium, or a yeast.

Example 54

The microbial cell of Example 53, wherein the microbial cell is from a bacterium.

Example 55

The microbial cell of Example 54, wherein the bacterium is from the genus *Psuedomonas*.

Example 56

The microbial cell of Example 55, wherein the bacterium comprises a strain from at least one of *P. putida, P. fluorescens*, or *P. stutzeri*.

Example 57

The microbial cell of Example 56, wherein the strain comprises *P. putida* KT2440.

Example 58

The microbial cell of Example 1, wherein the cellulose decomposition molecule comprises a sugar molecule.

Example 59

The microbial cell of Example 58, wherein the sugar molecule comprises at least one of D-xylose or D-glucose.

Example 60

The microbial cell of Example 1, wherein the lignin decomposition molecule comprises an aromatic molecule.

Example 61

The microbial cell of Example 60, wherein the aromatic molecule comprises at least one of protocatechuate, ferulate, p-coumarate, vanillate, or 4-hydroxybenzoate

Example 62

The microbial cell of Example 61, wherein the aromatic molecule comprises protocatechuate.

Example 63

The microbial cell of Example 60, wherein the aromatic molecule comprises at least one of catechol, protocatechuate, benzoate, phenol, or guaiacol.

Example 64

The microbial cell of Example 63, wherein the aromatic molecule comprises catechol and protocatechuate.

Example 65

The microbial cell of Example 1, wherein the first genetic modification comprises at least one of a full deletion of the endogenous transferase, a partial deletion of the endogenous transferase, an insertion into the endogenous transferase, or a replacement of the endogenous transferase.

Example 66

The microbial cell of Example 1, further comprising a gene encoding an exogenous carboxylase.

Example 67

The microbial cell of Example 66, wherein the exogenous carboxylase is AroY.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A non-naturally occurring *Pseudomonas* not capable of expressing 3-oxoadipate CoA-transferase, and capable of producing 3-oxohexanedioic acid,
   wherein the *Pseudomonas* is capable of growing on at least one of a cellulose decomposition molecule or a lignin decomposition molecule, and
   wherein the *Pseudomonas* lacks genes encoding for PcaI and/or PcaJ.

2. The *Pseudomonas* of claim 1, wherein the *Pseudomonas* lacks the genes encoding for PcaI and PcaJ.

3. The *Pseudomonas* of claim 1, wherein the *Pseudomonas* lacks a gene encoding for PcaI.

4. The *Pseudomonas* of claim 1, wherein the *Pseudomonas* lacks a gene encoding for PcaJ.

5. The *Pseudomonas* of claim 1, wherein the *Pseudomonas* is *P. putida* KT2440.

6. The *Pseudomonas* of claim 1, wherein the cellulose decomposition molecule comprises a sugar molecule.

7. The *Pseudomonas* of claim 6, wherein the sugar molecule is at least one of D-xylose or D-glucose.

8. The *Pseudomonas* of claim 1, wherein the lignin decomposition molecule comprises an aromatic molecule.

9. The *Pseudomonas* of claim 8, wherein the aromatic molecule is at least one of catechol, benzoate, phenol, guaiacol, protecatechuate, ferulate, p-coumarate, vanillate, or 4-hydroxybenzoate.

10. The *Pseudomonas* of claim 9, wherein the aromatic molecule is protocatechuate.

11. The *Pseudomonas* of claim 1, further comprising an exogenous gene encoding a carboxylase.

12. The *Pseudomonas* of claim 11, wherein the exogenous gene encodes for AroY.

* * * * *

SEQUENCE LISTING

<160> NUMBER OF SEQ ID NOS: 148

<210> SEQ ID NO 1
<211> LENGTH: 417
<212> TYPE: DNA
<213> ORGANISM: Sphingobium sp. SYK-6
<220> FEATURE:
<221> NAME/KEY: CDS
<222> LOCATION: (1)..(417)

<400> SEQUENCE: 1

| | | | | | | | | | | | | | | | | |
|---|---|---|---|---|---|---|---|---|---|---|---|---|---|---|---|---|
| atg | acc | gag | aag | aaa | gaa | cgc | atc | gac | gtg | cac | gcc | tac | ctg | gcc | gag | 48 |
| Met | Thr | Glu | Lys | Lys | Glu | Arg | Ile | Asp | Val | His | Ala | Tyr | Leu | Ala | Glu | |
| 1 | | | | 5 | | | | | 10 | | | | | 15 | | |
| ttc | gac | gac | atc | cca | ggc | acc | cgt | gtg | ttc | acc | gcc | cag | cgt | gcc | cgt | 96 |
| Phe | Asp | Asp | Ile | Pro | Gly | Thr | Arg | Val | Phe | Thr | Ala | Gln | Arg | Ala | Arg | |
| | | | 20 | | | | | 25 | | | | | 30 | | | |
| aag | ggc | tac | aac | ctg | aac | cag | ttc | gcc | atg | agc | ctg | atg | aag | gcc | gag | 144 |
| Lys | Gly | Tyr | Asn | Leu | Asn | Gln | Phe | Ala | Met | Ser | Leu | Met | Lys | Ala | Glu | |
| | | | | 35 | | | | | 40 | | | | | 45 | | |
| aac | cgc | gag | cgc | ttc | aag | gcc | gac | gag | agc | gcc | tac | ctg | gac | gaa | tgg | 192 |
| Asn | Arg | Glu | Arg | Phe | Lys | Ala | Asp | Glu | Ser | Ala | Tyr | Leu | Asp | Glu | Trp | |
| | 50 | | | | | 55 | | | | | 60 | | | | | |
| aac | ctg | acc | cca | gcc | gcc | aaa | gcc | gcc | gtg | ctg | gcc | cgt | gac | tac | aac | 240 |
| Asn | Leu | Thr | Pro | Ala | Ala | Lys | Ala | Ala | Val | Leu | Ala | Arg | Asp | Tyr | Asn | |
| 65 | | | | | 70 | | | | | 75 | | | | | 80 | |
| gcc | atg | atc | gac | gag | ggt | ggc | aac | gtg | tac | ttc | ctg | agc | aag | ctg | ttc | 288 |
| Ala | Met | Ile | Asp | Glu | Gly | Gly | Asn | Val | Tyr | Phe | Leu | Ser | Lys | Leu | Phe | |
| | | | | 85 | | | | | 90 | | | | | 95 | | |
| agc | acc | gac | ggc | aag | agc | ttc | cag | ttc | gcc | gcc | ggt | agc | atg | acc | ggc | 336 |
| Ser | Thr | Asp | Gly | Lys | Ser | Phe | Gln | Phe | Ala | Ala | Gly | Ser | Met | Thr | Gly | |
| | | | 100 | | | | | 105 | | | | | 110 | | | |
| atg | acc | caa | gag | gaa | tac | gcc | cag | atg | atg | atc | gat | ggc | ggt | cgc | agc | 384 |
| Met | Thr | Gln | Glu | Glu | Tyr | Ala | Gln | Met | Met | Ile | Asp | Gly | Gly | Arg | Ser | |
| | | | | 115 | | | | | 120 | | | | | 125 | | |
| cca | gcc | ggt | gtg | cgc | agc | atc | aag | ggt | ggc | tac | | | | | | 417 |
| Pro | Ala | Gly | Val | Arg | Ser | Ile | Lys | Gly | Gly | Tyr | | | | | | |
| | 130 | | | | | 135 | | | | | | | | | | |

<210> SEQ ID NO 2
<211> LENGTH: 139
<212> TYPE: PRT
<213> ORGANISM: Sphingobium sp. SYK-6

<400> SEQUENCE: 2

Met Thr Glu Lys Lys Glu Arg Ile Asp Val His Ala Tyr Leu Ala Glu
1               5                   10                  15

Phe Asp Asp Ile Pro Gly Thr Arg Val Phe Thr Ala Gln Arg Ala Arg
            20                  25                  30

Lys Gly Tyr Asn Leu Asn Gln Phe Ala Met Ser Leu Met Lys Ala Glu
        35                  40                  45

Asn Arg Glu Arg Phe Lys Ala Asp Glu Ser Ala Tyr Leu Asp Glu Trp
    50                  55                  60

Asn Leu Thr Pro Ala Ala Lys Ala Ala Val Leu Ala Arg Asp Tyr Asn
65                  70                  75                  80

Ala Met Ile Asp Glu Gly Gly Asn Val Tyr Phe Leu Ser Lys Leu Phe
                85                  90                  95

Ser Thr Asp Gly Lys Ser Phe Gln Phe Ala Ala Gly Ser Met Thr Gly
            100                 105                 110

Met Thr Gln Glu Glu Tyr Ala Gln Met Met Ile Asp Gly Gly Arg Ser

-continued

```
                115                 120                 125
Pro Ala Gly Val Arg Ser Ile Lys Gly Gly Tyr
    130                 135

<210> SEQ ID NO 3
<211> LENGTH: 906
<212> TYPE: DNA
<213> ORGANISM: Sphingobium sp. SYK-6
<220> FEATURE:
<221> NAME/KEY: CDS
<222> LOCATION: (1)..(906)

<400> SEQUENCE: 3 atg gcc cgt gtg acc acc ggc atc acc agc agc cac atc cca gcc ctg        48
Met Ala Arg Val Thr Thr Gly Ile Thr Ser Ser His Ile Pro Ala Leu
1               5                   10                  15 ggt gcc gcc atc caa acc ggc acc agc gac aac gac tac tgg ggt ccg        96
Gly Ala Ala Ile Gln Thr Gly Thr Ser Asp Asn Asp Tyr Trp Gly Pro
            20                  25                  30 gtg ttc aag ggc tac cag ccg atc cgc gac tgg atc aag cag cca ggc       144
Val Phe Lys Gly Tyr Gln Pro Ile Arg Asp Trp Ile Lys Gln Pro Gly
        35                  40                  45 aac atg ccg gac gtg gtg atc ctg gtg tac aac gac cac gcc agc gcc       192
Asn Met Pro Asp Val Val Ile Leu Val Tyr Asn Asp His Ala Ser Ala
    50                  55                  60 ttc gac atg aac atc atc ccg acc ttc gcc atc ggc tgc gcc gaa acc       240
Phe Asp Met Asn Ile Ile Pro Thr Phe Ala Ile Gly Cys Ala Glu Thr
65                  70                  75                  80 ttc aag cca gcc gac gag ggc tgg ggt ccg cgt cca gtg ccg gat gtg       288
Phe Lys Pro Ala Asp Glu Gly Trp Gly Pro Arg Pro Val Pro Asp Val
                85                  90                  95 aag ggc cat ccg gac ctg gcc tgg cat atc gcc cag agc ctg atc ctg       336
Lys Gly His Pro Asp Leu Ala Trp His Ile Ala Gln Ser Leu Ile Leu
            100                 105                 110 gac gaa ttc gat atg acc atc atg aac cag atg gac gtg gac cac ggc       384
Asp Glu Phe Asp Met Thr Ile Met Asn Gln Met Asp Val Asp His Gly
        115                 120                 125 tgc acc gtg ccg ctg agc atg atc ttc ggc gag ccg gaa gag tgg ccg       432
Cys Thr Val Pro Leu Ser Met Ile Phe Gly Glu Pro Glu Glu Trp Pro
    130                 135                 140 tgc aag gtg atc ccg ttc ccg gtg aac gtg gtg acc tat ccg cca ccg       480
Cys Lys Val Ile Pro Phe Pro Val Asn Val Val Thr Tyr Pro Pro Pro
145                 150                 155                 160 agc ggc aag cgc tgc ttc gcc ctg ggc gac agc atc cgt gcc gcc gtg       528
Ser Gly Lys Arg Cys Phe Ala Leu Gly Asp Ser Ile Arg Ala Ala Val
                165                 170                 175 gaa agc ttc ccc gag gac ctg aac gtg cac gtg tgg ggc acc ggt ggc       576
Glu Ser Phe Pro Glu Asp Leu Asn Val His Val Trp Gly Thr Gly Gly
            180                 185                 190 atg tcg cac cag ctg caa ggt ccg cgt gcc ggt ctg atc aac aaa gag       624
Met Ser His Gln Leu Gln Gly Pro Arg Ala Gly Leu Ile Asn Lys Glu
        195                 200                 205 ttc gac ctg aac ttc atc gac aag ctg atc agc gac ccg gaa gaa ctg       672
Phe Asp Leu Asn Phe Ile Asp Lys Leu Ile Ser Asp Pro Glu Glu Leu
    210                 215                 220 agc aag atg ccg cac atc cag tac ctg cgc gag agc ggc agc gag ggc       720
Ser Lys Met Pro His Ile Gln Tyr Leu Arg Glu Ser Gly Ser Glu Gly
225                 230                 235                 240 gtg gaa ctg gtg atg tgg ctg atc atg cgt ggt gcc ctg ccg gaa aag       768
Val Glu Leu Val Met Trp Leu Ile Met Arg Gly Ala Leu Pro Glu Lys
                245                 250                 255
```

```
gtg cgc gac ctg tac acc ttc tac cat atc cca gcc agc aac acc gcg     816
Val Arg Asp Leu Tyr Thr Phe Tyr His Ile Pro Ala Ser Asn Thr Ala
        260                 265                 270 ctg ggt gcc atg atc ctg cag ccg gaa gaa acc gcc ggc acc cca ctg     864
Leu Gly Ala Met Ile Leu Gln Pro Glu Glu Thr Ala Gly Thr Pro Leu
        275                 280                 285 gaa ccg cgt aag gtg atg agc ggt cac agc ctg gcc cag gcc             906
Glu Pro Arg Lys Val Met Ser Gly His Ser Leu Ala Gln Ala
        290                 295                 300
```

<210> SEQ ID NO 4
<211> LENGTH: 302
<212> TYPE: PRT
<213> ORGANISM: Sphingobium sp. SYK-6

<400> SEQUENCE: 4

```
Met Ala Arg Val Thr Thr Gly Ile Thr Ser His Ile Pro Ala Leu
1               5                   10                  15

Gly Ala Ala Ile Gln Thr Gly Thr Ser Asp Asn Asp Tyr Trp Gly Pro
                20                  25                  30

Val Phe Lys Gly Tyr Gln Pro Ile Arg Asp Trp Ile Lys Gln Pro Gly
                35                  40                  45

Asn Met Pro Asp Val Val Ile Leu Val Tyr Asn Asp His Ala Ser Ala
50                  55                  60

Phe Asp Met Asn Ile Ile Pro Thr Phe Ala Ile Gly Cys Ala Glu Thr
65                  70                  75                  80

Phe Lys Pro Ala Asp Glu Gly Trp Gly Pro Arg Pro Val Pro Asp Val
                85                  90                  95

Lys Gly His Pro Asp Leu Ala Trp His Ile Ala Gln Ser Leu Ile Leu
                100                 105                 110

Asp Glu Phe Asp Met Thr Ile Met Asn Gln Met Asp Val Asp His Gly
                115                 120                 125

Cys Thr Val Pro Leu Ser Met Ile Phe Gly Pro Glu Glu Trp Pro
        130                 135                 140

Cys Lys Val Ile Pro Phe Pro Val Asn Val Val Thr Tyr Pro Pro
145                 150                 155                 160

Ser Gly Lys Arg Cys Phe Ala Leu Gly Asp Ser Ile Arg Ala Ala Val
                165                 170                 175

Glu Ser Phe Pro Glu Asp Leu Asn Val His Val Trp Gly Thr Gly Gly
                180                 185                 190

Met Ser His Gln Leu Gln Gly Pro Arg Ala Gly Leu Ile Asn Lys Glu
        195                 200                 205

Phe Asp Leu Asn Phe Ile Asp Lys Leu Ile Ser Asp Pro Glu Glu Leu
        210                 215                 220

Ser Lys Met Pro His Ile Gln Tyr Leu Arg Glu Ser Gly Ser Glu Gly
225                 230                 235                 240

Val Glu Leu Val Met Trp Leu Ile Met Arg Gly Ala Leu Pro Glu Lys
                245                 250                 255

Val Arg Asp Leu Tyr Thr Phe Tyr His Ile Pro Ala Ser Asn Thr Ala
                260                 265                 270

Leu Gly Ala Met Ile Leu Gln Pro Glu Glu Thr Ala Gly Thr Pro Leu
        275                 280                 285

Glu Pro Arg Lys Val Met Ser Gly His Ser Leu Ala Gln Ala
        290                 295                 300
```

```
<210> SEQ ID NO 5
<211> LENGTH: 945
<212> TYPE: DNA
<213> ORGANISM: Sphingobium sp. SYK-6
<220> FEATURE:
<221> NAME/KEY: CDS
<222> LOCATION: (1)..(945)

<400> SEQUENCE: 5 atg cgt atc gcc ctg gcc ggt gcc ggt gcc ttc ggc gaa aag cat ctg      48
Met Arg Ile Ala Leu Ala Gly Ala Gly Ala Phe Gly Glu Lys His Leu
1               5                   10                  15 gac ggc ctg aag aac atc gac ggc gtg gaa atc gtg agc atc atc agc      96
Asp Gly Leu Lys Asn Ile Asp Gly Val Glu Ile Val Ser Ile Ile Ser
            20                  25                  30 cgc aag gcc gag caa gcc gcc gag gtg gcc gcc aag tac ggt gcc aaa     144
Arg Lys Ala Glu Gln Ala Ala Glu Val Ala Ala Lys Tyr Gly Ala Lys
        35                  40                  45 cac agc ggc acc gac ctg agc gaa gcc ctg gcc cgt gat gac gtg gac     192
His Ser Gly Thr Asp Leu Ser Glu Ala Leu Ala Arg Asp Asp Val Asp
    50                  55                  60 gcc gtg atc ctg tgc acc ccg acc cag atg cac gcc gag caa gcg atc     240
Ala Val Ile Leu Cys Thr Pro Thr Gln Met His Ala Glu Gln Ala Ile
65                  70                  75                  80 gcc tgc atg aac gcc ggt aag cac gtg cag gtc gag atc ccg ctg gcc     288
Ala Cys Met Asn Ala Gly Lys His Val Gln Val Glu Ile Pro Leu Ala
                85                  90                  95 gac agc tgg gcc gac gcc gag gcc gtg atg aag aag tcg caa gaa acc     336
Asp Ser Trp Ala Asp Ala Glu Ala Val Met Lys Lys Ser Gln Glu Thr
            100                 105                 110 ggt ctg gtg tgc atg gtg ggc cac acc cgt cgc ttc aac ccg agc cac     384
Gly Leu Val Cys Met Val Gly His Thr Arg Arg Phe Asn Pro Ser His
        115                 120                 125 cag tac atc cac aac aag atc gtg gcc ggt gag ctg gcc atc cag cag     432
Gln Tyr Ile His Asn Lys Ile Val Ala Gly Glu Leu Ala Ile Gln Gln
    130                 135                 140 atg gac gtc cag acc tac ttc ttc cgt cgc aag aac atg aac gcc aag     480
Met Asp Val Gln Thr Tyr Phe Phe Arg Arg Lys Asn Met Asn Ala Lys
145                 150                 155                 160 ggc gaa ccg cgt agc tgg acc gac cat ctg ctg tgg cac cat gcc gcc     528
Gly Glu Pro Arg Ser Trp Thr Asp His Leu Leu Trp His His Ala Ala
                165                 170                 175 cac acc gtg gac ctg ttc gcc tac caa gcc ggt aag atc gtc cag gcc     576
His Thr Val Asp Leu Phe Ala Tyr Gln Ala Gly Lys Ile Val Gln Ala
            180                 185                 190 aac gcc gtg cag ggt ccg atc cac ccg gaa ctg ggt atc gcc atg gac     624
Asn Ala Val Gln Gly Pro Ile His Pro Glu Leu Gly Ile Ala Met Asp
        195                 200                 205 atg agc atc cag ctg aag tcg gaa acc ggt gcc atc tgc acc ctg agc     672
Met Ser Ile Gln Leu Lys Ser Glu Thr Gly Ala Ile Cys Thr Leu Ser
    210                 215                 220 ctg agc ttc aac aac gac ggt ccg ctg ggc acc ttc ttc cgc tac atc     720
Leu Ser Phe Asn Asn Asp Gly Pro Leu Gly Thr Phe Phe Arg Tyr Ile
225                 230                 235                 240 tgc gac aac ggc acc tgg atc gcc cgt tac gac gac ctg gtg acc ggc     768
Cys Asp Asn Gly Thr Trp Ile Ala Arg Tyr Asp Asp Leu Val Thr Gly
                245                 250                 255 aaa gag gaa ccg gtc gac gtc agc aag gtg gac gtg agc atg aac ggc     816
Lys Glu Glu Pro Val Asp Val Ser Lys Val Asp Val Ser Met Asn Gly
            260                 265                 270 atc gag ctg cag gac cgc gag ttc atc gcc gcc atc cgc gaa ggc cgt     864
Ile Glu Leu Gln Asp Arg Glu Phe Ile Ala Ala Ile Arg Glu Gly Arg
```

```
Ile Glu Leu Gln Asp Arg Glu Phe Ile Ala Ala Ile Arg Glu Gly Arg
            275                 280                 285 gag ccg aac agc agc gtg gcc cgt gtg ctg gac tgc tac cgc gtg ctg      912
Glu Pro Asn Ser Ser Val Ala Arg Val Leu Asp Cys Tyr Arg Val Leu
        290                 295                 300 ggc gag ctg gaa gtg cag ctg gaa aag cag ggc                          945
Gly Glu Leu Glu Val Gln Leu Glu Lys Gln Gly
305                 310                 315

<210> SEQ ID NO 6
<211> LENGTH: 315
<212> TYPE: PRT
<213> ORGANISM: Sphingobium sp. SYK-6

<400> SEQUENCE: 6

Met Arg Ile Ala Leu Ala Gly Ala Gly Ala Phe Gly Glu Lys His Leu
1               5                   10                  15

Asp Gly Leu Lys Asn Ile Asp Gly Val Glu Ile Val Ser Ile Ile Ser
            20                  25                  30

Arg Lys Ala Glu Gln Ala Ala Glu Val Ala Ala Lys Tyr Gly Ala Lys
        35                  40                  45

His Ser Gly Thr Asp Leu Ser Glu Ala Leu Ala Arg Asp Asp Val Asp
50                  55                  60

Ala Val Ile Leu Cys Thr Pro Thr Gln Met His Ala Glu Gln Ala Ile
65                  70                  75                  80

Ala Cys Met Asn Ala Gly Lys His Val Gln Val Glu Ile Pro Leu Ala
                85                  90                  95

Asp Ser Trp Ala Asp Ala Glu Ala Val Met Lys Lys Ser Gln Glu Thr
            100                 105                 110

Gly Leu Val Cys Met Val Gly His Thr Arg Arg Phe Asn Pro Ser His
        115                 120                 125

Gln Tyr Ile His Asn Lys Ile Val Ala Gly Glu Leu Ala Ile Gln Gln
130                 135                 140

Met Asp Val Gln Thr Tyr Phe Phe Arg Arg Lys Asn Met Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Lys Ile Val Gln Ala
            180                 185                 190

Asn Ala Val Gln Gly Pro Ile His Pro Glu Leu Gly Ile Ala Met Asp
        195                 200                 205

Met Ser Ile Gln Leu Lys Ser Glu Thr Gly Ala Ile Cys Thr Leu Ser
210                 215                 220

Leu Ser Phe Asn Asn Asp Gly Pro Leu Gly Thr Phe Phe Arg Tyr Ile
225                 230                 235                 240

Cys Asp Asn Gly Thr Trp Ile Ala Arg Tyr Asp Asp Leu Val Thr Gly
                245                 250                 255

Lys Glu Glu Pro Val Asp Val Ser Lys Val Asp Val Ser Met Asn Gly
            260                 265                 270

Ile Glu Leu Gln Asp Arg Glu Phe Ile Ala Ala Ile Arg Glu Gly Arg
        275                 280                 285

Glu Pro Asn Ser Ser Val Ala Arg Val Leu Asp Cys Tyr Arg Val Leu
290                 295                 300

Gly Glu Leu Glu Val Gln Leu Glu Lys Gln Gly
305                 310                 315
```

<210> SEQ ID NO 7
<211> LENGTH: 879
<212> TYPE: DNA
<213> ORGANISM: Sphingobium sp. SYK-6
<220> FEATURE:
<221> NAME/KEY: CDS
<222> LOCATION: (1)..(879)

<400> SEQUENCE: 7

| | | | | | | | | | | | | | | | | |
|---|---|---|---|---|---|---|---|---|---|---|---|---|---|---|---|---|
| atg | acc | aac | gac | gag | cgc | atc | ctg | agc | tgg | aac | gaa | acc | ccg | agc | aag | 48 |
| Met | Thr | Asn | Asp | Glu | Arg | Ile | Leu | Ser | Trp | Asn | Glu | Thr | Pro | Ser | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cca | cgc | tac | acc | cca | ccg | cca | ggt | gcc | atc | gac | gcc | cac | tgc | cat | gtg | 96 |
| Pro | Arg | Tyr | Thr | Pro | Pro | Pro | Gly | Ala | Ile | Asp | Ala | His | Cys | His | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | ggt | ccg | atg | gcc | cag | ttc | ccg | ttc | agc | ccg | aag | gcc | aag | tac | ctg | 144 |
| Phe | Gly | Pro | Met | Ala | Gln | Phe | Pro | Phe | Ser | Pro | Lys | Ala | Lys | Tyr | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | cgt | gat | gcc | ggt | ccg | gac | atg | ctg | ttc | gcg | ctg | cgc | gac | cat | ctg | 192 |
| Pro | Arg | Asp | Ala | Gly | Pro | Asp | Met | Leu | Phe | Ala | Leu | Arg | Asp | His | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| ggc | ttc | gcc | cgt | aac | gtg | atc | gtg | cag | gcc | agc | tgc | cac | ggc | acc | gat | 240 |
| Gly | Phe | Ala | Arg | Asn | Val | Ile | Val | Gln | Ala | Ser | Cys | His | Gly | Thr | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aac | gcc | gcc | acc | ctg | gat | gcg | atc | gcc | cgt | gcc | caa | ggc | aaa | gcc | cgt | 288 |
| Asn | Ala | Ala | Thr | Leu | Asp | Ala | Ile | Ala | Arg | Ala | Gln | Gly | Lys | Ala | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | atc | gcc | gtg | gtg | gac | cca | gcc | atc | gac | gag | gcc | gaa | ctg | gcc | gcc | 336 |
| Gly | Ile | Ala | Val | Val | Asp | Pro | Ala | Ile | Asp | Glu | Ala | Glu | Leu | Ala | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | cac | gaa | ggc | ggt | atg | cgt | ggt | atc | cgc | ttc | aac | ttc | ctg | aag | cgc | 384 |
| Leu | His | Glu | Gly | Gly | Met | Arg | Gly | Ile | Arg | Phe | Asn | Phe | Leu | Lys | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| ctg | gtg | gac | gat | gcc | cca | aag | gac | aag | ttc | ctg | gaa | gtg | gcc | ggt | cgc | 432 |
| Leu | Val | Asp | Asp | Ala | Pro | Lys | Asp | Lys | Phe | Leu | Glu | Val | Ala | Gly | Arg | |
| 130 | | | | | 135 | | | | | 140 | | | | | | |

| | | | | | | | | | | | | | | | | |
|---|---|---|---|---|---|---|---|---|---|---|---|---|---|---|---|---|
| ctg | cca | gcc | ggt | tgg | cac | gtg | gtg | atc | tac | ttc | gag | gcc | gac | atc | ctg | 480 |
| Leu | Pro | Ala | Gly | Trp | His | Val | Val | Ile | Tyr | Phe | Glu | Ala | Asp | Ile | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gaa | gaa | ctg | cgt | ccg | ttc | atg | gac | gcc | atc | ccg | gtg | ccg | atc | gtg | atc | 528 |
| Glu | Glu | Leu | Arg | Pro | Phe | Met | Asp | Ala | Ile | Pro | Val | Pro | Ile | Val | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | cac | atg | ggt | cgt | ccg | gac | gtg | cgc | cag | ggt | cca | gac | ggt | gcc | gac | 576 |
| Asp | His | Met | Gly | Arg | Pro | Asp | Val | Arg | Gln | Gly | Pro | Asp | Gly | Ala | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| atg | aag | gcc | ttc | cgt | cgc | ctg | ctg | gac | agc | cgt | gag | gac | atc | tgg | ttc | 624 |
| Met | Lys | Ala | Phe | Arg | Arg | Leu | Leu | Asp | Ser | Arg | Glu | Asp | Ile | Trp | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | gcg | acc | tgc | cca | gac | cgc | ctg | gac | cca | gcc | ggt | ccg | cca | tgg | gat | 672 |
| Lys | Ala | Thr | Cys | Pro | Asp | Arg | Leu | Asp | Pro | Ala | Gly | Pro | Pro | Trp | Asp | |
| 210 | | | | | 215 | | | | | 220 | | | | | | |

| | | | | | | | | | | | | | | | | |
|---|---|---|---|---|---|---|---|---|---|---|---|---|---|---|---|---|
| gat | ttc | gcc | cgt | agc | gtg | gcc | cca | ctg | gtg | gcc | gat | tat | gcc | gac | cgc | 720 |
| Asp | Phe | Ala | Arg | Ser | Val | Ala | Pro | Leu | Val | Ala | Asp | Tyr | Ala | Asp | Arg | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gtg | atc | tgg | ggc | acc | gac | tgg | cca | cac | ccg | aac | atg | cag | gac | gcg | atc | 768 |
| Val | Ile | Trp | Gly | Thr | Asp | Trp | Pro | His | Pro | Asn | Met | Gln | Asp | Ala | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| ccg | gac | gac | ggc | ctg | gtg | gtg | gac | atg | atc | cca | cgt | atc | gcc | cca | acc | 816 |
| Pro | Asp | Asp | Gly | Leu | Val | Val | Asp | Met | Ile | Pro | Arg | Ile | Ala | Pro | Thr | |
| | | | 260 | | | | | 265 | | | | | 270 | | | |

```
cca gag ctg cag cac aag atg ctg gtg acc aac ccg atg cgc ctg tac      864
Pro Glu Leu Gln His Lys Met Leu Val Thr Asn Pro Met Arg Leu Tyr
        275                 280                 285 tgg tcg gag gaa atg                                                   879
Trp Ser Glu Glu Met
        290
```

<210> SEQ ID NO 8
<211> LENGTH: 293
<212> TYPE: PRT
<213> ORGANISM: Sphingobium sp. SYK-6

<400> SEQUENCE: 8

```
Met Thr Asn Asp Glu Arg Ile Leu Ser Trp Asn Glu Thr Pro Ser Lys
1               5                   10                  15

Pro Arg Tyr Thr Pro Pro Gly Ala Ile Asp Ala His Cys His Val
            20                  25                  30

Phe Gly Pro Met Ala Gln Phe Pro Phe Ser Pro Lys Ala Lys Tyr Leu
            35                  40                  45

Pro Arg Asp Ala Gly Pro Asp Met Leu Phe Ala Leu Arg Asp His Leu
        50                  55                  60

Gly Phe Ala Arg Asn Val Ile Val Gln Ala Ser Cys His Gly Thr Asp
65                  70                  75                  80

Asn Ala Ala Thr Leu Asp Ala Ile Ala Arg Ala Gln Gly Lys Ala Arg
                85                  90                  95

Gly Ile Ala Val Val Asp Pro Ala Ile Asp Glu Ala Glu Leu Ala Ala
            100                 105                 110

Leu His Glu Gly Gly Met Arg Gly Ile Arg Phe Asn Phe Leu Lys Arg
        115                 120                 125

Leu Val Asp Asp Ala Pro Lys Asp Lys Phe Leu Glu Val Ala Gly Arg
    130                 135                 140

Leu Pro Ala Gly Trp His Val Val Ile Tyr Phe Glu Ala Asp Ile Leu
145                 150                 155                 160

Glu Glu Leu Arg Pro Phe Met Asp Ala Ile Pro Val Pro Ile Val Ile
                165                 170                 175

Asp His Met Gly Arg Pro Asp Val Arg Gln Gly Pro Asp Gly Ala Asp
            180                 185                 190

Met Lys Ala Phe Arg Arg Leu Leu Asp Ser Arg Glu Asp Ile Trp Phe
        195                 200                 205

Lys Ala Thr Cys Pro Asp Arg Leu Asp Pro Ala Gly Pro Pro Trp Asp
    210                 215                 220

Asp Phe Ala Arg Ser Val Ala Pro Leu Val Ala Asp Tyr Ala Asp Arg
225                 230                 235                 240

Val Ile Trp Gly Thr Asp Trp Pro His Pro Asn Met Gln Asp Ala Ile
                245                 250                 255

Pro Asp Asp Gly Leu Val Val Asp Met Ile Pro Arg Ile Ala Pro Thr
            260                 265                 270

Pro Glu Leu Gln His Lys Met Leu Val Thr Asn Pro Met Arg Leu Tyr
        275                 280                 285

Trp Ser Glu Glu Met
        290
```

<210> SEQ ID NO 9
<211> LENGTH: 1053
<212> TYPE: DNA
<213> ORGANISM: Sphingobium sp. SYK-6
<220> FEATURE:

<221> NAME/KEY: CDS
<222> LOCATION: (1)..(1053)

<400> SEQUENCE: 9

```
atg cca ggc ggt gtg cgc tgc atg tgg atg cgt ggt ggc acc agc aaa      48
Met Pro Gly Gly Val Arg Cys Met Trp Met Arg Gly Gly Thr Ser Lys
1               5                   10                  15 ggc ggt tac ttc ctg gcc gag gac ctg cca gcc gac acc gcg acc cgt      96
Gly Gly Tyr Phe Leu Ala Glu Asp Leu Pro Ala Asp Thr Ala Thr Arg
            20                  25                  30 gat gcc ttc ctg ctg cgc gtg atg ggc agc cca gac cca cgc cag atc     144
Asp Ala Phe Leu Leu Arg Val Met Gly Ser Pro Asp Pro Arg Gln Ile
        35                  40                  45 gac ggc atg ggt ggt gcc gat ccg ctg acc tcg aag gtg gcc gtg gtg     192
Asp Gly Met Gly Gly Ala Asp Pro Leu Thr Ser Lys Val Ala Val Val
    50                  55                  60 aag aaa agc gcc cgt gag ggc gtg gac gtg gac tac ctg ttc ctg caa     240
Lys Lys Ser Ala Arg Glu Gly Val Asp Val Asp Tyr Leu Phe Leu Gln
65                  70                  75                  80 gtg ttc gtg gac cag gcc atc gtg acc gac gcc cag aac tgc ggc aac     288
Val Phe Val Asp Gln Ala Ile Val Thr Asp Ala Gln Asn Cys Gly Asn
                85                  90                  95 atc ctg gcc ggt atc ggt ccg ttc gcc atc gag cgt ggt ctg gtg gcc     336
Ile Leu Ala Gly Ile Gly Pro Phe Ala Ile Glu Arg Gly Leu Val Ala
            100                 105                 110 cca acc ggt gac gaa acc cgt gtg gcc atc ttc atg gaa aac acc ggt     384
Pro Thr Gly Asp Glu Thr Arg Val Ala Ile Phe Met Glu Asn Thr Gly
        115                 120                 125 cag atc gcc gtg gcc acc gtg cag acc cca ggt ggc acc gtg acc tac     432
Gln Ile Ala Val Ala Thr Val Gln Thr Pro Gly Gly Thr Val Thr Tyr
    130                 135                 140 gat ggc gaa gcc gcc atc acc ggt gtg cca ggc acc gcc gcc cca gtg     480
Asp Gly Glu Ala Ala Ile Thr Gly Val Pro Gly Thr Ala Ala Pro Val
145                 150                 155                 160 ccg ctg ctg ttc cgc gac acc gcc ggt agc tcg tgc ggt gcc ctg ctg     528
Pro Leu Leu Phe Arg Asp Thr Ala Gly Ser Ser Cys Gly Ala Leu Leu
                165                 170                 175 cca acc ggc aac ggc gtg gac gaa atc gac ggc gtc cgc gtg acc atg     576
Pro Thr Gly Asn Gly Val Asp Glu Ile Asp Gly Val Arg Val Thr Met
            180                 185                 190 atc gac aac ggc atg ccc tgc gtg gtg atg ctg gcc agc gac gtg ggc     624
Ile Asp Asn Gly Met Pro Cys Val Val Met Leu Ala Ser Asp Val Gly
        195                 200                 205 gtg acc ggc tac gaa gat cgc gac acc ctg gac gcc aac gcc gag atg     672
Val Thr Gly Tyr Glu Asp Arg Asp Thr Leu Asp Ala Asn Ala Glu Met
    210                 215                 220 aag gcc aag gtg gaa gcc atc cgc ctg aag gtc ggt gcc atg atg aac     720
Lys Ala Lys Val Glu Ala Ile Arg Leu Lys Val Gly Ala Met Met Asn
225                 230                 235                 240 ctg ggc gac gtg acc gag aag tcg gtg ccg aag atg atg ctg gtc gcc     768
Leu Gly Asp Val Thr Glu Lys Ser Val Pro Lys Met Met Leu Val Ala
                245                 250                 255 cca ccg cgt gaa ggc ggt gcg atc acc gtg cgt agc ctg atc ccg cac     816
Pro Pro Arg Glu Gly Gly Ala Ile Thr Val Arg Ser Leu Ile Pro His
            260                 265                 270 cgc gtg cat gcc agc atc ggt gtg ctg ggt gcc gtg agc gtg gcc acc     864
Arg Val His Ala Ser Ile Gly Val Leu Gly Ala Val Ser Val Ala Thr
        275                 280                 285 gcc tgc ctg atc gaa ggc tcg cca gcc gcc agc gtc gcc acc gtg cca     912
Ala Cys Leu Ile Glu Gly Ser Pro Ala Ala Ser Val Ala Thr Val Pro
```

```
                        290                     295                     300
gac ggt gcc acc aaa acc ctg ggc gtg gaa cac ccg acc ggt gtg acc        960
Asp Gly Ala Thr Lys Thr Leu Gly Val Glu His Pro Thr Gly Val Thr
305                     310                     315                     320 gag tgc gtg gtg acc gtg gat gcc gcc ggt caa ccg gtg gaa gcc ggt       1008
Glu Cys Val Val Thr Val Asp Ala Ala Gly Gln Pro Val Glu Ala Gly
                        325                     330                     335 atg ctg cgc acc gcc cgt aag ctg atg gac ggc atc gtg ttc ggc           1053
Met Leu Arg Thr Ala Arg Lys Leu Met Asp Gly Ile Val Phe Gly
                340                     345                     350

<210> SEQ ID NO 10
<211> LENGTH: 351
<212> TYPE: PRT
<213> ORGANISM: Sphingobium sp. SYK-6

<400> SEQUENCE: 10

Met Pro Gly Gly Val Arg Cys Met Trp Met Arg Gly Gly Thr Ser Lys
1               5                   10                  15

Gly Gly Tyr Phe Leu Ala Glu Asp Leu Pro Ala Asp Thr Ala Thr Arg
            20                  25                  30

Asp Ala Phe Leu Leu Arg Val Met Gly Ser Pro Asp Pro Arg Gln Ile
        35                  40                  45

Asp Gly Met Gly Gly Ala Asp Pro Leu Thr Ser Lys Val Ala Val Val
    50                  55                  60

Lys Lys Ser Ala Arg Glu Gly Val Asp Val Asp Tyr Leu Phe Leu Gln
65                  70                  75                  80

Val Phe Val Asp Gln Ala Ile Val Thr Asp Ala Gln Asn Cys Gly Asn
                85                  90                  95

Ile Leu Ala Gly Ile Gly Pro Phe Ala Ile Glu Arg Gly Leu Val Ala
            100                 105                 110

Pro Thr Gly Asp Glu Thr Arg Val Ala Ile Phe Met Glu Asn Thr Gly
        115                 120                 125

Gln Ile Ala Val Ala Thr Val Gln Thr Pro Gly Gly Thr Val Thr Tyr
    130                 135                 140

Asp Gly Glu Ala Ala Ile Thr Gly Val Pro Gly Thr Ala Ala Pro Val
145                 150                 155                 160

Pro Leu Leu Phe Arg Asp Thr Ala Gly Ser Cys Gly Ala Leu Leu
                165                 170                 175

Pro Thr Gly Asn Gly Val Asp Glu Ile Asp Gly Val Arg Val Thr Met
            180                 185                 190

Ile Asp Asn Gly Met Pro Cys Val Val Met Leu Ala Ser Asp Val Gly
        195                 200                 205

Val Thr Gly Tyr Glu Asp Arg Asp Thr Leu Asp Ala Asn Ala Glu Met
    210                 215                 220

Lys Ala Lys Val Glu Ala Ile Arg Leu Lys Val Gly Ala Met Met Asn
225                 230                 235                 240

Leu Gly Asp Val Thr Glu Lys Ser Val Pro Lys Met Met Leu Val Ala
                245                 250                 255

Pro Pro Arg Glu Gly Gly Ala Ile Thr Val Arg Ser Leu Ile Pro His
            260                 265                 270

Arg Val His Ala Ser Ile Gly Val Leu Gly Ala Val Ser Val Ala Thr
        275                 280                 285

Ala Cys Leu Ile Glu Gly Ser Pro Ala Ala Ser Val Ala Thr Val Pro
    290                 295                 300
```

```
Asp Gly Ala Thr Lys Thr Leu Gly Val Glu His Pro Thr Gly Val Thr
305                 310                 315                 320

Glu Cys Val Val Thr Val Asp Ala Ala Gly Gln Pro Val Glu Ala Gly
            325                 330                 335

Met Leu Arg Thr Ala Arg Lys Leu Met Asp Gly Ile Val Phe Gly
            340                 345                 350

<210> SEQ ID NO 11
<211> LENGTH: 1023
<212> TYPE: DNA
<213> ORGANISM: Sphingobium sp. SYK-6
<220> FEATURE:
<221> NAME/KEY: CDS
<222> LOCATION: (1)..(1023)

<400> SEQUENCE: 11 atg atg atg atc atc gac tgc cac ggc cac tac acc gtg ctg ccg aag       48
Met Met Met Ile Ile Asp Cys His Gly His Tyr Thr Val Leu Pro Lys
1               5                   10                  15 gcc cac gac gag tgg cgt gag cag cag aaa gcc gcc ttc aaa gcc ggt       96
Ala His Asp Glu Trp Arg Glu Gln Gln Lys Ala Ala Phe Lys Ala Gly
                20                  25                  30 cag cca gcc cca ccg tac ccg gaa atc agc gac gac gag atc cgc gaa      144
Gln Pro Ala Pro Pro Tyr Pro Glu Ile Ser Asp Asp Glu Ile Arg Glu
            35                  40                  45 acc atc gag gcc aac cag ctg cgc ctg atc aaa gaa cgc ggt gcg gac      192
Thr Ile Glu Ala Asn Gln Leu Arg Leu Ile Lys Glu Arg Gly Ala Asp
        50                  55                  60 atg acc atc ttc agc cca cgt gcc agc gcc atg gcc cca cat gtc ggc      240
Met Thr Ile Phe Ser Pro Arg Ala Ser Ala Met Ala Pro His Val Gly
65                  70                  75                  80 gat caa agc gtg gcc gtg ccg tgg gcc cag gcg tgc aac aac ctg atc      288
Asp Gln Ser Val Ala Val Pro Trp Ala Gln Ala Cys Asn Asn Leu Ile
                85                  90                  95 gcc cgt gtg gtc gac ctg ttc ccg gaa acc ttc gcc ggt gtg tgc atg      336
Ala Arg Val Val Asp Leu Phe Pro Glu Thr Phe Ala Gly Val Cys Met
            100                 105                 110 ctg ccg cag agc cca gag gcc gac atg acc agc tcg atc gcc gag ctg      384
Leu Pro Gln Ser Pro Glu Ala Asp Met Thr Ser Ser Ile Ala Glu Leu
        115                 120                 125 gaa cgc tgc gtg aac gag ctg ggc ttc atc ggc tgc aac ctg aac ccg      432
Glu Arg Cys Val Asn Glu Leu Gly Phe Ile Gly Cys Asn Leu Asn Pro
    130                 135                 140 gac cca ggc ggt ggt cac ttc aag cac cca ccg ctg acc gac cgt ttc      480
Asp Pro Gly Gly Gly His Phe Lys His Pro Pro Leu Thr Asp Arg Phe
145                 150                 155                 160 tgg tat ccg ttc tac gag aag atg gtg gaa ctg gac gtg cca gcc atg      528
Trp Tyr Pro Phe Tyr Glu Lys Met Val Glu Leu Asp Val Pro Ala Met
                165                 170                 175 atc cac gtg agc ggc agc tgc aac cca gcc atg cat gcg acc ggt gcc      576
Ile His Val Ser Gly Ser Cys Asn Pro Ala Met His Ala Thr Gly Ala
            180                 185                 190 tac tac ctg gcc gcc gac acc atc gcc ttc atg cag ctg ctg cag ggc      624
Tyr Tyr Leu Ala Ala Asp Thr Ile Ala Phe Met Gln Leu Leu Gln Gly
        195                 200                 205 aac ctg ttc gcc gac ttc ccg acc ctg cgc ttc atc atc ccg cac ggt      672
Asn Leu Phe Ala Asp Phe Pro Thr Leu Arg Phe Ile Ile Pro His Gly
    210                 215                 220 ggt ggc gcc gtg ccg tac cac tgg ggt cgt ttc cgt ggc ctg gcc gac      720
Gly Gly Ala Val Pro Tyr His Trp Gly Arg Phe Arg Gly Leu Ala Asp
225                 230                 235                 240
```

```
atg ctg aag cag ccg agc ctg gac acc ctg ctg atg aac aac gtg ttc       768
Met Leu Lys Gln Pro Ser Leu Asp Thr Leu Leu Met Asn Asn Val Phe
            245                 250                 255 ttc gat acc tgc gtg tac cat cag cca ggc atc aac ctg ctg gcc gac       816
Phe Asp Thr Cys Val Tyr His Gln Pro Gly Ile Asn Leu Leu Ala Asp
        260                 265                 270 gtc atc gac aac aag aac atc ctg ttc ggc agc gag atg gtg ggt gcc       864
Val Ile Asp Asn Lys Asn Ile Leu Phe Gly Ser Glu Met Val Gly Ala
    275                 280                 285 gtg cgt ggc atc gac ccg acc acc ggt cac tac ttc gac gac acc aag       912
Val Arg Gly Ile Asp Pro Thr Thr Gly His Tyr Phe Asp Asp Thr Lys
290                 295                 300 cgc tac atc gac gcc ctg gac atc agc gac caa gag cgc cac gcc atc       960
Arg Tyr Ile Asp Ala Leu Asp Ile Ser Asp Gln Glu Arg His Ala Ile
305                 310                 315                 320 ttc gag ggc aac acc cgt cgt gtg ttc cca cgt ctg gac gcc aag ctg      1008
Phe Glu Gly Asn Thr Arg Arg Val Phe Pro Arg Leu Asp Ala Lys Leu
                325                 330                 335 aaa gcc cgt ggc ctg                                                   1023
Lys Ala Arg Gly Leu
            340
```

<210> SEQ ID NO 12
<211> LENGTH: 341
<212> TYPE: PRT
<213> ORGANISM: Sphingobium sp. SYK-6

<400> SEQUENCE: 12

```
Met Met Met Ile Ile Asp Cys His Gly His Tyr Thr Val Leu Pro Lys
1               5                   10                  15

Ala His Asp Glu Trp Arg Glu Gln Gln Lys Ala Ala Phe Lys Ala Gly
            20                  25                  30

Gln Pro Ala Pro Pro Tyr Pro Glu Ile Ser Asp Asp Glu Ile Arg Glu
        35                  40                  45

Thr Ile Glu Ala Asn Gln Leu Arg Leu Ile Lys Glu Arg Gly Ala Asp
    50                  55                  60

Met Thr Ile Phe Ser Pro Arg Ala Ser Ala Met Ala Pro His Val Gly
65                  70                  75                  80

Asp Gln Ser Val Ala Val Pro Trp Ala Gln Ala Cys Asn Asn Leu Ile
                85                  90                  95

Ala Arg Val Val Asp Leu Phe Pro Glu Thr Phe Ala Gly Val Cys Met
            100                 105                 110

Leu Pro Gln Ser Pro Glu Ala Asp Met Thr Ser Ser Ile Ala Glu Leu
        115                 120                 125

Glu Arg Cys Val Asn Glu Leu Gly Phe Ile Gly Cys Asn Leu Asn Pro
    130                 135                 140

Asp Pro Gly Gly Gly His Phe Lys His Pro Leu Thr Asp Arg Phe
145                 150                 155                 160

Trp Tyr Pro Phe Tyr Glu Lys Met Val Glu Leu Asp Val Pro Ala Met
                165                 170                 175

Ile His Val Ser Gly Ser Cys Asn Pro Ala Met His Ala Thr Gly Ala
            180                 185                 190

Tyr Tyr Leu Ala Ala Asp Thr Ile Ala Phe Met Gln Leu Leu Gln Gly
        195                 200                 205

Asn Leu Phe Ala Asp Phe Pro Thr Leu Arg Phe Ile Ile Pro His Gly
    210                 215                 220
```

-continued

```
Gly Gly Ala Val Pro Tyr His Trp Gly Arg Phe Arg Gly Leu Ala Asp
225                 230                 235                 240

Met Leu Lys Gln Pro Ser Leu Asp Thr Leu Leu Met Asn Asn Val Phe
            245                 250                 255

Phe Asp Thr Cys Val Tyr His Gln Pro Gly Ile Asn Leu Leu Ala Asp
        260                 265                 270

Val Ile Asp Asn Lys Asn Ile Leu Phe Gly Ser Glu Met Val Gly Ala
    275                 280                 285

Val Arg Gly Ile Asp Pro Thr Gly His Tyr Phe Asp Asp Thr Lys
290                 295                 300

Arg Tyr Ile Asp Ala Leu Asp Ile Ser Asp Gln Glu Arg His Ala Ile
305                 310                 315                 320

Phe Glu Gly Asn Thr Arg Arg Val Phe Pro Arg Leu Asp Ala Lys Leu
            325                 330                 335

Lys Ala Arg Gly Leu
            340
```

```
<210> SEQ ID NO 13
<211> LENGTH: 684
<212> TYPE: DNA
<213> ORGANISM: Sphingobium sp. SYK-6
<220> FEATURE:
<221> NAME/KEY: CDS
<222> LOCATION: (1)..(684)

<400> SEQUENCE: 13
```

```
atg cgt ggt gcc gcc atg ggc gtg gtg gtg cag aac atc gag cgt gcg      48
Met Arg Gly Ala Ala Met Gly Val Val Val Gln Asn Ile Glu Arg Ala
1               5                   10                  15 cca ctg gaa gtg atc gac ggc ctg gcc gcc tgc ggt gtg gcc acc gtc      96
Pro Leu Glu Val Ile Asp Gly Leu Ala Ala Cys Gly Val Ala Thr Val
            20                  25                  30 cac gaa gcc caa ggc cgt acc ggt ctg ctg gcc agc tac atg cgt ccg     144
His Glu Ala Gln Gly Arg Thr Gly Leu Leu Ala Ser Tyr Met Arg Pro
        35                  40                  45 atc tat cgc ggt gcc cgt gtg gcc ggt agc gcc ctg acc atc agc gcc     192
Ile Tyr Arg Gly Ala Arg Val Ala Gly Ser Ala Leu Thr Ile Ser Ala
    50                  55                  60 cca ccg ggt gac aac tgg atg gtg cac gtg gcc atc gag cag ctg aaa     240
Pro Pro Gly Asp Asn Trp Met Val His Val Ala Ile Glu Gln Leu Lys
65                  70                  75                  80 gcg ggt gac atc ctg ctg ctg gcc cca acc agc ccg tgc gag gat ggc     288
Ala Gly Asp Ile Leu Leu Leu Ala Pro Thr Ser Pro Cys Glu Asp Gly
            85                  90                  95 tac ttc ggc gac ctg ctg gcg acc agc gcc caa gcc cgt ggc tgc cgt     336
Tyr Phe Gly Asp Leu Leu Ala Thr Ser Ala Gln Ala Arg Gly Cys Arg
        100                 105                 110 ggt ctg gtc atc gat gcc ggt gtg cgt gac gtc cgc gac ctg acc gag     384
Gly Leu Val Ile Asp Ala Gly Val Arg Asp Val Arg Asp Leu Thr Glu
    115                 120                 125 atg aac ttc ccg gtg tgg tcg aag gcc atc tac gcc cag ggc acc gtg     432
Met Asn Phe Pro Val Trp Ser Lys Ala Ile Tyr Ala Gln Gly Thr Val
130                 135                 140 aag aac acc ctg ggc agc gtg aac gtg ccg gtg gtg tgc gcc aac gcc     480
Lys Asn Thr Leu Gly Ser Val Asn Val Pro Val Val Cys Ala Asn Ala
145                 150                 155                 160 ctg gtg aac cca ggc gac gtg atc gtg gcc gac gac gac ggt gtg tgc     528
Leu Val Asn Pro Gly Asp Val Ile Val Ala Asp Asp Asp Gly Val Cys
            165                 170                 175
```

```
gtg gtc ccg ctg gcc aac gcc gaa aag gtg ctg gaa gcc gcc cgt gcc    576
Val Val Pro Leu Ala Asn Ala Glu Lys Val Leu Glu Ala Ala Arg Ala
        180                 185                 190 cgt gag gcc aac gaa ggc gac aag cgc gag aaa atg gcc aac ggc gtg    624
Arg Glu Ala Asn Glu Gly Asp Lys Arg Glu Lys Met Ala Asn Gly Val
            195                 200                 205 ctg ggc ctg gac ctg tac aag atg cgc gag cgc ctg gaa aaa gag ggc    672
Leu Gly Leu Asp Leu Tyr Lys Met Arg Glu Arg Leu Glu Lys Glu Gly
    210                 215                 220 ctg aag tac gtc                                                    684
Leu Lys Tyr Val
225
```

<210> SEQ ID NO 14
<211> LENGTH: 228
<212> TYPE: PRT
<213> ORGANISM: Sphingobium sp. SYK-6

<400> SEQUENCE: 14

```
Met Arg Gly Ala Ala Met Gly Val Val Gln Asn Ile Glu Arg Ala
1               5                   10                  15

Pro Leu Glu Val Ile Asp Gly Leu Ala Ala Cys Gly Val Ala Thr Val
            20                  25                  30

His Glu Ala Gln Gly Arg Thr Gly Leu Leu Ala Ser Tyr Met Arg Pro
        35                  40                  45

Ile Tyr Arg Gly Ala Arg Val Ala Gly Ser Ala Leu Thr Ile Ser Ala
    50                  55                  60

Pro Pro Gly Asp Asn Trp Met Val His Val Ala Ile Glu Gln Leu Lys
65                  70                  75                  80

Ala Gly Asp Ile Leu Leu Ala Pro Thr Ser Pro Cys Glu Asp Gly
                85                  90                  95

Tyr Phe Gly Asp Leu Leu Ala Thr Ser Ala Gln Ala Arg Gly Cys Arg
            100                 105                 110

Gly Leu Val Ile Asp Ala Gly Val Arg Asp Val Arg Asp Leu Thr Glu
        115                 120                 125

Met Asn Phe Pro Val Trp Ser Lys Ala Ile Tyr Ala Gln Gly Thr Val
    130                 135                 140

Lys Asn Thr Leu Gly Ser Val Asn Val Pro Val Val Cys Ala Asn Ala
145                 150                 155                 160

Leu Val Asn Pro Gly Asp Val Ile Val Ala Asp Asp Gly Val Cys
                165                 170                 175

Val Val Pro Leu Ala Asn Ala Glu Lys Val Leu Glu Ala Ala Arg Ala
            180                 185                 190

Arg Glu Ala Asn Glu Gly Asp Lys Arg Glu Lys Met Ala Asn Gly Val
        195                 200                 205

Leu Gly Leu Asp Leu Tyr Lys Met Arg Glu Arg Leu Glu Lys Glu Gly
    210                 215                 220

Leu Lys Tyr Val
225
```

<210> SEQ ID NO 15
<211> LENGTH: 1083
<212> TYPE: DNA
<213> ORGANISM: Pseudomonas putida
<220> FEATURE:
<221> NAME/KEY: CDS
<222> LOCATION: (1)..(1083)

<400> SEQUENCE: 15

-continued

| | | |
|---|---|---|
| atg ggc cag acc cgc ata ccc tgc ctg ctg atg cgc ggc ggc acc tcc<br>Met Gly Gln Thr Arg Ile Pro Cys Leu Leu Met Arg Gly Gly Thr Ser<br>1               5                   10                  15 | 48 | |
| aag ggc gcc tat ttt ttg cat gac gac ctg ccc gcc cct ggc ccg ctg<br>Lys Gly Ala Tyr Phe Leu His Asp Asp Leu Pro Ala Pro Gly Pro Leu<br>            20                  25                  30 | 96 | |
| cgt gac cgg gtg ctg ctg gcg gtg atg ggc tcg ccc gat gcc cgg cag<br>Arg Asp Arg Val Leu Leu Ala Val Met Gly Ser Pro Asp Ala Arg Gln<br>        35                  40                  45 | 144 | |
| att gac ggc atc ggc ggc gcc gac tcg ctc acc agc aaa gtc gcc atc<br>Ile Asp Gly Ile Gly Gly Ala Asp Ser Leu Thr Ser Lys Val Ala Ile<br>    50                  55                  60 | 192 | |
| atc cgc gct tcg cag cgc gat gac gcc gac gtg gac tac ctg ttc gct<br>Ile Arg Ala Ser Gln Arg Asp Asp Ala Asp Val Asp Tyr Leu Phe Ala<br>65                  70                  75                  80 | 240 | |
| cag gtg gtg gtg gac gag gcg cgg gtg gac tat ggg caa aac tgc ggc<br>Gln Val Val Val Asp Glu Ala Arg Val Asp Tyr Gly Gln Asn Cys Gly<br>                85                  90                  95 | 288 | |
| aac att ctg gcc ggc gta ggg ccg ttc gcc ctt gag cgc ggc ctg gtg<br>Asn Ile Leu Ala Gly Val Gly Pro Phe Ala Leu Glu Arg Gly Leu Val<br>            100                 105                 110 | 336 | |
| gcc gcc agc ggc gcg agc aca ccg gtg cgc atc ttc atg gaa aac acc<br>Ala Ala Ser Gly Ala Ser Thr Pro Val Arg Ile Phe Met Glu Asn Thr<br>        115                 120                 125 | 384 | |
| ggg cag atc gcc gtc gcc cag gtg ccg acc gcc gat ggc cag gtg gag<br>Gly Gln Ile Ala Val Ala Gln Val Pro Thr Ala Asp Gly Gln Val Glu<br>    130                 135                 140 | 432 | |
| tat gcc ggc gat acc cgt att gat ggg gtg ccg ggc cgt gcg gcg gcg<br>Tyr Ala Gly Asp Thr Arg Ile Asp Gly Val Pro Gly Arg Ala Ala Ala<br>145                 150                 155                 160 | 480 | |
| ctg gtg gtc acg ttt gcc gac gtg gcc ggc gcc agc tgc gga gca ctg<br>Leu Val Val Thr Phe Ala Asp Val Ala Gly Ala Ser Cys Gly Ala Leu<br>                165                 170                 175 | 528 | |
| ttg ccc acc ggc aac agc cgc gac tgt gtc gag ggt gtg gaa gtc acc<br>Leu Pro Thr Gly Asn Ser Arg Asp Cys Val Glu Gly Val Glu Val Thr<br>            180                 185                 190 | 576 | |
| tgc atc gac aac ggc atg ccg gtg gta ctg ctg tgt gcc gag gac ctt<br>Cys Ile Asp Asn Gly Met Pro Val Val Leu Leu Cys Ala Glu Asp Leu<br>        195                 200                 205 | 624 | |
| ggc gtg acc ggt tac gag ccg tgc gaa acg ctg gag gcc gac agc gca<br>Gly Val Thr Gly Tyr Glu Pro Cys Glu Thr Leu Glu Ala Asp Ser Ala<br>    210                 215                 220 | 672 | |
| ctg aaa aca cgc ctg gaa gcc atc cgc ctg caa ctg ggc cca cgc atg<br>Leu Lys Thr Arg Leu Glu Ala Ile Arg Leu Gln Leu Gly Pro Arg Met<br>225                 230                 235                 240 | 720 | |
| aac ctg ggt gat gtc agc cag cgc aat gtg ccg aag atg tgc ctg ctg<br>Asn Leu Gly Asp Val Ser Gln Arg Asn Val Pro Lys Met Cys Leu Leu<br>                245                 250                 255 | 768 | |
| tcg gca ccg cgc aac ggc ggc acg gtc aat acg cgc tcg ttc atc ccg<br>Ser Ala Pro Arg Asn Gly Gly Thr Val Asn Thr Arg Ser Phe Ile Pro<br>            260                 265                 270 | 816 | |
| cac cgc tgc cat gcg tcc atc ggg gtg ttt ggt gcg gtg agt gtt gct<br>His Arg Cys His Ala Ser Ile Gly Val Phe Gly Ala Val Ser Val Ala<br>        275                 280                 285 | 864 | |
| acg gcc tgc ttg att gaa ggg tcg gtt gca cag ggc ctt gcc agc acg<br>Thr Ala Cys Leu Ile Glu Gly Ser Val Ala Gln Gly Leu Ala Ser Thr<br>    290                 295                 300 | 912 | |
| tcc ggc ggt gat cgt cag cgt ttg gcg gtg gag cat ccg agt ggg gaa<br>Ser Gly Gly Asp Arg Gln Arg Leu Ala Val Glu His Pro Ser Gly Glu | 960 | |

```
                305                 310                 315                 320
ttt acg gtg gaa atc agc ctg gaa cat ggc gtg atc aag ggg tgc ggg              1008
Phe Thr Val Glu Ile Ser Leu Glu His Gly Val Ile Lys Gly Cys Gly
            325                 330                 335 ttg gtg agg acg gcc cgt ttg ctg ttt gac ggg gtt gtg tgc atc ggg              1056
Leu Val Arg Thr Ala Arg Leu Leu Phe Asp Gly Val Val Cys Ile Gly
            340                 345                 350 cga gat act tgg ggt ggg ccg gag aag                                          1083
Arg Asp Thr Trp Gly Gly Pro Glu Lys
            355                 360
```

<210> SEQ ID NO 16
<211> LENGTH: 361
<212> TYPE: PRT
<213> ORGANISM: Pseudomonas putida

<400> SEQUENCE: 16

```
Met Gly Gln Thr Arg Ile Pro Cys Leu Leu Met Arg Gly Gly Thr Ser
1               5                   10                  15

Lys Gly Ala Tyr Phe Leu His Asp Asp Leu Pro Ala Pro Gly Pro Leu
            20                  25                  30

Arg Asp Arg Val Leu Leu Ala Val Met Gly Ser Pro Asp Ala Arg Gln
        35                  40                  45

Ile Asp Gly Ile Gly Gly Ala Asp Ser Leu Thr Ser Lys Val Ala Ile
    50                  55                  60

Ile Arg Ala Ser Gln Arg Asp Asp Ala Asp Val Asp Tyr Leu Phe Ala
65                  70                  75                  80

Gln Val Val Val Asp Glu Ala Arg Val Asp Tyr Gly Gln Asn Cys Gly
                85                  90                  95

Asn Ile Leu Ala Gly Val Gly Pro Phe Ala Leu Glu Arg Gly Leu Val
            100                 105                 110

Ala Ala Ser Gly Ala Ser Thr Pro Val Arg Ile Phe Met Glu Asn Thr
        115                 120                 125

Gly Gln Ile Ala Val Ala Gln Val Pro Thr Ala Asp Gly Gln Val Glu
    130                 135                 140

Tyr Ala Gly Asp Thr Arg Ile Asp Gly Val Pro Gly Arg Ala Ala Ala
145                 150                 155                 160

Leu Val Val Thr Phe Ala Asp Val Ala Gly Ala Ser Cys Gly Ala Leu
                165                 170                 175

Leu Pro Thr Gly Asn Ser Arg Asp Cys Val Glu Gly Val Glu Val Thr
            180                 185                 190

Cys Ile Asp Asn Gly Met Pro Val Val Leu Leu Cys Ala Glu Asp Leu
        195                 200                 205

Gly Val Thr Gly Tyr Glu Pro Cys Glu Thr Leu Glu Ala Asp Ser Ala
    210                 215                 220

Leu Lys Thr Arg Leu Glu Ala Ile Arg Leu Gln Leu Gly Pro Arg Met
225                 230                 235                 240

Asn Leu Gly Asp Val Ser Gln Arg Asn Val Pro Lys Met Cys Leu Leu
                245                 250                 255

Ser Ala Pro Arg Asn Gly Gly Thr Val Asn Thr Arg Ser Phe Ile Pro
            260                 265                 270

His Arg Cys His Ala Ser Ile Gly Val Phe Gly Ala Val Ser Val Ala
        275                 280                 285

Thr Ala Cys Leu Ile Glu Gly Ser Val Ala Gln Gly Leu Ala Ser Thr
    290                 295                 300
```

```
Ser Gly Gly Asp Arg Gln Arg Leu Ala Val Glu His Pro Ser Gly Glu
305                 310                 315                 320

Phe Thr Val Glu Ile Ser Leu Glu His Gly Val Ile Lys Gly Cys Gly
            325                 330                 335

Leu Val Arg Thr Ala Arg Leu Leu Phe Asp Gly Val Val Cys Ile Gly
        340                 345                 350

Arg Asp Thr Trp Gly Gly Pro Glu Lys
    355                 360

<210> SEQ ID NO 17
<211> LENGTH: 774
<212> TYPE: DNA
<213> ORGANISM: Pseudomonas putida
<220> FEATURE:
<221> NAME/KEY: CDS
<222> LOCATION: (1)..(774)

<400> SEQUENCE: 17
```

| | | | | | | | | | | | | | | | | |
|---|---|---|---|---|---|---|---|---|---|---|---|---|---|---|---|---|
| atg | aca | tcc | tgc | gcc | cac | ccc | cac | tgc | agg | agc | caa | cga | aac | atg | aat | 48 |
| Met | Thr | Ser | Cys | Ala | His | Pro | His | Cys | Arg | Ser | Gln | Arg | Asn | Met | Asn | |
| 1 | | | | 5 | | | | | 10 | | | | | 15 | | |
| acc | cca | caa | aaa | tcc | gcc | ctg | gtg | gtc | agc | gca | cat | tcc | gcc | gac | ttt | 96 |
| Thr | Pro | Gln | Lys | Ser | Ala | Leu | Val | Val | Ser | Ala | His | Ser | Ala | Asp | Phe | |
| | | | 20 | | | | | 25 | | | | | 30 | | | |
| gtc | tgg | cgt | gcc | ggt | ggc | gcc | att | gcg | ctg | cac | gct | gag | caa | ggc | tat | 144 |
| Val | Trp | Arg | Ala | Gly | Gly | Ala | Ile | Ala | Leu | His | Ala | Glu | Gln | Gly | Tyr | |
| | | 35 | | | | | 40 | | | | | 45 | | | | |
| gcc | atg | cac | gtg | gtc | tgc | ctg | tct | ttc | ggt | gag | cgt | ggt | gag | tct | gcc | 192 |
| Ala | Met | His | Val | Val | Cys | Leu | Ser | Phe | Gly | Glu | Arg | Gly | Glu | Ser | Ala | |
| | 50 | | | | | 55 | | | | | 60 | | | | | |
| aag | ctg | tgg | cgc | aag | ggt | gaa | atg | acc | gaa | gcc | aag | gtc | aag | gac | gca | 240 |
| Lys | Leu | Trp | Arg | Lys | Gly | Glu | Met | Thr | Glu | Ala | Lys | Val | Lys | Asp | Ala | |
| 65 | | | | | 70 | | | | | 75 | | | | | 80 | |
| cgc | cgt | gaa | gag | gcc | atg | gcg | gcg | gcc | gaa | atc | ctc | ggt | gcc | agc | gtg | 288 |
| Arg | Arg | Glu | Glu | Ala | Met | Ala | Ala | Ala | Glu | Ile | Leu | Gly | Ala | Ser | Val | |
| | | | | 85 | | | | | 90 | | | | | 95 | | |
| gag | ttc | ttc | gac | atc | ggc | gac | tat | ccg | atg | cgc | gcc | gac | aag | gac | acc | 336 |
| Glu | Phe | Phe | Asp | Ile | Gly | Asp | Tyr | Pro | Met | Arg | Ala | Asp | Lys | Asp | Thr | |
| | | | 100 | | | | | 105 | | | | | 110 | | | |
| ctg | ttc | cgc | ctg | gcc | gat | gtg | tat | cgc | cgg | gta | caa | ccg | gag | ttc | gta | 384 |
| Leu | Phe | Arg | Leu | Ala | Asp | Val | Tyr | Arg | Arg | Val | Gln | Pro | Glu | Phe | Val | |
| | | 115 | | | | | 120 | | | | | 125 | | | | |
| ctc | agc | cac | tcc | ctc | aaa | gac | cct | tac | aac | tac | gac | cac | ccg | ctg | gcc | 432 |
| Leu | Ser | His | Ser | Leu | Lys | Asp | Pro | Tyr | Asn | Tyr | Asp | His | Pro | Leu | Ala | |
| | 130 | | | | | 135 | | | | | 140 | | | | | |
| atg | cac | ctg | gcc | cag | gaa | gcc | cgc | att | atc | gcg | cag | gct | gaa | ggc | tac | 480 |
| Met | His | Leu | Ala | Gln | Glu | Ala | Arg | Ile | Ile | Ala | Gln | Ala | Glu | Gly | Tyr | |
| 145 | | | | | 150 | | | | | 155 | | | | | 160 | |
| aag | ccg | ggc | gag | aag | atc | gtt | ggc | gca | ccg | ccg | gtc | tac | gcc | ttt | gag | 528 |
| Lys | Pro | Gly | Glu | Lys | Ile | Val | Gly | Ala | Pro | Pro | Val | Tyr | Ala | Phe | Glu | |
| | | | | 165 | | | | | 170 | | | | | 175 | | |
| ccg | cac | cag | ccc | gag | cag | tgc | gaa | tgg | cgc | ccg | gac | acg | ttc | ctg | gac | 576 |
| Pro | His | Gln | Pro | Glu | Gln | Cys | Glu | Trp | Arg | Pro | Asp | Thr | Phe | Leu | Asp | |
| | | | 180 | | | | | 185 | | | | | 190 | | | |
| att | acc | tcg | gtg | tgg | gac | aaa | aag | tat | gcc | gcc | atc | cag | tgc | atg | gcc | 624 |
| Ile | Thr | Ser | Val | Trp | Asp | Lys | Lys | Tyr | Ala | Ala | Ile | Gln | Cys | Met | Ala | |
| | | 195 | | | | | 200 | | | | | 205 | | | | |
| ggc | cag | gaa | cac | ctc | tgg | gag | tac | tac | acc | cgt | gta | gcc | ctg | cag | cgc | 672 |
| Gly | Gln | Glu | His | Leu | Trp | Glu | Tyr | Tyr | Thr | Arg | Val | Ala | Leu | Gln | Arg | |
| | 210 | | | | | 215 | | | | | 220 | | | | | |

```
ggc gtg cag gcc aag cgt aac gtg ggc ata acc agc gca cgc aac atc       720
Gly Val Gln Ala Lys Arg Asn Val Gly Ile Thr Ser Ala Arg Asn Ile
225                 230                 235                 240 gtc tac gcc gaa ggc ctg cag agc gtg ttc cca cgc gtg acg gag aac       768
Val Tyr Ala Glu Gly Leu Gln Ser Val Phe Pro Arg Val Thr Glu Asn
                245                 250                 255 ctg gca                                                                774
Leu Ala
```

<210> SEQ ID NO 18
<211> LENGTH: 258
<212> TYPE: PRT
<213> ORGANISM: Pseudomonas putida

<400> SEQUENCE: 18

```
Met Thr Ser Cys Ala His Pro His Cys Arg Ser Gln Arg Asn Met Asn
1               5                   10                  15

Thr Pro Gln Lys Ser Ala Leu Val Val Ser Ala His Ser Ala Asp Phe
            20                  25                  30

Val Trp Arg Ala Gly Gly Ala Ile Ala Leu His Ala Glu Gln Gly Tyr
        35                  40                  45

Ala Met His Val Val Cys Leu Ser Phe Gly Glu Arg Gly Glu Ser Ala
    50                  55                  60

Lys Leu Trp Arg Lys Gly Glu Met Thr Glu Ala Lys Val Lys Asp Ala
65                  70                  75                  80

Arg Arg Glu Glu Ala Met Ala Ala Glu Ile Leu Gly Ala Ser Val
                85                  90                  95

Glu Phe Phe Asp Ile Gly Asp Tyr Pro Met Arg Ala Asp Lys Asp Thr
            100                 105                 110

Leu Phe Arg Leu Ala Asp Val Tyr Arg Arg Val Gln Pro Glu Phe Val
        115                 120                 125

Leu Ser His Ser Leu Lys Asp Pro Tyr Asn Tyr Asp His Pro Leu Ala
    130                 135                 140

Met His Leu Ala Gln Glu Ala Arg Ile Ile Ala Gln Ala Glu Gly Tyr
145                 150                 155                 160

Lys Pro Gly Glu Lys Ile Val Gly Ala Pro Val Tyr Ala Phe Glu
                165                 170                 175

Pro His Gln Pro Glu Gln Cys Glu Trp Arg Pro Asp Thr Phe Leu Asp
            180                 185                 190

Ile Thr Ser Val Trp Asp Lys Lys Tyr Ala Ala Ile Gln Cys Met Ala
        195                 200                 205

Gly Gln Glu His Leu Trp Glu Tyr Tyr Thr Arg Val Ala Leu Gln Arg
    210                 215                 220

Gly Val Gln Ala Lys Arg Asn Val Gly Ile Thr Ser Ala Arg Asn Ile
225                 230                 235                 240

Val Tyr Ala Glu Gly Leu Gln Ser Val Phe Pro Arg Val Thr Glu Asn
                245                 250                 255

Leu Ala
```

<210> SEQ ID NO 19
<211> LENGTH: 714
<212> TYPE: DNA
<213> ORGANISM: Pseudomonas putida
<220> FEATURE:
<221> NAME/KEY: CDS
<222> LOCATION: (1)..(714)

<400> SEQUENCE: 19

```
atg agc ggg ctg atc ggc aag acc ggc atc gtc gtg cgt aat atc cca          48
Met Ser Gly Leu Ile Gly Lys Thr Gly Ile Val Val Arg Asn Ile Pro
1               5                   10                  15 cgc gtt gag cca cac atg atc gat gcc ctg ggc cgg ctg ggt gtc gcc          96
Arg Val Glu Pro His Met Ile Asp Ala Leu Gly Arg Leu Gly Val Ala
                20                  25                  30 acg gtg cat gag gcc caa ggt cgc aag ggg ctg ctc aat act gcc gtg          144
Thr Val His Glu Ala Gln Gly Arg Lys Gly Leu Leu Asn Thr Ala Val
            35                  40                  45 cgc cct atc cag caa ggt gtg gcg gtg gcc ggc agc gcg gta acc gtg          192
Arg Pro Ile Gln Gln Gly Val Ala Val Ala Gly Ser Ala Val Thr Val
        50                  55                  60 ctg gtg gcc cca ggc gac aac tgg atg ttc cat gtt gcc gtg gag cag          240
Leu Val Ala Pro Gly Asp Asn Trp Met Phe His Val Ala Val Glu Gln
65                  70                  75                  80 tgc cgc cca ggc gac gta ctg gtg gtg gcg ccc agc tcg ccg tgc agc          288
Cys Arg Pro Gly Asp Val Leu Val Val Ala Pro Ser Ser Pro Cys Ser
                85                  90                  95 gat ggc tat ttc ggc gac ctg ctg gcg acc tcg ctc cag gcc cgc ggc          336
Asp Gly Tyr Phe Gly Asp Leu Leu Ala Thr Ser Leu Gln Ala Arg Gly
                100                 105                 110 gtg ctc ggc ctg gtg atc gat gcg ggc gtg cgc gac agc cag aca ctg          384
Val Leu Gly Leu Val Ile Asp Ala Gly Val Arg Asp Ser Gln Thr Leu
            115                 120                 125 cgc gac atg ggc ttt gcc gtg tgg tcc cgc gcc atc aac gcc caa ggt          432
Arg Asp Met Gly Phe Ala Val Trp Ser Arg Ala Ile Asn Ala Gln Gly
        130                 135                 140 acg gtg aaa gag gtg ctg ggc tcg gtg aac ctg ccg ctg ctg tgt gcc          480
Thr Val Lys Glu Val Leu Gly Ser Val Asn Leu Pro Leu Leu Cys Ala
145                 150                 155                 160 ggg cag ctc gtc aat gcc ggt gac atc gtg gtg gcc gat gac gac ggc          528
Gly Gln Leu Val Asn Ala Gly Asp Ile Val Val Ala Asp Asp Asp Gly
                165                 170                 175 gta gtg gtg gtg cgc cat ggc gaa gcc cag gcg gta ctc gaa gcc gcc          576
Val Val Val Val Arg His Gly Glu Ala Gln Ala Val Leu Glu Ala Ala
                180                 185                 190 acc cag cgc gcc gac ctg gaa gaa cgc aaa cgc ctg cgc ctg gcc gcc          624
Thr Gln Arg Ala Asp Leu Glu Glu Arg Lys Arg Leu Arg Leu Ala Ala
            195                 200                 205 gga gag ctt ggc ctg gac atc tac gag atg cgc ccg cgc ctg gcg gcg          672
Gly Glu Leu Gly Leu Asp Ile Tyr Glu Met Arg Pro Arg Leu Ala Ala
        210                 215                 220 aag ggc ctg cgt tat gtc gac cac ctc acc gac ctg gaa ggc                  714
Lys Gly Leu Arg Tyr Val Asp His Leu Thr Asp Leu Glu Gly
225                 230                 235

<210> SEQ ID NO 20
<211> LENGTH: 238
<212> TYPE: PRT
<213> ORGANISM: Pseudomonas putida

<400> SEQUENCE: 20

Met Ser Gly Leu Ile Gly Lys Thr Gly Ile Val Val Arg Asn Ile Pro
1               5                   10                  15

Arg Val Glu Pro His Met Ile Asp Ala Leu Gly Arg Leu Gly Val Ala
                20                  25                  30

Thr Val His Glu Ala Gln Gly Arg Lys Gly Leu Leu Asn Thr Ala Val
            35                  40                  45

Arg Pro Ile Gln Gln Gly Val Ala Val Ala Gly Ser Ala Val Thr Val
```

```
                50                  55                  60
Leu Val Ala Pro Gly Asp Asn Trp Met Phe His Val Ala Val Glu Gln
 65                  70                  75                  80

Cys Arg Pro Gly Asp Val Leu Val Ala Pro Ser Ser Pro Cys Ser
                 85                  90                  95

Asp Gly Tyr Phe Gly Asp Leu Leu Ala Thr Ser Leu Gln Ala Arg Gly
                100                 105                 110

Val Leu Gly Leu Val Ile Asp Ala Gly Val Arg Asp Ser Gln Thr Leu
                115                 120                 125

Arg Asp Met Gly Phe Ala Val Trp Ser Arg Ala Ile Asn Ala Gln Gly
    130                 135                 140

Thr Val Lys Glu Val Leu Gly Ser Val Asn Leu Pro Leu Leu Cys Ala
145                 150                 155                 160

Gly Gln Leu Val Asn Ala Gly Asp Ile Val Val Ala Asp Asp Gly
                165                 170                 175

Val Val Val Val Arg His Gly Glu Ala Gln Ala Val Leu Glu Ala Ala
                180                 185                 190

Thr Gln Arg Ala Asp Leu Glu Glu Arg Lys Arg Leu Arg Leu Ala Ala
    195                 200                 205

Gly Glu Leu Gly Leu Asp Ile Tyr Glu Met Arg Pro Arg Leu Ala Ala
    210                 215                 220

Lys Gly Leu Arg Tyr Val Asp His Leu Thr Asp Leu Glu Gly
225                 230                 235

<210> SEQ ID NO 21
<211> LENGTH: 933
<212> TYPE: DNA
<213> ORGANISM: Pseudomonas putida
<220> FEATURE:
<221> NAME/KEY: CDS
<222> LOCATION: (1)..(933)

<400> SEQUENCE: 21 atg acc gtg aaa att tcc cac act gcc gac att caa gcc ttc ttc aac      48
Met Thr Val Lys Ile Ser His Thr Ala Asp Ile Gln Ala Phe Phe Asn
  1               5                  10                  15 cgg gta gct ggc ctg gac cat gcc gaa gga aac ccg cgc ttc aag cag      96
Arg Val Ala Gly Leu Asp His Ala Glu Gly Asn Pro Arg Phe Lys Gln
             20                  25                  30 atc att ctg cgc gtg ctg caa gac acc gcc cgc ctg atc gaa gac ctg     144
Ile Ile Leu Arg Val Leu Gln Asp Thr Ala Arg Leu Ile Glu Asp Leu
         35                  40                  45 gag att acc gag gac gag ttc tgg cac gcc gtc gac tac ctc aac cgc     192
Glu Ile Thr Glu Asp Glu Phe Trp His Ala Val Asp Tyr Leu Asn Arg
     50                  55                  60 ctg ggc ggc cgt aac gag gca ggc ctg ctg gct gct ggc ctg ggt atc     240
Leu Gly Gly Arg Asn Glu Ala Gly Leu Leu Ala Ala Gly Leu Gly Ile
 65                  70                  75                  80 gag cac ttc ctc gac ctg ctg cag gat gcc aag gat gcc gaa gcc ggc     288
Glu His Phe Leu Asp Leu Leu Gln Asp Ala Lys Asp Ala Glu Ala Gly
                 85                  90                  95 ctt ggc ggc ggc acc ccg cgc acc atc gaa ggc ccg ttg tac gtt gcc     336
Leu Gly Gly Gly Thr Pro Arg Thr Ile Glu Gly Pro Leu Tyr Val Ala
                100                 105                 110 ggg gcg ccg ctg gcc cag ggc gaa gcg cgc atg gac gac ggc act gac     384
Gly Ala Pro Leu Ala Gln Gly Glu Ala Arg Met Asp Asp Gly Thr Asp
                115                 120                 125 cca ggc gtg gtg atg ttc ctt cag ggc cag gtg ttc gat gcc gac ggc     432
```

```
                Pro Gly Val Val Met Phe Leu Gln Gly Gln Val Phe Asp Ala Asp Gly
                        130                 135                 140 aag ccg ttg gcc ggt gcc acc gtc gac ctg tgg cac gcc aat acc cag              480
Lys Pro Leu Ala Gly Ala Thr Val Asp Leu Trp His Ala Asn Thr Gln
145                 150                 155                 160 ggc acc tat tcg tac ttc gat tcg acc cag tcc gag ttc aac ctg cgt              528
Gly Thr Tyr Ser Tyr Phe Asp Ser Thr Gln Ser Glu Phe Asn Leu Arg
                165                 170                 175 cgg cgt atc atc acc gat gcc gag ggc cgc tac cgc gcg cgc tcg atc              576
Arg Arg Ile Ile Thr Asp Ala Glu Gly Arg Tyr Arg Ala Arg Ser Ile
            180                 185                 190 gtg ccg tcc ggg tat ggc tgc gac ccg cag ggc cca acc cag gaa tgc              624
Val Pro Ser Gly Tyr Gly Cys Asp Pro Gln Gly Pro Thr Gln Glu Cys
        195                 200                 205 ctg gac ctg ctc ggc cgc cac ggc cag cgc ccg gcg cac gtg cac ttc              672
Leu Asp Leu Leu Gly Arg His Gly Gln Arg Pro Ala His Val His Phe
    210                 215                 220 ttc atc tcg gca ccg ggg cac cgc cac ctg acc acg cag atc aac ttt              720
Phe Ile Ser Ala Pro Gly His Arg His Leu Thr Thr Gln Ile Asn Phe
225                 230                 235                 240 gct ggc gac aag tac ctg tgg gac gac ttt gcc tat gcc acc cgc gac              768
Ala Gly Asp Lys Tyr Leu Trp Asp Asp Phe Ala Tyr Ala Thr Arg Asp
                245                 250                 255 ggg ctg atc ggc gaa ctg cgt ttt gtc gag gat gcg gcg gcg gcg cgc              816
Gly Leu Ile Gly Glu Leu Arg Phe Val Glu Asp Ala Ala Ala Ala Arg
            260                 265                 270 gac cgc ggt gtg caa ggc gag cgc ttt gcc gag ctg tca ttc gac ttc              864
Asp Arg Gly Val Gln Gly Glu Arg Phe Ala Glu Leu Ser Phe Asp Phe
        275                 280                 285 cgc ttg cag ggt gcc aag tcg cct gac gcc gag gcg cga agc cat cgg              912
Arg Leu Gln Gly Ala Lys Ser Pro Asp Ala Glu Ala Arg Ser His Arg
    290                 295                 300 ccg cgg gcg ttg cag gag ggc                                                  933
Pro Arg Ala Leu Gln Glu Gly
305                 310

<210> SEQ ID NO 22
<211> LENGTH: 311
<212> TYPE: PRT
<213> ORGANISM: Pseudomonas putida

<400> SEQUENCE: 22

Met Thr Val Lys Ile Ser His Thr Ala Asp Ile Gln Ala Phe Phe Asn
1               5                   10                  15

Arg Val Ala Gly Leu Asp His Ala Glu Gly Asn Pro Arg Phe Lys Gln
                20                  25                  30

Ile Ile Leu Arg Val Leu Gln Asp Thr Ala Arg Leu Ile Glu Asp Leu
            35                  40                  45

Glu Ile Thr Glu Asp Glu Phe Trp His Ala Val Asp Tyr Leu Asn Arg
        50                  55                  60

Leu Gly Gly Arg Asn Glu Ala Gly Leu Leu Ala Gly Leu Gly Ile
65                  70                  75                  80

Glu His Phe Leu Asp Leu Leu Gln Asp Ala Lys Asp Ala Glu Ala Gly
                85                  90                  95

Leu Gly Gly Gly Thr Pro Arg Thr Ile Glu Gly Pro Leu Tyr Val Ala
            100                 105                 110

Gly Ala Pro Leu Ala Gln Gly Glu Ala Arg Met Asp Asp Gly Thr Asp
        115                 120                 125
```

```
Pro Gly Val Val Met Phe Leu Gln Gly Gln Val Phe Asp Ala Asp Gly
    130                 135                 140

Lys Pro Leu Ala Gly Ala Thr Val Asp Leu Trp His Ala Asn Thr Gln
145                 150                 155                 160

Gly Thr Tyr Ser Tyr Phe Asp Ser Thr Gln Ser Glu Phe Asn Leu Arg
                165                 170                 175

Arg Arg Ile Ile Thr Asp Ala Glu Gly Arg Tyr Arg Ala Arg Ser Ile
            180                 185                 190

Val Pro Ser Gly Tyr Gly Cys Asp Pro Gln Gly Pro Thr Gln Glu Cys
        195                 200                 205

Leu Asp Leu Leu Gly Arg His Gly Gln Arg Pro Ala His Val His Phe
    210                 215                 220

Phe Ile Ser Ala Pro Gly His Arg His Leu Thr Thr Gln Ile Asn Phe
225                 230                 235                 240

Ala Gly Asp Lys Tyr Leu Trp Asp Asp Phe Ala Tyr Ala Thr Arg Asp
                245                 250                 255

Gly Leu Ile Gly Glu Leu Arg Phe Val Glu Asp Ala Ala Ala Ala Arg
            260                 265                 270

Asp Arg Gly Val Gln Gly Glu Arg Phe Ala Glu Leu Ser Phe Asp Phe
        275                 280                 285

Arg Leu Gln Gly Ala Lys Ser Pro Asp Ala Glu Ala Arg Ser His Arg
    290                 295                 300

Pro Arg Ala Leu Gln Glu Gly
305                 310

<210> SEQ ID NO 23
<211> LENGTH: 912
<212> TYPE: DNA
<213> ORGANISM: Pseudomonas putida
<220> FEATURE:
<221> NAME/KEY: CDS
<222> LOCATION: (1)..(912)

<400> SEQUENCE: 23 atg acc gtg aac att tcc cat act gcc gag gta cag cag ttc ttc gag      48
Met Thr Val Asn Ile Ser His Thr Ala Glu Val Gln Gln Phe Phe Glu
1               5                   10                  15 cag gcc gca ggc ttt tgt aat gcg gcc ggc aac cca cgc ctc aaa cgc      96
Gln Ala Ala Gly Phe Cys Asn Ala Ala Gly Asn Pro Arg Leu Lys Arg
            20                  25                  30 atc gtg cag cgc ctg ctg cag gat acc gcg cgg ctg atc gaa gac ctg     144
Ile Val Gln Arg Leu Leu Gln Asp Thr Ala Arg Leu Ile Glu Asp Leu
        35                  40                  45 gac atc agc gaa gac gag ttc tgg cac gcc gtc gat tac ctc aac cgc     192
Asp Ile Ser Glu Asp Glu Phe Trp His Ala Val Asp Tyr Leu Asn Arg
    50                  55                  60 ctg ggc ggt cgc ggc gaa gcc ggg ttg ctg gtg gcg ggg ctg ggc atc     240
Leu Gly Gly Arg Gly Glu Ala Gly Leu Leu Val Ala Gly Leu Gly Ile
65                  70                  75                  80 gaa cac ttc ctc gac ctg ctg cag gat gcc aag gac cag gag gca ggg     288
Glu His Phe Leu Asp Leu Leu Gln Asp Ala Lys Asp Gln Glu Ala Gly
                85                  90                  95 cgc gtt ggc ggc acc cca cgc acc atc gaa ggc ccg ttg tac gtg gct     336
Arg Val Gly Gly Thr Pro Arg Thr Ile Glu Gly Pro Leu Tyr Val Ala
            100                 105                 110 ggc gca ccg att gcc caa ggt gaa gtg cgc atg gac gac ggc agc gag     384
Gly Ala Pro Ile Ala Gln Gly Glu Val Arg Met Asp Asp Gly Ser Glu
        115                 120                 125
```

| | | |
|---|---|---|
| gag ggc gtg gcc acg gtg atg ttc ctg gaa ggc cag gtg ctg gac ccg<br>Glu Gly Val Ala Thr Val Met Phe Leu Glu Gly Gln Val Leu Asp Pro<br>130                              135                           140 | | 432 |
| cac gga cgc ccg ctg ccg ggt gcc acg gtc gac ctg tgg cat gcc aat<br>His Gly Arg Pro Leu Pro Gly Ala Thr Val Asp Leu Trp His Ala Asn<br>145                            150                           155                       160 | | 480 |
| acc cgt ggt acc tac tcg ttc ttc gac caa agc cag tcg gcg tac aac<br>Thr Arg Gly Thr Tyr Ser Phe Phe Asp Gln Ser Gln Ser Ala Tyr Asn<br>                           165                           170                           175 | | 528 |
| ctg cgt cgg cgc atc gtt acc gat gcc cag ggg cgc tac cgc gcg cgc<br>Leu Arg Arg Arg Ile Val Thr Asp Ala Gln Gly Arg Tyr Arg Ala Arg<br>               180                           185                           190 | | 576 |
| tcc atc gtg cca tcg ggc tat ggc tgc gac ccg cag ggg cca acc cag<br>Ser Ile Val Pro Ser Gly Tyr Gly Cys Asp Pro Gln Gly Pro Thr Gln<br>                         195                          200                          205 | | 624 |
| gaa tgc ctg gac ctg ctg ggc cgt cat ggc cag cgc ccg gcg cac gtg<br>Glu Cys Leu Asp Leu Leu Gly Arg His Gly Gln Arg Pro Ala His Val<br>210                             215                           220 | | 672 |
| cac ttc ttt atc tcg gcc cca ggg tac cgg cac ctg acc acg cag ata<br>His Phe Phe Ile Ser Ala Pro Gly Tyr Arg His Leu Thr Thr Gln Ile<br>225                             230                           235                       240 | | 720 |
| aac ctg tcg ggg gac aag tac ctg tgg gat gac ttt gcc tat gcc aca<br>Asn Leu Ser Gly Asp Lys Tyr Leu Trp Asp Asp Phe Ala Tyr Ala Thr<br>                         245                          250                          255 | | 768 |
| cgg gat ggg ctg gtc ggg gag gtg gtg ttc gtc gaa ggg ccg gat ggt<br>Arg Asp Gly Leu Val Gly Glu Val Val Phe Val Glu Gly Pro Asp Gly<br>               260                           265                           270 | | 816 |
| cgg cat gcc gag ctg aag ttc gac ttc cag ttg cag cag gcc cag ggc<br>Arg His Ala Glu Leu Lys Phe Asp Phe Gln Leu Gln Gln Ala Gln Gly<br>275                             280                           285 | | 864 |
| ggt gcc gat gag cag cgc agc ggg cgg ccg cga gct ttg cag gag gcc<br>Gly Ala Asp Glu Gln Arg Ser Gly Arg Pro Arg Ala Leu Gln Glu Ala<br>               290                           295                           300 | | 912 |

```
<210> SEQ ID NO 24
<211> LENGTH: 304
<212> TYPE: PRT
<213> ORGANISM: Pseudomonas putida

<400> SEQUENCE: 24
```

Met Thr Val Asn Ile Ser His Thr Ala Glu Val Gln Gln Phe Phe Glu
1               5                   10                  15

Gln Ala Ala Gly Phe Cys Asn Ala Ala Gly Asn Pro Arg Leu Lys Arg
            20                  25                  30

Ile Val Gln Arg Leu Leu Gln Asp Thr Ala Arg Leu Ile Glu Asp Leu
        35                  40                  45

Asp Ile Ser Glu Asp Glu Phe Trp His Ala Val Asp Tyr Leu Asn Arg
    50                  55                  60

Leu Gly Gly Arg Gly Glu Ala Gly Leu Leu Val Ala Gly Leu Gly Ile
65                  70                  75                  80

Glu His Phe Leu Asp Leu Leu Gln Asp Ala Lys Asp Gln Glu Ala Gly
                85                  90                  95

Arg Val Gly Gly Thr Pro Arg Thr Ile Glu Gly Pro Leu Tyr Val Ala
            100                 105                 110

Gly Ala Pro Ile Ala Gln Gly Glu Val Arg Met Asp Asp Gly Ser Glu
        115                 120                 125

Glu Gly Val Ala Thr Val Met Phe Leu Glu Gly Gln Val Leu Asp Pro
    130                 135                 140

```
His Gly Arg Pro Leu Pro Gly Ala Thr Val Asp Leu Trp His Ala Asn
145                 150                 155                 160

Thr Arg Gly Thr Tyr Ser Phe Phe Asp Gln Ser Gln Ser Ala Tyr Asn
            165                 170                 175

Leu Arg Arg Arg Ile Val Thr Asp Ala Gln Gly Arg Tyr Arg Ala Arg
                180                 185                 190

Ser Ile Val Pro Ser Gly Tyr Gly Cys Asp Pro Gln Gly Pro Thr Gln
            195                 200                 205

Glu Cys Leu Asp Leu Leu Gly Arg His Gly Gln Arg Pro Ala His Val
210                 215                 220

His Phe Phe Ile Ser Ala Pro Gly Tyr Arg His Leu Thr Thr Gln Ile
225                 230                 235                 240

Asn Leu Ser Gly Asp Lys Tyr Leu Trp Asp Asp Phe Ala Tyr Ala Thr
                245                 250                 255

Arg Asp Gly Leu Val Gly Glu Val Val Phe Val Glu Gly Pro Asp Gly
                260                 265                 270

Arg His Ala Glu Leu Lys Phe Asp Phe Gln Leu Gln Gln Ala Gln Gly
                275                 280                 285

Gly Ala Asp Glu Gln Arg Ser Gly Arg Pro Arg Ala Leu Gln Glu Ala
290                 295                 300
```

<210> SEQ ID NO 25
<211> LENGTH: 1119
<212> TYPE: DNA
<213> ORGANISM: Pseudomonas putida
<220> FEATURE:
<221> NAME/KEY: CDS
<222> LOCATION: (1)..(1119)

<400> SEQUENCE: 25

```
atg aca agc gtg ctg att gaa cac ata gat gca att atc gtc gat ctc       48
Met Thr Ser Val Leu Ile Glu His Ile Asp Ala Ile Ile Val Asp Leu
1               5                   10                  15 ccg acc att cgc ccg cac aag ctg gcg atg cac acc atg cag cag cag       96
Pro Thr Ile Arg Pro His Lys Leu Ala Met His Thr Met Gln Gln Gln
            20                  25                  30 acc ctg gtg gta ttg cga ctg cgc tgc agc gat ggc gtg gaa ggc atc      144
Thr Leu Val Val Leu Arg Leu Arg Cys Ser Asp Gly Val Glu Gly Ile
        35                  40                  45 ggt gaa gcc acc acc atc ggt ggc ctg gcg tat ggc tac gaa agc ccc      192
Gly Glu Ala Thr Thr Ile Gly Gly Leu Ala Tyr Gly Tyr Glu Ser Pro
50                  55                  60 gaa ggg atc aag gcc aac atc gac gcg tac ctc gcc cca gcg ttg att      240
Glu Gly Ile Lys Ala Asn Ile Asp Ala Tyr Leu Ala Pro Ala Leu Ile
65                  70                  75                  80 ggc ctg ccg gca gac aac atc aat gcc gcc atg ctc aag ctg gac aag      288
Gly Leu Pro Ala Asp Asn Ile Asn Ala Ala Met Leu Lys Leu Asp Lys
                85                  90                  95 ctg gcc aag ggc aac acc ttc gcc aag tcc ggc atc gaa agc gcc ttg      336
Leu Ala Lys Gly Asn Thr Phe Ala Lys Ser Gly Ile Glu Ser Ala Leu
            100                 105                 110 ctc gac gcc cag ggc aaa cgc ctg ggc ctg ccg gtc agc gaa ctg ctg      384
Leu Asp Ala Gln Gly Lys Arg Leu Gly Leu Pro Val Ser Glu Leu Leu
        115                 120                 125 ggt ggc cgc gtg cgt gac agc ctg gaa gtg gcc tgg acc ctg gcc agc      432
Gly Gly Arg Val Arg Asp Ser Leu Glu Val Ala Trp Thr Leu Ala Ser
130                 135                 140 ggc gac acc gcc cgc gac atc gcc gaa gca cag cac atg ctg gac att      480
Gly Asp Thr Ala Arg Asp Ile Ala Glu Ala Gln His Met Leu Asp Ile
```

```
                 145                 150                 155                 160
cgc cgg cac cgc gtg ttc aag ctg aaa atc ggc gcc aac ccg gtg gcg        528
Arg Arg His Arg Val Phe Lys Leu Lys Ile Gly Ala Asn Pro Val Ala
                165                 170                 175 cag gac ctc aag cac gtg gtc gcg atc aag cgc gag ctg ggt gac agc        576
Gln Asp Leu Lys His Val Val Ala Ile Lys Arg Glu Leu Gly Asp Ser
            180                 185                 190 gcc agc gtg cgg gtc gac gtc aac cag tac tgg gac gag tcc cag gcc        624
Ala Ser Val Arg Val Asp Val Asn Gln Tyr Trp Asp Glu Ser Gln Ala
        195                 200                 205 atc cgc gcc tgc cag gta ttg ggc gac aac ggc atc gac ctg atc gag        672
Ile Arg Ala Cys Gln Val Leu Gly Asp Asn Gly Ile Asp Leu Ile Glu
    210                 215                 220 cag ccg att tcg cgc atc aac cgc gct ggc cag gtg cgc ctg aac cag        720
Gln Pro Ile Ser Arg Ile Asn Arg Ala Gly Gln Val Arg Leu Asn Gln
225                 230                 235                 240 cgc agt ccg gct ccg atc atg gcc gat gag tcg atc gaa agc gtc gag        768
Arg Ser Pro Ala Pro Ile Met Ala Asp Glu Ser Ile Glu Ser Val Glu
                245                 250                 255 gac gcc ttc agc ctg gcc gcc gac ggc gcc gcc agc atc ttc gcc ctg        816
Asp Ala Phe Ser Leu Ala Ala Asp Gly Ala Ala Ser Ile Phe Ala Leu
            260                 265                 270 aaa atc gcc aag aat ggt ggc ccg cgc gcg gtt ctg cgc act gca cag        864
Lys Ile Ala Lys Asn Gly Gly Pro Arg Ala Val Leu Arg Thr Ala Gln
        275                 280                 285 atc gcc gag gcc gct ggc atc gcc ttg tac ggc ggc acc atg ctc gaa        912
Ile Ala Glu Ala Ala Gly Ile Ala Leu Tyr Gly Gly Thr Met Leu Glu
    290                 295                 300 ggt tcg atc ggc acc ctg gct tcg gct cat gca ttc ctc acc ctg cgc        960
Gly Ser Ile Gly Thr Leu Ala Ser Ala His Ala Phe Leu Thr Leu Arg
305                 310                 315                 320 cag ctc acc tgg ggt aca gag ctg ttc ggg ccg ctg ctg acc gag          1008
Gln Leu Thr Trp Gly Thr Glu Leu Phe Gly Pro Leu Leu Thr Glu
                325                 330                 335 gag atc gtc aac gag ccg ccg caa tac cgc gac ttc cag ctg cac atc      1056
Glu Ile Val Asn Glu Pro Pro Gln Tyr Arg Asp Phe Gln Leu His Ile
            340                 345                 350 ccc cac acc cca ggc ctg ggc ctg acg ttg gac gaa cag cgc ctg gcg      1104
Pro His Thr Pro Gly Leu Gly Leu Thr Leu Asp Glu Gln Arg Leu Ala
        355                 360                 365 cgc ttc gcc cgt cgc                                                   1119
Arg Phe Ala Arg Arg
    370

<210> SEQ ID NO 26
<211> LENGTH: 373
<212> TYPE: PRT
<213> ORGANISM: Pseudomonas putida

<400> SEQUENCE: 26

Met Thr Ser Val Leu Ile Glu His Ile Asp Ala Ile Ile Val Asp Leu
1               5                   10                  15

Pro Thr Ile Arg Pro His Lys Leu Ala Met His Thr Met Gln Gln Gln
            20                  25                  30

Thr Leu Val Leu Arg Leu Arg Cys Ser Asp Gly Val Glu Gly Ile
        35                  40                  45

Gly Glu Ala Thr Thr Ile Gly Gly Leu Ala Tyr Gly Tyr Glu Ser Pro
    50                  55                  60

Glu Gly Ile Lys Ala Asn Ile Asp Ala Tyr Leu Ala Pro Ala Leu Ile
```

```
              65                  70                  75                  80
        Gly Leu Pro Ala Asp Asn Ile Asn Ala Ala Met Leu Lys Leu Asp Lys
                            85                  90                  95

Leu Ala Lys Gly Asn Thr Phe Ala Lys Ser Gly Ile Glu Ser Ala Leu
                        100                 105                 110

Leu Asp Ala Gln Gly Lys Arg Leu Gly Leu Pro Val Ser Glu Leu Leu
                    115                 120                 125

Gly Gly Arg Val Arg Asp Ser Leu Glu Val Ala Trp Thr Leu Ala Ser
                130                 135                 140

Gly Asp Thr Ala Arg Asp Ile Ala Glu Ala Gln His Met Leu Asp Ile
        145                 150                 155                 160

Arg Arg His Arg Val Phe Lys Leu Lys Ile Gly Ala Asn Pro Val Ala
                            165                 170                 175

Gln Asp Leu Lys His Val Val Ala Ile Lys Arg Glu Leu Gly Asp Ser
                        180                 185                 190

Ala Ser Val Arg Val Asp Val Asn Gln Tyr Trp Asp Glu Ser Gln Ala
                    195                 200                 205

Ile Arg Ala Cys Gln Val Leu Gly Asp Asn Gly Ile Asp Leu Ile Glu
                210                 215                 220

Gln Pro Ile Ser Arg Ile Asn Arg Ala Gly Gln Val Arg Leu Asn Gln
        225                 230                 235                 240

Arg Ser Pro Ala Pro Ile Met Ala Asp Glu Ser Ile Glu Ser Val Glu
                            245                 250                 255

Asp Ala Phe Ser Leu Ala Ala Asp Gly Ala Ala Ser Ile Phe Ala Leu
                        260                 265                 270

Lys Ile Ala Lys Asn Gly Gly Pro Arg Ala Val Leu Arg Thr Ala Gln
                    275                 280                 285

Ile Ala Glu Ala Ala Gly Ile Ala Leu Tyr Gly Gly Thr Met Leu Glu
                290                 295                 300

Gly Ser Ile Gly Thr Leu Ala Ser Ala His Ala Phe Leu Thr Leu Arg
        305                 310                 315                 320

Gln Leu Thr Trp Gly Thr Glu Leu Phe Gly Pro Leu Leu Thr Glu
                            325                 330                 335

Glu Ile Val Asn Glu Pro Pro Gln Tyr Arg Asp Phe Gln Leu His Ile
                        340                 345                 350

Pro His Thr Pro Gly Leu Gly Leu Thr Leu Asp Glu Gln Arg Leu Ala
                    355                 360                 365

Arg Phe Ala Arg Arg
            370

<210> SEQ ID NO 27
<211> LENGTH: 288
<212> TYPE: DNA
<213> ORGANISM: Pseudomonas putida
<220> FEATURE:
<221> NAME/KEY: CDS
<222> LOCATION: (1)..(288)

<400> SEQUENCE: 27 atg ttg ttc cac gtg aag atg acc gtg aag ctg ccg gtc gac atg gac    48
Met Leu Phe His Val Lys Met Thr Val Lys Leu Pro Val Asp Met Asp
1               5                   10                  15 ccg gcc aag gcc gcc cag ctc aag gcc gac gaa aag gaa ctg gcc cag    96
Pro Ala Lys Ala Ala Gln Leu Lys Ala Asp Glu Lys Glu Leu Ala Gln
            20                  25                  30 cgc ctg cag cgc gaa ggc atc tgg cgt cac ctg tgg cgc att gcc ggg   144
```

```
Arg Leu Gln Arg Glu Gly Ile Trp Arg His Leu Trp Arg Ile Ala Gly
             35                  40                  45 cat tac gcc aac tac agc gtg ttc gat gtg ccc agc gtc gag gca ttg    192
His Tyr Ala Asn Tyr Ser Val Phe Asp Val Pro Ser Val Glu Ala Leu
 50                  55                  60 cat gac acg ctg atg cag ctg ccg ctg ttc ccg tac atg gat atc gag    240
His Asp Thr Leu Met Gln Leu Pro Leu Phe Pro Tyr Met Asp Ile Glu
 65                  70                  75                  80 gtc gac ggc ctg tgt cgg cat ccc tcg tct att cac agc gac gat cgc    288
Val Asp Gly Leu Cys Arg His Pro Ser Ser Ile His Ser Asp Asp Arg
                 85                  90                  95

<210> SEQ ID NO 28
<211> LENGTH: 96
<212> TYPE: PRT
<213> ORGANISM: Pseudomonas putida

<400> SEQUENCE: 28

Met Leu Phe His Val Lys Met Thr Val Lys Leu Pro Val Asp Met Asp
 1               5                  10                  15

Pro Ala Lys Ala Ala Gln Leu Lys Ala Asp Glu Lys Glu Leu Ala Gln
             20                  25                  30

Arg Leu Gln Arg Glu Gly Ile Trp Arg His Leu Trp Arg Ile Ala Gly
             35                  40                  45

His Tyr Ala Asn Tyr Ser Val Phe Asp Val Pro Ser Val Glu Ala Leu
 50                  55                  60

His Asp Thr Leu Met Gln Leu Pro Leu Phe Pro Tyr Met Asp Ile Glu
 65                  70                  75                  80

Val Asp Gly Leu Cys Arg His Pro Ser Ser Ile His Ser Asp Asp Arg
                 85                  90                  95

<210> SEQ ID NO 29
<211> LENGTH: 717
<212> TYPE: DNA
<213> ORGANISM: Pseudomonas putida
<220> FEATURE:
<221> NAME/KEY: CDS
<222> LOCATION: (1)..(717)

<400> SEQUENCE: 29 atg ccc gcc cag gac aac agc cgc ttc gtg atc cgt gat cgc aac tgg     48
Met Pro Ala Gln Asp Asn Ser Arg Phe Val Ile Arg Asp Arg Asn Trp
 1               5                  10                  15 cac cct aaa gcc ctt acg cct gac tac aag acc tcc gtt gcc cgc tcg     96
His Pro Lys Ala Leu Thr Pro Asp Tyr Lys Thr Ser Val Ala Arg Ser
             20                  25                  30 ccg cgc cag gca ctg gtc agc att ccg cag tcg atc agc gaa acc act    144
Pro Arg Gln Ala Leu Val Ser Ile Pro Gln Ser Ile Ser Glu Thr Thr
             35                  40                  45 ggt ccg gac ttt tcc cat ctg ggc ttc ggc gcc cac gac cat gac ctg    192
Gly Pro Asp Phe Ser His Leu Gly Phe Gly Ala His Asp His Asp Leu
 50                  55                  60 ctg ctg aac ttc aat aac ggt ggc ctg ccc att ggc gag cgc atc atc    240
Leu Leu Asn Phe Asn Asn Gly Gly Leu Pro Ile Gly Glu Arg Ile Ile
 65                  70                  75                  80 gtc gcc ggc cgt gtc gtc gac cag tac ggc aag cct gtg ccg aac act    288
Val Ala Gly Arg Val Val Asp Gln Tyr Gly Lys Pro Val Pro Asn Thr
                 85                  90                  95 ttg gtg gag atg tgg caa gcc aac gcc ggc ggc cgc tat cgc cac aag    336
Leu Val Glu Met Trp Gln Ala Asn Ala Gly Gly Arg Tyr Arg His Lys
                100                 105                 110
```

```
aac gat cgc tac ctg gcg ccc ctg gac ccg aac ttc ggt ggt gtt ggg     384
Asn Asp Arg Tyr Leu Ala Pro Leu Asp Pro Asn Phe Gly Gly Val Gly
        115                 120                 125 cgg tgt ctg acc gac cgt gac ggc tat tac agc ttc cgc acc atc aag     432
Arg Cys Leu Thr Asp Arg Asp Gly Tyr Tyr Ser Phe Arg Thr Ile Lys
130                 135                 140 ccg ggc ccg tac cca tgg cgc aac ggc ccg aac gac tgg cgc ccg gcg     480
Pro Gly Pro Tyr Pro Trp Arg Asn Gly Pro Asn Asp Trp Arg Pro Ala
145                 150                 155                 160 cat atc cac ttc gcc atc agc ggc cca tcg atc gcc acc aag ctg atc     528
His Ile His Phe Ala Ile Ser Gly Pro Ser Ile Ala Thr Lys Leu Ile
                165                 170                 175 acc cag ttg tac ttc gaa ggt gac ccg ctg atc ccg atg tgc ccg atc     576
Thr Gln Leu Tyr Phe Glu Gly Asp Pro Leu Ile Pro Met Cys Pro Ile
            180                 185                 190 gtc aag tcg atc gcc aac ccg caa gcc gtg cag cag ttg atc gcc aag     624
Val Lys Ser Ile Ala Asn Pro Gln Ala Val Gln Gln Leu Ile Ala Lys
        195                 200                 205 ctc gac atg agc aac gcc aac ccg atg gac tgc ctg gcc tac cgc ttt     672
Leu Asp Met Ser Asn Ala Asn Pro Met Asp Cys Leu Ala Tyr Arg Phe
210                 215                 220 gac atc gtg ctg cgc ggc cag cgc aag acc cac ttc gaa aac tgc         717
Asp Ile Val Leu Arg Gly Gln Arg Lys Thr His Phe Glu Asn Cys
225                 230                 235
```

<210> SEQ ID NO 30
<211> LENGTH: 239
<212> TYPE: PRT
<213> ORGANISM: Pseudomonas putida

<400> SEQUENCE: 30

```
Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
        35                  40                  45

Gly Pro Asp Phe Ser His Leu Gly Phe Gly Ala His Asp His Asp Leu
    50                  55                  60

Leu Leu Asn Phe Asn Asn Gly Leu Pro Ile Gly Glu Arg Ile
65                  70                  75                  80

Val Ala Gly Arg Val Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205
```

```
Leu Asp Met Ser Asn Ala Asn Pro Met Asp Cys Leu Ala Tyr Arg Phe
    210                 215                 220

Asp Ile Val Leu Arg Gly Gln Arg Lys Thr His Phe Glu Asn Cys
225                 230                 235

<210> SEQ ID NO 31
<211> LENGTH: 603
<212> TYPE: DNA
<213> ORGANISM: Pseudomonas putida
<220> FEATURE:
<221> NAME/KEY: CDS
<222> LOCATION: (1)..(603)

<400> SEQUENCE: 31 atg cca atc gaa ctg ctg ccg gaa acc cct tcg cag act gcc ggc ccc      48
Met Pro Ile Glu Leu Leu Pro Glu Thr Pro Ser Gln Thr Ala Gly Pro
1               5                   10                  15 tac gtg cac atc ggc ctg gcc ctg gaa gcc gcc ggc aac ccg acc cgc      96
Tyr Val His Ile Gly Leu Ala Leu Glu Ala Ala Gly Asn Pro Thr Arg
            20                  25                  30 gac cag gaa atc tgg aac tgc ctg gcc aag cca gac gcc ccg ggc gag    144
Asp Gln Glu Ile Trp Asn Cys Leu Ala Lys Pro Asp Ala Pro Gly Glu
        35                  40                  45 cac att ctg ctg atc ggc cac gta tat gac gga aac ggc cac ctg gtg    192
His Ile Leu Leu Ile Gly His Val Tyr Asp Gly Asn Gly His Leu Val
    50                  55                  60 cgc gac tcg ttc ctg gaa gtg tgg cag gcc gac gcc aac ggt gag tac    240
Arg Asp Ser Phe Leu Glu Val Trp Gln Ala Asp Ala Asn Gly Glu Tyr
65                  70                  75                  80 cag gat gcc tac aac ctg gaa aac gcc ttc aac agc ttt ggc cgc acg    288
Gln Asp Ala Tyr Asn Leu Glu Asn Ala Phe Asn Ser Phe Gly Arg Thr
                85                  90                  95 gct acc acc ttc gat gcc ggt gag tgg acg ctg caa acg gtc aag ccg    336
Ala Thr Thr Phe Asp Ala Gly Glu Trp Thr Leu Gln Thr Val Lys Pro
            100                 105                 110 ggt gtg gtg aac aac gct gct ggc gtg ccg atg gcg ccg cac atc aac    384
Gly Val Val Asn Asn Ala Ala Gly Val Pro Met Ala Pro His Ile Asn
        115                 120                 125 atc agc ctg ttt gcc cgt ggc atc aac atc cac ctg cac acg cgc ctg    432
Ile Ser Leu Phe Ala Arg Gly Ile Asn Ile His Leu His Thr Arg Leu
    130                 135                 140 tat ttc gat gat gag gcc cag gcc aat gcc aag tgc ccg gtg ctc aac    480
Tyr Phe Asp Asp Glu Ala Gln Ala Asn Ala Lys Cys Pro Val Leu Asn
145                 150                 155                 160 ctg atc gag cag ccg cag cgg cgt gaa acc ttg att gcc aag cgt tgc    528
Leu Ile Glu Gln Pro Gln Arg Arg Glu Thr Leu Ile Ala Lys Arg Cys
                165                 170                 175 gaa gtg gat ggg aag acg gcg tac cgc ttt gat atc cgc att cag ggg    576
Glu Val Asp Gly Lys Thr Ala Tyr Arg Phe Asp Ile Arg Ile Gln Gly
            180                 185                 190 gaa ggg gag acc gtc ttc ttc gac ttc                                 603
Glu Gly Glu Thr Val Phe Phe Asp Phe
        195                 200

<210> SEQ ID NO 32
<211> LENGTH: 201
<212> TYPE: PRT
<213> ORGANISM: Pseudomonas putida

<400> SEQUENCE: 32

Met Pro Ile Glu Leu Leu Pro Glu Thr Pro Ser Gln Thr Ala Gly Pro
```

```
 1               5                   10                  15
Tyr Val His Ile Gly Leu Ala Leu Glu Ala Ala Gly Asn Pro Thr Arg
            20                  25                  30

Asp Gln Glu Ile Trp Asn Cys Leu Ala Lys Pro Asp Ala Pro Gly Glu
                35                  40                  45

His Ile Leu Leu Ile Gly His Val Tyr Asp Gly Asn Gly His Leu Val
    50                  55                  60

Arg Asp Ser Phe Leu Glu Val Trp Gln Ala Asp Ala Asn Gly Glu Tyr
65                  70                  75                  80

Gln Asp Ala Tyr Asn Leu Glu Asn Ala Phe Asn Ser Phe Gly Arg Thr
                85                  90                  95

Ala Thr Thr Phe Asp Ala Gly Glu Trp Thr Leu Gln Thr Val Lys Pro
                100                 105                 110

Gly Val Val Asn Asn Ala Ala Gly Val Pro Met Ala Pro His Ile Asn
            115                 120                 125

Ile Ser Leu Phe Ala Arg Gly Ile Asn Ile His Leu His Thr Arg Leu
130                 135                 140

Tyr Phe Asp Asp Glu Ala Gln Ala Asn Ala Lys Cys Pro Val Leu Asn
145                 150                 155                 160

Leu Ile Glu Gln Pro Gln Arg Arg Glu Thr Leu Ile Ala Lys Arg Cys
                165                 170                 175

Glu Val Asp Gly Lys Thr Ala Tyr Arg Phe Asp Ile Arg Ile Gln Gly
            180                 185                 190

Glu Gly Glu Thr Val Phe Phe Asp Phe
        195                 200

<210> SEQ ID NO 33
<211> LENGTH: 1350
<212> TYPE: DNA
<213> ORGANISM: Pseudomonas putida
<220> FEATURE:
<221> NAME/KEY: CDS
<222> LOCATION: (1)..(1350)

<400> SEQUENCE: 33 atg agc aac caa ctg ttc gac gcc tat ttc acc gcg ccg gcc atg cgc      48
Met Ser Asn Gln Leu Phe Asp Ala Tyr Phe Thr Ala Pro Ala Met Arg
1               5                   10                  15 gag att ttc tcc gac cga ggc cgc ctg cag ggc atg ctg gat ttc gaa      96
Glu Ile Phe Ser Asp Arg Gly Arg Leu Gln Gly Met Leu Asp Phe Glu
            20                  25                  30 gcc gcg ctt gcc cga gcc gaa gcc tct gcc ggt ttg gtc ccg cac agc     144
Ala Ala Leu Ala Arg Ala Glu Ala Ser Ala Gly Leu Val Pro His Ser
        35                  40                  45 gcg gta gcg gcc atc gag gcg gca tgc cag gcc gag cgc tat gac gtt     192
Ala Val Ala Ala Ile Glu Ala Ala Cys Gln Ala Glu Arg Tyr Asp Val
    50                  55                  60 ggc gcg ctg gcc aat gcc atc gcc acc gcg ggc aac tcg gcc att ccg     240
Gly Ala Leu Ala Asn Ala Ile Ala Thr Ala Gly Asn Ser Ala Ile Pro
65                  70                  75                  80 ctg gtg aaa gcg ttg ggc aag gtg atc gcc acc ggc gtg cca gag gct     288
Leu Val Lys Ala Leu Gly Lys Val Ile Ala Thr Gly Val Pro Glu Ala
                85                  90                  95 gag cgc tat gtg cac ctt ggg gcc acc agc cag gat gcg atg gat acc     336
Glu Arg Tyr Val His Leu Gly Ala Thr Ser Gln Asp Ala Met Asp Thr
            100                 105                 110 ggt ctg gtt ctg cag ctg cgc gat gcc ctc gat ttg atc gag gcc gac     384
Gly Leu Val Leu Gln Leu Arg Asp Ala Leu Asp Leu Ile Glu Ala Asp
```

```
                115                 120                 125
ctc ggc aag ctg gcc gat acc ctg tcg cag cag gcc ttg aag cac gcc         432
Leu Gly Lys Leu Ala Asp Thr Leu Ser Gln Gln Ala Leu Lys His Ala
        130                 135                 140 gat acg ccc ttg gtg ggt cgt acc tgg ttg caa cac gcc acc ccg gtg         480
Asp Thr Pro Leu Val Gly Arg Thr Trp Leu Gln His Ala Thr Pro Val
145                 150                 155                 160 acc ctg ggc atg aaa ctg gcc ggt gta ctg ggt gct ttg acc cgc cac         528
Thr Leu Gly Met Lys Leu Ala Gly Val Leu Gly Ala Leu Thr Arg His
                165                 170                 175 cgt cag cgc ctg cag gaa ctg cgc ccg cgc ctt ctg gtc ctg cag ttc         576
Arg Gln Arg Leu Gln Glu Leu Arg Pro Arg Leu Leu Val Leu Gln Phe
        180                 185                 190 ggc ggt gcc tcg ggc agc ctg gcg gcg ctg ggc agc aag gcg atg ccg         624
Gly Gly Ala Ser Gly Ser Leu Ala Ala Leu Gly Ser Lys Ala Met Pro
                195                 200                 205 gtg gcc gaa gcg ctg gcc gaa cag ctc aag ctg acc ctg ccc gag cag         672
Val Ala Glu Ala Leu Ala Glu Gln Leu Lys Leu Thr Leu Pro Glu Gln
        210                 215                 220 ccc tgg cac acc cag cgc gac cgc ctg gtg gag ttt gcc tcg gta ttg         720
Pro Trp His Thr Gln Arg Asp Arg Leu Val Glu Phe Ala Ser Val Leu
225                 230                 235                 240 ggc ctg gtt gcc ggc agc ctg ggc aag ttc ggc cgt gat atc agc ttg         768
Gly Leu Val Ala Gly Ser Leu Gly Lys Phe Gly Arg Asp Ile Ser Leu
                245                 250                 255 ctg atg caa acc gag gcg ggg gag gtg ttt gag cct tct gcg ccg ggc         816
Leu Met Gln Thr Glu Ala Gly Glu Val Phe Glu Pro Ser Ala Pro Gly
        260                 265                 270 aag ggt ggt tct tcg acc atg cca cac aag cgc aac ccg gtg ggt gcc         864
Lys Gly Gly Ser Ser Thr Met Pro His Lys Arg Asn Pro Val Gly Ala
                275                 280                 285 gcc gtg ttg atc ggt gcc gcg acc cgc gtg ccg ggc ctg ctg tcg acg         912
Ala Val Leu Ile Gly Ala Ala Thr Arg Val Pro Gly Leu Leu Ser Thr
        290                 295                 300 ctg ttc gca gcc atg cct cag gag cac gaa cgc agc ctg ggc cta tgg         960
Leu Phe Ala Ala Met Pro Gln Glu His Glu Arg Ser Leu Gly Leu Trp
305                 310                 315                 320 cat gcc gag tgg gaa acc ctg ccg gat atc tgc tgc ctg gtc tct ggc        1008
His Ala Glu Trp Glu Thr Leu Pro Asp Ile Cys Cys Leu Val Ser Gly
                325                 330                 335 gcc ctg cgc cag gct caa gtg att gcc gag ggc atg gag gtg gat gcc        1056
Ala Leu Arg Gln Ala Gln Val Ile Ala Glu Gly Met Glu Val Asp Ala
        340                 345                 350 gcg cgc atg cgc cgt aac ctc gac ctg acc caa ggc ctg gtg ctg gcc        1104
Ala Arg Met Arg Arg Asn Leu Asp Leu Thr Gln Gly Leu Val Leu Ala
                355                 360                 365 gaa gcg gtg agc atc gtc ctc gcc cag cgt ctg ggt cgc gac cgt gcc        1152
Glu Ala Val Ser Ile Val Leu Ala Gln Arg Leu Gly Arg Asp Arg Ala
        370                 375                 380 cac cac ctg ctg gaa caa tgc tgc caa cgc gcg gtg gcc gaa cag cgg        1200
His His Leu Leu Glu Gln Cys Cys Gln Arg Ala Val Ala Glu Gln Arg
385                 390                 395                 400 cac ctg cgt gcc gtg ctg ggt gac gag ccg cag gtc agc gcc gag ctg        1248
His Leu Arg Ala Val Leu Gly Asp Glu Pro Gln Val Ser Ala Glu Leu
                405                 410                 415 tct ggc gaa gaa ctc gat cgc ctg ctc gac cct gcc cat tac ctg ggc        1296
Ser Gly Glu Glu Leu Asp Arg Leu Leu Asp Pro Ala His Tyr Leu Gly
        420                 425                 430 cag gcc cgc gtc tgg gtg gcg cgc gcc gtg tcc gaa cat caa cgt ttc        1344
```

```
Gln Ala Arg Val Trp Val Ala Arg Ala Val Ser Glu His Gln Arg Phe
            435                 440                 445 act gcc                                                              1350
Thr Ala
    450

<210> SEQ ID NO 34
<211> LENGTH: 450
<212> TYPE: PRT
<213> ORGANISM: Pseudomonas putida

<400> SEQUENCE: 34

Met Ser Asn Gln Leu Phe Asp Ala Tyr Phe Thr Ala Pro Ala Met Arg
1               5                   10                  15

Glu Ile Phe Ser Asp Arg Gly Arg Leu Gln Gly Met Leu Asp Phe Glu
            20                  25                  30

Ala Ala Leu Ala Arg Ala Glu Ala Ser Ala Gly Leu Val Pro His Ser
        35                  40                  45

Ala Val Ala Ala Ile Glu Ala Ala Cys Gln Ala Glu Arg Tyr Asp Val
    50                  55                  60

Gly Ala Leu Ala Asn Ala Ile Ala Thr Ala Gly Asn Ser Ala Ile Pro
65                  70                  75                  80

Leu Val Lys Ala Leu Gly Lys Val Ile Ala Thr Gly Val Pro Glu Ala
                85                  90                  95

Glu Arg Tyr Val His Leu Gly Ala Thr Ser Gln Asp Ala Met Asp Thr
            100                 105                 110

Gly Leu Val Leu Gln Leu Arg Asp Ala Leu Asp Leu Ile Glu Ala Asp
        115                 120                 125

Leu Gly Lys Leu Ala Asp Thr Leu Ser Gln Gln Ala Leu Lys His Ala
    130                 135                 140

Asp Thr Pro Leu Val Gly Arg Thr Trp Leu Gln His Ala Thr Pro Val
145                 150                 155                 160

Thr Leu Gly Met Lys Leu Ala Gly Val Leu Gly Ala Leu Thr Arg His
                165                 170                 175

Arg Gln Arg Leu Gln Glu Leu Arg Pro Arg Leu Leu Val Leu Gln Phe
            180                 185                 190

Gly Gly Ala Ser Gly Ser Leu Ala Ala Leu Gly Ser Lys Ala Met Pro
        195                 200                 205

Val Ala Glu Ala Leu Ala Glu Gln Leu Lys Leu Thr Leu Pro Glu Gln
    210                 215                 220

Pro Trp His Thr Gln Arg Asp Arg Leu Val Glu Phe Ala Ser Val Leu
225                 230                 235                 240

Gly Leu Val Ala Gly Ser Leu Gly Lys Phe Gly Arg Asp Ile Ser Leu
                245                 250                 255

Leu Met Gln Thr Glu Ala Gly Glu Val Phe Glu Pro Ser Ala Pro Gly
            260                 265                 270

Lys Gly Gly Ser Ser Thr Met Pro His Lys Arg Asn Pro Val Gly Ala
        275                 280                 285

Ala Val Leu Ile Gly Ala Ala Thr Arg Val Pro Gly Leu Leu Ser Thr
    290                 295                 300

Leu Phe Ala Ala Met Pro Gln Glu His Glu Arg Ser Leu Gly Leu Trp
305                 310                 315                 320

His Ala Glu Trp Glu Thr Leu Pro Asp Ile Cys Cys Leu Val Ser Gly
                325                 330                 335

Ala Leu Arg Gln Ala Gln Val Ile Ala Glu Gly Met Glu Val Asp Ala
```

```
            340                 345                 350
Ala Arg Met Arg Arg Asn Leu Asp Leu Thr Gln Gly Leu Val Leu Ala
            355                 360                 365

Glu Ala Val Ser Ile Val Leu Ala Gln Arg Leu Gly Arg Asp Arg Ala
            370                 375                 380

His His Leu Leu Glu Gln Cys Cys Gln Arg Ala Val Ala Glu Gln Arg
385                 390                 395                 400

His Leu Arg Ala Val Leu Gly Asp Glu Pro Gln Val Ser Ala Glu Leu
                405                 410                 415

Ser Gly Glu Glu Leu Asp Arg Leu Leu Asp Pro Ala His Tyr Leu Gly
            420                 425                 430

Gln Ala Arg Val Trp Val Ala Arg Ala Val Ser Glu His Gln Arg Phe
            435                 440                 445

Thr Ala
    450

<210> SEQ ID NO 35
<211> LENGTH: 390
<212> TYPE: DNA
<213> ORGANISM: Pseudomonas putida
<220> FEATURE:
<221> NAME/KEY: CDS
<222> LOCATION: (1)..(390)

<400> SEQUENCE: 35 atg gac gag aaa caa cgt tac gac gct ggc atg caa gtg cgc cgc gca    48
Met Asp Glu Lys Gln Arg Tyr Asp Ala Gly Met Gln Val Arg Arg Ala
1               5                   10                  15 gtg ctg ggt gat gcc cac gtg gac cgc agc ctg gag aag ctc aac gac    96
Val Leu Gly Asp Ala His Val Asp Arg Ser Leu Glu Lys Leu Asn Asp
            20                  25                  30 ttc aat ggc gag ttc cag gaa atg atc acc cgc cac gcc tgg ggt gac   144
Phe Asn Gly Glu Phe Gln Glu Met Ile Thr Arg His Ala Trp Gly Asp
        35                  40                  45 atc tgg acc cgc ccg ggg ctg ccg cgc cat acc cgc agc ctg atc acc   192
Ile Trp Thr Arg Pro Gly Leu Pro Arg His Thr Arg Ser Leu Ile Thr
    50                  55                  60 atc gcc atg ctg att ggc atg aac cgc aac gac gag ctg aag ctg cac   240
Ile Ala Met Leu Ile Gly Met Asn Arg Asn Asp Glu Leu Lys Leu His
65                  70                  75                  80 ctg cgt gcg gcg gcc aac aat ggc gtg acc cgc gac gag atc aag gaa   288
Leu Arg Ala Ala Ala Asn Asn Gly Val Thr Arg Asp Glu Ile Lys Glu
                85                  90                  95 gtg ctg atg cag agc gcg atc tac tgc ggc att ccg gcg gcc aat gcc   336
Val Leu Met Gln Ser Ala Ile Tyr Cys Gly Ile Pro Ala Ala Asn Ala
            100                 105                 110 acg ttc cac ctg gct gag tcg gtg tgg gat gaa ctt ggc gta gag tct   384
Thr Phe His Leu Ala Glu Ser Val Trp Asp Glu Leu Gly Val Glu Ser
        115                 120                 125 cgc cag                                                             390
Arg Gln
    130

<210> SEQ ID NO 36
<211> LENGTH: 130
<212> TYPE: PRT
<213> ORGANISM: Pseudomonas putida

<400> SEQUENCE: 36

Met Asp Glu Lys Gln Arg Tyr Asp Ala Gly Met Gln Val Arg Arg Ala
```

```
                1               5                   10                  15
            Val Leu Gly Asp Ala His Val Asp Arg Ser Leu Glu Lys Leu Asn Asp
                        20                  25                  30

Phe Asn Gly Glu Phe Gln Glu Met Ile Thr Arg His Ala Trp Gly Asp
                        35                  40                  45

Ile Trp Thr Arg Pro Gly Leu Pro Arg His Thr Arg Ser Leu Ile Thr
             50                  55                  60

Ile Ala Met Leu Ile Gly Met Asn Arg Asn Asp Glu Leu Lys Leu His
             65                  70                  75                  80

Leu Arg Ala Ala Ala Asn Asn Gly Val Thr Arg Asp Glu Ile Lys Glu
                        85                  90                  95

Val Leu Met Gln Ser Ala Ile Tyr Cys Gly Ile Pro Ala Ala Asn Ala
                        100                 105                 110

Thr Phe His Leu Ala Glu Ser Val Trp Asp Glu Leu Gly Val Glu Ser
                        115                 120                 125

Arg Gln
                130

<210> SEQ ID NO 37
<211> LENGTH: 789
<212> TYPE: DNA
<213> ORGANISM: Pseudomonas putida
<220> FEATURE:
<221> NAME/KEY: CDS
<222> LOCATION: (1)..(789)

<400> SEQUENCE: 37 gtg gcg cac ttg caa ctg gcc gat ggc gtt ttg aat tac cag atc gat        48
Val Ala His Leu Gln Leu Ala Asp Gly Val Leu Asn Tyr Gln Ile Asp
  1               5                   10                  15 ggc ccg gat gac gcc ccg gtg ctg gtc ctg tcc aac tcg ctg ggt acc        96
Gly Pro Asp Asp Ala Pro Val Leu Val Leu Ser Asn Ser Leu Gly Thr
                20                  25                  30 gac ctg ggc atg tgg gac acc cag att ccg ctc tgg agt cag cac ttc        144
Asp Leu Gly Met Trp Asp Thr Gln Ile Pro Leu Trp Ser Gln His Phe
            35                  40                  45 cgg gtg ctg cgc tat gac acc cgt ggt cac ggc gca tcg ctg gtc act        192
Arg Val Leu Arg Tyr Asp Thr Arg Gly His Gly Ala Ser Leu Val Thr
 50                  55                  60 gaa ggc cct tac agc atc gaa cag ctg ggc cgc gac gtg ctg gcc ctg        240
Glu Gly Pro Tyr Ser Ile Glu Gln Leu Gly Arg Asp Val Leu Ala Leu
 65                  70                  75                  80 ctc gat ggc ctg gac att caa aag gct cac ttc gtc ggc ctg tcg atg        288
Leu Asp Gly Leu Asp Ile Gln Lys Ala His Phe Val Gly Leu Ser Met
                85                  90                  95 ggc ggc ctg atc ggc cag tgg ctg ggt atc cat gca ggt gag cgc ctg        336
Gly Gly Leu Ile Gly Gln Trp Leu Gly Ile His Ala Gly Glu Arg Leu
            100                 105                 110 cac agc ctg acc ctg tgc aac acg gcc gcc aag atc gcc aat gac gag        384
His Ser Leu Thr Leu Cys Asn Thr Ala Ala Lys Ile Ala Asn Asp Glu
            115                 120                 125 gtg tgg aac acc cgt atc gac acg gta ctc aaa ggc ggc cag cag gcc        432
Val Trp Asn Thr Arg Ile Asp Thr Val Leu Lys Gly Gly Gln Gln Ala
            130                 135                 140 atg gtc gac ctg cgc gat gcc tcc atc gcc cgc tgg ttc acc ccg ggc        480
Met Val Asp Leu Arg Asp Ala Ser Ile Ala Arg Trp Phe Thr Pro Gly
145                 150                 155                 160 ttt gcc cag gcg cag gcg gag cag gcc cag cgt atc tgc cag atg ctg        528
Phe Ala Gln Ala Gln Ala Glu Gln Ala Gln Arg Ile Cys Gln Met Leu
```

```
                              165                 170                 175
gcg caa acc agc ccg caa ggc tac gca ggc aac tgt gca gcg gta cgt         576
Ala Gln Thr Ser Pro Gln Gly Tyr Ala Gly Asn Cys Ala Ala Val Arg
            180                 185                 190 gac gct gat tat cgt gag caa ctg ggc cgc atc cag gtg cct gcg ctg         624
Asp Ala Asp Tyr Arg Glu Gln Leu Gly Arg Ile Gln Val Pro Ala Leu
        195                 200                 205 atc gtt gcc ggt acc caa gac gtg gtt acc acc cct gag cat ggc cgc         672
Ile Val Ala Gly Thr Gln Asp Val Val Thr Thr Pro Glu His Gly Arg
    210                 215                 220 ttc atg cag gcc ggt atc caa ggt gcc gag tac gtc gac ttc ccg gcg         720
Phe Met Gln Ala Gly Ile Gln Gly Ala Glu Tyr Val Asp Phe Pro Ala
225                 230                 235                 240 gcg cac ctg tcc aat gtc gag att ggc gag gcc ttc agc cgc cgc gtg         768
Ala His Leu Ser Asn Val Glu Ile Gly Glu Ala Phe Ser Arg Arg Val
                245                 250                 255 ctc gat ttc ctg ctg gct cac                                             789
Leu Asp Phe Leu Leu Ala His
                260
```

<210> SEQ ID NO 38
<211> LENGTH: 263
<212> TYPE: PRT
<213> ORGANISM: Pseudomonas putida

<400> SEQUENCE: 38

```
Val Ala His Leu Gln Leu Ala Asp Gly Val Leu Asn Tyr Gln Ile Asp
1               5                   10                  15

Gly Pro Asp Asp Ala Pro Val Leu Val Leu Ser Asn Ser Leu Gly Thr
                20                  25                  30

Asp Leu Gly Met Trp Asp Thr Gln Ile Pro Leu Trp Ser Gln His Phe
            35                  40                  45

Arg Val Leu Arg Tyr Asp Thr Arg Gly His Gly Ala Ser Leu Val Thr
        50                  55                  60

Glu Gly Pro Tyr Ser Ile Glu Gln Leu Gly Arg Asp Val Leu Ala Leu
65                  70                  75                  80

Leu Asp Gly Leu Asp Ile Gln Lys Ala His Phe Val Gly Leu Ser Met
                85                  90                  95

Gly Gly Leu Ile Gly Gln Trp Leu Gly Ile His Ala Gly Glu Arg Leu
            100                 105                 110

His Ser Leu Thr Leu Cys Asn Thr Ala Ala Lys Ile Ala Asn Asp Glu
        115                 120                 125

Val Trp Asn Thr Arg Ile Asp Thr Val Leu Lys Gly Gln Gln Ala
    130                 135                 140

Met Val Asp Leu Arg Asp Ala Ser Ile Ala Arg Trp Phe Thr Pro Gly
145                 150                 155                 160

Phe Ala Gln Ala Gln Ala Glu Gln Ala Gln Arg Ile Cys Gln Met Leu
                165                 170                 175

Ala Gln Thr Ser Pro Gln Gly Tyr Ala Gly Asn Cys Ala Ala Val Arg
            180                 185                 190

Asp Ala Asp Tyr Arg Glu Gln Leu Gly Arg Ile Gln Val Pro Ala Leu
        195                 200                 205

Ile Val Ala Gly Thr Gln Asp Val Val Thr Thr Pro Glu His Gly Arg
    210                 215                 220

Phe Met Gln Ala Gly Ile Gln Gly Ala Glu Tyr Val Asp Phe Pro Ala
225                 230                 235                 240
```

```
Ala His Leu Ser Asn Val Glu Ile Gly Glu Ala Phe Ser Arg Arg Val
                245                 250                 255

Leu Asp Phe Leu Leu Ala His
        260
```

<210> SEQ ID NO 39
<211> LENGTH: 693
<212> TYPE: DNA
<213> ORGANISM: Pseudomonas putida
<220> FEATURE:
<221> NAME/KEY: CDS
<222> LOCATION: (1)..(693)

<400> SEQUENCE: 39

```
ttg atc aat aaa acg tac gag tcc atc gcc agc gcg gtg gaa ggg att        48
Leu Ile Asn Lys Thr Tyr Glu Ser Ile Ala Ser Ala Val Glu Gly Ile
1               5                   10                  15 acc gac ggt tcg acc atc atg gtc ggt ggc ttc ggc acg gct ggc atg        96
Thr Asp Gly Ser Thr Ile Met Val Gly Gly Phe Gly Thr Ala Gly Met
            20                  25                  30 ccg tcc gag ctg atc gat ggc ctc att gcc acc ggt gcc cgc gac ctg       144
Pro Ser Glu Leu Ile Asp Gly Leu Ile Ala Thr Gly Ala Arg Asp Leu
        35                  40                  45 acc atc atc agc aac aac gcc ggc aac ggc gag atc ggc ctg gcc gcc       192
Thr Ile Ile Ser Asn Asn Ala Gly Asn Gly Glu Ile Gly Leu Ala Ala
    50                  55                  60 ctg ctc atg gca ggc agc gtg cgc aag gtg gtc tgc tcg ttc ccg cgc       240
Leu Leu Met Ala Gly Ser Val Arg Lys Val Val Cys Ser Phe Pro Arg
65                  70                  75                  80 cag tcc gac tcc tac gtg ttc gac gaa ctg tac cgc gcc ggc aag atc       288
Gln Ser Asp Ser Tyr Val Phe Asp Glu Leu Tyr Arg Ala Gly Lys Ile
                85                  90                  95 gag ctg gaa gtg gtc ccg cag ggc aac ctg gcc gag cgt atc cgc gcc       336
Glu Leu Glu Val Val Pro Gln Gly Asn Leu Ala Glu Arg Ile Arg Ala
            100                 105                 110 gca ggc tcc ggc att ggt gcg ttc ttc tcg cca acc ggc tac ggc acc       384
Ala Gly Ser Gly Ile Gly Ala Phe Phe Ser Pro Thr Gly Tyr Gly Thr
        115                 120                 125 ctg ctg gcc gag ggc aag gaa acc cgt gag atc gat ggc cgc atg tac       432
Leu Leu Ala Glu Gly Lys Glu Thr Arg Glu Ile Asp Gly Arg Met Tyr
    130                 135                 140 gtg ctg gaa atg ccg ctg cac gcc gac ttc gca ctg atc aag gcg cac       480
Val Leu Glu Met Pro Leu His Ala Asp Phe Ala Leu Ile Lys Ala His
145                 150                 155                 160 aag ggt gac cgt tgg ggc aac ctg acc tac cgc aag gcc gcc cgc aac       528
Lys Gly Asp Arg Trp Gly Asn Leu Thr Tyr Arg Lys Ala Ala Arg Asn
                165                 170                 175 ttc ggc ccg atc atg gcc atg gct gcc aag acc gcc atc gcc cag gtc       576
Phe Gly Pro Ile Met Ala Met Ala Ala Lys Thr Ala Ile Ala Gln Val
            180                 185                 190 gac cag gtc gtc gaa ctc ggt gaa ctg gac ccg gaa cac atc atc acc       624
Asp Gln Val Val Glu Leu Gly Glu Leu Asp Pro Glu His Ile Ile Thr
        195                 200                 205 ccg ggt atc ttc gtc cag cgc gtg gtc gcc gtc acc ggt gct gcc gct       672
Pro Gly Ile Phe Val Gln Arg Val Val Ala Val Thr Gly Ala Ala Ala
    210                 215                 220 tct tcg att gcc aaa gct gtc                                           693
Ser Ser Ile Ala Lys Ala Val
225                 230
```

<210> SEQ ID NO 40

<211> LENGTH: 231
<212> TYPE: PRT
<213> ORGANISM: Pseudomonas putida

<400> SEQUENCE: 40

```
Leu Ile Asn Lys Thr Tyr Glu Ser Ile Ala Ser Ala Val Glu Gly Ile
1               5                   10                  15

Thr Asp Gly Ser Thr Ile Met Val Gly Gly Phe Gly Thr Ala Gly Met
            20                  25                  30

Pro Ser Glu Leu Ile Asp Gly Leu Ile Ala Thr Gly Ala Arg Asp Leu
        35                  40                  45

Thr Ile Ile Ser Asn Asn Ala Gly Asn Gly Glu Ile Gly Leu Ala Ala
    50                  55                  60

Leu Leu Met Ala Gly Ser Val Arg Lys Val Val Cys Ser Phe Pro Arg
65                  70                  75                  80

Gln Ser Asp Ser Tyr Val Phe Asp Glu Leu Tyr Arg Ala Gly Lys Ile
                85                  90                  95

Glu Leu Glu Val Val Pro Gln Gly Asn Leu Ala Glu Arg Ile Arg Ala
            100                 105                 110

Ala Gly Ser Gly Ile Gly Ala Phe Phe Ser Pro Thr Gly Tyr Gly Thr
        115                 120                 125

Leu Leu Ala Glu Gly Lys Glu Thr Arg Glu Ile Asp Gly Arg Met Tyr
    130                 135                 140

Val Leu Glu Met Pro Leu His Ala Asp Phe Ala Leu Ile Lys Ala His
145                 150                 155                 160

Lys Gly Asp Arg Trp Gly Asn Leu Thr Tyr Arg Lys Ala Ala Arg Asn
                165                 170                 175

Phe Gly Pro Ile Met Ala Met Ala Ala Lys Thr Ala Ile Ala Gln Val
            180                 185                 190

Asp Gln Val Val Glu Leu Gly Glu Leu Asp Pro Glu His Ile Ile Thr
        195                 200                 205

Pro Gly Ile Phe Val Gln Arg Val Val Ala Val Thr Gly Ala Ala Ala
    210                 215                 220

Ser Ser Ile Ala Lys Ala Val
225                 230
```

<210> SEQ ID NO 41
<211> LENGTH: 639
<212> TYPE: DNA
<213> ORGANISM: Pseudomonas putida
<220> FEATURE:
<221> NAME/KEY: CDS
<222> LOCATION: (1)..(639)

<400> SEQUENCE: 41

```
atg acc atc acc aaa aag ctc tcc cgc acc gag atg gcc caa cgc gtg        48
Met Thr Ile Thr Lys Lys Leu Ser Arg Thr Glu Met Ala Gln Arg Val
1               5                   10                  15 gcc gca gac atc cag gaa ggc gcg tac gta aac ctg ggc atc ggc gca        96
Ala Ala Asp Ile Gln Glu Gly Ala Tyr Val Asn Leu Gly Ile Gly Ala
            20                  25                  30 ccg acc ctg gtg gcc aac tac ctg ggc gac aag gaa gtg ttc ctg cac       144
Pro Thr Leu Val Ala Asn Tyr Leu Gly Asp Lys Glu Val Phe Leu His
        35                  40                  45 agc gag aac ggc ctg ctg ggc atg ggc cca agc cct gcg ccg ggc gag       192
Ser Glu Asn Gly Leu Leu Gly Met Gly Pro Ser Pro Ala Pro Gly Glu
    50                  55                  60 gaa gac gat gac ctg atc aac gcc ggc aag cag cac gtc acc ctg ctg       240
```

```
Glu Asp Asp Asp Leu Ile Asn Ala Gly Lys Gln His Val Thr Leu Leu
65                  70                  75                  80 acc ggt ggt gcc ttc ttc cac cat gcc gat tcg ttc tcg atg atg cgt        288
Thr Gly Gly Ala Phe Phe His His Ala Asp Ser Phe Ser Met Met Arg
                    85                  90                  95 ggc ggc cac ctg gac atc gct gta ctg ggc gcc ttc cag gtg tcg gtc        336
Gly Gly His Leu Asp Ile Ala Val Leu Gly Ala Phe Gln Val Ser Val
                100                 105                 110 aag ggc gac ctg gcc aac tgg cac acg ggt gcc gaa ggc tcg atc ccg        384
Lys Gly Asp Leu Ala Asn Trp His Thr Gly Ala Glu Gly Ser Ile Pro
            115                 120                 125 gcc gta ggc ggt gca atg gac ctg gcc acc ggc gcc cgc cag gtg ttc        432
Ala Val Gly Gly Ala Met Asp Leu Ala Thr Gly Ala Arg Gln Val Phe
        130                 135                 140 gtg atg atg gac cac ctg acc aag acc ggc gaa agc aag ctg gtg ccc        480
Val Met Met Asp His Leu Thr Lys Thr Gly Glu Ser Lys Leu Val Pro
145                 150                 155                 160 gag tgc acc tac ccg ctg acc ggt atc gct tgc gtc agc cgc atc tac        528
Glu Cys Thr Tyr Pro Leu Thr Gly Ile Ala Cys Val Ser Arg Ile Tyr
                165                 170                 175 acc gac ctg gcc gta ctg gaa gtg aca cct gaa ggg ctg aaa gtg gtc        576
Thr Asp Leu Ala Val Leu Glu Val Thr Pro Glu Gly Leu Lys Val Val
            180                 185                 190 gaa atc tgc gcg gac atc gac ttt gac gag ctg cag aaa ctc agt ggc        624
Glu Ile Cys Ala Asp Ile Asp Phe Asp Glu Leu Gln Lys Leu Ser Gly
        195                 200                 205 gtg ccg ctg atc aag                                                    639
Val Pro Leu Ile Lys
    210

<210> SEQ ID NO 42
<211> LENGTH: 213
<212> TYPE: PRT
<213> ORGANISM: Pseudomonas putida

<400> SEQUENCE: 42

Met Thr Ile Thr Lys Lys Leu Ser Arg Thr Glu Met Ala Gln Arg Val
1               5                   10                  15

Ala Ala Asp Ile Gln Glu Gly Ala Tyr Val Asn Leu Gly Ile Gly Ala
                20                  25                  30

Pro Thr Leu Val Ala Asn Tyr Leu Gly Asp Lys Glu Val Phe Leu His
            35                  40                  45

Ser Glu Asn Gly Leu Leu Gly Met Gly Pro Ser Pro Ala Pro Gly Glu
        50                  55                  60

Glu Asp Asp Asp Leu Ile Asn Ala Gly Lys Gln His Val Thr Leu Leu
65                  70                  75                  80

Thr Gly Gly Ala Phe Phe His His Ala Asp Ser Phe Ser Met Met Arg
                85                  90                  95

Gly Gly His Leu Asp Ile Ala Val Leu Gly Ala Phe Gln Val Ser Val
                100                 105                 110

Lys Gly Asp Leu Ala Asn Trp His Thr Gly Ala Glu Gly Ser Ile Pro
            115                 120                 125

Ala Val Gly Gly Ala Met Asp Leu Ala Thr Gly Ala Arg Gln Val Phe
        130                 135                 140

Val Met Met Asp His Leu Thr Lys Thr Gly Glu Ser Lys Leu Val Pro
145                 150                 155                 160

Glu Cys Thr Tyr Pro Leu Thr Gly Ile Ala Cys Val Ser Arg Ile Tyr
                165                 170                 175
```

```
Thr Asp Leu Ala Val Leu Glu Val Thr Pro Glu Gly Leu Lys Val Val
            180                 185                 190

Glu Ile Cys Ala Asp Ile Asp Phe Asp Glu Leu Gln Lys Leu Ser Gly
            195                 200                 205

Val Pro Leu Ile Lys
        210

<210> SEQ ID NO 43
<211> LENGTH: 1200
<212> TYPE: DNA
<213> ORGANISM: Pseudomonas putida
<220> FEATURE:
<221> NAME/KEY: CDS
<222> LOCATION: (1)..(1200)

<400> SEQUENCE: 43 atg cac gac gta ttc atc tgt gac gcc atc cgt acc ccg atc ggc cgc      48
Met His Asp Val Phe Ile Cys Asp Ala Ile Arg Thr Pro Ile Gly Arg
1               5                   10                  15 ttc ggc ggc gcc ctg gcc agc gtg cgg gcc gac gac ctg gcc gcc gtg      96
Phe Gly Gly Ala Leu Ala Ser Val Arg Ala Asp Asp Leu Ala Ala Val
                20                  25                  30 ccg ctg aag gcg ctg atc gag cgc aac cct ggc gtg cag tgg gac cag     144
Pro Leu Lys Ala Leu Ile Glu Arg Asn Pro Gly Val Gln Trp Asp Gln
            35                  40                  45 gta gac gaa gtg ttc ttc ggc tgc gcc aac cag gcc ggt gaa gac aac     192
Val Asp Glu Val Phe Phe Gly Cys Ala Asn Gln Ala Gly Glu Asp Asn
        50                  55                  60 cgc aac gtg gcc cgc atg gca ctg ctg ctg gcc ggc ctg ccg gaa agc     240
Arg Asn Val Ala Arg Met Ala Leu Leu Leu Ala Gly Leu Pro Glu Ser
65                  70                  75                  80 atc ccg ggc gtc acc ctg aac cgt ctg tgc gcg tcg ggc atg gat gcc     288
Ile Pro Gly Val Thr Leu Asn Arg Leu Cys Ala Ser Gly Met Asp Ala
                85                  90                  95 gtc ggc acc gcg ttc cgc gcc atc gcc agc ggc gag atg gag ctg gtg     336
Val Gly Thr Ala Phe Arg Ala Ile Ala Ser Gly Glu Met Glu Leu Val
                100                 105                 110 att gcc ggt ggc gtc gag tcg atg tcg cgc gcc ccg ttc gtc atg ggc     384
Ile Ala Gly Gly Val Glu Ser Met Ser Arg Ala Pro Phe Val Met Gly
            115                 120                 125 aag gct gaa agc gcc tat tcg cgc aac atg aag ctg gaa gac acc acc     432
Lys Ala Glu Ser Ala Tyr Ser Arg Asn Met Lys Leu Glu Asp Thr Thr
        130                 135                 140 att ggc tgg cgt ttc atc aac ccg ctg atg aag agc cag tac ggt gtg     480
Ile Gly Trp Arg Phe Ile Asn Pro Leu Met Lys Ser Gln Tyr Gly Val
145                 150                 155                 160 gat tcc atg ccg gaa acc gcc gac aac gtg gcc gac gac tat cag gtt     528
Asp Ser Met Pro Glu Thr Ala Asp Asn Val Ala Asp Asp Tyr Gln Val
                165                 170                 175 tcg cgt gct gat cag gac gct ttc gcc ctg cgc agc cag cag aag gct     576
Ser Arg Ala Asp Gln Asp Ala Phe Ala Leu Arg Ser Gln Gln Lys Ala
                180                 185                 190 gcc gct gcg cag gct gcc ggc ttc ttt gcc gaa gaa atc gtg ccg gtg     624
Ala Ala Ala Gln Ala Ala Gly Phe Phe Ala Glu Glu Ile Val Pro Val
            195                 200                 205 cgt atc gct cac aag aag ggc gaa atc atc gtc gaa cgt gac gaa cac     672
Arg Ile Ala His Lys Lys Gly Glu Ile Ile Val Glu Arg Asp Glu His
        210                 215                 220 ctg cgc ccg gaa acc acg ctg gag gcg ctg acc aag ctc aaa ccg gtc     720
Leu Arg Pro Glu Thr Thr Leu Glu Ala Leu Thr Lys Leu Lys Pro Val
```

```
                      225                 230                 235                 240
aac ggc ccg gac aag acg gtc acc gcc ggc aac gcc tcg ggc gtg aac       768
Asn Gly Pro Asp Lys Thr Val Thr Ala Gly Asn Ala Ser Gly Val Asn
                245                 250                 255 gac ggt gct gcg gcg atg atc ctg gcc tcg gcc gca gcg gtg aag aaa       816
Asp Gly Ala Ala Ala Met Ile Leu Ala Ser Ala Ala Ala Val Lys Lys
                260                 265                 270 cac ggc ctg act ccg cgt gcc cgc gtt ctg ggc atg gcc agc ggc ggc       864
His Gly Leu Thr Pro Arg Ala Arg Val Leu Gly Met Ala Ser Gly Gly
                275                 280                 285 gtt gcg cca cgt gtc atg ggc att ggc ccg gtg ccg gcg gtg cgc aaa       912
Val Ala Pro Arg Val Met Gly Ile Gly Pro Val Pro Ala Val Arg Lys
                290                 295                 300 ctg acc gag cgt ctg ggg ata gcg gta agt gat ttc gac gtg atc gag       960
Leu Thr Glu Arg Leu Gly Ile Ala Val Ser Asp Phe Asp Val Ile Glu
305                 310                 315                 320 ctt aac gaa gcg ttt gcc agc caa ggc ctg gcg gtg ctg cgt gag ctg      1008
Leu Asn Glu Ala Phe Ala Ser Gln Gly Leu Ala Val Leu Arg Glu Leu
                325                 330                 335 ggt gtg gct gac gat gcg ccc cag gta aac cct aat ggc ggt gcc att      1056
Gly Val Ala Asp Asp Ala Pro Gln Val Asn Pro Asn Gly Gly Ala Ile
                340                 345                 350 gcc ctg ggc cac ccc ctg ggc atg agc ggt gca cgc ctg gta ctg act      1104
Ala Leu Gly His Pro Leu Gly Met Ser Gly Ala Arg Leu Val Leu Thr
                355                 360                 365 gcg ttg cac cag ctg gag aag agt ggc ggt cgc aag ggc ctg gcg acc      1152
Ala Leu His Gln Leu Glu Lys Ser Gly Gly Arg Lys Gly Leu Ala Thr
                370                 375                 380 atg tgt gtg ggt gtc ggc caa ggt ctg gcg ttg gcc atc gag cgg gtt      1200
Met Cys Val Gly Val Gly Gln Gly Leu Ala Leu Ala Ile Glu Arg Val
385                 390                 395                 400

<210> SEQ ID NO 44
<211> LENGTH: 400
<212> TYPE: PRT
<213> ORGANISM: Pseudomonas putida

<400> SEQUENCE: 44

Met His Asp Val Phe Ile Cys Asp Ala Ile Arg Thr Pro Ile Gly Arg
1               5                   10                  15

Phe Gly Gly Ala Leu Ala Ser Val Arg Ala Asp Asp Leu Ala Ala Val
                20                  25                  30

Pro Leu Lys Ala Leu Ile Glu Arg Asn Pro Gly Val Gln Trp Asp Gln
            35                  40                  45

Val Asp Glu Val Phe Phe Gly Cys Ala Asn Gln Ala Gly Glu Asp Asn
        50                  55                  60

Arg Asn Val Ala Arg Met Ala Leu Leu Leu Ala Gly Leu Pro Glu Ser
65                  70                  75                  80

Ile Pro Gly Val Thr Leu Asn Arg Leu Cys Ala Ser Gly Met Asp Ala
                85                  90                  95

Val Gly Thr Ala Phe Arg Ala Ile Ala Ser Gly Glu Met Glu Leu Val
                100                 105                 110

Ile Ala Gly Gly Val Glu Ser Met Ser Arg Ala Pro Phe Val Met Gly
            115                 120                 125

Lys Ala Glu Ser Ala Tyr Ser Arg Asn Met Lys Leu Glu Asp Thr Thr
        130                 135                 140

Ile Gly Trp Arg Phe Ile Asn Pro Leu Met Lys Ser Gln Tyr Gly Val
145                 150                 155                 160
```

```
Asp Ser Met Pro Glu Thr Ala Asp Asn Val Ala Asp Tyr Gln Val
                165                 170                 175

Ser Arg Ala Asp Gln Asp Ala Phe Ala Leu Arg Ser Gln Gln Lys Ala
            180                 185                 190

Ala Ala Ala Gln Ala Ala Gly Phe Phe Ala Glu Glu Ile Val Pro Val
        195                 200                 205

Arg Ile Ala His Lys Lys Gly Glu Ile Ile Val Glu Arg Asp Glu His
    210                 215                 220

Leu Arg Pro Glu Thr Thr Leu Glu Ala Leu Thr Lys Leu Lys Pro Val
225                 230                 235                 240

Asn Gly Pro Asp Lys Thr Val Thr Ala Gly Asn Ala Ser Gly Val Asn
                245                 250                 255

Asp Gly Ala Ala Ala Met Ile Leu Ala Ser Ala Ala Val Lys Lys
            260                 265                 270

His Gly Leu Thr Pro Arg Ala Arg Val Leu Gly Met Ala Ser Gly Gly
        275                 280                 285

Val Ala Pro Arg Val Met Gly Ile Gly Pro Val Pro Ala Val Arg Lys
    290                 295                 300

Leu Thr Glu Arg Leu Gly Ile Ala Val Ser Asp Phe Asp Val Ile Glu
305                 310                 315                 320

Leu Asn Glu Ala Phe Ala Ser Gln Gly Leu Ala Val Leu Arg Glu Leu
                325                 330                 335

Gly Val Ala Asp Asp Ala Pro Gln Val Asn Pro Asn Gly Gly Ala Ile
            340                 345                 350

Ala Leu Gly His Pro Leu Gly Met Ser Gly Ala Arg Leu Val Leu Thr
        355                 360                 365

Ala Leu His Gln Leu Glu Lys Ser Gly Gly Arg Lys Gly Leu Ala Thr
    370                 375                 380

Met Cys Val Gly Val Gly Gln Gly Leu Ala Leu Ala Ile Glu Arg Val
385                 390                 395                 400

<210> SEQ ID NO 45
<211> LENGTH: 798
<212> TYPE: DNA
<213> ORGANISM: Paenibacillus sp. JJ-1b
<220> FEATURE:
<221> NAME/KEY: CDS
<222> LOCATION: (1)..(789)

<400> SEQUENCE: 45 atg agc ctg gaa atg gca ctg ttg gcg gcc cac gta ccg agc atc tgt      48
Met Ser Leu Glu Met Ala Leu Leu Ala Ala His Val Pro Ser Ile Cys
1               5                   10                  15 cac gaa tca aac gtg cca gac ttc cag caa gac ctg gtg aag ggt ctg      96
His Glu Ser Asn Val Pro Asp Phe Gln Gln Asp Leu Val Lys Gly Leu
                20                  25                  30 aag cag atg cgc gac cgc atc aat gaa ctg cag act gac gtt att ctg     144
Lys Gln Met Arg Asp Arg Ile Asn Glu Leu Gln Thr Asp Val Ile Leu
            35                  40                  45 ctc atg tcc tgc cac ttc ccg gcc acg ttc cat cac tac gtg gac gca     192
Leu Met Ser Cys His Phe Pro Ala Thr Phe His His Tyr Val Asp Ala
        50                  55                  60 act ccc agg cac acc ggt atc ttg acc gcg atg gag tgc ccc gat ttg     240
Thr Pro Arg His Thr Gly Ile Leu Thr Ala Met Glu Cys Pro Asp Leu
65                  70                  75                  80 att tcc gac gtg cct tac gac tac ccg ggg gat gag gaa ctt gcc cgt     288
Ile Ser Asp Val Pro Tyr Asp Tyr Pro Gly Asp Glu Glu Leu Ala Arg
```

```
aag ctg gtc acg gct ggc cag gag gcc ggc ctg ccg atc gtg gaa att      336
Lys Leu Val Thr Ala Gly Gln Glu Ala Gly Leu Pro Ile Val Glu Ile
        100                 105                 110 aat gac cct acc tat atc tgg gac tac ggc acc gtg gtg cct ctt cgc      384
Asn Asp Pro Thr Tyr Ile Trp Asp Tyr Gly Thr Val Val Pro Leu Arg
            115                 120                 125 tat ctg gtg ccc aac caa gac aaa agc gtg atc tca ctg agt gtg tgc      432
Tyr Leu Val Pro Asn Gln Asp Lys Ser Val Ile Ser Leu Ser Val Cys
130                 135                 140 tgg gcc agc agt ctg gag gag agc tat cag tgg ggg gtg cag atc ggg      480
Trp Ala Ser Ser Leu Glu Glu Ser Tyr Gln Trp Gly Val Gln Ile Gly
145                 150                 155                 160 aag gtg ctg cgc gaa agc gag aag cgg gcg gtg ttc atc agc tcg ggc      528
Lys Val Leu Arg Glu Ser Glu Lys Arg Ala Val Phe Ile Ser Ser Gly
                165                 170                 175 gcc ttg tcc cac aac ctc gtg cgc ggg cgc cat cac atg ccg agc aga      576
Ala Leu Ser His Asn Leu Val Arg Gly Arg His His Met Pro Ser Arg
            180                 185                 190 tcc gag cag gca atg gac aat caa ttc atc gag tac ctg ctg aac ggt      624
Ser Glu Gln Ala Met Asp Asn Gln Phe Ile Glu Tyr Leu Leu Asn Gly
        195                 200                 205 gac tat aat gcc gcg cgt gaa atg ctg aat cag tac gcc cgc atc gcg      672
Asp Tyr Asn Ala Ala Arg Glu Met Leu Asn Gln Tyr Ala Arg Ile Ala
210                 215                 220 ggc gtc gaa tcg ggc ggt cgg cat ctg gca gcc ctg ctt ggg gtg ctg      720
Gly Val Glu Ser Gly Gly Arg His Leu Ala Ala Leu Leu Gly Val Leu
225                 230                 235                 240 gac gat aag caa cgg gcc gaa ttt tgg ggg tac ggg cag tcg tcc gga      768
Asp Asp Lys Gln Arg Ala Glu Phe Trp Gly Tyr Gly Gln Ser Ser Gly
                245                 250                 255 tcg ggg aac gcc atc atc tcc ttcgtcagc                                798
Ser Gly Asn Ala Ile Ile Ser
            260
```

<210> SEQ ID NO 46
<211> LENGTH: 263
<212> TYPE: PRT
<213> ORGANISM: Paenibacillus sp. JJ-1b

<400> SEQUENCE: 46

```
Met Ser Leu Glu Met Ala Leu Leu Ala Ala His Val Pro Ser Ile Cys
1               5                   10                  15

His Glu Ser Asn Val Pro Asp Phe Gln Gln Asp Leu Val Lys Gly Leu
            20                  25                  30

Lys Gln Met Arg Asp Arg Ile Asn Glu Leu Gln Thr Asp Val Ile Leu
        35                  40                  45

Leu Met Ser Cys His Phe Pro Ala Thr Phe His His Tyr Val Asp Ala
    50                  55                  60

Thr Pro Arg His Thr Gly Ile Leu Thr Ala Met Glu Cys Pro Asp Leu
65                  70                  75                  80

Ile Ser Asp Val Pro Tyr Asp Tyr Pro Gly Asp Glu Leu Ala Arg
                85                  90                  95

Lys Leu Val Thr Ala Gly Gln Glu Ala Gly Leu Pro Ile Val Glu Ile
            100                 105                 110

Asn Asp Pro Thr Tyr Ile Trp Asp Tyr Gly Thr Val Val Pro Leu Arg
        115                 120                 125

Tyr Leu Val Pro Asn Gln Asp Lys Ser Val Ile Ser Leu Ser Val Cys
```

```
                130                 135                 140
Trp Ala Ser Ser Leu Glu Glu Ser Tyr Gln Trp Gly Val Gln Ile Gly
145                 150                 155                 160

Lys Val Leu Arg Glu Ser Glu Lys Arg Ala Val Phe Ile Ser Ser Gly
                165                 170                 175

Ala Leu Ser His Asn Leu Val Arg Gly Arg His His Met Pro Ser Arg
                180                 185                 190

Ser Glu Gln Ala Met Asp Asn Gln Phe Ile Glu Tyr Leu Leu Asn Gly
            195                 200                 205

Asp Tyr Asn Ala Ala Arg Glu Met Leu Asn Gln Tyr Ala Arg Ile Ala
            210                 215                 220

Gly Val Glu Ser Gly Gly Arg His Leu Ala Ala Leu Leu Gly Val Leu
225                 230                 235                 240

Asp Asp Lys Gln Arg Ala Glu Phe Trp Gly Tyr Gly Gln Ser Ser Gly
                245                 250                 255

Ser Gly Asn Ala Ile Ile Ser
                260

<210> SEQ ID NO 47
<211> LENGTH: 939
<212> TYPE: DNA
<213> ORGANISM: Paenibacillus sp. JJ-1b
<220> FEATURE:
<221> NAME/KEY: CDS
<222> LOCATION: (1)..(939)

<400> SEQUENCE: 47 atg tac gac gtg cat acg cac ttc att cca cct gag gtc gtg cgg tgg      48
Met Tyr Asp Val His Thr His Phe Ile Pro Pro Glu Val Val Arg Trp
1               5                   10                  15 ctg cag gag aat cga gct tcc gtg aac gca aac tgg atc aag aag gac      96
Leu Gln Glu Asn Arg Ala Ser Val Asn Ala Asn Trp Ile Lys Lys Asp
                20                  25                  30 ccg cgt aag gcg gag ttc ttg agc gtc aac ggc aac tgg gag ttc gaa     144
Pro Arg Lys Ala Glu Phe Leu Ser Val Asn Gly Asn Trp Glu Phe Glu
            35                  40                  45 ctg aag gaa tcc ttc gtt aac ccc agc ctg tat tta gaa gag caa gga     192
Leu Lys Glu Ser Phe Val Asn Pro Ser Leu Tyr Leu Glu Glu Gln Gly
        50                  55                  60 aag cag ggc atc gag cat agc ctc atc tcc cca atc ccg cag ctt ttc     240
Lys Gln Gly Ile Glu His Ser Leu Ile Ser Pro Ile Pro Gln Leu Phe
65                  70                  75                  80 ctg tac gat ttt tct ccg aag atc acg aaa gag ctg gcg agc gtg tac     288
Leu Tyr Asp Phe Ser Pro Lys Ile Thr Lys Glu Leu Ala Ser Val Tyr
                85                  90                  95 aac gac tcg ctg gcc gat tgg gtg cag agg cat agc agc cgt ctg agc     336
Asn Asp Ser Leu Ala Asp Trp Val Gln Arg His Ser Ser Arg Leu Ser
            100                 105                 110 ggc ttg gcg act ctg ccg atg aat gac ccg gaa gcc gcc gca gta gag     384
Gly Leu Ala Thr Leu Pro Met Asn Asp Pro Glu Ala Ala Ala Val Glu
        115                 120                 125 ctg gaa cgc gcc atg gac cgc ggt ctc cgg ggc gcg atc gtg gcg agc     432
Leu Glu Arg Ala Met Asp Arg Gly Leu Arg Gly Ala Ile Val Ala Ser
    130                 135                 140 agc tgg tcc ggc cgc ttg cta tct gaa gaa cca ttc gcc cca ttc tgg     480
Ser Trp Ser Gly Arg Leu Leu Ser Glu Glu Pro Phe Ala Pro Phe Trp
145                 150                 155                 160 gaa gca gca aac cgc cgc aag gct att ctt ttc gtc cac cct ctg cta     528
Glu Ala Ala Asn Arg Arg Lys Ala Ile Leu Phe Val His Pro Leu Leu
```

-continued

```
                          165                 170                 175
tgc act gat ccc cgc ctg agc aaa cgc atg atg cca aat ctg atc ggc      576
Cys Thr Asp Pro Arg Leu Ser Lys Arg Met Met Pro Asn Leu Ile Gly
            180                 185                 190 gtg ccg tgg gag acc acc gtc tgc gcc gcc gac ctg ctg ctg tct ggt      624
Val Pro Trp Glu Thr Thr Val Cys Ala Ala Asp Leu Leu Leu Ser Gly
        195                 200                 205 acc ctg gag cgt tac ccc gaa gcc aag gtg ctc ctt gcc cat ggg ggt      672
Thr Leu Glu Arg Tyr Pro Glu Ala Lys Val Leu Leu Ala His Gly Gly
    210                 215                 220 ggc ttt ctg cct tat cag att ggt cgc ctg acc aaa ggt tat gag aag      720
Gly Phe Leu Pro Tyr Gln Ile Gly Arg Leu Thr Lys Gly Tyr Glu Lys
225                 230                 235                 240 tgg ggg gga gca ttc agc cat ctg gaa cag gcc cct cag gag ctg att      768
Trp Gly Gly Ala Phe Ser His Leu Glu Gln Ala Pro Gln Glu Leu Ile
                245                 250                 255 cgc cgt ttc tgg tac gac acc gtg ctg tgg aac ccg gag ggc ctt ggc      816
Arg Arg Phe Trp Tyr Asp Thr Val Leu Trp Asn Pro Glu Gly Leu Gly
            260                 265                 270 tac ctg act gag ctg gtg ggg gag gag cgg gtg gtg ccg ggg act gac      864
Tyr Leu Thr Glu Leu Val Gly Glu Glu Arg Val Val Pro Gly Thr Asp
        275                 280                 285 tac ccg ttt gac ctg tgc gag tgg ccg ccg gcg att gat ggc cgt aag      912
Tyr Pro Phe Asp Leu Cys Glu Trp Pro Pro Ala Ile Asp Gly Arg Lys
    290                 295                 300 ggc ttc cag gca ctg atg aac aag agc                                  939
Gly Phe Gln Ala Leu Met Asn Lys Ser
305                 310

<210> SEQ ID NO 48
<211> LENGTH: 313
<212> TYPE: PRT
<213> ORGANISM: Paenibacillus sp. JJ-1b

<400> SEQUENCE: 48

Met Tyr Asp Val His Thr His Phe Ile Pro Pro Glu Val Val Arg Trp
1               5                   10                  15

Leu Gln Glu Asn Arg Ala Ser Val Asn Ala Asn Trp Ile Lys Lys Asp
            20                  25                  30

Pro Arg Lys Ala Glu Phe Leu Ser Val Asn Gly Asn Trp Glu Phe Glu
        35                  40                  45

Leu Lys Glu Ser Phe Val Asn Pro Ser Leu Tyr Leu Glu Glu Gln Gly
    50                  55                  60

Lys Gln Gly Ile Glu His Ser Leu Ile Ser Pro Ile Pro Gln Leu Phe
65                  70                  75                  80

Leu Tyr Asp Phe Ser Pro Lys Ile Thr Lys Glu Leu Ala Ser Val Tyr
                85                  90                  95

Asn Asp Ser Leu Ala Asp Trp Val Gln Arg His Ser Ser Arg Leu Ser
            100                 105                 110

Gly Leu Ala Thr Leu Pro Met Asn Asp Pro Glu Ala Ala Val Glu
        115                 120                 125

Leu Glu Arg Ala Met Asp Arg Gly Leu Arg Gly Ala Ile Val Ala Ser
    130                 135                 140

Ser Trp Ser Gly Arg Leu Leu Ser Glu Glu Pro Phe Ala Pro Phe Trp
145                 150                 155                 160

Glu Ala Ala Asn Arg Arg Lys Ala Ile Leu Phe Val His Pro Leu Leu
                165                 170                 175
```

```
Cys Thr Asp Pro Arg Leu Ser Lys Arg Met Met Pro Asn Leu Ile Gly
            180                 185                 190

Val Pro Trp Glu Thr Thr Val Cys Ala Ala Asp Leu Leu Leu Ser Gly
        195                 200                 205

Thr Leu Glu Arg Tyr Pro Glu Ala Lys Val Leu Leu Ala His Gly Gly
    210                 215                 220

Gly Phe Leu Pro Tyr Gln Ile Gly Arg Leu Thr Lys Gly Tyr Glu Lys
225                 230                 235                 240

Trp Gly Gly Ala Phe Ser His Leu Glu Gln Ala Pro Gln Glu Leu Ile
                245                 250                 255

Arg Arg Phe Trp Tyr Asp Thr Val Leu Trp Asn Pro Glu Gly Leu Gly
            260                 265                 270

Tyr Leu Thr Glu Leu Val Gly Glu Arg Val Val Pro Gly Thr Asp
        275                 280                 285

Tyr Pro Phe Asp Leu Cys Glu Trp Pro Pro Ala Ile Asp Gly Arg Lys
    290                 295                 300

Gly Phe Gln Ala Leu Met Asn Lys Ser
305                 310

<210> SEQ ID NO 49
<211> LENGTH: 921
<212> TYPE: DNA
<213> ORGANISM: Pseudomonas putida
<220> FEATURE:
<221> NAME/KEY: CDS
<222> LOCATION: (1)..(921)

<400> SEQUENCE: 49 atg aac aaa ggt gta atg cga ccg ggc cat gtg cag ctg cgt gta ctg     48
Met Asn Lys Gly Val Met Arg Pro Gly His Val Gln Leu Arg Val Leu
1               5                   10                  15 gac atg agc aag gcc ctg gaa cac tac gtc gag ttg ctg ggc ctg atc     96
Asp Met Ser Lys Ala Leu Glu His Tyr Val Glu Leu Leu Gly Leu Ile
            20                  25                  30 gag atg gac cgt gac gac cag ggc cgt gtc tat ctg aag gct tgg acc    144
Glu Met Asp Arg Asp Asp Gln Gly Arg Val Tyr Leu Lys Ala Trp Thr
        35                  40                  45 gaa gtg gat aag ttt tcc ctg gtg cta cgc gag gct gac gag ccg ggc    192
Glu Val Asp Lys Phe Ser Leu Val Leu Arg Glu Ala Asp Glu Pro Gly
    50                  55                  60 atg gat ttt atg ggt ttc aag gtt gtg gat gag gat gct ctc cgg caa    240
Met Asp Phe Met Gly Phe Lys Val Val Asp Glu Asp Ala Leu Arg Gln
65                  70                  75                  80 ctg gag cgg gat ctg atg gca tat ggc tgt gcc gtt gag cag cta ccc    288
Leu Glu Arg Asp Leu Met Ala Tyr Gly Cys Ala Val Glu Gln Leu Pro
                85                  90                  95 gca ggt gaa ctg aac agt tgt ggc cgg cgc gtg cgc ttc cag gcc ccc    336
Ala Gly Glu Leu Asn Ser Cys Gly Arg Arg Val Arg Phe Gln Ala Pro
            100                 105                 110 tcc ggg cat cac ttc gag ttg tat gca gac aag gaa tat act gga aag    384
Ser Gly His His Phe Glu Leu Tyr Ala Asp Lys Glu Tyr Thr Gly Lys
        115                 120                 125 tgg ggt ttg aat gac gtc aat ccc gag gca tgg ccg cgc gat ctg aaa    432
Trp Gly Leu Asn Asp Val Asn Pro Glu Ala Trp Pro Arg Asp Leu Lys
    130                 135                 140 ggt atg gcg gct gtg cgt ttc gac cac gcc ctc atg tat ggc gac gaa    480
Gly Met Ala Ala Val Arg Phe Asp His Ala Leu Met Tyr Gly Asp Glu
145                 150                 155                 160 ttg ccg gcg acc tat gac ctg ttc acc aag gtg ctc ggt ttc tat ctg    528
Leu Pro Ala Thr Tyr Asp Leu Phe Thr Lys Val Leu Gly Phe Tyr Leu
```

| | | |
|---|---|---|
| Leu Pro Ala Thr Tyr Asp Leu Phe Thr Lys Val Leu Gly Phe Tyr Leu<br>165 170 175 | | |
| gcc gaa cag gtg ctg gac gaa aat ggc acg cgc gtc gcc cag ttt ctc<br>Ala Glu Gln Val Leu Asp Glu Asn Gly Thr Arg Val Ala Gln Phe Leu<br>180 185 190 | | 576 |
| agt ctg tcg acc aag gcc cac gac gtg gcc ttc att cac cat ccg gaa<br>Ser Leu Ser Thr Lys Ala His Asp Val Ala Phe Ile His His Pro Glu<br>195 200 205 | | 624 |
| aaa ggc cgc ctc cat cat gtg tcc ttc cac ctc gaa acc tgg gaa gac<br>Lys Gly Arg Leu His His Val Ser Phe His Leu Glu Thr Trp Glu Asp<br>210 215 220 | | 672 |
| ttg ctt cgc gcc gcc gac ctg atc tcc atg acc gac aca tct atc gat<br>Leu Leu Arg Ala Ala Asp Leu Ile Ser Met Thr Asp Thr Ser Ile Asp<br>225 230 235 240 | | 720 |
| atc ggc cca acc cgc cac ggc ctc act cac ggc aag acc atc tac ttc<br>Ile Gly Pro Thr Arg His Gly Leu Thr His Gly Lys Thr Ile Tyr Phe<br>245 250 255 | | 768 |
| ttc gac ccg tcc ggt aac cgc aac gaa gtg ttc tgc ggg gga gat tac<br>Phe Asp Pro Ser Gly Asn Arg Asn Glu Val Phe Cys Gly Gly Asp Tyr<br>260 265 270 | | 816 |
| aac tac ccg gac cac aaa ccg gtg acc tgg acc acc gac cag ctg ggc<br>Asn Tyr Pro Asp His Lys Pro Val Thr Trp Thr Thr Asp Gln Leu Gly<br>275 280 285 | | 864 |
| aag gcg atc ttt tac cac gac cgc att ctc aac gaa cga ttc atg acc<br>Lys Ala Ile Phe Tyr His Asp Arg Ile Leu Asn Glu Arg Phe Met Thr<br>290 295 300 | | 912 |
| gtg ctg acc<br>Val Leu Thr<br>305 | | 921 |

<210> SEQ ID NO 50
<211> LENGTH: 307
<212> TYPE: PRT
<213> ORGANISM: Pseudomonas putida

<400> SEQUENCE: 50

Met Asn Lys Gly Val Met Arg Pro Gly His Val Gln Leu Arg Val Leu
1               5                   10                  15

Asp Met Ser Lys Ala Leu Glu His Tyr Val Glu Leu Leu Gly Leu Ile
                20                  25                  30

Glu Met Asp Arg Asp Asp Gln Gly Arg Val Tyr Leu Lys Ala Trp Thr
            35                  40                  45

Glu Val Asp Lys Phe Ser Leu Val Leu Arg Glu Ala Asp Glu Pro Gly
        50                  55                  60

Met Asp Phe Met Gly Phe Lys Val Val Asp Glu Asp Ala Leu Arg Gln
65                  70                  75                  80

Leu Glu Arg Asp Leu Met Ala Tyr Gly Cys Ala Val Glu Gln Leu Pro
                85                  90                  95

Ala Gly Glu Leu Asn Ser Cys Gly Arg Arg Val Arg Phe Gln Ala Pro
            100                 105                 110

Ser Gly His His Phe Glu Leu Tyr Ala Asp Lys Glu Tyr Thr Gly Lys
        115                 120                 125

Trp Gly Leu Asn Asp Val Asn Pro Glu Ala Trp Pro Arg Asp Leu Lys
    130                 135                 140

Gly Met Ala Ala Val Arg Phe Asp His Ala Leu Met Tyr Gly Asp Glu
145                 150                 155                 160

Leu Pro Ala Thr Tyr Asp Leu Phe Thr Lys Val Leu Gly Phe Tyr Leu
                165                 170                 175

```
Ala Glu Gln Val Leu Asp Glu Asn Gly Thr Arg Val Ala Gln Phe Leu
            180                 185                 190

Ser Leu Ser Thr Lys Ala His Asp Val Ala Phe Ile His His Pro Glu
            195                 200                 205

Lys Gly Arg Leu His His Val Ser Phe His Leu Glu Thr Trp Glu Asp
            210                 215                 220

Leu Leu Arg Ala Ala Asp Leu Ile Ser Met Thr Asp Thr Ser Ile Asp
225                 230                 235                 240

Ile Gly Pro Thr Arg His Gly Leu Thr His Gly Lys Thr Ile Tyr Phe
                245                 250                 255

Phe Asp Pro Ser Gly Asn Arg Asn Glu Val Phe Cys Gly Gly Asp Tyr
                260                 265                 270

Asn Tyr Pro Asp His Lys Pro Val Thr Trp Thr Thr Asp Gln Leu Gly
            275                 280                 285

Lys Ala Ile Phe Tyr His Asp Arg Ile Leu Asn Glu Arg Phe Met Thr
            290                 295                 300

Val Leu Thr
305

<210> SEQ ID NO 51
<211> LENGTH: 843
<212> TYPE: DNA
<213> ORGANISM: Pseudomonas putida
<220> FEATURE:
<221> NAME/KEY: CDS
<222> LOCATION: (1)..(843)

<400> SEQUENCE: 51 atg aac gca ccg cag caa agc cct gaa atc ggt cgc gaa atc ctc gcc     48
Met Asn Ala Pro Gln Gln Ser Pro Glu Ile Gly Arg Glu Ile Leu Ala
1               5                  10                  15 gcc ggc tac cgc acc aac ctg cat gat cag ggc gaa ggc ttc ccg gct     96
Ala Gly Tyr Arg Thr Asn Leu His Asp Gln Gly Glu Gly Phe Pro Ala
                20                  25                  30 ctg ctg atc cac ggc tcc ggc ccc gcg tca ccg cct ggg cca act ggc    144
Leu Leu Ile His Gly Ser Gly Pro Ala Ser Pro Pro Gly Pro Thr Gly
            35                  40                  45 gcg gga tca ttc cgc agc tcg cag acg cgc cgg gtg atc gcc ccg gac    192
Ala Gly Ser Phe Arg Ser Ser Gln Thr Arg Arg Val Ile Ala Pro Asp
        50                  55                  60 atg ctc ggc ttc ggc tac agc gaa cgt ccg gcc gat ggc aag tac agc    240
Met Leu Gly Phe Gly Tyr Ser Glu Arg Pro Ala Asp Gly Lys Tyr Ser
65                  70                  75                  80 cag gcg cgc tgg gtc gag cat gcc atc ggc gtg ctc gac gcc ctc ggc    288
Gln Ala Arg Trp Val Glu His Ala Ile Gly Val Leu Asp Ala Leu Gly
                85                  90                  95 atc cag cag ggc gac atc gtc ggc aac tcg ttc ggc ggc ggg ctg gca    336
Ile Gln Gln Gly Asp Ile Val Gly Asn Ser Phe Gly Gly Gly Leu Ala
                100                 105                 110 ctg gca ctg gcc atc cgt cac ccc gag cgt gtg cgc cgg ctg gtg ctg    384
Leu Ala Leu Ala Ile Arg His Pro Glu Arg Val Arg Arg Leu Val Leu
            115                 120                 125 atg ggc agc gtc ggt gtg tct ttc ccc atc acc gca gga ctg gaa aca    432
Met Gly Ser Val Gly Val Ser Phe Pro Ile Thr Ala Gly Leu Glu Thr
        130                 135                 140 gcc tgg ggc tac acg ccg tcg ctg gcc aac atg cgc agg ctg ctc gat    480
Ala Trp Gly Tyr Thr Pro Ser Leu Ala Asn Met Arg Arg Leu Leu Asp
145                 150                 155                 160
```

```
ctg ttc gcc cac gac cgc acc ctg gtc aac gac gag ctg gcc gag ctg      528
Leu Phe Ala His Asp Arg Thr Leu Val Asn Asp Glu Leu Ala Glu Leu
            165                 170                 175 cgc tac cag gcc agc atc cgc ccc ggc ttt cag gag tcg ttc gcc gcg      576
Arg Tyr Gln Ala Ser Ile Arg Pro Gly Phe Gln Glu Ser Phe Ala Ala
        180                 185                 190 atg ttc ccg ccg cca cgg cag aac gga gtc gac gat ctg gcc agc aac      624
Met Phe Pro Pro Pro Arg Gln Asn Gly Val Asp Asp Leu Ala Ser Asn
    195                 200                 205 gag acc gat atc cgc gcc ctg ccc aac gaa acc ctg gtc atc cac ggc      672
Glu Thr Asp Ile Arg Ala Leu Pro Asn Glu Thr Leu Val Ile His Gly
210                 215                 220 cgc gag gat cgg atc atc ccg ctg cag gct tcg ctg acc ctc gcg cag      720
Arg Glu Asp Arg Ile Ile Pro Leu Gln Ala Ser Leu Thr Leu Ala Gln
225                 230                 235                 240 tgg att ccc aac gcc cag cta cac gtg ttc ggc cag tgc ggc cac tgg      768
Trp Ile Pro Asn Ala Gln Leu His Val Phe Gly Gln Cys Gly His Trp
                245                 250                 255 acc cag atc gaa cac gcc gag cgt ttc gcc cgc ttg gtc gag aat ttc      816
Thr Gln Ile Glu His Ala Glu Arg Phe Ala Arg Leu Val Glu Asn Phe
            260                 265                 270 ctc gcc gag gcc gac gcc ctc cat tcc                                  843
Leu Ala Glu Ala Asp Ala Leu His Ser
        275                 280
```

<210> SEQ ID NO 52
<211> LENGTH: 281
<212> TYPE: PRT
<213> ORGANISM: Pseudomonas putida

<400> SEQUENCE: 52

```
Met Asn Ala Pro Gln Gln Ser Pro Glu Ile Gly Arg Glu Ile Leu Ala
1               5                   10                  15

Ala Gly Tyr Arg Thr Asn Leu His Asp Gln Gly Glu Gly Phe Pro Ala
            20                  25                  30

Leu Leu Ile His Gly Ser Gly Pro Ala Ser Pro Pro Gly Pro Thr Gly
        35                  40                  45

Ala Gly Ser Phe Arg Ser Gln Thr Arg Arg Val Ile Ala Pro Asp
    50                  55                  60

Met Leu Gly Phe Gly Tyr Ser Glu Arg Pro Ala Asp Gly Lys Tyr Ser
65                  70                  75                  80

Gln Ala Arg Trp Val Glu His Ala Ile Gly Val Leu Asp Ala Leu Gly
                85                  90                  95

Ile Gln Gln Gly Asp Ile Val Gly Asn Ser Phe Gly Gly Leu Ala
            100                 105                 110

Leu Ala Leu Ala Ile Arg His Pro Glu Arg Val Arg Arg Leu Val Leu
        115                 120                 125

Met Gly Ser Val Gly Val Ser Phe Pro Ile Thr Ala Gly Leu Glu Thr
    130                 135                 140

Ala Trp Gly Tyr Thr Pro Ser Leu Ala Asn Met Arg Arg Leu Leu Asp
145                 150                 155                 160

Leu Phe Ala His Asp Arg Thr Leu Val Asn Asp Glu Leu Ala Glu Leu
                165                 170                 175

Arg Tyr Gln Ala Ser Ile Arg Pro Gly Phe Gln Glu Ser Phe Ala Ala
            180                 185                 190

Met Phe Pro Pro Pro Arg Gln Asn Gly Val Asp Asp Leu Ala Ser Asn
        195                 200                 205
```

-continued

```
Glu Thr Asp Ile Arg Ala Leu Pro Asn Glu Thr Leu Val Ile His Gly
    210                 215                 220

Arg Glu Asp Arg Ile Ile Pro Leu Gln Ala Ser Leu Thr Leu Ala Gln
225                 230                 235                 240

Trp Ile Pro Asn Ala Gln Leu His Val Phe Gly Gln Cys Gly His Trp
                245                 250                 255

Thr Gln Ile Glu His Ala Glu Arg Phe Ala Arg Leu Val Glu Asn Phe
            260                 265                 270

Leu Ala Glu Ala Asp Ala Leu His Ser
            275                 280

<210> SEQ ID NO 53
<211> LENGTH: 1458
<212> TYPE: DNA
<213> ORGANISM: Pseudomonas putida
<220> FEATURE:
<221> NAME/KEY: CDS
<222> LOCATION: (1)..(1458)

<400> SEQUENCE: 53 atg aaa gaa atc aag cat ttc att agc ggt gaa tta gtc ggt tcg gcc      48
Met Lys Glu Ile Lys His Phe Ile Ser Gly Glu Leu Val Gly Ser Ala
1               5                   10                  15 agc ggc aag ctg ttc gac aat gtc agc ccg gcc aac ggc cag gtg atc      96
Ser Gly Lys Leu Phe Asp Asn Val Ser Pro Ala Asn Gly Gln Val Ile
                20                  25                  30 ggc cgc gtc cac gag gcc ggc cgc gcc gag gtc gac gcc gcg gtc agg     144
Gly Arg Val His Glu Ala Gly Arg Ala Glu Val Asp Ala Ala Val Arg
            35                  40                  45 gcg gca cgc gct gcg ctg aag gga ccc tgg ggg aag atg acg gtg gcc     192
Ala Ala Arg Ala Ala Leu Lys Gly Pro Trp Gly Lys Met Thr Val Ala
        50                  55                  60 gag cgc gct gag att ctg cat cgc gtg gcc gat ggc atc acg gcg cgc     240
Glu Arg Ala Glu Ile Leu His Arg Val Ala Asp Gly Ile Thr Ala Arg
65                  70                  75                  80 ttc ggc gag ttt ctc gag gcc cga atg cct gga cac cgg caa gcc gaa     288
Phe Gly Glu Phe Leu Glu Ala Arg Met Pro Gly His Arg Gln Ala Glu
                85                  90                  95 gtc gct ggc cag cca cat cga cat tcc gcg cgg cgc gcc aat ttc aag     336
Val Ala Gly Gln Pro His Arg His Ser Ala Arg Arg Ala Asn Phe Lys
            100                 105                 110 gtg ttc gcc gac ctg ctc aag aat gtt gcc aat gaa gcc ttc gag atg     384
Val Phe Ala Asp Leu Leu Lys Asn Val Ala Asn Glu Ala Phe Glu Met
        115                 120                 125 gcc acc ccg gac ggc gcc ggt gca ctc aac tac ggc gtg cgc cgg ccc     432
Ala Thr Pro Asp Gly Ala Gly Ala Leu Asn Tyr Gly Val Arg Arg Pro
    130                 135                 140 aag ggg gtg atc ggg gtg atc agc ccg tgg aac ctg ccg ctg ctg ctg     480
Lys Gly Val Ile Gly Val Ile Ser Pro Trp Asn Leu Pro Leu Leu Leu
145                 150                 155                 160 atg acc tgg aaa gtc ggc ccg gcc ctg gcc tgc ggc aac tgc gtg gtg     528
Met Thr Trp Lys Val Gly Pro Ala Leu Ala Cys Gly Asn Cys Val Val
                165                 170                 175 gtc aaa cca tcc gag gaa acc ccg ctg acc gcc acc ctg ctc ggc gag     576
Val Lys Pro Ser Glu Glu Thr Pro Leu Thr Ala Thr Leu Leu Gly Glu
            180                 185                 190 gtg atg cag gcc gcc ggt gtg ccg gcc ggc gtg tac aac gtg gtg cac     624
Val Met Gln Ala Ala Gly Val Pro Ala Gly Val Tyr Asn Val Val His
        195                 200                 205 ggt ttc ggc ggc gat tcg gcc ggg gcc ttc ctc acc gag cac ccg gac     672
```

```
                Gly Phe Gly Gly Asp Ser Ala Gly Ala Phe Leu Thr Glu His Pro Asp
                    210             215                 220 gtc gac gcc tac acc ttc acc ggc gag acc ggc acc ggc gaa acc atc        720
Val Asp Ala Tyr Thr Phe Thr Gly Glu Thr Gly Thr Gly Glu Thr Ile
225                 230                 235                 240 atg cgc gcc gcg gcc aag ggc gtg cgc cag gtg tcg ctg gag ctg ggc        768
Met Arg Ala Ala Ala Lys Gly Val Arg Gln Val Ser Leu Glu Leu Gly
                    245                 250                 255 ggc aag aac gcc ggc atc gtc ttc gcc gac tgc gat atg gac aag gcc        816
Gly Lys Asn Ala Gly Ile Val Phe Ala Asp Cys Asp Met Asp Lys Ala
                260                 265                 270 atc gag ggc acc ctg cgc tcg gcc ttc gcc aac tgc ggc cag gtc tgc        864
Ile Glu Gly Thr Leu Arg Ser Ala Phe Ala Asn Cys Gly Gln Val Cys
            275                 280                 285 ctg ggc acc gag cgg gtg tat gtc gag cgg ccg atc ttc gac gcg ttc        912
Leu Gly Thr Glu Arg Val Tyr Val Glu Arg Pro Ile Phe Asp Ala Phe
        290                 295                 300 gtc gcc cgc ctg aag gcc ggc gcc gaa gcg ttg aag atc ggc gaa ccg        960
Val Ala Arg Leu Lys Ala Gly Ala Glu Ala Leu Lys Ile Gly Glu Pro
305                 310                 315                 320 aac gat cca gag gcc aat ttc ggc ccg ctg atc agc cat aag ccc cgt       1008
Asn Asp Pro Glu Ala Asn Phe Gly Pro Leu Ile Ser His Lys Pro Arg
                    325                 330                 335 gaa aaa gtc ccc agt tac tac cag cag gca gtc gac gac ggc gcc acc       1056
Glu Lys Val Pro Ser Tyr Tyr Gln Gln Ala Val Asp Asp Gly Ala Thr
                340                 345                 350 gtt gtc acc ggc ggc ggc gtg ccg gag atg ccg gcg cac ctg gcc ggc       1104
Val Val Thr Gly Gly Gly Val Pro Glu Met Pro Ala His Leu Ala Gly
            355                 360                 365 ggc gcc tgg gtg cag ccg act atc tgg acc ggc ctg gcc gac gat tcg       1152
Gly Ala Trp Val Gln Pro Thr Ile Trp Thr Gly Leu Ala Asp Asp Ser
        370                 375                 380 gcg gtg gtc acc gag gaa atc ttc ggc ccc tgc tgc cat atc cgc ccg       1200
Ala Val Val Thr Glu Glu Ile Phe Gly Pro Cys Cys His Ile Arg Pro
385                 390                 395                 400 ttc gac agc gag gag gaa gcc att gaa ctg gcc aac agc ctg cct tac       1248
Phe Asp Ser Glu Glu Glu Ala Ile Glu Leu Ala Asn Ser Leu Pro Tyr
                    405                 410                 415 ggc ctg gcc tcg gcg atc tgg acc gag aac gtt cgc cgc gcc cac cgc       1296
Gly Leu Ala Ser Ala Ile Trp Thr Glu Asn Val Arg Arg Ala His Arg
                420                 425                 430 gtc gcc ggg cag att gag gcc ggc atc gtc tgg gtc aac agc tgg ttc       1344
Val Ala Gly Gln Ile Glu Ala Gly Ile Val Trp Val Asn Ser Trp Phe
            435                 440                 445 ctg cgc gac ctg cgc acc gcc ttc ggc ggc agc aag cag tcg ggc atc       1392
Leu Arg Asp Leu Arg Thr Ala Phe Gly Gly Ser Lys Gln Ser Gly Ile
        450                 455                 460 ggg cgc gaa ggg ggt gtg cac tcg ctg gag ttc tac acc gag ctg aaa       1440
Gly Arg Glu Gly Gly Val His Ser Leu Glu Phe Tyr Thr Glu Leu Lys
465                 470                 475                 480 aac atc tgt gtg aaa ctt                                               1458
Asn Ile Cys Val Lys Leu
                485

<210> SEQ ID NO 54
<211> LENGTH: 486
<212> TYPE: PRT
<213> ORGANISM: Pseudomonas putida

<400> SEQUENCE: 54
```

```
Met Lys Glu Ile Lys His Phe Ile Ser Gly Glu Leu Val Gly Ser Ala
1               5                   10                  15

Ser Gly Lys Leu Phe Asp Asn Val Ser Pro Ala Asn Gly Gln Val Ile
            20                  25                  30

Gly Arg Val His Glu Ala Gly Arg Ala Glu Val Asp Ala Ala Val Arg
                35                  40                  45

Ala Ala Arg Ala Ala Leu Lys Gly Pro Trp Gly Lys Met Thr Val Ala
50                  55                  60

Glu Arg Ala Glu Ile Leu His Arg Val Ala Asp Gly Ile Thr Ala Arg
65                  70                  75                  80

Phe Gly Glu Phe Leu Glu Ala Arg Met Pro Gly His Arg Gln Ala Glu
                85                  90                  95

Val Ala Gly Gln Pro His Arg His Ser Ala Arg Arg Ala Asn Phe Lys
                100                 105                 110

Val Phe Ala Asp Leu Leu Lys Asn Val Ala Asn Glu Ala Phe Glu Met
                115                 120                 125

Ala Thr Pro Asp Gly Ala Gly Ala Leu Asn Tyr Gly Val Arg Arg Pro
            130                 135                 140

Lys Gly Val Ile Gly Val Ile Ser Pro Trp Asn Leu Pro Leu Leu Leu
145                 150                 155                 160

Met Thr Trp Lys Val Gly Pro Ala Leu Ala Cys Gly Asn Cys Val Val
                165                 170                 175

Val Lys Pro Ser Glu Glu Thr Pro Leu Thr Ala Thr Leu Leu Gly Glu
                180                 185                 190

Val Met Gln Ala Ala Gly Val Pro Ala Gly Val Tyr Asn Val Val His
                195                 200                 205

Gly Phe Gly Gly Asp Ser Ala Gly Ala Phe Leu Thr Glu His Pro Asp
            210                 215                 220

Val Asp Ala Tyr Thr Phe Thr Gly Glu Thr Gly Thr Gly Glu Thr Ile
225                 230                 235                 240

Met Arg Ala Ala Ala Lys Gly Val Arg Gln Val Ser Leu Glu Leu Gly
                245                 250                 255

Gly Lys Asn Ala Gly Ile Val Phe Ala Asp Cys Asp Met Asp Lys Ala
            260                 265                 270

Ile Glu Gly Thr Leu Arg Ser Ala Phe Ala Asn Cys Gly Gln Val Cys
            275                 280                 285

Leu Gly Thr Glu Arg Val Tyr Val Glu Arg Pro Ile Phe Asp Ala Phe
            290                 295                 300

Val Ala Arg Leu Lys Ala Gly Ala Glu Ala Leu Lys Ile Gly Glu Pro
305                 310                 315                 320

Asn Asp Pro Glu Ala Asn Phe Gly Pro Leu Ile Ser His Lys Pro Arg
                325                 330                 335

Glu Lys Val Pro Ser Tyr Tyr Gln Gln Ala Val Asp Asp Gly Ala Thr
                340                 345                 350

Val Val Thr Gly Gly Val Pro Glu Met Pro Ala His Leu Ala Gly
            355                 360                 365

Gly Ala Trp Val Gln Pro Thr Ile Trp Thr Gly Leu Ala Asp Asp Ser
        370                 375                 380

Ala Val Val Thr Glu Glu Ile Phe Gly Pro Cys Cys His Ile Arg Pro
385                 390                 395                 400

Phe Asp Ser Glu Glu Glu Ala Ile Glu Leu Ala Asn Ser Leu Pro Tyr
                405                 410                 415

Gly Leu Ala Ser Ala Ile Trp Thr Glu Asn Val Arg Arg Ala His Arg
```

```
                    420             425             430
Val Ala Gly Gln Ile Glu Ala Gly Ile Val Trp Val Asn Ser Trp Phe
            435                 440                 445

Leu Arg Asp Leu Arg Thr Ala Phe Gly Gly Ser Lys Gln Ser Gly Ile
    450                 455                 460

Gly Arg Glu Gly Gly Val His Ser Leu Glu Phe Tyr Thr Glu Leu Lys
465                 470                 475                 480

Asn Ile Cys Val Lys Leu
                485

<210> SEQ ID NO 55
<211> LENGTH: 189
<212> TYPE: DNA
<213> ORGANISM: Pseudomonas putida
<220> FEATURE:
<221> NAME/KEY: CDS
<222> LOCATION: (1)..(189)

<400> SEQUENCE: 55 atg cct att gcc cag atc cac atc ctt gaa ggc cgc agc gac gag cag     48
Met Pro Ile Ala Gln Ile His Ile Leu Glu Gly Arg Ser Asp Glu Gln
1               5                   10                  15 aag gaa acc ctc att cgg gaa gtc agc gag gcc atc tcg cgc tcc ctg     96
Lys Glu Thr Leu Ile Arg Glu Val Ser Glu Ala Ile Ser Arg Ser Leu
            20                  25                  30 gat gcg ccg ctg acc agc gtg cga gtg att atc acg gag atg gcc aag    144
Asp Ala Pro Leu Thr Ser Val Arg Val Ile Ile Thr Glu Met Ala Lys
        35                  40                  45 ggc cac ttc ggc atc ggc ggc gaa ctg gcc agc aag gtc aga cgc        189
Gly His Phe Gly Ile Gly Gly Glu Leu Ala Ser Lys Val Arg Arg
    50                  55                  60

<210> SEQ ID NO 56
<211> LENGTH: 63
<212> TYPE: PRT
<213> ORGANISM: Pseudomonas putida

<400> SEQUENCE: 56

Met Pro Ile Ala Gln Ile His Ile Leu Glu Gly Arg Ser Asp Glu Gln
1               5                   10                  15

Lys Glu Thr Leu Ile Arg Glu Val Ser Glu Ala Ile Ser Arg Ser Leu
            20                  25                  30

Asp Ala Pro Leu Thr Ser Val Arg Val Ile Ile Thr Glu Met Ala Lys
        35                  40                  45

Gly His Phe Gly Ile Gly Gly Glu Leu Ala Ser Lys Val Arg Arg
    50                  55                  60

<210> SEQ ID NO 57
<211> LENGTH: 792
<212> TYPE: DNA
<213> ORGANISM: Pseudomonas putida
<220> FEATURE:
<221> NAME/KEY: CDS
<222> LOCATION: (1)..(792)

<400> SEQUENCE: 57 atg aat cgt acc ctc aac cgc gag cag gtg ctg gca ctg gcc gag cac     48
Met Asn Arg Thr Leu Asn Arg Glu Gln Val Leu Ala Leu Ala Glu His
1               5                   10                  15 atc gag aac gcc gaa ctg cag gcc cat gac atc cac aag gtc acc aat     96
Ile Glu Asn Ala Glu Leu Gln Ala His Asp Ile His Lys Val Thr Asn
            20                  25                  30
```

```
gat tat ccg gag atg acc ttt gcc gat gcc tac acg atc cag tgg gaa      144
Asp Tyr Pro Glu Met Thr Phe Ala Asp Ala Tyr Thr Ile Gln Trp Glu
        35                  40                  45 atc cgc cgc cgc aag gag gag cgc ggc aac aag atc gtc ggc ctg aag      192
Ile Arg Arg Arg Lys Glu Glu Arg Gly Asn Lys Ile Val Gly Leu Lys
 50                  55                  60 atg ggc ctg acc tcc tgg gcg aag atg gca cag atg ggc gtg gag acg      240
Met Gly Leu Thr Ser Trp Ala Lys Met Ala Gln Met Gly Val Glu Thr
 65                  70                  75                  80 ccg atc tac ggc ttt ctc gcc gac tac ttc agc gtg ccc gac ggt ggc      288
Pro Ile Tyr Gly Phe Leu Ala Asp Tyr Phe Ser Val Pro Asp Gly Gly
                 85                  90                  95 gtg gtg gat tgc tcc aag ctg atc cat ccg aag atc gag gcg gaa atc      336
Val Val Asp Cys Ser Lys Leu Ile His Pro Lys Ile Glu Ala Glu Ile
            100                 105                 110 gcg gtg gtc acc aag gca ccg ctg gtc ggg cct ggt tgc cat atc ggc      384
Ala Val Val Thr Lys Ala Pro Leu Val Gly Pro Gly Cys His Ile Gly
        115                 120                 125 gac gtg atc gcc gcg gtc gac tac gtg atc ccc acc gtc gag gta atc      432
Asp Val Ile Ala Ala Val Asp Tyr Val Ile Pro Thr Val Glu Val Ile
130                 135                 140 gac tcg cgc tat gag aac ttc aag ttc gac ctg atc agc gtg gtg gcc      480
Asp Ser Arg Tyr Glu Asn Phe Lys Phe Asp Leu Ile Ser Val Val Ala
145                 150                 155                 160 gac aac gcc tcg tcg acc cgc tat atc act gga ggc cgc atg gcc aat      528
Asp Asn Ala Ser Ser Thr Arg Tyr Ile Thr Gly Gly Arg Met Ala Asn
                165                 170                 175 ctc gag gat gtc gac ctg cgc acc ctt ggc gtg gtg atg gag aag aac      576
Leu Glu Asp Val Asp Leu Arg Thr Leu Gly Val Val Met Glu Lys Asn
            180                 185                 190 ggc gag gtg gtg gaa ctc ggt gcc ggt gcc gcg gtg ctc ggc cat ccg      624
Gly Glu Val Val Glu Leu Gly Ala Gly Ala Ala Val Leu Gly His Pro
        195                 200                 205 ctg tcc agc gtg gcg atg ctc gcc aac ctg ctg gcc gag cgc ggc gag      672
Leu Ser Ser Val Ala Met Leu Ala Asn Leu Leu Ala Glu Arg Gly Glu
210                 215                 220 cac ata ccg gcc ggc acc ttc atc atg acc ggc ggc atc acc gcc gcc      720
His Ile Pro Ala Gly Thr Phe Ile Met Thr Gly Gly Ile Thr Ala Ala
225                 230                 235                 240 gtc gca gta gcg ccg ggc gac aac atc acc gtg cgc tac cag ggg ctt      768
Val Ala Val Ala Pro Gly Asp Asn Ile Thr Val Arg Tyr Gln Gly Leu
                245                 250                 255 ggc agc gtc tcc gcg cgc ttc gtc                                      792
Gly Ser Val Ser Ala Arg Phe Val
            260

<210> SEQ ID NO 58
<211> LENGTH: 264
<212> TYPE: PRT
<213> ORGANISM: Pseudomonas putida

<400> SEQUENCE: 58

Met Asn Arg Thr Leu Asn Arg Glu Gln Val Leu Ala Leu Ala Glu His
 1               5                  10                  15

Ile Glu Asn Ala Glu Leu Gln Ala His Asp Ile His Lys Val Thr Asn
             20                  25                  30

Asp Tyr Pro Glu Met Thr Phe Ala Asp Ala Tyr Thr Ile Gln Trp Glu
         35                  40                  45

Ile Arg Arg Arg Lys Glu Glu Arg Gly Asn Lys Ile Val Gly Leu Lys
```

```
                50                  55                  60
Met Gly Leu Thr Ser Trp Ala Lys Met Ala Gln Met Gly Val Glu Thr
 65                  70                  75                  80

Pro Ile Tyr Gly Phe Leu Ala Asp Tyr Phe Ser Val Pro Asp Gly Gly
                 85                  90                  95

Val Val Asp Cys Ser Lys Leu Ile His Pro Lys Ile Glu Ala Glu Ile
                100                 105                 110

Ala Val Val Thr Lys Ala Pro Leu Val Gly Pro Gly Cys His Ile Gly
            115                 120                 125

Asp Val Ile Ala Ala Val Asp Tyr Val Ile Pro Thr Val Glu Val Ile
        130                 135                 140

Asp Ser Arg Tyr Glu Asn Phe Lys Phe Asp Leu Ile Ser Val Val Ala
145                 150                 155                 160

Asp Asn Ala Ser Ser Thr Arg Tyr Ile Thr Gly Gly Arg Met Ala Asn
                165                 170                 175

Leu Glu Asp Val Asp Leu Arg Thr Leu Gly Val Val Met Glu Lys Asn
            180                 185                 190

Gly Glu Val Val Glu Leu Gly Ala Gly Ala Ala Val Leu Gly His Pro
        195                 200                 205

Leu Ser Ser Val Ala Met Leu Ala Asn Leu Leu Ala Glu Arg Gly Glu
210                 215                 220

His Ile Pro Ala Gly Thr Phe Ile Met Thr Gly Gly Ile Thr Ala Ala
225                 230                 235                 240

Val Ala Val Ala Pro Gly Asp Asn Ile Thr Val Arg Tyr Gln Gly Leu
                245                 250                 255

Gly Ser Val Ser Ala Arg Phe Val
            260

<210> SEQ ID NO 59
<211> LENGTH: 666
<212> TYPE: DNA
<213> ORGANISM: Pseudomonas putida
<220> FEATURE:
<221> NAME/KEY: CDS
<222> LOCATION: (1)..(666)

<400> SEQUENCE: 59 atg gac aag aca ttg atc aac gaa ctc ggc gac gag ctc tac cag gcg      48
Met Asp Lys Thr Leu Ile Asn Glu Leu Gly Asp Glu Leu Tyr Gln Ala
  1               5                  10                  15 atg gtc cag cgc gag acc gtc acg ccg ctg acc agc cgc ggc ttc gac      96
Met Val Gln Arg Glu Thr Val Thr Pro Leu Thr Ser Arg Gly Phe Asp
                 20                  25                  30 atc agc gtc gag gac gcc tac cac att tcc ctg cgc atg ctg gaa cgg     144
Ile Ser Val Glu Asp Ala Tyr His Ile Ser Leu Arg Met Leu Glu Arg
             35                  40                  45 cgc ctg gcc gcc ggc gag cgg gtg atc ggc aag aag atc ggc gtc acc     192
Arg Leu Ala Ala Gly Glu Arg Val Ile Gly Lys Lys Ile Gly Val Thr
         50                  55                  60 agc aag gcc gtg cag aac atg ctc ggc gtg cac cag ccg gac ttc ggc     240
Ser Lys Ala Val Gln Asn Met Leu Gly Val His Gln Pro Asp Phe Gly
 65                  70                  75                  80 tac ctc acc gat gcc atg gtc tac aac agc ggc gaa gcc atg ccg atc     288
Tyr Leu Thr Asp Ala Met Val Tyr Asn Ser Gly Glu Ala Met Pro Ile
                 85                  90                  95 agc gag aag ctg atc cag ccg cgc gcc gag ggc gag atc gcc ttc atc     336
Ser Glu Lys Leu Ile Gln Pro Arg Ala Glu Gly Glu Ile Ala Phe Ile
                100                 105                 110
```

```
ctc aag aag gac ctg atg ggg ccg ggc gtg acc aac gcc gac gtg ctg      384
Leu Lys Lys Asp Leu Met Gly Pro Gly Val Thr Asn Ala Asp Val Leu
        115                 120                 125 gct gcc acc gaa tgc gtg atc ccc tgc ttc gaa gtg gtc gat tcg cgc      432
Ala Ala Thr Glu Cys Val Ile Pro Cys Phe Glu Val Val Asp Ser Arg
130                 135                 140 atc cag gac tgg aag atc aag atc cag gac acc gtg gcg gac aac gcc      480
Ile Gln Asp Trp Lys Ile Lys Ile Gln Asp Thr Val Ala Asp Asn Ala
145                 150                 155                 160 tcc tgc ggg ctg ttc gtg ctc ggc gac cag gcc gtc tca ccg cgc cag      528
Ser Cys Gly Leu Phe Val Leu Gly Asp Gln Ala Val Ser Pro Arg Gln
                165                 170                 175 gtc gat ctg gtc acc tgc ggc atg ctg gtc gag aag aac ggc cag ctg      576
Val Asp Leu Val Thr Cys Gly Met Leu Val Glu Lys Asn Gly Gln Leu
            180                 185                 190 ctc tcc acc ggc gct gga gcg gct gcg ctc ggc tcg ccg gtc aat tgc      624
Leu Ser Thr Gly Ala Gly Ala Ala Ala Leu Gly Ser Pro Val Asn Cys
        195                 200                 205 gtc gcc tgg ttg gcc aac acc ctc ggc cac ttc ggc atc gcc              666
Val Ala Trp Leu Ala Asn Thr Leu Gly His Phe Gly Ile Ala
210                 215                 220
```

<210> SEQ ID NO 60
<211> LENGTH: 222
<212> TYPE: PRT
<213> ORGANISM: Pseudomonas putida

<400> SEQUENCE: 60

```
Met Asp Lys Thr Leu Ile Asn Glu Leu Gly Asp Glu Leu Tyr Gln Ala
1               5                   10                  15

Met Val Gln Arg Glu Thr Val Thr Pro Leu Thr Ser Arg Gly Phe Asp
            20                  25                  30

Ile Ser Val Glu Asp Ala Tyr His Ile Ser Leu Arg Met Leu Glu Arg
        35                  40                  45

Arg Leu Ala Ala Gly Glu Arg Val Ile Gly Lys Lys Ile Gly Val Thr
    50                  55                  60

Ser Lys Ala Val Gln Asn Met Leu Gly Val His Gln Pro Asp Phe Gly
65                  70                  75                  80

Tyr Leu Thr Asp Ala Met Val Tyr Asn Ser Gly Glu Ala Met Pro Ile
                85                  90                  95

Ser Glu Lys Leu Ile Gln Pro Arg Ala Glu Gly Glu Ile Ala Phe Ile
            100                 105                 110

Leu Lys Lys Asp Leu Met Gly Pro Gly Val Thr Asn Ala Asp Val Leu
        115                 120                 125

Ala Ala Thr Glu Cys Val Ile Pro Cys Phe Glu Val Val Asp Ser Arg
    130                 135                 140

Ile Gln Asp Trp Lys Ile Lys Ile Gln Asp Thr Val Ala Asp Asn Ala
145                 150                 155                 160

Ser Cys Gly Leu Phe Val Leu Gly Asp Gln Ala Val Ser Pro Arg Gln
                165                 170                 175

Val Asp Leu Val Thr Cys Gly Met Leu Val Glu Lys Asn Gly Gln Leu
            180                 185                 190

Leu Ser Thr Gly Ala Gly Ala Ala Ala Leu Gly Ser Pro Val Asn Cys
        195                 200                 205

Val Ala Trp Leu Ala Asn Thr Leu Gly His Phe Gly Ile Ala
    210                 215                 220
```

-continued

```
<210> SEQ ID NO 61
<211> LENGTH: 1035
<212> TYPE: DNA
<213> ORGANISM: Pseudomonas putida
<220> FEATURE:
<221> NAME/KEY: CDS
<222> LOCATION: (1)..(1035)

<400> SEQUENCE: 61 atg acc ttc aac ccc ggc aag aaa ctc tat atc tcc gac gta acc ctg       48
Met Thr Phe Asn Pro Gly Lys Lys Leu Tyr Ile Ser Asp Val Thr Leu
 1               5                  10                  15 cgc gac ggc agc cat gcg att cgt cac cag tac tcg atc cag aat gtt       96
Arg Asp Gly Ser His Ala Ile Arg His Gln Tyr Ser Ile Gln Asn Val
             20                  25                  30 cag gac atc gcc cgc gcg ctg gac aag gcc cgt gtc gac tcc atc gaa      144
Gln Asp Ile Ala Arg Ala Leu Asp Lys Ala Arg Val Asp Ser Ile Glu
         35                  40                  45 gtg acc cac ggt gat ggc ctg cag ggc tcc agc ttc aat tac ggt ttc      192
Val Thr His Gly Asp Gly Leu Gln Gly Ser Ser Phe Asn Tyr Gly Phe
     50                  55                  60 ggt gcg cac agc gac ctg gag tgg atc gag gcc gcc gcc gat gtg atc      240
Gly Ala His Ser Asp Leu Glu Trp Ile Glu Ala Ala Ala Asp Val Ile
 65                  70                  75                  80 cag cac gcc cgg gtc aca gtg ctg ctg gta ccc gga atc ggc acc gtg      288
Gln His Ala Arg Val Thr Val Leu Leu Val Pro Gly Ile Gly Thr Val
                 85                  90                  95 cat gac ctg aaa gcc gcc tat gac gcc ggc gcc cgc tcg gtc gcc gtg      336
His Asp Leu Lys Ala Ala Tyr Asp Ala Gly Ala Arg Ser Val Arg Val
            100                 105                 110 gcc aca cac tgc acc gag gcg gat gtc tcg cga cag cac att gag tat      384
Ala Thr His Cys Thr Glu Ala Asp Val Ser Arg Gln His Ile Glu Tyr
        115                 120                 125 gcc cgt gaa ctg ggc atg gac acc gtc ggc ttt cta atg atg agc cac      432
Ala Arg Glu Leu Gly Met Asp Thr Val Gly Phe Leu Met Met Ser His
    130                 135                 140 atg att ccg gct gag caa ctg gca gcg caa ggc aag ttg atg gag acc      480
Met Ile Pro Ala Glu Gln Leu Ala Ala Gln Gly Lys Leu Met Glu Thr
145                 150                 155                 160 tac ggc gca cag tgc atc tac atg gcc gat tcc ggt ggc gcg atg aac      528
Tyr Gly Ala Gln Cys Ile Tyr Met Ala Asp Ser Gly Gly Ala Met Asn
                165                 170                 175 atg aac gac atc cgc gac cgc atg cgc gct ttc aag gcg gtg ctg aat      576
Met Asn Asp Ile Arg Asp Arg Met Arg Ala Phe Lys Ala Val Leu Asn
            180                 185                 190 ccg cag acc cag acc ggc atg cat gcg cac cac aac ctc agc ctc ggc      624
Pro Gln Thr Gln Thr Gly Met His Ala His His Asn Leu Ser Leu Gly
        195                 200                 205 gtg gcc aat tcc atc atc gcg gtg gaa gag ggc tgc gac cgc atc gac      672
Val Ala Asn Ser Ile Ile Ala Val Glu Glu Gly Cys Asp Arg Ile Asp
    210                 215                 220 gcc tcg ctg gct gga atg ggc gct ggc gcc ggc aac gcg ccg ctg gag      720
Ala Ser Leu Ala Gly Met Gly Ala Gly Ala Gly Asn Ala Pro Leu Glu
225                 230                 235                 240 gtg ttc atc gcc gcc gcg gag cgc ctc ggc tgg aac cat ggc acc gat      768
Val Phe Ile Ala Ala Ala Glu Arg Leu Gly Trp Asn His Gly Thr Asp
                245                 250                 255 ctc tac acg ctg atg gac gcc gcc gac gat atc gtc agg ccg ttg cag      816
Leu Tyr Thr Leu Met Asp Ala Ala Asp Asp Ile Val Arg Pro Leu Gln
            260                 265                 270
```

| | | | | | | | | | | | | | | | | |
|---|---|---|---|---|---|---|---|---|---|---|---|---|---|---|---|---|
| gac | cgt | ccg | gtg | aga | gtt | gat | cgc | gaa | acc | ctc | ggc | ctg | ggt | tat | gcc | 864 |
| Asp | Arg | Pro | Val | Arg | Val | Asp | Arg | Glu | Thr | Leu | Gly | Leu | Gly | Tyr | Ala | |
| | | 275 | | | | 280 | | | | | 285 | | | | | |
| ggg | gtc | tac | tcc | agc | ttc | ctg | cgc | cac | gcc | gag | gtg | gca | gcc | gcg | aag | 912 |
| Gly | Val | Tyr | Ser | Ser | Phe | Leu | Arg | His | Ala | Glu | Val | Ala | Ala | Ala | Lys | |
| | 290 | | | | | 295 | | | | 300 | | | | | | |
| tat | ggg | ctg | aag | acc | ctg | gac | atc | ctc | gta | gaa | ctg | ggc | agg | cgc | cgg | 960 |
| Tyr | Gly | Leu | Lys | Thr | Leu | Asp | Ile | Leu | Val | Glu | Leu | Gly | Arg | Arg | Arg | |
| 305 | | | | 310 | | | | 315 | | | | 320 | | | | |
| atg | gtc | ggt | ggc | cag | gaa | gac | atg | atc | gtc | gac | gtc | gcc | ctc | gat | ctg | 1008 |
| Met | Val | Gly | Gly | Gln | Glu | Asp | Met | Ile | Val | Asp | Val | Ala | Leu | Asp | Leu | |
| | | | 325 | | | | 330 | | | | 335 | | | | | |
| ctg | gca | gcc | cgc | aag | gag | caa | cag | gca | | | | | | | | 1035 |
| Leu | Ala | Ala | Arg | Lys | Glu | Gln | Gln | Ala | | | | | | | | |
| | 340 | | | | | 345 | | | | | | | | | | |

<210> SEQ ID NO 62
<211> LENGTH: 345
<212> TYPE: PRT
<213> ORGANISM: Pseudomonas putida

<400> SEQUENCE: 62

Met Thr Phe Asn Pro Gly Lys Lys Leu Tyr Ile Ser Asp Val Thr Leu
1               5                   10                  15

Arg Asp Gly Ser His Ala Ile Arg His Gln Tyr Ser Ile Gln Asn Val
            20                  25                  30

Gln Asp Ile Ala Arg Ala Leu Asp Lys Ala Arg Val Asp Ser Ile Glu
        35                  40                  45

Val Thr His Gly Asp Gly Leu Gln Gly Ser Ser Phe Asn Tyr Gly Phe
    50                  55                  60

Gly Ala His Ser Asp Leu Glu Trp Ile Glu Ala Ala Asp Val Ile
65                  70                  75                  80

Gln His Ala Arg Val Thr Val Leu Leu Val Pro Gly Ile Gly Thr Val
                85                  90                  95

His Asp Leu Lys Ala Ala Tyr Asp Ala Gly Ala Arg Ser Val Arg Val
            100                 105                 110

Ala Thr His Cys Thr Glu Ala Asp Val Ser Arg Gln His Ile Glu Tyr
        115                 120                 125

Ala Arg Glu Leu Gly Met Asp Thr Val Gly Phe Leu Met Met Ser His
    130                 135                 140

Met Ile Pro Ala Glu Gln Leu Ala Ala Gln Gly Lys Leu Met Glu Thr
145                 150                 155                 160

Tyr Gly Ala Gln Cys Ile Tyr Met Ala Asp Ser Gly Gly Ala Met Asn
                165                 170                 175

Met Asn Asp Ile Arg Asp Arg Met Arg Ala Phe Lys Ala Val Leu Asn
            180                 185                 190

Pro Gln Thr Gln Thr Gly Met His Ala His His Asn Leu Ser Leu Gly
        195                 200                 205

Val Ala Asn Ser Ile Ile Ala Val Glu Glu Gly Cys Asp Arg Ile Asp
    210                 215                 220

Ala Ser Leu Ala Gly Met Gly Ala Gly Ala Asn Ala Pro Leu Glu
225                 230                 235                 240

Val Phe Ile Ala Ala Ala Glu Arg Leu Gly Trp Asn His Gly Thr Asp
                245                 250                 255

Leu Tyr Thr Leu Met Asp Ala Ala Asp Asp Ile Val Arg Pro Leu Gln
            260                 265                 270

```
        Asp Arg Pro Val Arg Val Asp Arg Glu Thr Leu Gly Leu Gly Tyr Ala
                    275                 280                 285

Gly Val Tyr Ser Ser Phe Leu Arg His Ala Glu Val Ala Ala Ala Lys
                290                 295                 300

Tyr Gly Leu Lys Thr Leu Asp Ile Leu Val Glu Leu Gly Arg Arg
        305                 310                 315                 320

Met Val Gly Gly Gln Glu Asp Met Ile Val Asp Val Ala Leu Asp Leu
                        325                 330                 335

Leu Ala Ala Arg Lys Glu Gln Gln Ala
                        340                 345

<210> SEQ ID NO 63
<211> LENGTH: 936
<212> TYPE: DNA
<213> ORGANISM: Pseudomonas putida
<220> FEATURE:
<221> NAME/KEY: CDS
<222> LOCATION: (1)..(936)

<400> SEQUENCE: 63 atg aac aag aaa ctg aaa gta gcg atc ata ggc cca ggc aac atc ggc      48
Met Asn Lys Lys Leu Lys Val Ala Ile Ile Gly Pro Gly Asn Ile Gly
1               5                   10                  15 aca gac ctg atg atc aag gtg atg cgc aac gca cag tac ttg gaa atg      96
Thr Asp Leu Met Ile Lys Val Met Arg Asn Ala Gln Tyr Leu Glu Met
                20                  25                  30 ggg gcc atg gtg ggt atc gac ccg gcc tcc gat ggc ttg gcc cgt gct     144
Gly Ala Met Val Gly Ile Asp Pro Ala Ser Asp Gly Leu Ala Arg Ala
            35                  40                  45 cag cgc atg ggc gtg gcg acc acc cat gaa ggc gtc gaa ggg ttc atc     192
Gln Arg Met Gly Val Ala Thr Thr His Glu Gly Val Glu Gly Phe Ile
        50                  55                  60 aac ctg ccg gaa ttc gcc gac atc gat ttt gtc ttc gat gcc act agc     240
Asn Leu Pro Glu Phe Ala Asp Ile Asp Phe Val Phe Asp Ala Thr Ser
65                  70                  75                  80 gcc tcc gcc cat gtg cag aac gat gcc ttg ctg cgt cgt gct aaa ccc     288
Ala Ser Ala His Val Gln Asn Asp Ala Leu Leu Arg Arg Ala Lys Pro
                85                  90                  95 ggc atc cgc ctg atc gac ctg acc ccg gcg gcc atc ggc ccc tac tgc     336
Gly Ile Arg Leu Ile Asp Leu Thr Pro Ala Ala Ile Gly Pro Tyr Cys
            100                 105                 110 gta ccg gta gtg aat ctg gaa gag cac ctc gcc aaa ctc aac gtc aac     384
Val Pro Val Val Asn Leu Glu Glu His Leu Ala Lys Leu Asn Val Asn
        115                 120                 125 atg gtc acc tgc ggt ggc cag gcc acc atc cct atg gtc gcc gcg gtc     432
Met Val Thr Cys Gly Gly Gln Ala Thr Ile Pro Met Val Ala Ala Val
130                 135                 140 tcg cgt gtg gcc aag gtg cat tat gcc gaa atc gtc gcc tcg atc gcg     480
Ser Arg Val Ala Lys Val His Tyr Ala Glu Ile Val Ala Ser Ile Ala
145                 150                 155                 160 tcg aaa tcg gct ggt ccc ggc act cgc gcc aat atc gac gag ttc acc     528
Ser Lys Ser Ala Gly Pro Gly Thr Arg Ala Asn Ile Asp Glu Phe Thr
                165                 170                 175 gag acc acc agc aag gcc atc gaa gtg att ggc ggc gcc gcc aag ggc     576
Glu Thr Thr Ser Lys Ala Ile Glu Val Ile Gly Gly Ala Ala Lys Gly
            180                 185                 190 aag gcg atc atc gtc atg aac ccg gcc gag ccg ccg ctg atc atg cgt     624
Lys Ala Ile Ile Val Met Asn Pro Ala Glu Pro Pro Leu Ile Met Arg
        195                 200                 205 gac acg gtg ttt gta ctg tcc gaa acc gtc gac cag gca cag gtc gag     672
Asp Thr Val Phe Val Leu Ser Glu Thr Val Asp Gln Ala Gln Val Glu
```

```
Asp Thr Val Phe Val Leu Ser Glu Thr Val Asp Gln Ala Gln Val Glu
    210                 215                 220 gcc agc gta gag gag atg acc agc gcc gtg cag gcc tac gtg ccg ggc    720
Ala Ser Val Glu Glu Met Thr Ser Ala Val Gln Ala Tyr Val Pro Gly
225                 230                 235                 240 tat cgt ctc aag cag aag gtg cag ttc gac gtg att ccc gaa tcc gcg    768
Tyr Arg Leu Lys Gln Lys Val Gln Phe Asp Val Ile Pro Glu Ser Ala
                245                 250                 255 ccg ctg cat atc cca ggc ctc ggc aca ttc agc ggt ttg aag acc tcg    816
Pro Leu His Ile Pro Gly Leu Gly Thr Phe Ser Gly Leu Lys Thr Ser
            260                 265                 270 atc tac ctc gaa gtc gaa ggt gcc gcc cac tat ttg ccg gcc tac gcc    864
Ile Tyr Leu Glu Val Glu Gly Ala Ala His Tyr Leu Pro Ala Tyr Ala
        275                 280                 285 agc agc ctc gac atc atg acc tcc gcc gcg ctg gct acc gcc gaa cgc    912
Ser Ser Leu Asp Ile Met Thr Ser Ala Ala Leu Ala Thr Ala Glu Arg
    290                 295                 300 atg gcg cag tcg ctg ctg aac gcc                                    936
Met Ala Gln Ser Leu Leu Asn Ala
305                 310

<210> SEQ ID NO 64
<211> LENGTH: 312
<212> TYPE: PRT
<213> ORGANISM: Pseudomonas putida

<400> SEQUENCE: 64

Met Asn Lys Lys Leu Lys Val Ala Ile Ile Gly Pro Gly Asn Ile Gly
1               5                   10                  15

Thr Asp Leu Met Ile Lys Val Met Arg Asn Ala Gln Tyr Leu Glu Met
                20                  25                  30

Gly Ala Met Val Gly Ile Asp Pro Ala Ser Asp Gly Leu Ala Arg Ala
            35                  40                  45

Gln Arg Met Gly Val Ala Thr Thr His Glu Gly Val Glu Gly Phe Ile
        50                  55                  60

Asn Leu Pro Glu Phe Ala Asp Ile Asp Phe Val Phe Asp Ala Thr Ser
65                  70                  75                  80

Ala Ser Ala His Val Gln Asn Asp Ala Leu Leu Arg Arg Ala Lys Pro
                85                  90                  95

Gly Ile Arg Leu Ile Asp Leu Thr Pro Ala Ala Ile Gly Pro Tyr Cys
            100                 105                 110

Val Pro Val Val Asn Leu Glu Glu His Leu Ala Lys Leu Asn Val Asn
        115                 120                 125

Met Val Thr Cys Gly Gly Gln Ala Thr Ile Pro Met Val Ala Ala Val
    130                 135                 140

Ser Arg Val Ala Lys Val His Tyr Ala Glu Ile Val Ala Ser Ile Ala
145                 150                 155                 160

Ser Lys Ser Ala Gly Pro Gly Thr Arg Ala Asn Ile Asp Glu Phe Thr
                165                 170                 175

Glu Thr Thr Ser Lys Ala Ile Glu Val Ile Gly Gly Ala Ala Lys Gly
            180                 185                 190

Lys Ala Ile Ile Val Met Asn Pro Ala Glu Pro Pro Leu Ile Met Arg
        195                 200                 205

Asp Thr Val Phe Val Leu Ser Glu Thr Val Asp Gln Ala Gln Val Glu
    210                 215                 220

Ala Ser Val Glu Glu Met Thr Ser Ala Val Gln Ala Tyr Val Pro Gly
225                 230                 235                 240
```

```
Tyr Arg Leu Lys Gln Lys Val Gln Phe Asp Val Ile Pro Glu Ser Ala
                245                 250                 255

Pro Leu His Ile Pro Gly Leu Gly Thr Phe Ser Gly Leu Lys Thr Ser
            260                 265                 270

Ile Tyr Leu Glu Val Glu Gly Ala Ala His Tyr Leu Pro Ala Tyr Ala
        275                 280                 285

Ser Ser Leu Asp Ile Met Thr Ser Ala Ala Leu Ala Thr Ala Glu Arg
    290                 295                 300

Met Ala Gln Ser Leu Leu Asn Ala
305                 310

<210> SEQ ID NO 65
<211> LENGTH: 1485
<212> TYPE: DNA
<213> ORGANISM: Enterobacter cloacae
<220> FEATURE:
<221> NAME/KEY: CDS
<222> LOCATION: (1)..(1485)

<400> SEQUENCE: 65 atg cag aac ccg atc aac gac ctg cgc tcc gcg atc gcg ctg ctg caa      48
Met Gln Asn Pro Ile Asn Asp Leu Arg Ser Ala Ile Ala Leu Leu Gln
1               5                   10                  15 cgc cat ccg ggt cac tac atc gaa acc gac cac ccg gtc gac ccg aac      96
Arg His Pro Gly His Tyr Ile Glu Thr Asp His Pro Val Asp Pro Asn
            20                  25                  30 gcc gaa ctg gcc ggt gtg tac cgc cac atc ggt gcg ggt ggc acc gtg     144
Ala Glu Leu Ala Gly Val Tyr Arg His Ile Gly Ala Gly Gly Thr Val
        35                  40                  45 aaa cgt ccg acc cgc acc ggt cca gcc atg atg ttc aac agc gtg aag     192
Lys Arg Pro Thr Arg Thr Gly Pro Ala Met Met Phe Asn Ser Val Lys
50                  55                  60 ggc tac cca ggc agc cgc atc ctg gtg ggc atg cac gcc agc cgt gaa     240
Gly Tyr Pro Gly Ser Arg Ile Leu Val Gly Met His Ala Ser Arg Glu
65                  70                  75                  80 cgt gcc gcc ctg ctg ctg ggc tgc gtg cca agc aaa ctg gcg cag cac     288
Arg Ala Ala Leu Leu Leu Gly Cys Val Pro Ser Lys Leu Ala Gln His
                85                  90                  95 gtg ggc cag gcc gtg aag aac ccg gtg gcc cca gtg gtg gtg cca gcc     336
Val Gly Gln Ala Val Lys Asn Pro Val Ala Pro Val Val Val Pro Ala
            100                 105                 110 agc caa gcc cca tgc caa gaa cag gtg ttc tac gcc gac gac ccg gac     384
Ser Gln Ala Pro Cys Gln Glu Gln Val Phe Tyr Ala Asp Asp Pro Asp
        115                 120                 125 ttc gac ctg cgc aag ctg ctg cca gcc cca acc aac acc ccg atc gat     432
Phe Asp Leu Arg Lys Leu Leu Pro Ala Pro Thr Asn Thr Pro Ile Asp
130                 135                 140 gcc ggt ccg ttc ttc tgc ctg ggc ctg gtg ctg gcg agc gac ccg gaa     480
Ala Gly Pro Phe Phe Cys Leu Gly Leu Val Leu Ala Ser Asp Pro Glu
145                 150                 155                 160 gat acc agc ctg acc gac gtg acc atc cac cgc ctg tgc gtg caa gag     528
Asp Thr Ser Leu Thr Asp Val Thr Ile His Arg Leu Cys Val Gln Glu
                165                 170                 175 cgc gac gag ctg agc atg ttc ctg gcc gcc ggt cgc cac atc gag gtg     576
Arg Asp Glu Leu Ser Met Phe Leu Ala Ala Gly Arg His Ile Glu Val
            180                 185                 190 ttc cgc aag aag gcc gaa gcc gcc ggt aag ccg ctg ccg gtg acc atc     624
Phe Arg Lys Lys Ala Glu Ala Ala Gly Lys Pro Leu Pro Val Thr Ile
        195                 200                 205
```

```
aac atg ggc ctg gac cca gcc atc tac atc ggt gcc tgc ttc gaa gcg    672
Asn Met Gly Leu Asp Pro Ala Ile Tyr Ile Gly Ala Cys Phe Glu Ala
    210                 215                 220 cca acc acc ccg ttc ggc tac aac gag ctg ggt gtg gcc ggt gcc ctg    720
Pro Thr Thr Pro Phe Gly Tyr Asn Glu Leu Gly Val Ala Gly Ala Leu
225                 230                 235                 240 cgt cag caa ccg gtg gaa ctg gtg cag ggc gtg gcc gtg aaa gag aag    768
Arg Gln Gln Pro Val Glu Leu Val Gln Gly Val Ala Val Lys Glu Lys
                245                 250                 255 gcg atc gcg cgt gcc gag atc atc atc gag ggc gaa ctg ctg cca ggc    816
Ala Ile Ala Arg Ala Glu Ile Ile Ile Glu Gly Glu Leu Leu Pro Gly
            260                 265                 270 gtg cgc gtg cgc gaa gat cag cac acc aac acc ggt cac gcc atg ccg    864
Val Arg Val Arg Glu Asp Gln His Thr Asn Thr Gly His Ala Met Pro
        275                 280                 285 gaa ttc cca ggc tac tgc ggt gag gcc aac ccg agc ctg ccg gtg atc    912
Glu Phe Pro Gly Tyr Cys Gly Glu Ala Asn Pro Ser Leu Pro Val Ile
    290                 295                 300 aag gtg aag gcc gtg acc atg cgc aac cac gcc atc ctg cag acc ctg    960
Lys Val Lys Ala Val Thr Met Arg Asn His Ala Ile Leu Gln Thr Leu
305                 310                 315                 320 gtg ggt ccg ggt gag gaa cac acc acc ctg gcg ggt ctg ccg acc gaa   1008
Val Gly Pro Gly Glu Glu His Thr Thr Leu Ala Gly Leu Pro Thr Glu
                325                 330                 335 gcc agc atc cgc aac gcc gtg gaa gag gcg atc cca ggc ttc ctg cag   1056
Ala Ser Ile Arg Asn Ala Val Glu Glu Ala Ile Pro Gly Phe Leu Gln
            340                 345                 350 aac gtg tac gcc cac acc gcc ggt ggc ggt aag ttc ctg ggc atc ctg   1104
Asn Val Tyr Ala His Thr Ala Gly Gly Gly Lys Phe Leu Gly Ile Leu
        355                 360                 365 cag gtc aag aag cgc cag ccg agc gac gaa ggc cgt cag ggc caa gcc   1152
Gln Val Lys Lys Arg Gln Pro Ser Asp Glu Gly Arg Gln Gly Gln Ala
    370                 375                 380 gcc ctg atc gcc ctg gcc acc tac agc gag ctg aag aac atc atc ctg   1200
Ala Leu Ile Ala Leu Ala Thr Tyr Ser Glu Leu Lys Asn Ile Ile Leu
385                 390                 395                 400 gtg gac gag gac gtg gac atc ttc gac agc gac gac atc ctg tgg gcc   1248
Val Asp Glu Asp Val Asp Ile Phe Asp Ser Asp Asp Ile Leu Trp Ala
                405                 410                 415 atg acc acc cgc atg cag ggc gac gtg agc atc acc acc ctg cca ggc   1296
Met Thr Thr Arg Met Gln Gly Asp Val Ser Ile Thr Thr Leu Pro Gly
            420                 425                 430 atc cgt ggc cat cag ctg gac ccg agc cag agc cca gac tac agc acc   1344
Ile Arg Gly His Gln Leu Asp Pro Ser Gln Ser Pro Asp Tyr Ser Thr
        435                 440                 445 agc atc cgt ggc aac ggc atc agc tgc aag acc atc ttc gac tgc acc   1392
Ser Ile Arg Gly Asn Gly Ile Ser Cys Lys Thr Ile Phe Asp Cys Thr
    450                 455                 460 gtg ccg tgg gcc ctg aaa gcc cgt ttc gag cgt gcc cca ttc atg gaa   1440
Val Pro Trp Ala Leu Lys Ala Arg Phe Glu Arg Ala Pro Phe Met Glu
465                 470                 475                 480 gtg gac ccg acc ccg tgg gcc cca gag ctg ttc agc gac aag aag        1485
Val Asp Pro Thr Pro Trp Ala Pro Glu Leu Phe Ser Asp Lys Lys
                485                 490                 495

<210> SEQ ID NO 66
<211> LENGTH: 495
<212> TYPE: PRT
<213> ORGANISM: Enterobacter cloacae

<400> SEQUENCE: 66
```

```
Met Gln Asn Pro Ile Asn Asp Leu Arg Ser Ala Ile Ala Leu Leu Gln
1               5                   10                  15

Arg His Pro Gly His Tyr Ile Glu Thr Asp His Pro Val Asp Pro Asn
            20                  25                  30

Ala Glu Leu Ala Gly Val Tyr Arg His Ile Gly Ala Gly Gly Thr Val
        35                  40                  45

Lys Arg Pro Thr Arg Thr Gly Pro Ala Met Met Phe Asn Ser Val Lys
50                  55                  60

Gly Tyr Pro Gly Ser Arg Ile Leu Val Gly Met His Ala Ser Arg Glu
65              70                  75                  80

Arg Ala Ala Leu Leu Leu Gly Cys Val Pro Ser Lys Leu Ala Gln His
                85                  90                  95

Val Gly Gln Ala Val Lys Asn Pro Val Ala Pro Val Val Pro Ala
                100                 105                 110

Ser Gln Ala Pro Cys Gln Glu Gln Val Phe Tyr Ala Asp Asp Pro Asp
        115                 120                 125

Phe Asp Leu Arg Lys Leu Leu Pro Ala Pro Thr Asn Thr Pro Ile Asp
    130                 135                 140

Ala Gly Pro Phe Phe Cys Leu Gly Leu Val Leu Ala Ser Asp Pro Glu
145                 150                 155                 160

Asp Thr Ser Leu Thr Asp Val Thr Ile His Arg Leu Cys Val Gln Glu
                165                 170                 175

Arg Asp Glu Leu Ser Met Phe Leu Ala Ala Gly Arg His Ile Glu Val
            180                 185                 190

Phe Arg Lys Lys Ala Glu Ala Ala Gly Lys Pro Leu Pro Val Thr Ile
        195                 200                 205

Asn Met Gly Leu Asp Pro Ala Ile Tyr Ile Gly Ala Cys Phe Glu Ala
210                 215                 220

Pro Thr Thr Pro Phe Gly Tyr Asn Glu Leu Gly Val Ala Gly Ala Leu
225                 230                 235                 240

Arg Gln Gln Pro Val Glu Leu Val Gln Gly Val Ala Val Lys Glu Lys
            245                 250                 255

Ala Ile Ala Arg Ala Glu Ile Ile Ile Glu Gly Glu Leu Leu Pro Gly
        260                 265                 270

Val Arg Val Arg Glu Asp Gln His Thr Asn Thr Gly His Ala Met Pro
            275                 280                 285

Glu Phe Pro Gly Tyr Cys Gly Glu Ala Asn Pro Ser Leu Pro Val Ile
    290                 295                 300

Lys Val Lys Ala Val Thr Met Arg Asn His Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Arg Asn Ala Val Glu Glu Ala Ile Pro Gly Phe Leu Gln
            340                 345                 350

Asn Val Tyr Ala His Thr Ala Gly Gly Lys Phe Leu Gly Ile Leu
        355                 360                 365

Gln Val Lys Lys Arg Gln Pro Ser Asp Glu Gly Arg Gln Gly Gln Ala
    370                 375                 380

Ala Leu Ile Ala Leu Ala Thr Tyr Ser Glu Leu Lys Asn Ile Ile Leu
385                 390                 395                 400

Val Asp Glu Asp Val Asp Ile Phe Asp Ser Asp Asp Ile Leu Trp Ala
            405                 410                 415
```

```
Met Thr Thr Arg Met Gln Gly Asp Val Ser Ile Thr Thr Leu Pro Gly
            420                 425                 430

Ile Arg Gly His Gln Leu Asp Pro Ser Gln Ser Pro Tyr Ser Thr
        435                 440                 445

Ser Ile Arg Gly Asn Gly Ile Ser Cys Lys Thr Ile Phe Asp Cys Thr
450                 455                 460

Val Pro Trp Ala Leu Lys Ala Arg Phe Glu Arg Ala Pro Phe Met Glu
465                 470                 475                 480

Val Asp Pro Thr Pro Trp Ala Pro Glu Leu Phe Ser Asp Lys Lys
            485                 490                 495

<210> SEQ ID NO 67
<211> LENGTH: 82
<212> TYPE: DNA
<213> ORGANISM: Artificial Sequence
<220> FEATURE:
<223> OTHER INFORMATION: Synthetic Promoter

<400> SEQUENCE: 67
gagctgttga caattaatca tcggctcgta taatgtgtgg aattgtgagc ggataacaat    60
ttcacacagg aaacagaatt ct                                             82

<210> SEQ ID NO 68
<211> LENGTH: 98
<212> TYPE: DNA
<213> ORGANISM: Escherichia coli

<400> SEQUENCE: 68
ttgcattagg caccccaggc tttacacttt atgcttccgg ctcgtatgtt gtgtggaatt    60
gtgagcggat aacaatttca caggaaac agaattct                              98

<210> SEQ ID NO 69
<211> LENGTH: 268
<212> TYPE: DNA
<213> ORGANISM: Escherichia coli

<400> SEQUENCE: 69
tgccgtcact gcgtctttta ctggctcttc tcgctaacca aaccggtaac cccgcttatt    60
aaaagcattc tgtaacaaag cgggaccaaa gccatgacaa aaacgcgtaa caaaagtgtc   120
tataatcacg gcagaaaagt ccacattgat tatttgcacg gcgtcacact ttgctatgcc   180
ataacatttt tatccataag attagcggat cctacctgac gctttttatc gcaactctct   240
actgtttctc catacccgtt ttttggg                                       268

<210> SEQ ID NO 70
<211> LENGTH: 135
<212> TYPE: DNA
<213> ORGANISM: Pseudomonas putida

<400> SEQUENCE: 70
cagacctcca gggtatggtg ggagattcat ttgatattgg acggtcgtca gggtctcgcg    60
caatccttca gcaatcaagt aaacgcatca ctcgggcctg caactgaaag cccgacctga   120
cgggacctgg caaca                                                    135

<210> SEQ ID NO 71
<211> LENGTH: 133
<212> TYPE: DNA
<213> ORGANISM: Pseudomonas putida
```

<400> SEQUENCE: 71
aggtgttaag acatcaccat ttggttatgt atgagttggt cgatttcaat attcatcacg    60
cgcgacctgc cggaaactgc aagtccgcct gccacgccca ggcgttctca caattccaag   120
agaggaaacc ggc                                                      133

<210> SEQ ID NO 72
<211> LENGTH: 38
<212> TYPE: DNA
<213> ORGANISM: Artificial Sequence
<220> FEATURE:
<223> OTHER INFORMATION: PCR Primer

<400> SEQUENCE: 72
ccgaaaagtg ccacctgacg tccttcatcg ccggcctg                            38

<210> SEQ ID NO 73
<211> LENGTH: 39
<212> TYPE: DNA
<213> ORGANISM: Artificial Sequence
<220> FEATURE:
<223> OTHER INFORMATION: PCR Primer

<400> SEQUENCE: 73
gccgcagctc gagatctgtc ttgttctgtt cggttcagg                           39

<210> SEQ ID NO 74
<211> LENGTH: 36
<212> TYPE: DNA
<213> ORGANISM: Artificial Sequence
<220> FEATURE:
<223> OTHER INFORMATION: PCR Primer

<400> SEQUENCE: 74
agatctcgag ctgcggccgc tccaccgagt gggctg                              36

<210> SEQ ID NO 75
<211> LENGTH: 42
<212> TYPE: DNA
<213> ORGANISM: Artificial Sequence
<220> FEATURE:
<223> OTHER INFORMATION: PCR Primer

<400> SEQUENCE: 75
gctggatcct ctagtgagct cggttttcat gggcttcatg gc                       42

<210> SEQ ID NO 76
<211> LENGTH: 41
<212> TYPE: DNA
<213> ORGANISM: Artificial Sequence
<220> FEATURE:
<223> OTHER INFORMATION: PCR Primer

<400> SEQUENCE: 76
ccgaaaagtg ccacctgacg tccctgttgc tcgatcaacg c                        41

<210> SEQ ID NO 77
<211> LENGTH: 100
<212> TYPE: DNA
<213> ORGANISM: Artificial Sequence
<220> FEATURE:
<223> OTHER INFORMATION: PCR Primer

<400> SEQUENCE: 77
tcataagatc tctcctgtgt gaaattgtta tccgctcaca attccacaca ttatacgagc    60

```
cgatgattaa ttgtcaacag ctctgttgcc aggtcccgtc                            100

<210> SEQ ID NO 78
<211> LENGTH: 35
<212> TYPE: DNA
<213> ORGANISM: Artificial Sequence
<220> FEATURE:
<223> OTHER INFORMATION: PCR Primer

<400> SEQUENCE: 78
aggagagatc ttatgaacaa aggtgtaatg cgacc                                 35

<210> SEQ ID NO 79
<211> LENGTH: 36
<212> TYPE: DNA
<213> ORGANISM: Artificial Sequence
<220> FEATURE:
<223> OTHER INFORMATION: PCR Primer

<400> SEQUENCE: 79
cgaacgcggc cgcgcaataa gtcgtaccgg accatc                                36

<210> SEQ ID NO 80
<211> LENGTH: 40
<212> TYPE: DNA
<213> ORGANISM: Artificial Sequence
<220> FEATURE:
<223> OTHER INFORMATION: PCR Primer

<400> SEQUENCE: 80
attgcgcggc cgcgttcgag gttatgtcac tgtgattttg                            40

<210> SEQ ID NO 81
<211> LENGTH: 37
<212> TYPE: DNA
<213> ORGANISM: Artificial Sequence
<220> FEATURE:
<223> OTHER INFORMATION: PCR Primer

<400> SEQUENCE: 81
gctggatcct ctagtgagct ccgcctgctc caggttg                               37

<210> SEQ ID NO 82
<211> LENGTH: 37
<212> TYPE: DNA
<213> ORGANISM: Artificial Sequence
<220> FEATURE:
<223> OTHER INFORMATION: PCR Primer

<400> SEQUENCE: 82
cgaacgcggc cgcgcaattc agcgtctgac cttgctg                               37

<210> SEQ ID NO 83
<211> LENGTH: 21
<212> TYPE: DNA
<213> ORGANISM: Artificial Sequence
<220> FEATURE:
<223> OTHER INFORMATION: PCR Primer

<400> SEQUENCE: 83
atcggctcgt ataatgtgtg g                                                21

<210> SEQ ID NO 84
<211> LENGTH: 19
<212> TYPE: DNA
```

<210> SEQ ID NO 85
<211> LENGTH: 18
<212> TYPE: DNA
<213> ORGANISM: Artificial Sequence
<220> FEATURE:
<223> OTHER INFORMATION: PCR Primer

<400> SEQUENCE: 84
tccgctcaca attccacac                                                 19

<210> SEQ ID NO 85
<211> LENGTH: 18
<212> TYPE: DNA
<213> ORGANISM: Artificial Sequence
<220> FEATURE:
<223> OTHER INFORMATION: PCR Primer

<400> SEQUENCE: 85
aatttcggcc cgctgatc                                                  18

<210> SEQ ID NO 86
<211> LENGTH: 19
<212> TYPE: DNA
<213> ORGANISM: Artificial Sequence
<220> FEATURE:
<223> OTHER INFORMATION: PCR Primer

<400> SEQUENCE: 86
gcagcaaagc cctgaaatc                                                 19

<210> SEQ ID NO 87
<211> LENGTH: 18
<212> TYPE: DNA
<213> ORGANISM: Artificial Sequence
<220> FEATURE:
<223> OTHER INFORMATION: PCR Primer

<400> SEQUENCE: 87
aacatcaccg tgcgctac                                                  18

<210> SEQ ID NO 88
<211> LENGTH: 18
<212> TYPE: DNA
<213> ORGANISM: Artificial Sequence
<220> FEATURE:
<223> OTHER INFORMATION: PCR Primer

<400> SEQUENCE: 88
cctcaatggc tttgccag                                                  18

<210> SEQ ID NO 89
<211> LENGTH: 18
<212> TYPE: DNA
<213> ORGANISM: Artificial Sequence
<220> FEATURE:
<223> OTHER INFORMATION: PCR Primer

<400> SEQUENCE: 89
gtacaacaca ctgccagc                                                  18

<210> SEQ ID NO 90
<211> LENGTH: 18
<212> TYPE: DNA
<213> ORGANISM: Artificial Sequence
<220> FEATURE:
<223> OTHER INFORMATION: PCR Primer

<400> SEQUENCE: 90
tgtgggcatg gtgtgttc                                                  18

```
<210> SEQ ID NO 91
<211> LENGTH: 18
<212> TYPE: DNA
<213> ORGANISM: Artificial Sequence
<220> FEATURE:
<223> OTHER INFORMATION: PCR Primer

<400> SEQUENCE: 91
tcttcaaagc gtccggtg                                                 18

<210> SEQ ID NO 92
<211> LENGTH: 18
<212> TYPE: DNA
<213> ORGANISM: Artificial Sequence
<220> FEATURE:
<223> OTHER INFORMATION: PCR Primer

<400> SEQUENCE: 92
acgaaggcac cgctaatg                                                 18

<210> SEQ ID NO 93
<211> LENGTH: 38
<212> TYPE: DNA
<213> ORGANISM: Artificial Sequence
<220> FEATURE:
<223> OTHER INFORMATION: PCR Primer

<400> SEQUENCE: 93
ccgaaaagtg ccacctgacg tcggccttgc tgctgcag                           38

<210> SEQ ID NO 94
<211> LENGTH: 37
<212> TYPE: DNA
<213> ORGANISM: Artificial Sequence
<220> FEATURE:
<223> OTHER INFORMATION: PCR Primer

<400> SEQUENCE: 94
gccgcagctc gagatctgga attgtgagaa cgcctgg                            37

<210> SEQ ID NO 95
<211> LENGTH: 36
<212> TYPE: DNA
<213> ORGANISM: Artificial Sequence
<220> FEATURE:
<223> OTHER INFORMATION: PCR Primer

<400> SEQUENCE: 95
agatctcgag ctgcggccgc ggtgaagctt ggggcc                             36

<210> SEQ ID NO 96
<211> LENGTH: 40
<212> TYPE: DNA
<213> ORGANISM: Artificial Sequence
<220> FEATURE:
<223> OTHER INFORMATION: PCR Primer

<400> SEQUENCE: 96
gctggatcct ctagtgagct cacgatttcc ccattgccag                         40

<210> SEQ ID NO 97
<211> LENGTH: 18
<212> TYPE: DNA
<213> ORGANISM: Artificial Sequence
<220> FEATURE:
```

<223> OTHER INFORMATION: PCR Primer

<400> SEQUENCE: 97
atcttgaacc aacgcacc                                                18

<210> SEQ ID NO 98
<211> LENGTH: 19
<212> TYPE: DNA
<213> ORGANISM: Artificial Sequence
<220> FEATURE:
<223> OTHER INFORMATION: PCR Primer

<400> SEQUENCE: 98
cacaaggcaa tcctgatcg                                               19

<210> SEQ ID NO 99
<211> LENGTH: 127
<212> TYPE: DNA
<213> ORGANISM: Artificial Sequence
<220> FEATURE:
<223> OTHER INFORMATION: PCR Primer

<400> SEQUENCE: 99
ggcgttctca caattccaga tctgagctgt tgacaattaa tcatcggctc gtataatgtg     60
tggaattgtg agcggataac aatttcacac aggaggacag ctatgaccga agaaagaa     120 cgcatcg                                                            127

<210> SEQ ID NO 100
<211> LENGTH: 47
<212> TYPE: DNA
<213> ORGANISM: Artificial Sequence
<220> FEATURE:
<223> OTHER INFORMATION: PCR Primer

<400> SEQUENCE: 100
gcggccccaa gcttcaccgc ggccgctcag acgtacttca ggccctc                 47

<210> SEQ ID NO 101
<211> LENGTH: 24
<212> TYPE: DNA
<213> ORGANISM: Artificial Sequence
<220> FEATURE:
<223> OTHER INFORMATION: PCR Primer

<400> SEQUENCE: 101
tcacatttcc tccgaccagt acag                                          24

<210> SEQ ID NO 102
<211> LENGTH: 41
<212> TYPE: DNA
<213> ORGANISM: Artificial Sequence
<220> FEATURE:
<223> OTHER INFORMATION: PCR Primer

<400> SEQUENCE: 102
actggtcgga ggaaatgtga aggaggacag ctatgccagg c                       41

<210> SEQ ID NO 103
<211> LENGTH: 50
<212> TYPE: DNA
<213> ORGANISM: Artificial Sequence
<220> FEATURE:
<223> OTHER INFORMATION: PCR Primer

<400> SEQUENCE: 103

```
ccaggcgttc tcacaattcc agatctgagc tgttgacaat taatcatcgg          50
```

<210> SEQ ID NO 104
<211> LENGTH: 29
<212> TYPE: DNA
<213> ORGANISM: Artificial Sequence
<220> FEATURE:
<223> OTHER INFORMATION: PCR Primer

<400> SEQUENCE: 104

```
gagcggcccc aagcttcacc gcggccgct                                 29
```

<210> SEQ ID NO 105
<211> LENGTH: 31
<212> TYPE: DNA
<213> ORGANISM: Artificial Sequence
<220> FEATURE:
<223> OTHER INFORMATION: PCR Primer

<400> SEQUENCE: 105

```
ctaactcaca ttaattgcgt tgcgctcact g                              31
```

<210> SEQ ID NO 106
<211> LENGTH: 22
<212> TYPE: DNA
<213> ORGANISM: Artificial Sequence
<220> FEATURE:
<223> OTHER INFORMATION: PCR Primer

<400> SEQUENCE: 106

```
gcccaggcgt tctcacaatt cc                                        22
```

<210> SEQ ID NO 107
<211> LENGTH: 48
<212> TYPE: DNA
<213> ORGANISM: Artificial Sequence
<220> FEATURE:
<223> OTHER INFORMATION: PCR Primer

<400> SEQUENCE: 107

```
cgcagagcgg ccccaagctt caccgcggcc gctcaggcct gggccagg            48
```

<210> SEQ ID NO 108
<211> LENGTH: 53
<212> TYPE: DNA
<213> ORGANISM: Artificial Sequence
<220> FEATURE:
<223> OTHER INFORMATION: PCR Primer

<400> SEQUENCE: 108

```
cgcagagcgg ccccaagctt caccgcggcc gctcagccct gcttttccag ctg      53
```

<210> SEQ ID NO 109
<211> LENGTH: 57
<212> TYPE: DNA
<213> ORGANISM: Artificial Sequence
<220> FEATURE:
<223> OTHER INFORMATION: PCR Primer

<400> SEQUENCE: 109

```
cgcagagcgg ccccaagctt caccgcggcc gctcacattt cctccgacca gtacagg  57
```

<210> SEQ ID NO 110
<211> LENGTH: 51
<212> TYPE: DNA

<213> ORGANISM: Artificial Sequence
<220> FEATURE:
<223> OTHER INFORMATION: PCR Primer

<400> SEQUENCE: 110
cgcagagcgg ccccaagctt caccgcggcc gctcagccga acacgatgcc g    51

<210> SEQ ID NO 111
<211> LENGTH: 52
<212> TYPE: DNA
<213> ORGANISM: Artificial Sequence
<220> FEATURE:
<223> OTHER INFORMATION: PCR Primer

<400> SEQUENCE: 111
cgcagagcgg ccccaagctt caccgcggcc gctcacaggc cacgggcttt ca    52

<210> SEQ ID NO 112
<211> LENGTH: 22
<212> TYPE: DNA
<213> ORGANISM: Artificial Sequence
<220> FEATURE:
<223> OTHER INFORMATION: PCR Primer

<400> SEQUENCE: 112
aactggagcg ggatctgatg gc    22

<210> SEQ ID NO 113
<211> LENGTH: 64
<212> TYPE: DNA
<213> ORGANISM: Artificial Sequence
<220> FEATURE:
<223> OTHER INFORMATION: PCR Primer

<400> SEQUENCE: 113
aatcacagtg acataacctc gaacgcggcc gctcaaagtt tcacacagat gttttcagc    60 tcgg    64

<210> SEQ ID NO 114
<211> LENGTH: 80
<212> TYPE: DNA
<213> ORGANISM: Artificial Sequence
<220> FEATURE:
<223> OTHER INFORMATION: PCR Primer

<400> SEQUENCE: 114
ggtgtgcctc ctgaagaaga ggccgcccgg gcaggcggc cggatggctc aaagtttcac    60
acagatgttt ttcagctcgg    80

<210> SEQ ID NO 115
<211> LENGTH: 22
<212> TYPE: DNA
<213> ORGANISM: Artificial Sequence
<220> FEATURE:
<223> OTHER INFORMATION: PCR Primer

<400> SEQUENCE: 115
tgacataacc tcgaacgcgg cc    22

<210> SEQ ID NO 116
<211> LENGTH: 52
<212> TYPE: DNA
<213> ORGANISM: Artificial Sequence
<220> FEATURE:
<223> OTHER INFORMATION: PCR Primer -continued

```
<400> SEQUENCE: 116
aatcacagtg acataacctc gaacgcggcc gctcaggaat ggagggcgtc gg          52

<210> SEQ ID NO 117
<211> LENGTH: 38
<212> TYPE: DNA
<213> ORGANISM: Artificial Sequence
<220> FEATURE:
<223> OTHER INFORMATION: PCR Primer

<400> SEQUENCE: 117
tcatgcctgt tgctccttca gatgaagcgc acggaggc                          38

<210> SEQ ID NO 118
<211> LENGTH: 38
<212> TYPE: DNA
<213> ORGANISM: Artificial Sequence
<220> FEATURE:
<223> OTHER INFORMATION: PCR Primer

<400> SEQUENCE: 118
gcgcttcatc tgaaggagca acaggcatga atcgtacc                          38

<210> SEQ ID NO 119
<211> LENGTH: 45
<212> TYPE: DNA
<213> ORGANISM: Artificial Sequence
<220> FEATURE:
<223> OTHER INFORMATION: PCR Primer

<400> SEQUENCE: 119
gaattcctgc agtctagagg atccctagct tcacgctgcc gcaag                  45

<210> SEQ ID NO 120
<211> LENGTH: 52
<212> TYPE: DNA
<213> ORGANISM: Artificial Sequence
<220> FEATURE:
<223> OTHER INFORMATION: PCR Primer

<400> SEQUENCE: 120
cgcaacgcaa ttaatgtgag ttaggaattc gtgcttcggc tccctgatga tc          52

<210> SEQ ID NO 121
<211> LENGTH: 41
<212> TYPE: DNA
<213> ORGANISM: Artificial Sequence
<220> FEATURE:
<223> OTHER INFORMATION: PCR Primer

<400> SEQUENCE: 121
tcacggtgcg gccgcttaat catcatggtg caggtacgcc g                      41

<210> SEQ ID NO 122
<211> LENGTH: 41
<212> TYPE: DNA
<213> ORGANISM: Artificial Sequence
<220> FEATURE:
<223> OTHER INFORMATION: PCR Primer

<400> SEQUENCE: 122
caccatgatg attaagcggc cgcaccgtga tcacgggcag g                      41

<210> SEQ ID NO 123
```

```
<210> SEQ ID NO 123
<211> LENGTH: 58
<212> TYPE: DNA
<213> ORGANISM: Artificial Sequence
<220> FEATURE:
<223> OTHER INFORMATION: PCR Primer

<400> SEQUENCE: 123
gtgcttgcgg cagcgtgaag ctagggatcc gaaccgctat atcaagggtg acaacgtc      58

<210> SEQ ID NO 124
<211> LENGTH: 52
<212> TYPE: DNA
<213> ORGANISM: Artificial Sequence
<220> FEATURE:
<223> OTHER INFORMATION: PCR Primer

<400> SEQUENCE: 124
cgcaacgcaa ttaatgtgag ttaggaattc gcgcgatgcc ctcgatttga tc            52

<210> SEQ ID NO 125
<211> LENGTH: 41
<212> TYPE: DNA
<213> ORGANISM: Artificial Sequence
<220> FEATURE:
<223> OTHER INFORMATION: PCR Primer

<400> SEQUENCE: 125
tcacggtgcg gccgctcagg cagtgaaacg ttgatgttcg g                        41

<210> SEQ ID NO 126
<211> LENGTH: 40
<212> TYPE: DNA
<213> ORGANISM: Artificial Sequence
<220> FEATURE:
<223> OTHER INFORMATION: PCR Primer

<400> SEQUENCE: 126
gtttcactgc ctgagcggcc gcaccgtgat cacgggcagg                          40

<210> SEQ ID NO 127
<211> LENGTH: 55
<212> TYPE: DNA
<213> ORGANISM: Artificial Sequence
<220> FEATURE:
<223> OTHER INFORMATION: PCR Primer

<400> SEQUENCE: 127
cagagcggcc ccaagcttca ccgcggccgc ttagctgacg aaggagatga tggcg         55

<210> SEQ ID NO 128
<211> LENGTH: 18
<212> TYPE: DNA
<213> ORGANISM: Artificial Sequence
<220> FEATURE:
<223> OTHER INFORMATION: PCR Primer

<400> SEQUENCE: 128
ctgatgatct cggtgctg                                                  18

<210> SEQ ID NO 129
<211> LENGTH: 18
<212> TYPE: DNA
<213> ORGANISM: Artificial Sequence
<220> FEATURE:
<223> OTHER INFORMATION: PCR Primer

<400> SEQUENCE: 129
```

```
gacttcaact tcgccacc                                              18
```

<210> SEQ ID NO 130
<211> LENGTH: 42
<212> TYPE: DNA
<213> ORGANISM: Artificial Sequence
<220> FEATURE:
<223> OTHER INFORMATION: PCR Primer

<400> SEQUENCE: 130

```
tgtcctcagc ggccgctcag gcagtgaaac gttgatgttc gg                   42
```

<210> SEQ ID NO 131
<211> LENGTH: 44
<212> TYPE: DNA
<213> ORGANISM: Artificial Sequence
<220> FEATURE:
<223> OTHER INFORMATION: PCR Primer

<400> SEQUENCE: 131

```
gtttcactgc ctgagcggcc gctgaggaca acgccatgga cgag                 44
```

<210> SEQ ID NO 132
<211> LENGTH: 57
<212> TYPE: DNA
<213> ORGANISM: Artificial Sequence
<220> FEATURE:
<223> OTHER INFORMATION: PCR Primer

<400> SEQUENCE: 132

```
gtgcttgcgg cagcgtgaag ctagggatcc aacagggagg cacaacaatg aaaaccc   57
```

<210> SEQ ID NO 133
<211> LENGTH: 50
<212> TYPE: DNA
<213> ORGANISM: Artificial Sequence
<220> FEATURE:
<223> OTHER INFORMATION: PCR Primer

<400> SEQUENCE: 133

```
cgcaacgcaa ttaatgtgag ttaggaattc gtagttgtcg cccgactcgg           50
```

<210> SEQ ID NO 134
<211> LENGTH: 44
<212> TYPE: DNA
<213> ORGANISM: Artificial Sequence
<220> FEATURE:
<223> OTHER INFORMATION: PCR Primer

<400> SEQUENCE: 134

```
gtcttcctgg agcggccgcg gttgttcctg gagttgtggt tgtc                 44
```

<210> SEQ ID NO 135
<211> LENGTH: 45
<212> TYPE: DNA
<213> ORGANISM: Artificial Sequence
<220> FEATURE:
<223> OTHER INFORMATION: PCR Primer

<400> SEQUENCE: 135

```
caggaacaac cgcggccgct ccaggaagac ttagggcttt ccatg                45
```

<210> SEQ ID NO 136
<211> LENGTH: 50
<212> TYPE: DNA

<213> ORGANISM: Artificial Sequence
<220> FEATURE:
<223> OTHER INFORMATION: PCR Primer

<400> SEQUENCE: 136
gtgcttgcgg cagcgtgaag ctagggatcc tgaccacagc cacccagtgc        50

<210> SEQ ID NO 137
<211> LENGTH: 20
<212> TYPE: DNA
<213> ORGANISM: Artificial Sequence
<220> FEATURE:
<223> OTHER INFORMATION: PCR Primer

<400> SEQUENCE: 137
cccagcccat gctgaatttg        20

<210> SEQ ID NO 138
<211> LENGTH: 18
<212> TYPE: DNA
<213> ORGANISM: Artificial Sequence
<220> FEATURE:
<223> OTHER INFORMATION: PCR Primer

<400> SEQUENCE: 138
cgattgcgcc atgaacag        18

<210> SEQ ID NO 139
<211> LENGTH: 51
<212> TYPE: DNA
<213> ORGANISM: Artificial Sequence
<220> FEATURE:
<223> OTHER INFORMATION: PCR Primer

<400> SEQUENCE: 139
agtgagcgca acgcaattaa tgtgagttag gaattcgccc gcggcaacac c        51

<210> SEQ ID NO 140
<211> LENGTH: 46
<212> TYPE: DNA
<213> ORGANISM: Artificial Sequence
<220> FEATURE:
<223> OTHER INFORMATION: PCR Primer

<400> SEQUENCE: 140
agcaaccatt gatgaggcgg ccgctggcct gtgcagggca ctaatg        46

<210> SEQ ID NO 141
<211> LENGTH: 46
<212> TYPE: DNA
<213> ORGANISM: Artificial Sequence
<220> FEATURE:
<223> OTHER INFORMATION: PCR Primer

<400> SEQUENCE: 141
aggccagcgg ccgcctcatc aatggttgct tggggtttca aaaatg        46

<210> SEQ ID NO 142
<211> LENGTH: 52
<212> TYPE: DNA
<213> ORGANISM: Artificial Sequence
<220> FEATURE:
<223> OTHER INFORMATION: PCR Primer

<400> SEQUENCE: 142
ccctgagtgc ttgcggcagc gtgaagctag ggatccgaca ccccccggcg tg        52

<210> SEQ ID NO 143
<211> LENGTH: 18
<212> TYPE: DNA
<213> ORGANISM: Artificial Sequence
<220> FEATURE:
<223> OTHER INFORMATION: PCR Primer

<400> SEQUENCE: 143
gaagcagttg tcgagcag                                                     18

<210> SEQ ID NO 144
<211> LENGTH: 18
<212> TYPE: DNA
<213> ORGANISM: Artificial Sequence
<220> FEATURE:
<223> OTHER INFORMATION: PCR Primer

<400> SEQUENCE: 144
attggtgaaa acccgcag                                                     18

<210> SEQ ID NO 145
<211> LENGTH: 136
<212> TYPE: DNA
<213> ORGANISM: Artificial Sequence
<220> FEATURE:
<223> OTHER INFORMATION: PCR Primer

<400> SEQUENCE: 145
tgaacgcatt agtgccctgc acaggccagc gagctgttga caattaatca tcggctcgta       60
taatgtgtgg aattgtgagc ggataacaat ttcacactag tcctaaggag atctaaatgg      120
gccagacccg catacc                                                      136

<210> SEQ ID NO 146
<211> LENGTH: 55
<212> TYPE: DNA
<213> ORGANISM: Artificial Sequence
<220> FEATURE:
<223> OTHER INFORMATION: PCR Primer

<400> SEQUENCE: 146
ccctgagtgc ttgcggcagc gtgaagctag ggatcctcac ttctccggcc caccc           55

<210> SEQ ID NO 147
<211> LENGTH: 60
<212> TYPE: DNA
<213> ORGANISM: Artificial Sequence
<220> FEATURE:
<223> OTHER INFORMATION: PCR Primer

<400> SEQUENCE: 147
tgtgagcgga taacaatttc acactagtta aggggaaaa atgacatcct gcgcccaccc       60

<210> SEQ ID NO 148
<211> LENGTH: 60
<212> TYPE: DNA
<213> ORGANISM: Artificial Sequence
<220> FEATURE:
<223> OTHER INFORMATION: PCR Primer

<400> SEQUENCE: 148
aggcagggta tgcgggtctg gcccattttt tcctccgttc atgccaggtt ctccgtcacg      60